United States Patent
Blanchette et al.

(10) Patent No.: US 12,378,592 B2
(45) Date of Patent: *Aug. 5, 2025

(54) SAMPLE PREP FOR DNA LINKAGE RECOVERY

(71) Applicant: DOVETAIL GENOMICS, LLC, Scotts Valley, CA (US)

(72) Inventors: Marco Blanchette, Santa Cruz, CA (US); Christopher John Troll, Santa Cruz, CA (US)

(73) Assignee: DOVETAIL GENOMICS, LLC., Scotts Valley, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/966,354

(22) PCT Filed: Jan. 30, 2019

(86) PCT No.: PCT/US2019/015886
§ 371 (c)(1),
(2) Date: Jul. 30, 2020

(87) PCT Pub. No.: WO2019/152543
PCT Pub. Date: Aug. 8, 2019

(65) Prior Publication Data
US 2020/0370096 A1    Nov. 26, 2020

Related U.S. Application Data

(60) Provisional application No. 62/654,896, filed on Apr. 9, 2018, provisional application No. 62/625,215, filed on Feb. 1, 2018, provisional application No. 62/625,212, filed on Feb. 1, 2018, provisional application No. 62/624,634, filed on Jan. 31, 2018.

(51) Int. Cl.
*C12Q 1/6806* (2018.01)

(52) U.S. Cl.
CPC .................... *C12Q 1/6806* (2013.01)

(58) Field of Classification Search
CPC ............ C12Q 1/6806; C12Q 2521/537
See application file for complete search history.

(56) References Cited

U.S. PATENT DOCUMENTS

| | | | |
|---|---|---|---|
| 3,817,837 | A | 6/1974 | Rubenstein et al. |
| 3,850,752 | A | 11/1974 | Schuurs et al. |
| 3,939,350 | A | 2/1976 | Kronick et al. |
| 3,996,345 | A | 12/1976 | Ullman et al. |
| 4,275,149 | A | 6/1981 | Litman et al. |
| 4,277,437 | A | 7/1981 | Maggio |
| 4,366,241 | A | 12/1982 | Tom et al. |
| 4,882,268 | A * | 11/1989 | Penman .............. G01N 33/6875 530/358 |
| 4,988,617 | A | 1/1991 | Landegren et al. |
| 5,143,854 | A | 9/1992 | Pirrung et al. |
| 5,234,809 | A | 8/1993 | Boom et al. |
| 5,242,794 | A | 9/1993 | Whiteley et al. |
| 5,348,853 | A | 9/1994 | Wang et al. |
| 5,476,930 | A | 12/1995 | Letsinger et al. |
| 5,494,810 | A | 2/1996 | Barany et al. |
| 5,567,583 | A | 10/1996 | Wang et al. |
| 5,571,639 | A | 11/1996 | Hubbell et al. |
| 5,593,839 | A | 1/1997 | Hubbell et al. |
| 5,705,628 | A | 1/1998 | Hawkins |
| 5,780,613 | A | 7/1998 | Letsinger et al. |
| 5,786,146 | A | 7/1998 | Herman et al. |
| 5,837,832 | A | 11/1998 | Chee et al. |
| 5,989,823 | A | 11/1999 | Jayasena et al. |
| 5,994,056 | A | 11/1999 | Higuchi |
| 6,033,854 | A | 3/2000 | Kurnit et al. |
| 6,110,709 | A | 8/2000 | Ausubel et al. |
| 6,117,635 | A | 9/2000 | Nazarenko et al. |
| 6,171,785 | B1 | 1/2001 | Higuchi |
| 6,174,670 | B1 | 1/2001 | Wittwer et al. |
| 6,225,109 | B1 | 5/2001 | Juncosa et al. |
| 6,287,766 | B1 | 9/2001 | Nolan et al. |
| 6,326,145 | B1 | 12/2001 | Whitcombe et al. |
| 6,416,950 | B1 | 7/2002 | Lohse et al. |
| 6,449,562 | B1 | 9/2002 | Chandler et al. |
| 6,582,938 | B1 | 6/2003 | Su et al. |
| 6,787,308 | B2 | 9/2004 | Balasubramanian et al. |
| 6,833,246 | B2 | 12/2004 | Balasubramanian |

(Continued)

FOREIGN PATENT DOCUMENTS

| | | | | |
|---|---|---|---|---|
| CN | 107073474 A | * | 8/2017 | ............ B01D 15/08 |
| DE | 10149786 A1 | | 7/2003 | |

(Continued)

OTHER PUBLICATIONS

Dejica et al., Cleavage of Type II Collagen by Cathepsin K in Human Osteoarthritic Cartilage, 2008, Am. J. Pathol., 173(1), 161-169. (Year: 2008).*

Higashi-Fujime et al., Muscle Actin Cleaved by Proteinase K: Its Polymerization and In Vitro Motility, 1992, J. Biochem., 112(4), 568-572. (Year: 1992).*

Mornet et al., Proteolysis and the domain organization of myosin subfragment 1, 1984, Proc. Natl. Acad. Sci. U.S.A., 81(3), 736-739. (Year: 1984).*

Nagaki et al., Chromatin Immunoprecipitation Reveals That the 180-bp Satellite Repeat Is the Key Functional DNA Element of *Arabidopsis thaliana* Centromeres, 2003, Genetics, 163, 1221-1225. (Year: 2003).*

Adams, et al. The Genome Sequence of *Drosophila melanogaster*. Science Mar. 24, 2000, 287.5461: 2185-2195.

(Continued)

*Primary Examiner* — Joseph G. Dauner
(74) *Attorney, Agent, or Firm* — WILSON SONSINI GOODRICH & ROSATI

(57) ABSTRACT

Provided herein are methods of releasing nucleic acids from a fixed biological sample comprising contacting the fixed tissue sample to an enzyme. The disclosure further provides methods to quantify and deconvolute a population of mRNA spliced variant isoforms from a cellular transcriptome. Additionally provided herein are methods delivering a barcode to a nucleic acid sample using integrases, nucleic acid samples having barcodes, and nucleic acid libraries thereof.

14 Claims, 7 Drawing Sheets

Specification includes a Sequence Listing.

(56) References Cited

U.S. PATENT DOCUMENTS

| | | |
|---|---|---|
| 6,897,023 B2 | 5/2005 | Fu et al. |
| 6,969,488 B2 | 11/2005 | Bridgham et al. |
| 7,001,724 B1 | 2/2006 | Greenfield |
| 7,361,468 B2 | 4/2008 | Liu et al. |
| 7,414,117 B2 | 8/2008 | Saito et al. |
| 7,425,415 B2 | 9/2008 | Pfeifer et al. |
| 7,709,179 B2 | 5/2010 | Iwashita |
| 7,709,197 B2 | 5/2010 | Drmanac |
| 7,901,891 B2 | 3/2011 | Drmanac |
| 7,985,546 B2 | 7/2011 | Church et al. |
| 8,058,004 B2 | 11/2011 | Oleinikov |
| 8,071,296 B2 | 12/2011 | Ruan et al. |
| 8,076,070 B2 | 12/2011 | Chen et al. |
| 8,153,373 B2 | 4/2012 | De Laat et al. |
| 8,278,112 B2 | 10/2012 | Shokat et al. |
| 8,367,322 B2 | 2/2013 | Barany et al. |
| 8,642,295 B2 | 2/2014 | De Laat et al. |
| 8,652,810 B2 | 2/2014 | Adessi et al. |
| 8,673,562 B2 | 3/2014 | Drmanac et al. |
| 8,841,075 B1 | 9/2014 | Borner et al. |
| 9,411,930 B2 | 8/2016 | Green, Jr. et al. |
| 9,663,826 B2 | 5/2017 | Barrett et al. |
| 9,715,573 B2 | 7/2017 | Putnam et al. |
| 9,910,955 B2 | 3/2018 | Green, Jr. et al. |
| 10,059,989 B2 | 8/2018 | Giresi et al. |
| 10,089,437 B2 | 10/2018 | Green, Jr. et al. |
| 10,529,443 B2 | 1/2020 | Green, Jr. et al. |
| 10,825,553 B2 | 11/2020 | Green, Jr. et al. |
| 10,947,579 B2 * | 3/2021 | Troll ................. C12Q 1/6806 |
| 11,081,209 B2 | 8/2021 | Green, Jr. et al. |
| 11,935,626 B2 | 3/2024 | Green, Jr. et al. |
| 12,065,691 B2 | 8/2024 | Troll et al. |
| 2002/0012930 A1 | 1/2002 | Rothberg et al. |
| 2002/0190663 A1 | 12/2002 | Rasmussen |
| 2003/0022207 A1 | 1/2003 | Balasubramanian et al. |
| 2003/0044781 A1 | 3/2003 | Korlach et al. |
| 2003/0064398 A1 | 4/2003 | Barnes |
| 2003/0068629 A1 | 4/2003 | Rothberg et al. |
| 2003/0100102 A1 | 5/2003 | Rothberg et al. |
| 2003/0148344 A1 | 8/2003 | Rothberg et al. |
| 2004/0106110 A1 | 6/2004 | Balasubramanian et al. |
| 2004/0248161 A1 | 12/2004 | Rothberg et al. |
| 2005/0079510 A1 | 4/2005 | Berka et al. |
| 2005/0100932 A1 | 5/2005 | Lapidus et al. |
| 2005/0124022 A1 | 6/2005 | Srinivasan et al. |
| 2005/0130161 A1 | 6/2005 | Fraser et al. |
| 2005/0130173 A1 * | 6/2005 | Leamon ............ C12N 15/1075 435/5 |
| 2005/0227231 A1 | 10/2005 | Tcherkassov |
| 2006/0012784 A1 | 1/2006 | Ulmer |
| 2006/0012793 A1 | 1/2006 | Harris |
| 2006/0024678 A1 | 2/2006 | Buzby |
| 2006/0024711 A1 | 2/2006 | Lapidus et al. |
| 2006/0078909 A1 | 4/2006 | Srinivasan et al. |
| 2006/0078937 A1 | 4/2006 | Korlach et al. |
| 2007/0172839 A1 | 7/2007 | Smith et al. |
| 2009/0111115 A1 | 4/2009 | Drmanac et al. |
| 2009/0186352 A1 | 7/2009 | Akoulitchev et al. |
| 2009/0233291 A1 | 9/2009 | Chen et al. |
| 2009/0298064 A1 | 12/2009 | Batzoglou et al. |
| 2010/0062947 A1 | 3/2010 | De Laat et al. |
| 2010/0081141 A1 | 4/2010 | Chen et al. |
| 2010/0093986 A1 | 4/2010 | Zwick et al. |
| 2010/0130373 A1 | 5/2010 | Dekker et al. |
| 2011/0033854 A1 | 2/2011 | Drmanac et al. |
| 2011/0124851 A1 * | 5/2011 | Guo ................. C12N 15/1006 536/23.1 |
| 2011/0287947 A1 | 11/2011 | Chen et al. |
| 2012/0197533 A1 | 8/2012 | Nazarenko et al. |
| 2012/0302449 A1 | 11/2012 | Dong et al. |
| 2013/0096009 A1 | 4/2013 | Dekker et al. |
| 2013/0183672 A1 | 7/2013 | De Laat et al. |
| 2013/0203605 A1 | 8/2013 | Shendure et al. |
| 2015/0126396 A1 | 5/2015 | Manaresi et al. |
| 2015/0363550 A1 | 12/2015 | Green, Jr. et al. |
| 2018/0200379 A1 * | 7/2018 | Sherman ................. A61P 35/00 |
| 2018/0365376 A1 | 12/2018 | Green, Jr. et al. |
| 2019/0080050 A1 | 3/2019 | Green, Jr. et al. |
| 2020/0370096 A1 * | 11/2020 | Blanchette ........... C12Q 1/6806 |
| 2022/0172799 A1 | 6/2022 | Green, Jr. et al. |
| 2024/0395360 A1 | 11/2024 | Green, Jr. et al. |

FOREIGN PATENT DOCUMENTS

| | | |
|---|---|---|
| DE | 10214395 A1 | 10/2003 |
| DE | 10356837 A1 | 6/2005 |
| DE | 102004009704 A1 | 9/2005 |
| DE | 102004025744 A1 | 12/2005 |
| DE | 102004025745 A1 | 12/2005 |
| DE | 102004025746 A1 | 12/2005 |
| DE | 102004025694 A1 | 2/2006 |
| DE | 102004025695 A1 | 2/2006 |
| DE | 102004025696 A1 | 2/2006 |
| EP | 0476014 A1 | 3/1992 |
| EP | 0624059 A1 | 11/1994 |
| EP | 0717113 A2 | 6/1996 |
| EP | 0728520 A1 | 8/1996 |
| EP | 2624059 A1 | 8/2013 |
| GB | 2519255 A | 4/2015 |
| JP | 2019088295 A | 6/2019 |
| KR | 20170054130 A | 5/2017 |
| WO | WO-9015070 A1 | 12/1990 |
| WO | WO-9210092 A1 | 6/1992 |
| WO | WO-9309668 A1 | 5/1993 |
| WO | WO-9511995 A1 | 5/1995 |
| WO | WO-9729212 A1 | 8/1997 |
| WO | WO-9841651 A1 | 9/1998 |
| WO | WO-02059731 A2 | 8/2002 |
| WO | WO-02088382 A2 | 11/2002 |
| WO | WO-02103046 A2 | 12/2002 |
| WO | WO-03020968 A2 | 3/2003 |
| WO | WO-03031947 A2 | 4/2003 |
| WO | WO-2005001113 A2 | 1/2005 |
| WO | WO-2005005655 A1 | 1/2005 |
| WO | WO-2005005657 A1 | 1/2005 |
| WO | WO-2005044836 A2 | 5/2005 |
| WO | WO-2004046305 A8 | 6/2005 |
| WO | WO-2007093819 A2 | 8/2007 |
| WO | WO-2008024473 A2 | 2/2008 |
| WO | WO-2009053039 A1 | 4/2009 |
| WO | WO-2009147386 A1 | 12/2009 |
| WO | WO-2010036323 A1 | 4/2010 |
| WO | WO-2011106546 A1 | 9/2011 |
| WO | WO-2011127297 A1 | 10/2011 |
| WO | WO-2012005595 A2 | 1/2012 |
| WO | WO-2012047726 A1 | 4/2012 |
| WO | WO-2012106546 A2 | 8/2012 |
| WO | WO-2012116331 A2 | 8/2012 |
| WO | WO-2012142531 A2 | 10/2012 |
| WO | WO-2012142611 A2 | 10/2012 |
| WO | WO-2012150317 A1 | 11/2012 |
| WO | WO-2013123463 A1 * | 8/2013 | ........... C12Q 1/6806 |
| WO | WO-2014121091 A1 | 8/2014 |
| WO | WO-2015071748 A1 * | 5/2015 | ........... C12Q 1/6806 |
| WO | WO-2015123588 A1 | 8/2015 |
| WO | WO-2016019360 A1 | 2/2016 |
| WO | WO-2016033160 A2 * | 3/2016 | ........... C12N 15/113 |
| WO | WO-2016061517 A2 | 4/2016 |
| WO | WO-2016149350 A1 * | 9/2016 | ........... C12Q 1/6886 |
| WO | WO-2016154540 A1 | 9/2016 |
| WO | WO-2016164313 A1 | 10/2016 |
| WO | WO-2016196360 A1 | 12/2016 |
| WO | WO-2016207647 A1 | 12/2016 |
| WO | WO-2016207653 A1 | 12/2016 |
| WO | WO-2016207661 A1 | 12/2016 |
| WO | WO-2017147435 A1 * | 8/2017 | ........... C08L 101/14 |
| WO | WO-2017197300 A1 * | 11/2017 | ........... C12Q 1/6806 |
| WO | WO-2018031902 A1 * | 2/2018 | ........... A61K 31/353 |
| WO | WO-2018148501 A1 * | 8/2018 | ........... C07K 14/705 |

(56) References Cited

FOREIGN PATENT DOCUMENTS

| WO | WO-2018157074 A1 * | 8/2018 | ............... G01N 1/36 |
| WO | WO-2018209324 A2 * | 11/2018 | ............. A61K 38/45 |

OTHER PUBLICATIONS

Ausubel, et al., eds. 1993. Current Protocols in Molecular Biology. Part 1: *E. coli*, plasmids, and bacteriophages, pp. 1-15.
Belaghzal et al., Hi—C 2.0: An optimized Hi—C procedure for high-resolution genome-wide mapping of chromosome conformation. Methods. 123:56-65 (2017).
Burton, et al. Chromosome-scale scaffolding of de novo genome assemblies based on chromatin interactions. Nat. Biotechnol. 2013, 31: 1119-1125.
Cai et al., "SATB1 packages densely looped transcriptionally active chromatin for coordinated expression of cytokine genes," Nature Genetics, 2006, vol. 38, No. 11, pp. 1278-1288.
Chapman, et al. Meraculous: de novo genome assembly with short paired-end reads. PloS one. 2011, 6.8: e23501.
Constans, A. All in the Family Scientist 13: 36 (2003).
Constans. Beyond Sanger: Toward the $1,000 Genome—The Scientist—Magazine of the Life Sciences. The Scientist. Jun. 30, 2003; 17(13):36.
Cortese, J. Array of options. Scientist. 2000, 14.11: 26.
Cortese, J. The array of today. Scientist. 2000, 14.17: 25.
Dekker et al., A closer look at long-range chromosomal interactions. Trends in Biochemical Science (Jun. 2003) 28(6):277-280.
Dekker et al., "Capturing chromosome conformation," Science, 2002, vol. 295, pp. 1306-1311.
Dostie et al., "Chromosome Conformation Capture Carbon Copy (5C): a massively parallel solution for mapping interaction between genomic elements," Genome research, 2006, vol. 16, No. 10, pp. 1299-1309.
Dower, et al. Recombinant and synthetic randomized peptide libraries. Ann. Rep. Med. Chem. 1991, 26:271-280.
Drmanac et al. Human genome sequencing using unchained base reads on self-assembling DNA nanoarrays. Science. 327: 78-81 (2010).
Ekins, R. et al. Microarrays: Their Origins and applications. Trends in Biotechnology, 17(6); 217-218 (Jun. 1999).
Fan et al. "A versatile assay for high-throughput gene expression profiling on universal array matrices." Genome Research, 2004, vol. 14 No. 5 pp. 878-885.
Fangman, et al. Activation of replication origins within yeast chromosomes, Annual Review of Cell Biology, 7(1); 375-402 (1991).
Fodor, et al. Light-directed, spatially addressable parallel chemical synthesis. Science. Feb. 15, 1991, 251.4995: 767-773.
Fullwood, MJ et al. Chromatin interaction analysis using paired-end tag sequencing. Jan. 2010. Curr. Prot. In Mol. Biol. Chapter 21; unit 21 . 15.1-25.
Fyodorov, et al. Chromatin assembly in vitro with purified recombinant ACF and NAP-1. Methods in enzymology. 2002, 371: 499-515.
Garaj, et al. Graphene as a sub-nanometer trans-electrode membrane. Nature. Sep. 9, 2010, 467.7312: 190-193.
Gilmour, David S., et al. Detecting protein-DNA interactions in vivo: distribution of RNA polymerase on specific bacterial genes. Proceedings of the National Academy of Sciences. (1984) 81(14): 4275-4279.
Grunenwald et al., "Rapid, high-throughput library preparation for next-generation sequencing" 2010 Nature Methods, vol. 7.
Gwynne, P. et al. Microarray analysis: the next revolution in molecular biology. Science. pp. 1-6 (Aug. 6, 1999).
Heid, C.A. et al. Real time quantitative PCR. Genome Research, 6(10): 986-994 (1996).
Herschleb, J. et al. Pulsed-field gel electrophoresis. Pulsed-field gel electrophoresis. Nature Protocols 2(3):677-84 (Mar. 29, 2007).
Jansen, et al. Nucleosome Positioning in *Saccharomyces cerevisiae*. Microbiology and Molecular Biology Reviews, Jun. 2011, pp. 301-320.
Kalhor, R. et al. Genome architectures revealed by tethered chromosome conformation capture and population-based modeling, Nature Biotechnology, 30(1): 90-98 (Jan. 2012).
Kaplan, N. et al. High-throughput genome scaffolding from in vivo DNA interaction frequency. Nat. Biotechnol., 31(12):1143-1147 (Dec. 2013).
Kitzman, Jacob O. et al. Haplotype-resolved genome sequencing of a Gujarati Indian individual, Nature Biotechnology, 29(1): 59-63 (Jan. 2011).
Kotoulas, S. et al. The chipping forecast. Special supplement to Nature Genetics vol. 21; pp. 1-6 (1999).
Kundu et al. Activator-dependent transcription from chromatin in vitro involving targeted histone acetylation by p300. Molecular cell. 2000, 6.3: 551-561.
Lasken, Roger S. et al. Mechanism of chimera formation during the Multiple Displacement Amplification reaction. BMC biotechnology. 7(19): 1-11 (Apr. 12, 2007).
Lemieux, B. et al. Overview of DNA chip technology. Molecular Breeding 4: 277-289 (1998).
Levene, et al. Zero-mode waveguides for single-molecule analysis at high concentrations. Science. Jan. 31, 2003;299(5607):682-6.
Lieberman-Aiden, et al. "Comprehensive mapping of long range interactions reveals folding principles of the human genome." Science. Oct. 9, 2009; 326(5950): 289-293. doi:10.1126/science. 1181369.
Lupski, James R. et al. Whole-genome sequencing in a patient with Charcot-Marie-Tooth neuropathy. New England Journal of Medicine, 362(13): 1181-1191 (Apr. 1, 2010).
Lusser, Alexandra et al. Strategies for the reconstitution of chromatin. Nature Methods, 1(1):19-26 (Oct. 2004).
Ma, H. et al. Application of Real-time Polymerase Chain Reaction (RT-PCR), The Journal of American Science, 2 (3):1-15 (Aug. 10, 2006).
Maniatis, et al. Molecular Cloning: A Laboratory Manual, Cold Spring Harbor, N.Y., pp. 280-281 (1982).
Margulies, M. et al. Genome sequencing in open microfabricated high density picolitre reactors. Nature 437(7057):376-380 (Sep. 15, 2005).
Marshall, A. et al. DNA chips: an array of possibilities. Nature Biotechnology, 16(1): 27-31 (Jan. 1998).
Mary, I. et al. Metaproteomic and metagenomic analyses of defined oceanic microbial populations using microwave cell fixation and flow cytometric sorting. FEMS Microbiol Ecol. 74(1):10-18 (Oct. 2010). E-Pub. Jul. 5, 2010.
Miller et al. A Simple salting out procedure for extracting DNA from human nucleated cells. Nucleic Acids Research vol. 16, No. 3, 1215 (1988).
Myers, E.W. et al. A Whole-Genome Assembly of *Drosohila*. Science, 287(5461):2196-2204 (Mar. 24, 2000).
Nazarenko, I.A. et al. A closed tube format for amplification and detection of DNA based on energy transfer. Nucleic acids research, 25(12):2516-2521 (Jun. 15, 1997).
PCT/US2014/014184 International Preliminary Report on Patentability dated Aug. 13, 2015.
PCT/US2014/014184 International Search Report dated Apr. 23, 2014.
PCT/US2019/015886 International Preliminary Report on Patentability dated Aug. 4, 2020.
PCT/US2019/015886 International Search Report and Written Opinion dated Jun. 3, 2019.
Peng, Z. et al. Generation of long insert pairs using a Cre-LoxP Inverse PCR approach, PLoS One, 7(1): e29437 (2012) E-Pub Jan. 9, 2012.
Peters, B.A. et al. Accurate whole-genome sequencing and haplotyping from 10 to 20 human cells. Nature, 487(7406):190-195 (Jul. 11, 2012).
Rios, J. et al. Identification by whole-genome resequencing of gene defect responsible for severe hypercholesterolemia. Human Molecular Genetics, 19(22): 4313-4318 (Nov. 15, 2010). E-Pub Aug. 18, 2010.

(56) References Cited

OTHER PUBLICATIONS

Sambrook, et al. Mixed Oligonucleotide-primed Amplification of cDNA (MOPAC). Cold Spring Harbor Protocols, pp. 1-30 (2006).
Schena M. (ed.), Microarray Biochip Technology (2000), ISBN-10: 1881299376 ISBN-13: 978-1881299370.
Schena, M. et al. PCR applications: protocols for functional genomics. Chapter 28: Parallel analysis with biological chips. Eds. Michael A. Innis, David H. Gelfand, John J. Sninsky. Academic Press. ISBN: 0-12-372185-7. pp. 445-456 (1999).
Schena, Mark et al. Genes, genomes, and chips. DNA microarrays: A practical approach. Oxford University Press, pp. 1-18 (1999); ISBN-10: 1881299376 ISBN-13: 978-1881299370.
Schwartz, D.C. et al. Separation of yeast chromosome-sized DNAs by pulsed field gradient gel electrophoresis. Cell 37(1): 67-75 (May 1984).
Selvaraj et al. Whole-genome haplotype reconstruction using proximity-ligation and shotgun sequencing. Nat. Biotechnol. 2013, 31:1113-1119.
Sewards, Richard, Combined Search and Examination Report under Sections 17 & 18(3), Great Britain Patent Application No. GB1520448.0, Date of Report: May 31, 2016.
Shalon, D. et al. A DNA microarray system for analyzing complex DNA samples using two-color fluorescent probe hybridization. Genome research, 6(7): 639-645 (Jul. 1996).
Simpson, J.T. et al. Efficient de novo assembly of large genomes using compressed data structures. Genome Res, 22(3): 549-556 (Mar. 2012). E-Pub Dec. 7, 2011. doi: 10.1101/gr.126953.111.
Solomon, M.J. et al. Formaldehyde-mediated DNA-protein crosslinking: a probe for in vivo chromatin structures. Proceedings of the National Academy of Sciences, 82(19): 6470-6474 (Oct. 1985).
Solomon, M.J. et al. Mapping protein-DNA interactions in vivo with formaldehyde: evidence that histone H4 is retained on a highly transcribed gene. Cell, 53(6):937-947 (Jun. 17, 1988).
Soni, et al. Progress toward ultrafast DNA sequencing using solid-state nanopores. Clin Chem, 53(11):1996-2001 (Nov. 2007). Epub Sep. 21, 2007.
Splinter, E. 3C Technology: Analyzing the Spatial Organization of Genomic Loci In Vivo Methods in Enzymology, 375:493-507 (2004).
Sridhara et al., Preparation and properties of chromatin from the silk glands of the silkworm *Bombyx mori*. European Journal of Biochemistry. 75(1): 107-119 (1977).
Syed, F. et al. Optimized library preparation method for next-generation sequencing. Application Note Abstract, Nature Methods 6:i-ii (Oct. 2009).
Tanizawa, H. et al., Mapping of long-range associations throughout the fission yeast genome reveals global genome organization linked to transcriptional regulation. Nucleic Acid Research, 38(22):8164-8177 (Dec. 2010). Epub Oct. 28, 2010.
Tazi et al., Alternative splicing and disease. Biochim Biophys Acta. 1792(1):14-26 (2009).
Teague, B. et al. High-resolution human genome structure by single-molecule analysis. Proceedings of the National Academy of Sciences, 107(24): 10848-10853 (Jun. 15, 2010).
Tyagi, S. et al. Molecular beacons: probes that fluoresce upon hybridization. Nature Biotechnology, 14(3):303-308 (Mar. 1996).
Umbarger, M.A. Chromosome conformation capture assays in bacteria. Methods 58(3):212-220 (Nov. 2012).
Venter, J.C. et al. The sequence of the human genome. Science, 291(5507):1304-1351 (Feb. 16, 2001).
Whitcombe, D. et al. Detection of PCR Products Using Self-probing Amplicons and Fluorescence. Nature Biotechnology, 17(8):804-807 (Aug. 1999).
Wing, R.D., et al. An improved method of plant megabase DNA isolation in agarose microbeads suitable for physical mapping and YAC cloning. The Plant Journal, 4(5):893-898 (1993).
Zhou, S. et al. A single molecule scaffold for the maize genome. PLoS Genetics, 5(11): e1000711; pp. 1-14 (Nov. 20, 2009).
Zinchenko, A. et al. Compaction of Single-Chain DNA by Histone-Inspired Nanoparticles. Physical Review Letters, 95(22); 228101 (2005).
Constans A., "Microarrays in Microtubes," Scientist. 2003 17.13: 36.
Korbel et al., Genome assembly and haplotyping with Hi—C. Nat Biotechnol. 31(12):1099-1101 (2013).
O'Neill LP, Turner BM. Immunoprecipitation of native chromatin: NChIP. Methods. Sep. 2003;31(1):76-82.
Putnam, N. H. et al. Supplemental Material—Chromosome-scale shotgun assembly using an in vitro method for long-range linkage. Genome Research 26:342-350 (2016). E-Pub Feb. 4, 2016.
Putnam, Nicholas H. et al. Chromosome-scale shotgun assembly using an in vitro method for long-range linkage. Genome Research, 26(3):342-350 (Mar. 2016).
Bansal et al. HapCUT : an efficient and accurate algorithm for the haplotype assembly problem, Bioinformatics (2008) 24:i153-i159.
De Koning et al., Repetitive elements may comprise over two-thirds of the human genome. PLoS Genet., 7(12):e1002384 (pp. 1-12) (2011).
Dixon, J. R. et al. Topological domains in mammalian genomes identified by analysis of chromatin interactions. Nature, 485(7398):376-380 (May 2012).
Fang et al., Mapping of long-range chromatin interactions by proximity ligation-assisted ChIP-seq. Letter to the Editor—Cell Research 26:1345-1348 (2016).
Fullwood, et al. An oestrogen-receptor-alpha-bound human chromatin interactome. Nature 462(7269):58-64 (2009).
Fullwood et al. ChIP-based methods for the identification of long-range chromatin interactions. J Cell Biochem. 107(1):30-39 (2009).
Gnerre, S. et al. High-quality draft assemblies of mammalian genomes from massively parallel sequence data. PNAS USA 108 (4):1513-1518 (Jan. 2011).
Goodwin, S. et al. Oxford nanopore sequencing and de novo assembly of a eukaryotic genome. bioRxiv, pp. 1-28 (Jul. 15, 2015).
Green et al., Three crocodilian genomes reveal ancestral patterns of evolution among archosaurs. Science. 346(6215):1254449 (pp. 1-11) (2014).
Haussler, D., et al. Genome 10K: a proposal to obtain whole-genome sequence for 10,000 vertebrate species. J. Hered., 100(6):659-674 (2009).
Hsieh et al., Mapping nucleosome resolution chromosome folding in yeast by Micro-C. Cell. 162(1):108-119 (2015).
Juric et al., MAPS: Model-based analysis of long-range chromatin interactions from PLAC-seq and HiChIP experiments. PLoS Comput Biol. 15(4):e1006982, pp. 1-24 (2019).
Krietenstein et al., Ultrastructural details of mammalian chromosome architecture. bioRxiv preprint 639922, pp. 1-15 (2019). https://www.biorxiv.org/content/10.1101/639922v1 http://dx.doi_org/10.1101/639922.
Li et al., OCEAN-C: mapping hubs of open chromatin interactions across the genome reveals gene regulatory networks. Genome Biol. 19(1):54, pp. 1-14 (2018).
Li, Guoqiang et al. Simultaneous profiling of DNA methylation and chromatin architecture in mixed populations and in single Cells. bioRxiv pp. 1-35 (2018).
Ma et al., Fine-scale chromatin interaction maps reveal the cis-regulatory landscape of human lincRNA genes. Nat Methods 12(1):71-78 (2015).
Ma et al., Using DNase Hi—C techniques to map global and local three-dimensional genome architecture at high resolution. bioRxiv preprint184846, pp. 1-55 (2018).
Mifsud et al., Mapping long-range promoter contacts in human cells with high-resolution capture Hi—C. Nat Genet. 47(6):598-606 (2015).
PCT/US2014/014184 International Search Report and Written Opinion dated Apr. 23, 2014.
PCT/US2020/039656 International Search Report and Written Opinion dated Oct. 8, 2020.
Quail, M.A. et al. A tale of three next generation sequencing platforms: comparison of Ion Torrent, Pacific Biosciences and Illumina MiSeq sequencers. BMC Genomics, 13:341 (Jul. 24, 2012).

(56) References Cited

OTHER PUBLICATIONS

Ramani et al., Mapping 3D genome architecture through in situ DNase Hi—C. Nat Protoc. 11(11):2104-2121 (2016).
Ramani, et al. Massively multiplex single-cell Hi—C. Nat Methods. Mar. 2017; 14(3):263-266. Published online Jan. 30, 2017.
Rao et al., A 3D map of the human genome at kilobase resolution reveals principles of chromatin looping. Cell. 159:1665-1680 (2014).
Rozowsky, J. et al. AlleleSeq: analysis of allele-specific expression and binding in a network framework. Mol. Syst. Biol., 7:522 (pp. 1-15) (Aug. 2, 2011).
Salzberg, S.L. et al. GAGE: A critical evaluation of genome assemblies and assembly algorithms. Genome Res., 22(3):557-567 (Mar. 2012) (E-Pub Jan. 6, 2012).
Schena, Mark., Microarray Biochip Technology. A BioTechniques Books Publication. Eaton Publishing pp. 1-4 (2000).
Schmitt, Anthony D. et al. A Compendium of Chromatin Contact Maps Reveals Spatially Active Regions in the Human Genome. Cell Reports 17(8):2042-2059 (2016).
Selvaraj, S. et al. Complete haplotype phasing of the MHC and KIR loci with targeted HaploSeq. BMC Genomics 16:900 (pp. 1-7) (Nov. 5, 2015).
Shedlock, A.M. et al. Phylogenomics of nonavian reptiles and the structure of the ancestral amniote genome. PNAS USA 104(8):2767-2772 (Feb. 20, 2007) (E-Pub Feb. 16, 2007).
Sheridan, C. Milestone approval lifts Illumina's NGS from research into clinic. Nature Biotechnology, 32(2):111-112 (Feb. 2014).
Torjesen, I. Genomes of 100,000 people will be sequenced to create an open access research resource. BMJ, 347:f6690 (Nov. 6, 2013).
Tuzun et al. Fine-scale structural variation of the human genome. Nat. Genet., 37(7):727-732 (Jul. 2005).
Tyagi S, et al. Molecular beacons: hybridization probes for detection of nucleic acids in homogeneous solutions. In: Kessler, C. (eds) Nonradioactive Analysis of Biomolecules. Springer Lab Manuals. Springer, Berlin, Heidelberg (pp. 1-8) (2000).
U.S. Appl. No. 14/170,339 Office Action dated Mar. 24, 2015.
U.S. Appl. No. 14/170,339 Office Action dated Oct. 20, 2014.
U.S. Appl. No. 14/764,945 Office Action dated Mar. 2, 2018.
U.S. Appl. No. 14/764,945 Office Action dated Sep. 22, 2017.
U.S. Appl. No. 15/167,880 Office Action dated Jul. 3, 2017.
U.S. Appl. No. 15/900,723 Office Action dated Jul. 31, 2019.
U.S. Appl. No. 15/900,723 Office Action dated Mar. 20, 2020.
U.S. Appl. No. 16/128,297 Office Action dated Nov. 18, 2020.
U.S. Appl. No. 16/202,042 Office Action dated Jul. 26, 2019.
Voskoboynik, A. et al. The genome sequence of the colonial chordate, *Botryllus schlosseri*. eLife 2:e00569 (2013).
Wang et al., The 3D Genome Browser: a web-based browser for visualizing 3D genome organization and long-range chromatin interactions. Genome Biol. 19(1):151, pp. 1-12 (2018).
Weisenfeld N.I., et al. Comprehensive variation discovery in single human genomes. Nat. Genet. 46(12):1350-1355 (Dec. 2014).
Williams et al., Paired-end sequencing of Fosmid libraries by Illumina. Genome Res. 22(11):2241-2249 (2012).
Wu, C.C. et al. Long-span, mate-pair scaffolding and other methods for faster next-generation sequencing library creation. Nat. Methods pp. i-ii (Sep. 2012).
Wu, T.D. et al. GMAP: a genomic mapping and alignment program for mRNA and EST sequences. Bioinformatics, 21(9):1859-1875 (May 1, 2005) (Epub Feb. 22, 2005).
U.S. Appl. No. 17/369,429 Office Action dated Dec. 17, 2024.
U.S. Appl. No. 18/436,754 Office Action dated Nov. 4, 2024.

\* cited by examiner

SAMPLE PREP FOR DNA LINKAGE RECOVERY

CROSS-REFERENCE

This application is a 371 U.S. National Stage Application of PCT/US2019/015886, which claims the benefit of U.S. Provisional Application No. 62/624,634, filed Jan. 31, 2018; U.S. Provisional Application No. 62/654,896, filed Apr. 9, 2018; U.S. Provisional Application No. 62/625,212, filed Feb. 1, 2018; and U.S. Provisional Application No. 62/625,215, filed Feb. 1, 2018; each of which applications are incorporated herein by reference in their entirety.

BACKGROUND OF THE INVENTION

Assembly and phasing of nucleic acid sequence data is facilitated by obtaining linkage information, for example, linkage information determined using read-pair data obtained from cross-linked chromatin, reconstituted chromatin, cross-linked RNA, and nucleic acids isolated from recalcitrant biological samples.

Isolation of nucleic acids from certain recalcitrant biological samples, such as fixed biological samples, samples with extra-cellular matrices, and samples with resilient cell walls, poses challenges in obtaining nucleic acids amenable to certain sequencing applications. Recalcitrant biological samples, such as fixed biological samples, samples with extra-cellular matrices, and samples with resilient cell walls, can require disruption of intermolecular bonds, such as crosslinking found in fixed samples, or disruption of extra-cellular matrices or cell walls, in order to isolate nucleic acids. Fixed biological samples are often obtained in surgery, for example in a surgery to remove a suspected cancerous tissue, such as a tumor. Typically, conventional methods use harsh mechanical means to homogenize the biological sample and isolate the nucleic acids. These harsh methods lead to nucleic acid strand breakage and result in a lower quality nucleic acid sample that can pose challenges in sequencing and other applications.

RNA sequencing, also called whole transcriptome shotgun sequencing, utilizes next-generation sequencing to reveal the presence and quantity of RNA in a biological sample at a given moment in time. Next-generation sequencing technologies have introduced the advantages of high-throughput, high-sensitivity, and high-speed processing to advanced sequence-based research. However, the present methods for RNA sequencing remain expensive and challenging to execute. Improved methods are needed to address these concerns.

Obtaining accurate assembly and phasing information from genomic sequencing data remains a challenge. Most sequencing technologies produce relatively short read lengths. Without unique identifiers in a chromosomal sequence, it is difficult to infer a haplotype from such sequencing data. It is also difficult to accurately discern the sequence in a repetitive genomic region. The present disclosure provides methods and compositions to associate polynucleotide segments to acquire long-range DNA sequence information, which can be used for applications such as genomic assembly and haplotype phasing.

SUMMARY OF THE INVENTION

Provided herein are methods and compositions related to obtaining linkage information from nucleic acid samples, including methods of sample preparation for obtaining nucleic acids, methods and compositions relating to obtaining linkage information from RNA samples, and methods and compositions relating to phase determination in nucleic acid sequences.

Provided herein are embodiments related to sample preparation, such as sample preparation related to extraction of nucleic acid information. Sample treatments such as enzymatic treatment, for example using cellulase or collagenase, is used to preserve nucleic acid integrity such as DNA integrity so that long range linkage information is recovered from a treated sample such as a crosslinked sample.

Embodiments disclosed herein relate to enzymatic procedures and related compositions to produce chromatin or other long, intact, or modestly fragmented nucleic acid material from a sample independent of or without relying upon mechanical disruption of the sample. Representative samples include but are not limited to animal tissue, plant tissue, fungal tissue, bacterial or other tissue comprising nucleic acids. Non-mechanical approaches often have the benefits of being relatively more reproducible, easier to perform without specialized equipment, improved removing of extracellular material, and more conducive to high throughput implementation, resulting in less shearing of the isolated nucleic acids. The compositions and approaches herein do not preclude mechanical manipulation and may be used in concert therewith. However, the disclosure herein is not reliant upon mechanical disruption for the release of intact or long nucleic acids from a sample, such that damage to nucleic acids pursuant to some mechanical disruption approaches is avoided or reduced.

By using a non-mechanical approach such as a composition comprising an enzyme that degrades non-nucleic acid material such as structural material (conjunctive or connective tissue found in areolar tissue, adipose tissue, tendon, ligament, cartilage, bone, blood vessels, and lymph tissue in animals, for example; fixed or cross-linked tissue obtained from a surgical sample, for example; or tissue containing cellulose in plants, though other examples are contemplated), fixed cells are liberated and can be directly process in our standard assay.

Some approaches comprise contacting a fixed tissue comprising nucleic acids to an enzyme that is capable of digesting proteins, such as cross-linked proteins, in the tissue and incubating the reaction mixture where the enzyme is active in order to isolate the nucleic acids from the fixed tissue. In some cases, 10-50 mg of tissue obtained from different sources, such as a fixed tumor sample, is contacted to a buffered solution containing an enzyme having collagenase activity, such as 1 mg/ml of collagenase at a time and temperature suitable for collagenase activity, such as 60 mins at 37° C. The remaining tissue is discarded and a detergent such as SDS is added to the solution to solubilize cellular membrane and release the fixed chromatin. At this stage raw chromatin from the fixed sample (700 ng in the case of a 10-50 mg sample) is loaded on chromatin capture beads and a standard library prep such as a Hi-C library prep is done.

This disclosure also describes processes and compositions for determining sequences of RNA molecules contained within a sample. The processes and compositions can apply to identifying individual species of RNA sequences within a population of RNA transcripts, such as a transcriptome. The processes and compositions are particularly helpful when trying to identify sequences of segments of a molecule that are too far apart to be captured by the same read-pair. The methods and compositions can determine this information without long reads and with nearly any sequencing platform.

The processes and compositions include extracting RNA from a sample, binding RNA molecules to RNA binding moieties, breaking longer RNA molecules into fragments while still bound to the RNA binding moieties, tagging the fragments so they can be identified as originating from the same RNA molecule, sequencing the rearranged molecules, and combining sequences from the same transcript to gain information regarding the identity of the original RNA molecule. As a result, fragments that ordinarily occur long distances apart from each other can be read using the same sequence read and identified as belonging to the same molecule. The compositions and processes disclosed herein can, therefore, be useful in identifying individual RNA species within a population that may contain several splice variants, mutations, and RNA editing events.

Methods disclosed herein include extracting cellular RNA and incubating it with an RNA binding moiety. An example RNA binding molecule includes a recombinant RNA binding protein, but native RNA binding proteins and nanoparticles are also contemplated. The RNA binding protein generally has broad specificity and can include an affinity tag, such as a polyhistidine tag. Once the RNA binding protein is attached to the RNA, the sample is treated with formaldehyde to crosslink the RNA and RNA binding proteins. The RNA and RNA binding proteins are crosslinked to form RNA-protein crosslinks such that two or more RNA segments can be bound together via one or more RNA binding proteins. The methods generally bind RNA segments that are closer in physical space. Thus, the crosslinking can preferentially bind two RNA segments from the same molecule together compared to binding RNA from two different molecules. The crosslinking serves to maintain this proximity information throughout the process of manipulating the RNA molecule.

Once the RNA and RNA binding proteins are bound to each other, the RNA molecule can be fragmented using, for example, alkaline hydrolysis or enzymes. Crosslinking stabilizes the RNA-RNA binding protein complexes such that a first RNA segment and a second RNA segment from the same molecule remain bound together after the fragmentation step. Molecules that are closer in proximity are more likely to be ligated together or tagged with the same molecular tag than molecules that are free-floating.

Fragmenting allows the molecule to be rearranged while retaining the proximity of fragments originating from the same RNA molecule. For example, segments of the original molecule that aren't adjacent to each other can be ligated together so they are both captured by the same sequencing read. Furthermore, segments of the molecule that aren't bound by RNA binding proteins can be washed away.

The fragmented RNA is generally labeled with a tag. The tag allows fragments generated from a common molecule to be identified as originating from that common molecule with confidence. For example, the segments can be tagged by being ligated to each other. This process allows a single sequencing read to capture information from different parts of the same RNA molecule that would otherwise be too far apart to capture at the same time. This information can include segments from exons that are included or excluded from various transcripts due to alternative splicing events and mutations that are more than one read length apart. Segments can also be tagged with a barcode.

The RNA fragments can be further manipulated by adding sequencing primers or adapters to the molecules and reverse transcribing the molecules into DNA. The DNA molecules can then be sequenced by methods known in the art, including by high-throughput or "next-gen" sequencing techniques.

Sequencing information can then be reassembled to identify variant species within the transcriptome by identifying fragments that originated from the same original RNA transcript using the molecular tagging information. This information can assist in identifying variants caused by alternative splicing, mutations, and RNA editing. In some cases, this information can be used to determine if changes are mutually exclusive or frequently accompany one another.

This disclosure also describes processes and compositions for determining phase information for DNA sequences that are too long to be captured in a single sequencing read. The processes and compositions can improve genomic assemblies by generating sequences that retain linkage information. The methods and compositions can determine this information without long reads and with nearly any sequencing platform.

The methods and compositions use recombinases, such as integrases, to deliver barcodes to fragments of DNA, such as genomic DNA. The methods generally include labeling fragments of genomic DNA with a first integrase recognition site. The methods also generally include labeling the sample DNA in a manner that retains linkage information. This can include forming chains of sample DNA fragments that originated from the same DNA molecule. The chains are generally interrupted by integrase recognition sites that allow for the insertion of barcodes.

These sites are then annealed to compatible sites on a second polynucleotide comprising a label. The second sites are capable of undergoing a recombination event with the first sites. The second polynucleotides generally comprise a barcode that labels the sample DNA fragments in a manner that indicates they arose from a common molecule. The second sites are typically a second integrase recognition site that is compatible with the first integrase recognition site. A plurality of these barcoded polynucleotides can be bound to a solid support, such as a bead or a chip. Thus, a chain containing several first integrase recognition sequences and several DNA fragments can anneal to several barcoded polynucleotides containing the second integrase recognition sequences on the same bead. The barcodes often differ between beads, regions on a chip, or sample, and in some cases are unique to a bead, region on a chip, or a sample. The barcodes need not be unique in all cases, however, so long as they are informative of possible linkage information. An integrase is introduced, which leads to the recombination of the annealed integrase recognition sequences. The integrase produces DNA fragments containing the barcodes from the second polynucleotide.

Of significant importance is the use of reconstituted chromatin in forming associations among very distant, but molecularly-linked, segments of DNA. The disclosure enables distant segments to be labeled with the same barcode using chromatin conformation, thereby enabling the identification of distant portions of the DNA molecule. Subsequent processing allows sequences that contain the same barcoding information to be identified as associated segments, yielding sequences whose separation on the genome extends up to the full length of the input DNA molecules. Since the sequences are identified as originating from the same molecule, these sequence reads also contain phase information.

Thus, the processes and compositions include extracting DNA from a sample, binding DNA molecules to DNA binding moieties, such as by reconstituting chromatin, breaking longer DNA molecules into fragments while still bound to the DNA binding moieties, tagging the fragments so they can be identified as originating from the same DNA molecule, sequencing the tagged molecules, and combining sequences containing the same tags to gain information regarding the identity of the original DNA molecule. As a result, fragments that ordinarily occur long distances apart from each other can nevertheless be identified as having originated from the same molecule. The compositions and processes disclosed herein can, therefore, be useful in determining haplotype information over long stretches of a chromosome, up to and including a full-length chromosome.

For example, a typical method begins by extracting genomic DNA and incubating it with a DNA binding moiety to generate reconstituted chromatin. An example DNA binding molecule includes a recombinant histone complex, but native DNA binding proteins and nanoparticles are also contemplated. Once the DNA binding protein is attached to the DNA, the sample is treated with formaldehyde to crosslink the DNA and DNA binding proteins. The DNA and DNA binding proteins are crosslinked to form DNA-protein crosslinks such that two or more DNA segments can be bound together via one or more DNA binding proteins. The methods generally bind DNA segments that are closer in physical space. Thus, the crosslinking can preferentially bind together two DNA segments from the same molecule, such as the same chromosome, compared to binding DNA from two different molecules or chromosomes. The crosslinking serves to maintain this proximity information throughout the process of manipulating the DNA molecule.

Once the DNA and DNA binding proteins are crosslinked, the DNA molecule can be fragmented using, for example, a restriction enzyme like MboI. Crosslinking stabilizes the DNA-DNA binding protein complexes such that the various crosslinked segments remain bound to each other even after their common phosphodiester bond has been cleaved. The segments are then ligated to adapters containing a first integrase recognition sequence. Fragments that are closer in proximity are more likely to be ligated to adapters and to each other than fragments that are not bound to the same crosslinked chromatin complex or that are free-floating. Thus, the process generally favors ligating fragments together that originated from the same DNA molecule or the same chromosome. It is generally desirable to produce chains comprising a plurality of genomic fragments and adapters.

Alternately, samples are not contacted to an explicit fragmenting agent, but are fragmented pursuant to partial or total extraction of nucleic acids from a sample such as a preserved sample, such as extraction that destroys intercellular binding agents such as collagenase but that leaves at least some nuclear protein-nucleic acid complexes intact. Nucleic acids, again, that are held in closer proximity are likely to have arisen from a common molecule and are more likely to be commonly tagged or to ligate to one another through exposed ends held in proximity in the complex.

Fragmenting, therefore, allows the molecule or its constituents to be rearranged while retaining the proximity of fragments originating from the same DNA molecule. For example, segments of the original molecule that are not adjacent to each other can be ligated together or to the same adapter so they are both captured by the same sequencing read or that they can be assigned to a common scaffold due to their common labeling. Furthermore, segments of the molecule that are not bound by DNA binding proteins or other binding agent can be washed away.

The fragmented DNA or RNA segments chains are generally ligated to one another or are labeled with a tag as described above. For example, the segments arising from the same molecule can be tagged using a common barcode. The tag allows fragments generated from a common molecule to be identified as originating from that common molecule with confidence. This allows shorter sequencing reads to be reassembled into larger molecules, like alleles or chromosomes.

The barcoded DNA fragments can be further manipulated by adding sequencing primers or adapters to the molecule. The DNA molecules can then be sequenced by methods known in the art, including by high-throughput or "next-gen" sequencing techniques. Similarly, junctions of a first segment and a second segment of a nucleic acid molecule that are ligated to one another can be packaged for sequencing by, for example, adding sequencing primers or adapters to the molecule.

Sequencing information can then be direct assignment of contigs to which sequence reads map into larger contigs, scaffolds comprising sequence gaps, up to and including scaffolds or contigs representing an entire chromosome. As one exemplary advantage, the methods are often able produce high quality assemblies with far less data than previously required. For example, the methods disclosed herein often provide for genomic assembly from only two lanes of Illumina® HiSeq™ data. As another exemplary advantage, the disclosure provides methods and compositions that can generate chromosome-level phasing using a long-distance read pair approach. For example, some methods disclosed herein phase 90% or more of the heterozygous single nucleotide polymorphisms (SNPs) for that individual to an accuracy of at least 99% or greater. This accuracy is on par with phasing produced by substantially more costly and laborious methods. As another exemplary advantage, the disclosure provides methods and compositions that can barcode individual DNA molecules without the need for complex microfluidics devices or emulsions.

INCORPORATION BY REFERENCE

All publications, patents, and patent applications mentioned in this specification are herein incorporated by reference to the same extent as if each individual publication, patent, or patent application was specifically and individually indicated to be incorporated by reference. U.S. Pat. No. 9,715,573, issued Jul. 25, 2017, is hereby incorporated by reference in its entirety. U.S. Pat. No. 9,411,930, issued Aug. 9, 2016, is hereby incorporated by reference in its entirety.

BRIEF DESCRIPTION OF THE DRAWINGS

Some understanding of the features and advantages of the present invention will be obtained by reference to the following detailed description that sets forth illustrative embodiments, in which the principles of the invention are utilized, and the accompanying drawings of which.

DETAILED DESCRIPTION OF THE INVENTION

Figure 1:
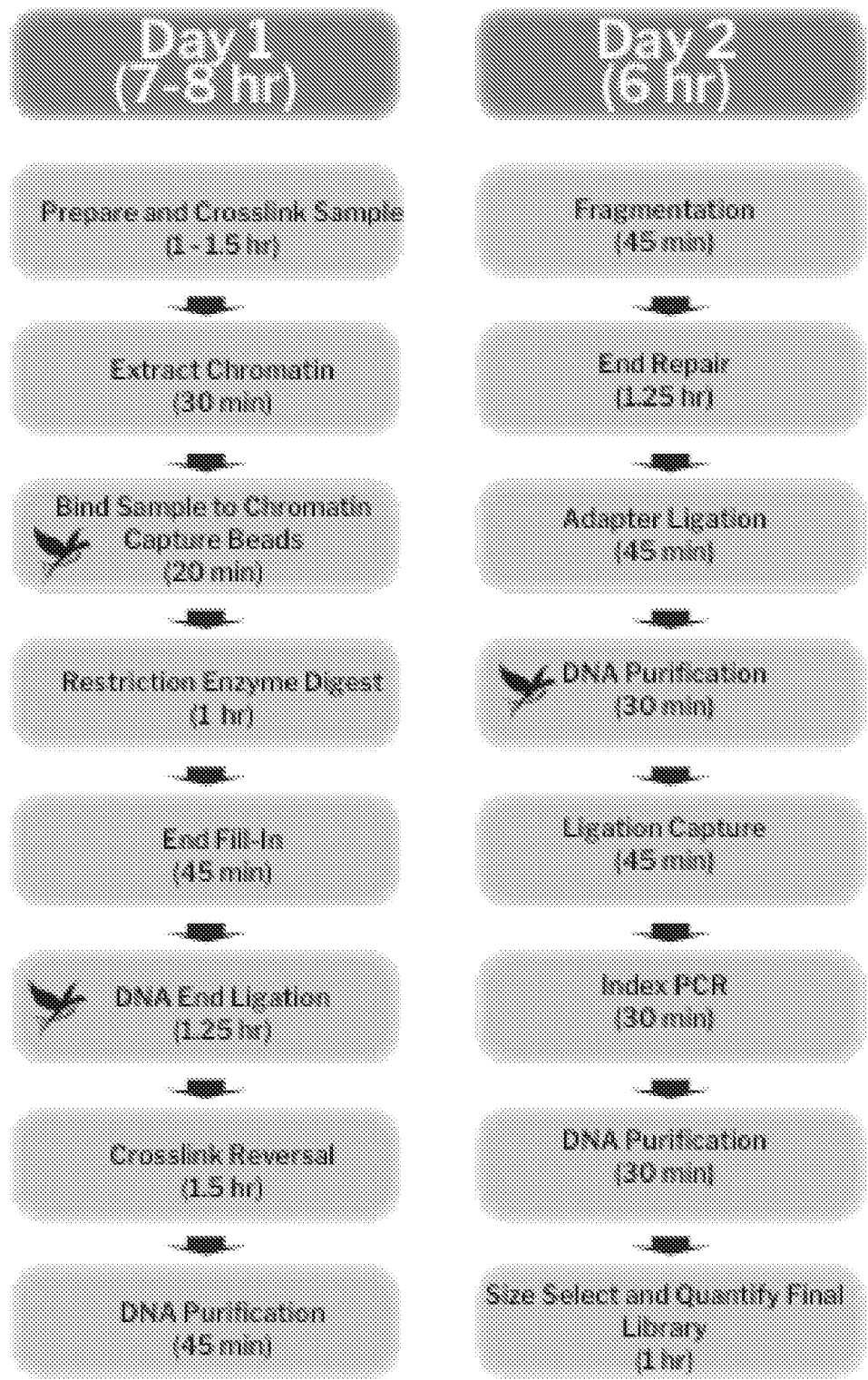
FIG. 1 depicts an exemplary workflow for the protocols herein.
Figure 2A:
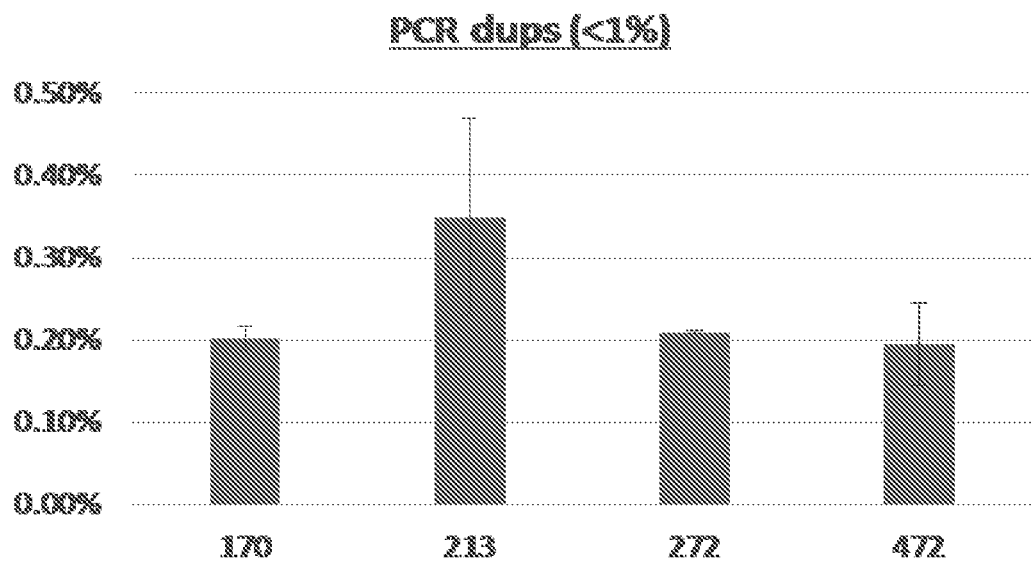
FIG. 2A presents analysis of paired end read data generated from fixed samples from which chromatin was extracted using collagenase.
Figure 2B:
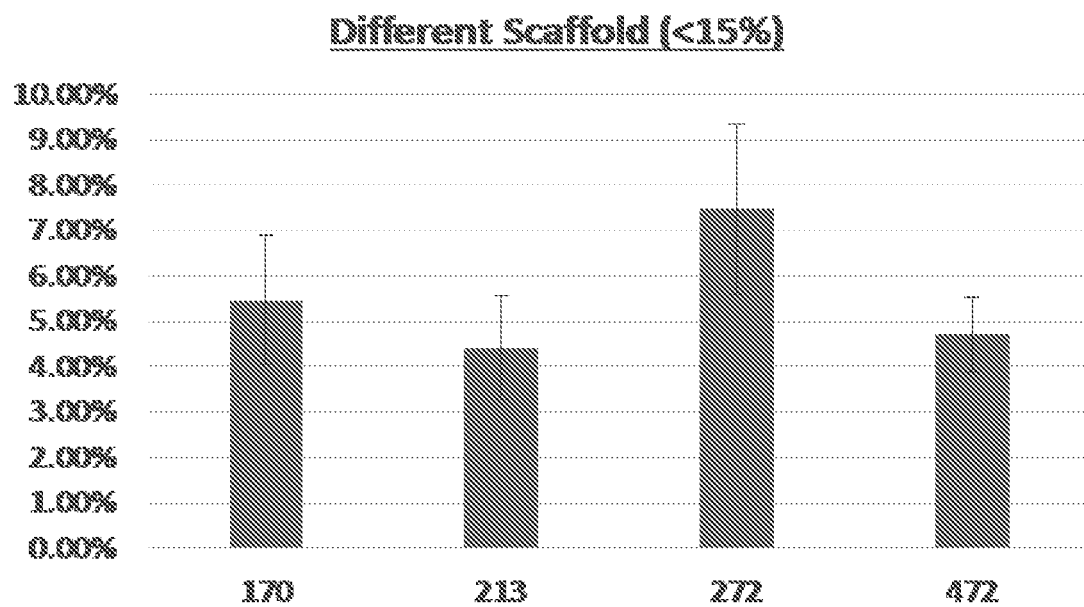
FIG. 2B presents analysis of paired end read data generated from fixed samples from which chromatin was extracted using collagenase.
Figure 2C:
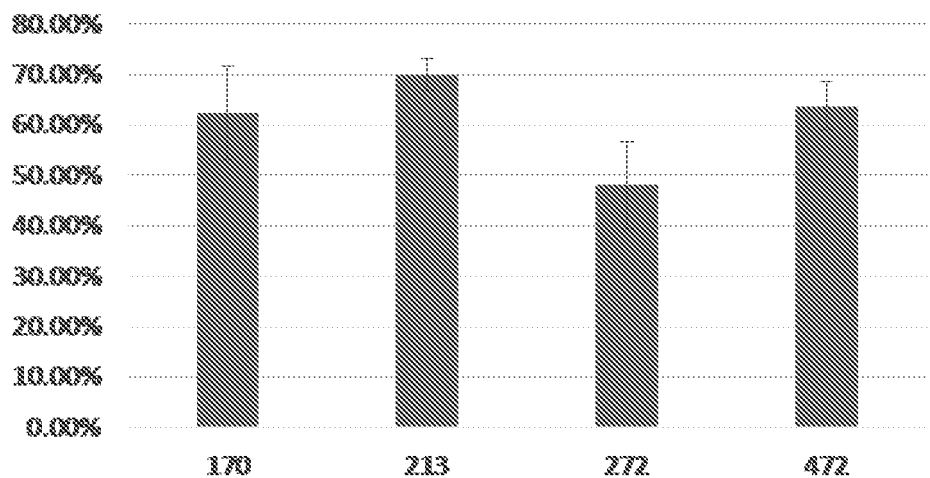
FIG. 2C presents analysis of paired end read data generated from fixed samples from which chromatin was extracted using collagenase.
Figure 2D:
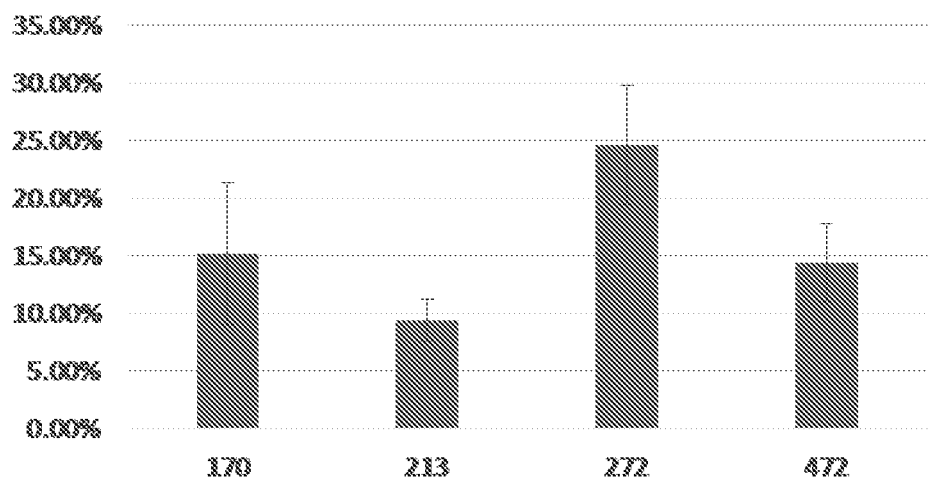
FIG. 2D presents analysis of paired end read data generated from fixed samples from which chromatin was extracted using collagenase.

Obtaining high quality sequence data from nucleic acid samples is valuable to biological and medical applications. A number of aspects present challenges including preparing a quality nucleic acid sample, sequencing the transcriptome or RNA samples, and phasing sequences obtained from long nucleic acid molecules. Provided herein are methods and compositions that address these and other challenges, improving quality of sequence data across broad applications.

Nucleic Acid Sample Preparation Methods

Preparation of high-quality nucleic acids, such as DNA and RNA, from biological samples is an important step in obtaining high quality nucleic acid, such as DNA sequences. In some cases, biological samples comprise tissues or cells that have been fixed. In some cases, biological samples comprise a tissue sample from an individual. Often, isolation of nucleic acids such as DNA and RNA from fixed biological samples or resected tissue samples requires homogenization of the biological sample in order to isolate the cells from extracellular proteins, such as an extracellular matrix. Such homogenization enables efficient isolation of chromatin DNA useful in sequencing applications. In previously described methods, physical methods have been used to obtain a homogenous mixture of cells from a biological sample, such as a tissue sample. However, such methods create high shear forces that can result in shearing of the DNA in the sample leading to a lower quality sample and lower quality sequence information. Such methods can also be more labor intensive, more difficult to scale up, and more difficult to automate.

Disclosed herein are compositions, methods, kits and systems for nucleic acid manipulation, extraction, and sequencing that individually or in combination provide nucleic acids suitable for analysis yielding long range linkage information, up to and including a comprehensive genome assembly pipeline. Genome assembly is effected in some cases using a contig or scaffold dataset that is independently obtained or concurrently generated. In an exemplary application, paired-end reads are generated from extracted nucleic acids, and are taken to be indicative that contigs to which each end of a paired end read set map are present on a common scaffold, or on a common molecule in the sample. Nucleic acids obtained using methods disclosed herein are also suitable for long-read sequencing applications and other applications requiring intact or largely intact chromatin.

Methods and compositions herein also provide for isolation of intact nuclei from recalcitrant or fixed biological samples. A benefit of nuclei isolation is that preserving an intact nucleus in an extraction protocol increases the likelihood that the nucleic acids contained therein are undamaged or only moderately damaged in the extraction process, so that use of these nucleic acids in a downstream sequence protocol is more likely to yield long range linkage information, such as information consistent with a sequence contig or scaffold set having an increased N50, The compositions, methods, kits, and systems disclosed herein are suitable for mammalian cell culture, blood, or tissue sample, and in some cases for non-mammalian samples such as other animal samples, fungal samples, viral, eukaryotic, bacterial, plant, algal, soil, or other sample sources. Samples are fresh or are preserved, such as through freezing, drying, or formaldehyde fixation.

Kits disclosed herein comprise buffers, enzymes, and instructions for preparation of nucleic acids from recalcitrant biological samples, such as fixed biological samples or samples with extracellular matrixes or cell walls, using methods disclosed herein. Exemplary kits disclosed herein enable users to generate up to 8 Illumina®-ready Hi-C sequencing libraries in no more than 2 days. The Hi-C library is validated using, for example, 1-2 million reads and Dovetail™'s QC software. Validated Hi-C libraries are sequenced to generate up to 100M read-pairs or more per Gbp of genome.

In certain applications, analysis of nucleic acids isolated via methods disclosed herein yield a sequenced library and input assembly, exemplarily with a N50 of >1 Mbp. Such sequenced library and input assembly are run through a computational scaffolding pipeline such as that disclosed in U.S. Pat. No. 9,715,573, issued Jul. 25, 2017, which is hereby incorporated by reference in its entirety.

Compositions, methods, kits, and systems disclosed herein provide nucleic acid isolated from biological samples, for example fixed tissue samples or cells, using enzymes to dissociate the cells and extracellular components rather than physical methods that are typically used in the art. Advantages to such enzymatic preparation include but are not limited to increased nucleic acid sample quality, isolation of intact or near intact chromatin, and increased quality of nucleic acid sequence data. Nucleic acid isolation from certain biological samples can require dissociation of the cells in order to separate the nucleic acid from the remaining cellular components. Enzymatic methods disclosed herein disperse cells in the biological sample to overcome issues observed in conventional homogenization techniques, such as shearing of the isolated nucleic acids.

Compositions, methods, kits, and systems herein isolate high-quality nucleic acids from a variety of biological samples, including tissues or organs, such as fixed tissues or organs, biological fluids such as blood, such as coagulated or fixed blood, and cultured cells. Biological samples herein also include fixed surgical samples, such as fixed tumor samples. In some instances, 2 to 400 mg of tissue is used, for example 2 to 200 mg, 200 to 400 mg, 2 to 100 mg, 100 to 200 mg, 200 to 300 mg, 300 to 400 mg, 2 to 50 mg, 50 to 100 mg, 100 to 150 mg, 150 to 200 mg, 200 to 250 mg, 250 to 300 mg, 300 to 350 mg, 350 to 400 mg, 2 to 10 mg, 10 to 20 mg, 20 to 30 mg, 30 to 40 mg, 40 to 50 mg, 50 to 60 mg, 60 to 70 mg, 70 to 80 mg, 80 to 90 mg, 90 to 100 mg, 100 to 110 mg, 110 to 120 mg, 120 to 130 mg, 130 to 140 mg, 140 to 150 mg, 150 to 160 mg, 160 to 170 mg, 170 to 180 mg, 180 to 190 mg, 190 to 200 mg, 200 to 220 mg, 220 to 240 mg, 240 to 260 mg, 260 to 280 mg, 280 to 300 mg, 300 to 320 mg, 320 to 340 mg, 340 to 360 mg, 360 to 380 mg, or 380 to 400 mg of tissue is used. In some instances, 10 to 50 mg, 10 to 40 mg, 20 to 50 mg, or 20 to 40 mg of tissue is used. In some instances, 20 to 40 mg of tissue is used. In some instances at least about 2 mg, at least about 10 mg, at least about 20 mg, at least about 30 mg, at least about 40 mg, at least about 50 mg, at least about 60 mg, at least about 70 mg, at least about 80 mg, at least about 90 mg, at least about 100 mg, at least about 110 mg, at least about 120 mg, at least about 130 mg, at least about 140 mg, at least about 150 mg, at least about 160 mg, at least about 170 mg, at least about 180 mg, at least about 190 mg, at least about 200 mg, at least about 210 mg, at least about 220 mg, at least about 230 mg, at least about 240 mg, at least about 250 mg, at least about 260 mg, at least about 270 mg, at least about 280 mg, at least about 290 mg, at least about 300 mg, at least about 310 mg, at least about 320 mg, at least about 330 mg, at least about 340 mg, at least about 350 mg, at least about 360 mg, at least about 370 mg, at least about 380 mg, at least about 390 mg, or at least about 400 mg of tissue is used. In some cases, up to about 2 mg, up to about 10 mg, up to about 20 mg, up to about 30 mg, up to about 40 mg, up to about 50 mg, up to about 60 mg, up to about 70 mg, up to about 80 mg, up to about 90 mg, up to about 100 mg, up to about 110 mg, up to about 120 mg, up to about 130 mg, up to about 140 mg, up to about 150 mg, up to about 160 mg, up to about 170 mg, up to about 180 mg, up to about 190 mg, up to about 200 mg, up to about 210 mg, up to about 220 mg, up to about 230 mg, up to about 240 mg, up to about 250 mg, up to about 260 mg, up to about 270 mg, up to about 280 mg, up to about 290 mg, up to about 300 mg, up to about 310 mg, up to about 320 mg, up to about 330 mg, up to about 340 mg, up to about 350 mg, up to about 360 mg, up to about 370 mg, up to about 380 mg, up to about 390 mg, or up to about 400 mg of tissue is used.

Often, biological samples for use in methods isolation of nucleic acids disclosed herein, are preserved biological samples. In some cases, the biological sample is frozen. In some cases, the biological sample is cryogenically frozen in liquid nitrogen, frozen in dry ice, or frozen using other methods to stabilize the sample. In some instances, the biological sample is frozen prior to fixing using a fixative. In some cases, the biological sample is fixed in a fixative immediately after isolating the biological sample from the organism. In some cases, the biological sample is perfused with a fixative. In some cases, fixation is performed on a biological sample that has been cut into small pieces, for example with a razor blade or by grinding the biological sample with a mortar and pestle. The sample is then fixed using a fixative agent, such as formaldehyde, paraformaldehyde, glutaraldehyde, formalin, or other chemical cross-linking agent. The sample is then placed into a solution of about 1.5% formaldehyde in a buffered saline, such as phosphate buffered saline. In some cases, a buffered solution of about or no more than 0.5% formaldehyde is used. In some cases, a buffered solution of about or no more than 1% formaldehyde is used. In some cases, a buffered solution of about or no more than 2% formaldehyde is used. In some cases, a buffered solution of about or no more than 3% formaldehyde is used. In some cases, a buffered solution of about or no more than 4% formaldehyde is used. In some cases, a buffered solution of about or no more than 5% formaldehyde is used. In some cases, a buffered solution of about or no more than 6% formaldehyde is used. In some cases, a buffered solution of about or no more than 7% formaldehyde is used. In some cases, a buffered solution of about or no more than 8% formaldehyde is used. In some cases, a buffered solution of about or no more than 9% formaldehyde is used. In some cases, a buffered solution of about or no more than 10% formaldehyde is used. Alternately, a buffered solution of at least 10% formaldehyde is preferred in some cases. Fixation proceeds at an appropriate temperature, optimized for the isolated tissue, for example at about or no more than 4° C. to about or no more than 25° C. In some cases, the tissue is fixed at room temperature. In some cases, the tissue is fixed at about or no more than 4° C. In some cases, the tissue is fixed at about or no more than 10° C. In some cases, the tissue is fixed at about or no more than 15° C. In some cases, the tissue is fixed about at or no more than 20° C. In some cases, the tissue is fixed at or no more than 25° C. Fixation proceeds at an amount of time needed to fix the entire tissue and may depend on a number of factors, such as the permeability of the tissue, the size of the tissue sample, and other factors. In some instances, fixation proceeds for about 20 minutes to about 12 hours, or longer. In some cases, fixation proceeds for about 20 minutes at room temperature. In some cases, fixation proceeds for about 12 hours at 4° C. The fixed tissue is then washed and ready for enzymatic treatment.

Methods of isolating nucleic acids from recalcitrant biological samples provided herein often use an enzymatic treatment of the biological sample, such as a fixed biological sample. Enzyme treatment of the biological sample facilitates isolation of nucleic acids from the biological sample without damaging the nucleic acids such that at least some phase or physical linkage information is preserved. Alternately, some enzymatic isolation comprises or results in cleavage between at least some segments of a nucleic acid molecule, such that internal ends are exposed form tagging or ligation as described herein. In some cases, intact or nearly intact chromatin is isolated from the fixed biological sample. Alternately, complexes are isolated such that a first segment and a second segment are held together independent of a phosphodiester backbone, or are held together such that a first segment and a second segment are held in physical proximity despite no longer being tethered by a common phosphodiester backbone.

Enzymes useful in isolation of nucleic acids often target intercellular matrix components or cellular components, but that leave at least some nucleoprotein complexes intact, such as some chromatin constituents or some nucleosomes, or some riboprotein complexes, such that physical proximity or physical linkage information is preserved even upon enzymatic degradation of extracellular or cellular components.

As used herein, a first segment of a first nucleic acid region and a second segment of a second nucleic acid region are in physical proximity if they are physically closer to one another than either is to linearly-following nucleic acid segments of the first nucleic acid region and the second nucleic acid region, respectively.

Some enzymes include enzymes capable of degrading extracellular components such as proteins such as collagen and polysaccharides such as cellulose or chitin. Similarly, enzymes that exhibit actin, myosin or other structural component degradation are in some cases preferred. Alternately, nonspecific enzymes are in some cases employed under reaction conditions such that extracellular components are selectively degraded, or such that at least some leave at least some nucleoprotein complexes intact, such as some chromatin constituents or some nucleosomes, or some riboprotein complexes, such that physical proximity or physical linkage information is preserved even upon enzymatic degradation of extracellular or cellular components.

A variety of enzymes are available from many sources that are capable of digesting extracellular components such as proteins or polysaccharides addressed in more detail below. Enzymatic treatment is carried out at a temperature optimized or otherwise suitable for the biological sample and the selected enzyme. Exemplary temperatures for treatment of biological samples are from about 4° C. to about 90° C., for example about 4-40° C., about 40-90° C., about 4-20° C., about 20-40° C., about 40-60° C., about 60-80° C., about 70-90° C., about 20-30° C., about 30-40° C., about 40-50° C., about 50-60° C., about 60-70° C., about 70-80° C., or about 80-90° C. In some cases, enzymatic treatment is carried out at a temperature of at least about 4° C., at least about 15° C., at least about 20° C., at least about 25° C., at least about 30° C., at least about 35° C., at least about 37° C., at least about 40° C., at least about 50° C., at least about 55° C., at least about 60° C., at least about 65° C., at least about 70° C., at least about 75° C., at least about 80° C., at least about 85° C., or at least about 90° C. In some cases, enzymatic treatment is carried out at about 37° C. In some cases, enzymatic treatment is carried out about or at 55° C. After enzymatic treatment, the isolated nucleic acids are in solution and the remaining tissue is discarded.

Methods herein optionally proceed to normalize the amount of nucleic acids in each sample prior to use in further applications, such as chromatin capture or sequencing. In some cases, about 50 to about 5000 ng of nucleic acid is used in further applications, such as chromatin capture or sequencing, for example about 50 ng, about 60 ng, about 70 ng, about 80 ng, about 90 ng, about 100 ng, about 200 ng, about 300 ng, about 400 ng, about 500 ng, about 600 ng, about 700 ng, about 800 ng, about 900 ng, about 1000 ng, about 1200 ng, about 1400 ng, about 1600 ng, about 1800 ng, about 2000 ng, about 2500 ng, about 3000 ng, about 3500 ng, about 4000 ng, about 4500 ng, or about 5000 ng nucleic acids is used. In some cases, at least about 50 to at least about 5000 ng of nucleic acid is used in further applications, such as chromatin capture or sequencing, for example at least about 50 ng, at least about 60 ng, at least about 70 ng, at least about 80 ng, at least about 90 ng, at least about 100 ng, at least about 200 ng, at least about 300 ng, at least about 400 ng, at least about 500 ng, at least about 600 ng, at least about 700 ng, at least about 800 ng, at least about 900 ng, at least about 1000 ng, at least about 1200 ng, at least about 1400 ng, at least about 1600 ng, at least about 1800 ng, at least about 2000 ng, at least about 2500 ng, at least about 3000 ng, at least about 3500 ng, at least about 4000 ng, at least about 4500 ng, or at least about 5000 ng nucleic acids is used. In some cases, no more than about 50 to no more than about 5000 ng of nucleic acid is used in further applications, such as chromatin capture or sequencing, for example no more than about 50 ng, no more than about 60 ng, no more than about 70 ng, no more than about 80 ng, no more than about 90 ng, no more than about 100 ng, no more than about 200 ng, no more than about 300 ng, no more than about 400 ng, no more than about 500 ng, no more than about 600 ng, no more than about 700 ng, no more than about 800 ng, no more than about 900 ng, no more than about 1000 ng, no more than about 1200 ng, no more than about 1400 ng, no more than about 1600 ng, no more than about 1800 ng, no more than about 2000 ng, no more than about 2500 ng, no more than about 3000 ng, no more than about 3500 ng, no more than about 4000 ng, no more than about 4500 ng, or no more than about 5000 ng nucleic acids is used. In some cases, about 50 to about 500 ng is used. In some cases, about 500 ng is used.

In some applications of methods of preparation of nucleic acids provided herein, further applications, such as chromatin capture or sequencing is performed on a fixed amount of nucleic acids as described above. In some cases, chromatin capture is performed using beads that have been functionalized to bind to a target, such as a nucleic acid or a nucleic acid binding protein. In some embodiments, chromatin capture is performed using chromatin capture beads provided by a kit designed for performing methods herein. In some cases, chromatin capture is performed on intact nuclei isolated from recalcitrant or fixed biological samples using methods provided herein.

Biological Samples for Preparation of Nucleic Acids

Methods, compositions, systems, and kits for preparing nucleic acids herein are amenable to preparation of nucleic acids from recalcitrant biological samples having nucleic acids, such as fixed biological samples, for sequencing. Such biological samples include but are not limited to biological samples from animal, plant, fungal, or bacterial sources. Often biological samples are isolated from an animal, such as a mammal. In some cases, biological samples are isolated from a human, such as a human patient. In some cases, biological samples are tumor tissues isolated from a cancer patient. Often biological samples are fixed tumor tissues isolated from a cancer patient and then fixed for further analysis and long-term storage.

Biological samples for preparation of nucleic acids using methods described herein include mammalian tissue samples. Mammalian tissue samples include but are not limited to skin, bone, cartilage, skeletal muscle, brain, spinal cord, tongue, esophagus, lung, stomach, intestine, smooth muscle, uterus, ovary, testes, kidney, spleen, bone marrow, thymus, pituitary, thyroid, and other mammalian tissue samples. In some cases, mammalian tissue samples are tumor samples. In some cases, the biological sample is blood, such as coagulated or fixed blood. In some cases, the biological sample is cultured cells, including fixed or preserved cultured cells.

Some samples are freshly obtained, such as samples obtained pursuant to surgery, preserved, and promptly subjected to analysis. Alternately, some samples are obtained and preserved over a substantial period of time, such as a period of time necessary to perform a clinical drug trial or to initiate or proceed with a therapeutic treatment or symptom amelioration regimen, and are subjected to analysis so as to obtain information relevant to assessment of regimen performance.

Homogeneous and heterogeneous samples are consistent with the compositions and methods disclosed herein. Some samples are heterogeneous due to mutations occurring at varying levels of abundance, such as may occur in cancer or tumor tissue. Alternately or in combination, sample heterogeneity is often due to presence of distinct nucleic acid sources, such as pathogens or nonpathogenic organisms in a sample.

Enzymes for Preparation of Nucleic Acids

Disclosed herein are improved methods for preparing nucleic acids from recalcitrant biological samples, such as fixed biological samples, samples with extra-cellular matrices, and samples with resilient cell walls, for use in sequencing methods, such as those described herein. Some methods of preparing nucleic acids provided herein use enzymes to gently dissociate cells and unwanted cellular proteins from nucleic acids. Exemplary enzymes include enzymes suitable for digestion of cellular proteins, such as extracellular proteins or extracellular matrix proteins in order to improve the quantity and quality of the isolated nucleic acid. Some enzymes consistent with the disclosure herein are specific for or largely target extracellular matrix constituents such as collagen. Alternately or in combination, some enzymes consistent with the disclosure herein degrade multiple constituents but leave at least some nucleic acid-protein constituents at least partially intact so as to facilitate the preservation of linkage information as discussed herein. This is accomplished through enzymatic specificity, enzymatic differential or selective nonactivity as to nucleoprotein complexes, or manipulation of reaction conditions such that enzymes lacking protein specificity are contacted to samples under conditions such that protease activity, even nonspecific protease activity, is arrested prior to degradation of all or a substantial portion of nucleoprotein complexes. That is, in various embodiments of enzymes consistent with the disclosure herein, preservation of a substantial portion of nucleoprotein complexes is effected through selection of enzymes having selective protease activity, selective nonactivity as to nucleoprotein complexes, or in some cases through selection or reaction conditions that lead to substantial nonspecific protein degradation, particularly of extracellular matrix proteins such as collagen, but that leave a substantial portion of nucleoprotein complexes in tact or otherwise suitable for the ligation or labeling methods disclosed herein. That is, specificity that leads to at least partial preservation of nucleoprotein complexes is effected through enzyme specificity or, alternately, reaction conditions. Accordingly, some enzymes consistent with the methods herein act on preserved samples without substantially disrupting nucleoprotein complexes, or without disrupting preserved cells, or without disrupting preserved nuclei, or without disrupting at least some nucleosomes bound to nucleic acids, or without disrupting at least some nucleoprotein complexes.

Enzymes useful in method herein include but are not limited to collagenases, cellulases, proteinases, metalloproteases, metallopeptidases, matrix metalloproteinases, a disintegrin and metalloproteinase with thrombospondin motifs (ADAMTS), proteases, sulfhydryl proteases, seine proteinases, cysteine proteinases, cysteine endopeptidases, and combinations thereof. In some cases, enzymes useful in methods herein include but are not limited to matrix metallopeptidase 1, matrix metallopeptidase 8, peptidase M9, peptidase M9A, peptidase M9B, *Vibrio* collagenase, *Clostridium* collagenase, papain, bromelain, ficain, interstitial collagenase, gelatinase-A, stromeysin 1, matrilysin, neutrophil collagenase, gelatinase-B, stromelysin 2, stromelysin 3, macrophage metalloelastase, collagenase 3, collagenase 4, stromelysin 4, enamelysin, matrix metallopeptidase 21, matrilysin 2, matrix metallopeptidase 27, epilysin, plasmin, cathepsin G, cathepsin B, cathepsin L, neutrophil elastase, ADAMTS-1, ADAMTS-2, ADAMTS-4, ADAMTS-5, ADAMTS-8, and ADAMTS-9. Collagenases useful in methods herein include but are not limited to *Vibrio* collagenase, *Clostridium* collagenase, interstitial collagenase, and neutrophil collagenase. Metalloproteinases useful in methods herein include but are not limited to matrix metalloproteinase 1, matrix metalloproteinase 2, matrix metalloproteinase 3, matrix metalloproteinase 7, matrix metalloproteinase 8, matrix metalloproteinase 9, matrix metalloproteinase 10, matrix metalloproteinase 11, matrix metalloproteinase 12, matrix metalloproteinase 13, matrix metalloproteinase 21, matrix metalloproteinase 26, and matrix metalloproteinase 27. A disintegrin and metalloproteinase with thrombospondin motifs (ADAMTS) useful in methods provided herein include but are not limited to ADAMTS-1, ADAMTS-2, ADAMTS-4, ADAMTS-5, ADAMTS-8, and ADAMTS-9. Additional enzymes useful in methods herein include but are not limited to endocellulases, exocellulases, cellobiases, oxidative cellulases, cellulose phosphorylases, avicelase, progressive cellulase, nonprogressive cellulase, beta glucosidases, amylase, glycase, and cellbiose dehydrogenase. Exemplary enzymes consistent with the disclosure herein comprise collagenases.

Alternately or in combination, some embodiments such as those relying on reaction conditions to effect partial or selective degradation or selective preservation are nonspecific proteases such as proteinase k.

Nucleic Acids Isolated from Recalcitrant Samples

Methods provided herein isolate nucleic acids from recalcitrant samples, such as fixed samples or samples with extracellular matrixes or cell walls, that comprise intact or largely intact nucleic acids, for example intact or largely intact chromatin. For example, some nucleic acids prepared using methods provided herein comprise chromosome fragments having a length at least 10%, 20%, 30%, at least about 40%, at least about 50%, at least about 60%, at least about 70%, at least about 80%, at least about 90%, at least about 95%, at least about 99% or greater up to and including 100% of the length of an entire chromosome from which they originated. Often, nucleic acids prepared using methods provided herein produce very long nucleic acids, for example greater than about 200 kb, about 300 kb, about 400 kb, about 500 kb, about 600 kb, about 700 kb, about 800 kb, about 900 kb, about 1 Mb, about 2 Mb, about 3 Mb, about 4 Mb, about 5 Mb, or about 10 Mb, or longer than about 10 Mb, up to and including the entire length of a chromosome. Nucleic acids isolated from recalcitrant biological samples using methods herein often display a larger N50 of the physical molecules observed, by sequencing or by other approach such as visualization via size separation on an electrophoresis gel, for example. An N50 of the molecules of a protected sample is increased relative to a control sample, such as a sample subjected to complete or substantially complete protease treatment, by in some cases 2×, 3×, 4×, 5×, 6×, 7×, 8×, 9×, 10×, 20×, 50×, 100×, 200×, 500×, 1000×, 2000×, 5000×, 10,000×, 100,000×, or more than 100,000×. A control sample is in some cases an aliquot of nucleic acids purified from a portion of the biological sample using conventional methods. In some embodiments, a control sample is a sample of known N50 from experience using a sample processing method. Methods disclosed herein also provide for isolation of intact nuclei from a recalcitrant biological sample, such as a fixed biological sample or samples with extracellular matrix or cell walls.

Sequencing Nucleic Acids

Nucleic acids isolated from recalcitrant or fixed biological samples via enzymatic methods disclosed herein are useful samples for existing sequencing technology. The improved quality of nucleic acids prepared using methods disclosed herein leads to improved sequencing results using a variety of sequencing technologies. Cases of sequencing technologies that can be used in analysis of nucleic acids isolated using methods herein include, but are not limited to, the Illumina® sequencing-by-synthesis platform (Illumina®, San Diego, Calif), the SOLiD™ system (Applied Biosystems Corp.), pyrosequencing (e.g., 454 Life Sciences™, subsidiary of Roche Diagnostics), a sequencing technique based on semiconductor detectors (e.g., the Ion Torrent® platform), nanopore sequencing (e.g., the Oxford Nanopore™ sequencing platform), DNA nanoball sequencing methods (e.g. Complete Genomics™), long-read sequencing such as Pacific Biosciences™ (PacBio™), sequencing by hybridization and any other suitable technology, or any technology that may be derived from any of the above technologies.

Chromatin Reassembly of Nucleic Acids Isolated Through Segment Preserving Methods Disclosed herein are methods, compositions, systems, and kits for preparing nucleic acids from recalcitrant biological samples, such as fixed biological samples or samples with extracellular matrix or cell walls. Some methods herein purify nucleic acid molecules using enzymatic techniques described herein resulting in less damage that is often observed during conventional sample preparation techniques.

Nucleic acid isolation is in many cases effected so as to preserve nucleoprotein complexes to facilitate physical proximity or phase determination analyses such as those known in the art or disclosed herein. Alternately, in some embodiments, DNA is isolated using enzymes as disclosed herein so as to increase the size of nucleic acid fragments recovered from preserved or recalcitrant samples, such that, even if nucleoprotein complexes are not preserved, nucleic acids are recovered so as to facilitate scaffold constructions. Segments are treated using techniques provided herein or disclosed in the art such that chromatin or nucleoprotein complexes or other complexes are assembled in vitro by contacting to DNA-binding agents to generate reconstituted chromatin. DNA binding agents include, for example, DNA-binding proteins, nanoparticles, DNA-binding beads, and beads coated with DNA-binding substances, polymers, synthetic DNA-binding molecules, and other affinity molecules. In some cases, SPRI beads are used in 'chromatin' reconstitution. In many cases the bound DNA sample is referred to as reconstituted chromatin, either in the strict sense of reconstitution of native chromatin constituents onto isolated DNA, or as herein, more broadly to refer to reconstitution of a nucleic acid into a heterogeneous complex such that a first segment and a second segment are held together independent of their common phosphodiester backbone.

Reconstituted chromatin prepared from nucleic acid samples from recalcitrant biological samples obtained by methods provided herein is optionally contacted to a cross-linking agent. Cross-linking occurs through contact with a cross-linking agent such as formaldehyde, though many other cross-linking agents are recited herein or are well known in the field. Often, after the DNA complex, such as the reconstituted chromatin, has been cross-linked, tagging information is added to further preserve phase and/or physical linkage information in the event that DNA damage causes degradation to the cross-linked complex. Disclosed herein and incorporated herein are methods for adding such tagging information. In many cases, exposed internal ends are generated by intentionally contacting the cross-linked complex with a DNA-cleaving agent. DNA cleaving agents include, but are not limited to, restriction enzymes, topoisomerases, non-specific endonucleases, DNA repair enzymes, RNA-guided nucleases, and alternate enzymes. The exposed internal ends are then tagged using known methods in the art or by the methods described below. Tagging information allows one to map tagged segments to a common phase of a common molecule of origin. Thus, tagged nucleic acids retain their physical linkage information as to segments adjacent to the tag.

Reconstituted chromatin prepared from nucleic acid samples from recalcitrant biological samples obtained by methods provided herein results in a higher quality sequence assembly upon the removal of the reconstituted chromatin and sequencing of the sample. This protection manifests itself in a larger N50 of the physical molecules observed, by sequencing or by other approach such as visualization via size separation on an electrophoresis gel, for example. An N50 of the molecules of a protected sample is increased relative to a control sample by in some cases 2×, 3×, 4×, 5×, 6×, 7×, 8×, 9×, 10×, 20×, 50×, 100×, 200×, 500×, 1000×, 2000×, 5000×, 10,000×, 100,000×, or more than 100,000×. A control sample is in some cases an aliquot of nucleic acids purified from a portion of the biological sample using conventional methods. In some embodiments, a control sample is a sample of known N50 from experience using a sample processing method.

In some cases, phase information and/or physical linkage is preserved despite physical molecules of a reconstituted chromatin complex. Physical linkage information is preserved such that a first segment and a second segment of a common molecule of the sample are held in proximity by the reconstituted chromatin such that they are assigned to a common phase or common molecule, for example by being similarly tagged or by being ligated to one another subsequent to double strand cleavage due to degradation or in sample preparation. In these cases, an N50 of the contigs and/or scaffolds obtained from sequencing the sample is increased relative to the N50 of contigs and/or scaffolds obtained from a control sample. The extent of preservation relative to a control sample's sequenced contig and/or scaffold N50 is an increase of in some cases 2×, 3×, 4×, 5×, 6×, 7×, 8×, 9×, 10×, 20×, 50×, 100×, 200×, 500×, 1000×, 2000×, 5000×, 10,000×, 100,000×, or more than 100,000×. A control sample is in some cases a nucleic acid sample prepared from a biological sample using conventional techniques but otherwise subjected to the same or a comparable treatment regimen. In some embodiments, a control sample is a sample of known N50 from experience using a sample preparation method.

N50 improvements are determined in some cases by comparison to a control sample or N50 value. In some cases, the control is defined strictly, that is by aliquoting a portion of an initial sample, and subjecting it to a treatment comparable to that of the sample prepared using methods herein but changing a single parameter of the preparation method, such as the enzyme used for biological sample preparation. Alternately, in some cases the 'control' is more broadly defined, such that a control value or control N50 distribution is that previously experimentally observed to result from a particular sample preparation method. For example, if a sample preparation method is known or expected to yield sample information having an N50 of the resultant contigs and/or scaffolds of a particular low value or range of low values, then a control need not be generated in the individual practice of a method as disclosed herein. Exclusion of a control in sample preparation may in some cases result in more efficient use of reagents, in particular when a large number of samples are collected, transported, and sequenced. Alternately, in some cases a control aliquot is regularly taken for each sample.

Following chromatin reconstitution around a nucleic acid sample and subjecting to nucleic acid degradation, the chromatin assembly is reversed and the nucleic acids are optionally subjected to further analysis. Chromatin assembly is reversed by any of a number of approaches known to one of skill in the art, for example treatment of the sample using a protease such as proteinase K. In some cases, samples are processed, for example to tag exposed ends of cleaved nucleic acids, prior to removal of reconstituted chromatin, for example so as to preserve physical linkage information.

Samples are then available to be assayed directly for nucleic acid size, via size selection or size visualization on an electrophoresis gel or other approach. Alternately, samples are subjected to a sequencing regimen so as to determine the sequence and phase of the nucleic acid source material.

Sequencing is achieved by any number of approaches available to one of skill in the art. In some cases, samples are shotgun sequenced and then subjected to additional methods such as those disclosed herein or elsewhere to assign physical linkage information to shotgun sequence reads or assembled shotgun contigs and/or scaffolds. Alternately, samples are subjected to a long-read sequence approach, alone or in combination with an approach to assign physical linkage information to the resultant long-range sequence reads or contigs and/or scaffolds.

Chromatin reconstitution is not, however, an essential step of all methods disclosed herein. Rather, as disclosed above and throughout, in many cases samples are treated (for example using a collagenase or other specific enzyme or treatment regimen) so as to preserve at least some nucleoprotein complexes, such that chromatin reconstitution is not essential for the preservation of proximity, physical linkage or phase information.

Nucleic Acid Labeling

Nucleic acid samples isolated from recalcitrant biological samples obtained by methods provided herein are also used for labeling of a nucleic acid sample such that nucleic acid segments of a common phase or common molecule are commonly labeled prior to sample degradation, such that sample degradation does not result in loss of label-associated physical linkage information for a labeled segment. Methods herein purify nucleic acid molecules using enzymatic techniques described herein resulting in less damage that is often observed during traditional sample preparation techniques.

Samples are labeled as described below and elsewhere herein. Briefly, a nucleic acid sample is isolated from a recalcitrant biological sample, such as a fixed biological sample, using enzymatic methods described herein. This isolated nucleic acid sample is optionally assembled into reconstituted chromatin such that some, the majority, substantially all or all of the nucleic acid molecules are assembled into reconstituted chromatin complexes having a single nucleic acid fragment per complex. Reconstituted chromatin is assembled by addition of polypeptides such as nucleic acid binding proteins, histones, nuclear proteins, or other suitable proteins that bind nucleic acids and are amenable to crosslinking. Alternately, reconstituted chromatin is assembled using nanoparticles or other nonpolypeptide moieties such as spermine or spermidine.

Alternately or in combination, nucleoprotein complexes are preferably isolated at least partially intact, such that many embodiments may rely upon such complexes and do not need or rely upon chromatin reassembly.

Assembled or recovered complexes are beneficially constituted such that a first segment and a second segment of a common phase of a nucleic acid molecule are bound such that they are held together independent of their common phosphodiester backbone, or are held together such that segments derived from a common original source such as an original chromosome are held in physical proximity despite no longer possessing a common phosphodiester backbone. Complexes are optionally crosslinked subsequent to isolation or assembly.

In some methods, exposed nucleic acid loops of a complex are cleaved such that internal double strand ends are exposed. Cleavage preferably comprises contacting to a sequence specific restriction endonuclease, although other cleavage and tagging approaches are contemplated, such as contacting to a tagmentation enzyme, to a tag-loaded transposase, or to a nonspecific endonuclease. Nonenzymatic methods, such as sonication or shearing, are also contemplated. Often, nucleic acids are sheared pursuant to nucleoprotein complex isolation or are subject to degradation in preservation, such that an additional cleavage step is not required or is performed only supplementally to partially cleaved complexes. Exposed ends are labeled, for example using a tag that commonly or uniquely tags the exposed ends of a complex relative to other complexes. That is, preferably, exposed ends of a complex are commonly tagged for a given complex, and distinct complexes are distinctly tagged. In some cases, two complexes share a common tag, or a single complex receives more than one species of tag. Provided that these events are relatively rare, physical linkage information is still readily derived from tagged complexes in these situations.

Alternately, exposed ends are tagged or labelled by randomly cross-ligating to one another within a complex, such that an exposed end of a first segment is labeled with sequence of a second segment in phase with it in the original molecule but randomly positioned relative to the first fragment.

Labeled nucleic acids are optionally removed from their reconstituted chromatin environment, for example using proteinase K treatment.

Labeled nucleic acids are then subjected to degradation. Sequence independent double-strand breaks are introduced, but physical linkage information that is marked by fragment border tags or by fragment borders being ligated to adjacent fragments is not lost during degradation. Accordingly, upon sequencing of a degraded, labeled sample, fragments are often found to be comparable in size to an unlabeled sample, but contig N50 is substantially larger due to the preservation of physical linkage information associated with fragment-adjacent label sequence. In some cases, contig length is 2×, 5×, 10×, 50×, 100×, 500×, 1000× or greater than 1000× improved relative to an unlabeled control sample. Similarly, upon sequencing of a degraded, labeled sample, fragments are often found to be comparable in size to an unlabeled sample, but scaffold N50 is substantially larger due to the preservation of physical linkage information associated with fragment-adjacent label sequence. In some cases, scaffold length is 2×, 5×, 10×, 50×, 100×, 500×, 1000× or greater than 1000× improved relative to an unlabeled control sample.

Physical Linkage Preservation and Sequencing Approaches

Nucleic acid isolated from recalcitrant biological samples, such as fixed biological samples are useful in obtaining physical linkage information through any number of approaches known to one of skill in the art. For example, reconstituted chromatin created from nucleic acid isolated from recalcitrant biological samples as described herein is optionally subjected to controlled cleavage separate from the degradation to which it is subjected, so that regular exposed ends amenable to downstream analysis are generated. Exposed ends are optionally attached to tagged oligonucleotides which identify the tagged exposed ends as originating from the same DNA molecule. This attachment often occurs through ligation or polymerase extension. In some cases the tagged oligonucleotides are barcoded to identify molecules originating from a common DNA molecule and/or biotinylated for downstream isolation.

Exposed ends optionally are partially filled, for example with dNTPs or labeled dNTPs, in to prevent religation. Oligonucleotides, such as punctuation oligonucleotides, with ends compatible with the partially filled-in sticky ends are added to the chromatin sample along with a DNA ligase. In some instances, the punctuation oligonucleotides are dephosphorylated in order to avoid concatemerization of the oligonucleotides. Alternatively, oligonucleotide tags are added through transposase activity. In these cases, transposase bound to two punctuation oligonucleotides is added to the cross-linked DNA complex. The transposase cleaves exposed DNA segments and inserts the two punctuation oligonucleotides into the DNA. In some cases, the transposase-bound oligonucleotides are linked. In other cases, the transposase-bound oligonucleotides are unlinked. When the oligonucleotides are unlinked, the insertion results in two free DNA ends, each terminated by one of the two punctuation oligonucleotides. Many times, DNA ligase is added to the sample to ligate blunt DNA ends together, resulting in a rearrangement of DNA segments, though physical linkage information is maintained since the DNA molecule is bound to the chromatin proteins throughout this process.

In yet other examples, exposed ends are filled-in with labeled dNTPs, such as an alpha-thio-dGTP and a biotinylated dCTP to generate blunt ends. In many of these examples, the cross-linked DNA complex is biotinylated prior to exposure of the internal DNA ends. After filling in the exposed ends, the blunt ends are often ligated to generate paired-ends. Though, other methods of attaching the paired ends are envisioned such as polymerase extension transposase activity.

Tagging information is be added to the cross-linked DNA complex as disclosed herein or by other tagging methods well known in the art. Tagging information is ideally added prior to exposure to DNA damage; however, in many circumstances it can be necessary to add tagging information after DNA damage has occurred. In the latter cases, it is often preferred to remove non-complexed DNA prior to adding tagging information. Non-complexed DNA is removed by washing, differential centrifugation, gel-electrophoresis, chromatography, other traditional methods, or any combination thereof. In some cases, non-complex DNA is removed from samples prior to DNA damage occurring.

Disclosed herein are methods for isolating and enriching phase-informative or physical linkage-informative fragments of DNA isolated from recalcitrant samples via enzymatic methods provided herein. Long DNA molecules are needed to determine physical linkage information. Following DNA extraction, DNA molecules of different sizes are included in the DNA sample. Furthermore, DNA damage caused by some preparation methods as discussed herein causes further fragmentation of the DNA sample and the DNA damage will accumulate over time. In many of the methods disclosed herein, to isolate or enrich for phase-informative or physical linkage-informative DNA fragments, the DNA sample is assembled in vitro into reconstituted chromatin as disclosed herein. Only the DNA molecules long enough to wrap about the DNA binding agent are incorporated into the chromatin complex. In many instances, after reconstitution, the sample is washed to remove non-complexed DNA molecules, leaving only the reconstituted chromatin complexes. The complexed DNA molecules which contain important phasing information are protected against further degradation by DNA damaging agents. Alternatively, the enriched complexed DNA molecules can be directly sequenced to generate physical linkage information. In some examples, prior to sequencing, the enriched DNA complex is processed in order to add tagging information. For example, the DNA sample has tagging information added through any of the methods disclosed herein. Additionally or alternatively, tagging information is added such that the sample is compatible for sequencing with PacBio™, Illumina®, Oxford Nanopore™, or other well-known sequencing technologies.

Methods of preparing nucleic acids from recalcitrant biological samples, such as fixed biological samples or samples with extracellular matrix, disclosed herein produce fragments of genomic DNA up to megabase scale. Long DNA fragments may be generated to confirm the ability of the present methods to generate read pairs spanning the longest fragments offered by those extractions. In some cases, DNA fragments beyond 150 kb in length may be extracted and used to generate XLRP libraries.

Methods disclosed herein utilize data analysis that allows for rapid and inexpensive de novo assembly of genome sequence information from one or more subjects. Some methods disclosed herein produce high quality sequence assemblies with far less data than previously required. The methods disclosed herein may be used in a variety of applications, including haplotype phasing and metagenomics analysis. The disclosure provides methods that generate chromosome-level phasing using a long-distance read pair approach. For example, some methods disclosed herein phase at least 10%, at least 20%, at least 30%, at least 40%, at least 50%, at least 60%, at least 70%, at least 80%, at least 90% or more of the heterozygous loci such as single nucleotide polymorphisms (SNPs), indels, or other allelic polymorphisms at heterozygous loci in a sample for that individual to an accuracy of at least 50%, at least 60%, at least 70%, at least 80%, at least 90%, at least 95%, at least 99% or greater.

In various examples, the disclosure provides methods to determine haplotype phasing comprising a step of identifying one or more sites of heterozygosity in the plurality of read pairs, wherein phasing data for allelic variants may be determined by identifying read pairs that comprise a pair of heterozygous sites. In various cases, the disclosure provides methods for high-throughput bacterial genome assembly, comprising a step of generating a plurality of read pairs by probing the physical layout of a plurality of microbial chromosomes using a modified Hi-C based method, comprising the modified steps of: collecting microbes from an environment; adding a fixative agent, such as formaldehyde, so as to form cross-links within each microbial cell, and wherein read pairs mapping to different contigs indicate which contigs are from the same species. In some examples, the disclosed provides methods for generating labeled polynucleotides from a plurality of DNA molecules. Methods, compositions, and kits for generating read pairs, labeling polynucleotides, assembling genomes, and determining phasing information disclosed herein, such as, but not limited to those found in Patent Publication Number WO2014/121091 A1, and PCT Patent Application Number PCT/US2015/043327, which published as International Publication Number WO2016/019360, both of which are hereby incorporated by reference in their entirety.

In various examples, nucleic acid obtained from biological samples are fragmented after isolation to produce suitable fragments for analysis. Template nucleic acids are fragmented or sheared to desired length in some cases, using a variety of mechanical, chemical and/or enzymatic methods. For example, DNA is randomly sheared via sonication, e.g. Covaris method, brief exposure to a DNase, or using a mixture of one or more restriction enzymes, or a transposase or nicking enzyme. In further examples, RNA is fragmented by brief exposure to an RNase, heat plus magnesium, or by shearing. The RNA in some cases is converted to cDNA. If fragmentation is employed, the RNA is often converted to cDNA before or after fragmentation. In some examples, nucleic acid from a biological sample is fragmented by sonication. In other cases, nucleic acid is fragmented by a hydroshear instrument. Generally, individual nucleic acid template molecules are from about 2 kb to about 1 Mb. In various instances, nucleic acids may be about 6 kb to about 10 kb fragments. Nucleic acid molecules may be single-stranded, double-stranded, or double-stranded with single-stranded regions (for example, stem- and loop-structures).

Disclosed herein are methods wherein cross-linked DNA complexes prepared from nucleic acids isolated from recalcitrant or fixed biological samples are subjected to a size selection step. Size selection of the nucleic acids is performed, for example, to cross-linked DNA complexes below or above a certain size. Size selection is affected by the frequency of cross-links and/or by the fragmentation method, for example, by choosing a frequent or rare cutter restriction enzyme. At times, a composition is prepared comprising cross-linking a DNA complex in the range of about 1 kb to 5 Mb, about 5 kb to 5 Mb, about 5 kb to 2 Mb, about 10 kb to 2 Mb, about 10 kb to 1 Mb, about 20 kb to 1 Mb about 20 kb to 500 kb, about 50 kb to 500 kb, about 50 kb to 200 kb, about 60 kb to 200 kb, about 60 kb to 150 kb, about 80 kb to 150 kb, about 80 kb to 120 kb, or about 100 kb to 120 kb, or any range bounded by any of these values (e.g. about 150 kb to 1 Mb).

In some methods disclosed herein, sample polynucleotides are fragmented into a population of fragmented DNA molecules of one or more specific size range (s). In various examples, fragments are generated from at least about 1, about 2, about 5, about 10, about 20, about 50, about 100, about 200, about 500, about 1000, about 2000, about 5000, about 10,000, about 20,000, about 50,000, about 100,000, about 200,000, about 500,000, about 1,000,000, about 2,000,000, about 5,000,000, about 10,000,000, or more genome-equivalents of starting DNA. Fragmentation is accomplished by methods known in the art, including chemical, enzymatic, and mechanical fragmentation. In some cases, the fragments have an average length from about 10 to about 10,000, about 20,000, about 30,000, about 40,000, about 50,000, about 60,000, about 70,000, about 80,000, about 90,000, about 100,000, about 150,000, about 200,000, about 300,000, about 400,000, about 500,000, about 600,000, about 700,000, about 800,000, about 900, 000, about 1,000,000, about 2,000,000, about 5,000,000, about 10,000,000, or more nucleotides. Sometimes the fragments have an average length from about 1 kb to about 10 Mb. Additionally or alternatively the fragments have an average length from about 1 kb to 5 Mb, about 5 kb to 5 Mb, about 5 kb to 2 Mb, about 10 kb to 2 Mb, about 10 kb to 1 Mb, about 20 kb to 1 Mb about 20 kb to 500 kb, about 50 kb to 500 kb, about 50 kb to 200 kb, about 60 kb to 200 kb, about 60 kb to 150 kb, about 80 kb to 150 kb, about 80 kb to 120 kb, or about 100 kb to 120 kb, or any range bounded by any of these values (e.g. about 60 to 120 kb). In some cases, the fragments have an average length less than about 10 Mb, less than about 5 Mb, less than about 1 Mb, less than about 500 kb, less than about 200 kb, less than about 100 kb, or less than about 50 kb. The fragments may have an average length more than about 5 kb, more than about 10 kb, more than about 50 kb, more than about 100 kb, more than about 200 kb, more than about 500 kb, more than about 1 Mb, more than about 5 Mb, or more than about 10 Mb. In many cases, fragmentation is accomplished mechanically comprising subjection sample DNA molecules to acoustic sonication. Alternatively, the fragmentation comprises treating the sample DNA molecules with one or more enzymes under conditions suitable for the one or more enzymes to generate double-stranded nucleic acid breaks. Examples of enzymes useful in the generation of DNA fragments include sequence specific and non-sequence specific nucleases. Non-limiting examples of nucleases include DNase I, Fragmentase, restriction endonucleases, variants thereof, and combinations thereof. For example, digestion with DNase I induces random double-stranded breaks in DNA in the absence of Mg++ and in the presence of Mn++. Additionally or alternatively, fragmentation comprises treating the sample DNA molecules with one or more restriction endonucleases. In some cases, fragmentation produces fragments having 5' overhangs, 3' overhangs, blunt ends, or a combination thereof. In other cases, such as when fragmentation comprises the use of one or more restriction endonucleases, cleavage of sample DNA molecules leaves overhangs having a predictable sequence. In some cases, the method includes the step of size selecting the fragments via standard methods such as column purification or isolation from an agarose gel.

Often, the 5' and/or 3' end nucleotide sequences of fragmented DNA are not modified prior to ligation. For example, fragmentation by a restriction endonuclease is used to leave a predictable overhang, followed by ligation with a nucleic acid end comprising an overhang complementary to the predictable overhang on a DNA fragment. In other examples, cleavage by an enzyme that leaves a predictable blunt end is followed by ligation of blunt-ended DNA fragments to nucleic acids, such as adapters, oligonucleotides, or polynucleotides, comprising a blunt end. In some cases, the fragmented DNA molecules are blunt-end polished (or "end repaired") to produce DNA fragments having blunt ends, prior to being joined to adapters. The blunt-end polishing step is accomplished, for example, by incubation with a suitable enzyme, such as a DNA polymerase that has both 3' to 5' exonuclease activity and 5' to 3' polymerase activity, for example T4 polymerase. Often, end repair is followed by an addition of 1, 2, 3, 4, 5, 6, 7, 8, 9, 10, 11, 12, 13, 14, 15, 16, 17, 18, 19, 20 or more nucleotides, such as one or more adenine, one or more thymine, one or more guanine, or one or more cytosine, to produce an overhang. For example, the end pair is followed by an addition of 1, 2, 3, 4, 5, or 6 nucleotides. In some cases, DNA fragments having an overhang is joined to one or more nucleic acids, such as oligonucleotides, adapter oligonucleotides, punctuation oligonucleotides, or polynucleotides, having a complementary overhang, such as in a ligation reaction. For example, a single adenine is added to the 3' ends of end repaired DNA fragments using a template independent polymerase, followed by ligation to one or more adapters each having a thymine at a 3' end. In some embodiments, nucleic acids, such as oligonucleotides or polynucleotides are joined to blunt end double-stranded DNA molecules which have been modified by extension of the 3' end with one or more nucleotides followed by 5' phosphorylation. In some cases, extension of the 3' end is performed with a polymerase such as, Klenow polymerase or any of the suitable polymerases provided herein, or by use of a terminal deoxynucleotide transferase, in the presence of one or more dNTPs in a suitable buffer that can contain magnesium. In some examples, target polynucleotides having blunt ends are joined to one or more adapters comprising a blunt end. Phosphorylation of 5' ends of DNA fragment molecules is performed for example with T4 polynucleotide kinase in a suitable buffer containing ATP and magnesium. The fragmented DNA molecules are optionally treated to dephosphorylate 5' ends or 3' ends, for example, by using enzymes known in the art, such as phosphatases.

The terms "connecting", "joining" and "ligation" as used herein, with respect to two polynucleotides, such as an adapter oligonucleotide and a target polynucleotide, refers to the covalent attachment of two separate DNA segments to produce a single larger polynucleotide with a contiguous backbone. Methods for joining two DNA segments are known in the art, and include without limitation, enzymatic and non-enzymatic (e.g. chemical) methods. Examples of ligation reactions that are non-enzymatic include the non-enzymatic ligation techniques described in U.S. Pat. No. 5,780,613 issued Jul. 14, 1998, and U.S. Pat. No. 5,476,930 issued Dec. 19, 1995, which are herein incorporated by reference in their entirety. In some examples, an adapter oligonucleotide is joined to a target polynucleotide by a ligase, for example a DNA ligase or RNA ligase. Multiple ligases, each having characterized reaction conditions, are known in the art, and include, without limitation $NAD^+$-dependent ligases including tRNA ligase, Taq DNA ligase, *Thermus filiformis* DNA ligase, *Escherichia coli* DNA ligase, Tth DNA ligase, *Thermus scotoductus* DNA ligase (I and II), thermostable ligase, Ampligase thermostable DNA ligase, VanC-type ligase, 9° N DNA Ligase, Tsp DNA ligase, and novel ligases discovered by bioprospecting; ATP-dependent ligases including T4 RNA ligase, T4 DNA ligase, T3 DNA ligase, T7 DNA ligase, Pfu DNA ligase, DNA ligase 1, DNA ligase III, DNA ligase IV, and novel ligases discovered by bioprospecting; and wild-type, mutant isoforms, and genetically engineered variants thereof.

Alternatively, "ligation" is achieved by synthesizing a new molecule that comprises the segments to be attached to one another attached into a single molecule.

In some methods disclosed herein, ligation is between DNA segments having hybridizable sequences, such as complementary overhangs. Alternatively, ligation is between two blunt ends. Generally, a 5' phosphate is utilized in a ligation reaction. In these cases, the 5' phosphate is provided by the target polynucleotide, the adapter oligonucleotide, or both. 5' phosphates can be added to or removed from DNA segments to be joined, as needed. Methods for the addition or removal of 5' phosphates are known in the art and include without limitation enzymatic and chemical processes. Enzymes useful in the addition and/or removal of 5' phosphates include kinases, phosphatases, and polymerases. In some examples, both of the two ends joined in a ligation reaction (e.g. an adapter end and a target polynucleotide end) provide a 5' phosphate, such that two covalent linkages are made in joining the two ends. In other examples, only one of the two ends joined in a ligation reaction (e.g. only one of an adapter end and a target polynucleotide end) provides a 5' phosphate, such that only one covalent linkage is made in joining the two ends.

An adaptor oligonucleotide is joined to only one strand at one or both ends of a target polynucleotide. Alternatively, both strands at one or both ends of a target polynucleotide are joined to an adapter oligonucleotide. In some cases, 3' phosphates are removed prior to ligation. Additionally or alternatively, an adapter oligonucleotide is added to both ends of a target polynucleotide, wherein one or both strands at each end are joined to one or more adapter oligonucleotides. When both strands at both ends are joined to an adapter oligonucleotide, joining is followed in some examples by a cleavage reaction that leaves a 5' overhang that can serve as a template for the extension of the corresponding 3' end, which 3' end may or may not include one or more nucleotides derived from the adapter oligonucleotide. Sometimes, a target polynucleotide is joined to a first adapter oligonucleotide on one end and a second adapter oligonucleotide on the other end. Alternatively, two ends of a target polynucleotide are joined to the opposite ends of a single adapter oligonucleotide. In some cases, the target polynucleotide and the adapter oligonucleotide to which it is joined comprise blunt ends. In many examples, separate ligation reactions are carried out for each sample, using a different first adapter oligonucleotide comprising at least one barcode sequence for each sample, such that no barcode sequence is joined to the target polynucleotides of more than one sample. A DNA segment or a target polynucleotide that has an adapter oligonucleotide joined to it is considered "tagged" by the joined adapter.

The ligation reaction is performed at a DNA segment or target polynucleotide concentration of about 0.1 ng/µl, about 0.2 ng/µl, about 0.3 ng/µl, about 0.4 ng/µl, about 0.5 ng/µl, about 0.6 ng/µl, about 0.7 ng/µl, about 0.8 ng/µl, about 0.9 ng/µl, about 1.0 ng/µl, about 1.2 ng/µl, about 1.4 ng/µl, about 1.6 ng/µl, about 1.8 ng/µl, about 2.0 ng/µl, about 2.5 ng/µl, about 3.0 ng/µl, about 3.5 ng/µl, about 4.0 ng/µl, about 4.5 ng/µl, about 5.0 ng/µl, about 6.0 ng/µl, about 7.0 ng/µl, about 8.0 ng/µl, about 9.0 ng/µl, about 10 ng/µl, about 15 ng/µl, about 20 ng/µl, about 30 ng/µl, about 40 ng/µl, about 50 ng/µl, about 60 ng/µl, about 70 ng/µl, about 80 ng/µl, about 90 ng/µl, about 100 ng/µl, about 150 ng/µl, about 200 ng/µl, about 300 ng/µl, about 400 ng/µl, about 500 ng/µl, about 600 ng/µl, about 800 ng/µl, about 1000 ng/µl, or a higher concentration. For example, the ligation is performed at a DNA segment or target polynucleotide concentration of about 100 ng/µl, about 150 ng/µl, about 200 ng/µl, about 300 ng/µl, about 400 ng/µl, or about 500 ng/µl.

In some cases, the ligation reaction is performed at a DNA segment or target polynucleotide concentration of about 0.1 to 1000 ng/µl, about 1 to 1000 ng/µl, about 1 to 800 ng/µl, about 10 to 800 ng/µl, about 10 to 600 ng/µl, about 100 to 600 ng/µl, or about 100 to 500 ng/µl.

In many cases, the ligation reaction is performed for more than about 5 minutes, about 10 minutes, about 20 minutes, about 30 minutes, about 40 minutes, about 50 minutes, about 60 minutes, about 90 minutes, about 2 hours, about 3 hours, about 4 hours, about 5 hours, about 6 hours, about 8 hours, about 10 hours, about 12 hours, about 18 hours, about 24 hours, about 36 hours, about 48 hours, or about 96 hours. In other cases, the ligation reaction can be performed for less than about 5 minutes, about 10 minutes, about 20 minutes, about 30 minutes, about 40 minutes, about 50 minutes, about 60 minutes, about 90 minutes, about 2 hours, about 3 hours, about 4 hours, about 5 hours, about 6 hours, about 8 hours, about 10 hours, about 12 hours, about 18 hours, about 24 hours, about 36 hours, about 48 hours, about 96 hours, or a greater length of time. For example, the ligation reaction is performed for about 30 minutes to about 90 minutes. In some instances, joining of an adapter to a target polynucleotide produces a joined product polynucleotide having a 3' overhang comprising a nucleotide sequence derived from the adapter.

In some examples, after joining at least one adapter oligonucleotide to a target polynucleotide, the 3' end of one or more target polynucleotides is extended using the one or more joined adapter oligonucleotides as template. For example, an adapter comprising two hybridized oligonucleotides that is joined to only the 5' end of a target polynucleotide allows for the extension of the unjoined 3' end of the target using the joined strand of the adapter as template, concurrently with or following displacement of the unjoined strand. Both strands of an adapter comprising two hybridized oligonucleotides are joined to a target polynucleotide such that the joined product has a 5' overhang, and the complementary 3' end can be extended using the 5' overhang as template. As a further example, a hairpin adapter oligonucleotide is joined to the 5' end of a target polynucleotide. In some examples, the 3' end of the target polynucleotide that is extended comprises one or more nucleotides from an adapter oligonucleotide. For target polynucleotides to which adapters are joined on both ends, extension is, in some examples, carried out for both 3' ends of a double-stranded target polynucleotide having 5' overhangs. This 3' end extension, or "fill-in" reaction, generates a complementary sequence, or "complement," to the adapter oligonucleotide template that is hybridized to the template, thus filling in the 5' overhang to produce a double-stranded sequence region. Where both ends of a double-stranded target polynucleotide have 5' overhangs that are filled in by extension of the complementary strands' 3' ends, the product is completely double-stranded. In many examples, extension is carried out by any suitable polymerase known in the art, such as a DNA polymerase, many of which are commercially available. DNA polymerases can comprise DNA-dependent DNA polymerase activity, RNA-dependent DNA polymerase activity, or DNA-dependent and RNA-dependent DNA polymerase activity. DNA polymerases are thermostable or non-thermostable.

Examples of DNA polymerases include, but are not limited to, Taq polymerase, Tth polymerase, Tli polymerase, Pfu polymerase, Pfutubo polymerase, Pyrobest polymerase, Pwo polymerase, KOD polymerase, Bst polymerase, Sac polymerase, Sso polymerase, Poc polymerase, Pab polymerase, Mth polymerase, Pho polymerase, ES4 polymerase, VENT polymerase, DEEPVENT polymerase, EX-Taq polymerase, LA-Taq polymerase, Expand polymerases, Platinum Taq polymerases, Hi-Fi polymerase, Tbr polymerase, Tfl polymerase, Tru polymerase, Tac polymerase, Tne polymerase, Tma polymerase, Tih polymerase, Tfi polymerase, Klenow fragment, and variants, modified products and derivatives thereof 3' end extension can be performed before or after pooling of target polynucleotides from independent samples.

The present disclosure provides methods for generating labeled polynucleotides from nucleic acids isolated from recalcitrant or fixed biological samples, such as a first DNA molecule comprising a first sequence segment and a second sequence segment. In some cases, the present disclosure provides methods for preserving these labeled polynucleotides. For example, the method comprises: a. crosslinking the first sequence segment and the second sequence segment outside of a cell; b. adding the first sequence segment and the second sequence segment to a first resolved locus comprising a plurality of binding probes; and c. generating a first labeled polynucleotide comprising a first label and a first complement sequence, and a second labeled polynucleotide comprising a second label and a second complement sequence.

The present disclosure provides methods for labeling DNA segments. In some cases, the method comprises: a. crosslinking a first DNA molecule to yield a DNA complex; b. severing the DNA complex to form a plurality of sequence segments comprising a first sequence segment and a second sequence segment, wherein the first sequence segment comprises a first segment end and the second sequence segment comprises a second segment end; and c. attaching a first label to the first segment end and a second label to the second segment end.

In some examples, the first DNA molecule isolated from a recalcitrant or fixed biological sample is severed by any of a number of known methods in the art, including but not limited to the chemical, enzymatic, and mechanical fragmentation methods disclosed in the present application. For example, the first DNA molecule is severed using a restriction enzyme or nonspecific endonuclease. Alternatively, the first DNA molecule is severed by a nonenzymatic approach such as shearing, sonication or ultraviolet irradiation. Alternately, in the majority of cases herein, nucleoprotein complexes are isolated substantially in tact but partially degraded, such that double-strand breaks are already present pursuant to preservation or extraction, such that additional cleavage is accessory rather than required.

The first segment end and the second segment end often comprise blunt ends. Other times, the first segment end and the second segment end comprise overhang sequences. In some cases, the overhang sequences are filled in to generate blunt ends (e.g. using a DNA polymerase). In some of these cases, the overhangs are filled in by modified nucleotides, such as sulfated or biotinylated nucleotides. In other cases, the overhang sequences are cut with an exonuclease to generate blunt ends.

In some cases, the first DNA molecule isolated from a recalcitrant or fixed biological sample is contacted to a cross-linking agent within a cell. Alternatively, the first DNA molecule is part of chromatin obtained from whole cell or nuclear extracts. In preferred examples, the first DNA molecule contacted to a cross-linking agent outside of a cell. For example, the first DNA molecule is isolated and contacted to a cross-linking agent in vitro. The cross-linking is performed using photo-irradiation methods (e.g. UV irradiation) or chemical agents (e.g. formaldehyde) as non-limiting examples.

In some examples, the first DNA molecule isolated from a recalcitrant or fixed biological sample is contacted to a plurality of association molecules prior to cross-linking. In many cases, the association molecules comprise amino acids. In some of these cases, the association molecules comprise peptides, proteins or, amino acids. In certain examples, the association molecules comprise peptides or proteins such as DNA binding proteins. Exemplary DNA binding proteins include native chromatin constituents such as histone, for example Histones 2A, 2B, 3A, 3B, 4A, or 4B. In some examples, the binding proteins comprise transcription factors. Non-protein organic molecules are also compatible with the disclosure herein, such as protamine, spermine, spermidine or other positively charged molecules. In further cases, the association molecules are from a different source than the first DNA molecule. In some cases, the first DNA molecule is from a first human subject, whereas the association molecules are from a second human subject. In other examples, the first DNA molecule is from a mammal (e.g. human), whereas the association molecules are from another eukaryotic organism. In further examples, the first DNA molecule is from a eubacterium or an archaea organism, whereas the association molecules are from a eukaryotic organism.

Additionally or alternatively, the association molecules comprise nanoparticles, such as nanoparticles having a positively charged surface. A number of nanoparticle compositions are compatible with the disclosure herein. In some cases, the nanoparticle is a platinum-based nanoparticle. In certain cases, the platinum-based nanoparticle is selected from the group consisting of cisplatin, oxaliplatin, and transplatin. In other examples, the nanoparticle is a DNA intercalator, or any derivatives thereof. In further examples, the nanoparticle is a bisintercalator, or any derivatives thereof. In further cases, the nanoparticle is a bisintercalator, or any derivatives thereof. In some cases, the DNA intercalator is a bis-intercalator. In further cases, the bis-intercalator is bisacridine. In some embodiments the nanoparticles comprise silica, such as silica coated with a positive coating so as to bind negatively charged nucleic acids. In further examples, the nanoparticles are magnetic or paramagnetic, which may facilitate the isolation of the cross-linked sequence segments. In some cases, the nanoparticles are coated with amine groups, and/or amine-containing molecules. In certain cases, the DNA and the nanoparticles aggregate and condense. In further cases, the nanoparticle-bound DNA is induced to aggregate in a fashion that mimics the ordered arrays of biological nucleosomes (e.g. chromatin). In some cases, the association molecules are from a different source than the first DNA molecule. In some cases, the first DNA molecule is obtained from a first human subject, whereas the association molecules are from a second human subject. In other examples, the first DNA molecule is from a mammal (e.g. human), whereas the association molecules are from another eukaryotic organism. In further examples, the first DNA molecule is obtained from a plant cell, another non-mammalian eukaryote, a eubacterium or an archaeal cell, whereas the association molecules are from a eukaryotic organism.

In some examples, nanoparticles are used to generate read pairs from a single DNA molecule for assembling a contig, scaffold or a genome as described in PCT Patent Application Number PCT/US2015/043327, which published as International Publication No. WO2016/019360, and which is hereby incorporated by reference in its entirety. In general, single DNA molecule is cross-contacted to a plurality of nanoparticles in vitro or in vivo, and the complex is then cross-linked. A plurality of contigs and/or scaffolds of the single DNA molecule are assembled using the read pairs, wherein at least 1% of the read pairs spans a distance of at least 10 kb, at least 20 kb, at least 30 kb, at least 50 kb, or more on the single DNA molecule, and wherein the haplotype phasing is performed at greater than 70% accuracy. In certain cases, at least 10% of the read pairs span a distance of at least 50 kb on the single DNA molecule. In further cases, at least 1% of the read pairs span a distance of at least 100 kb on the single DNA molecule. In various cases, the haplotype phasing is performed at greater than 90% accuracy. In some cases, the crosslinking is reversible. In certain cases, the crosslinking is reversed using heat. In other cases, the crosslinking is reversed using a chemical agent such as thiourea.

A number of factors are varied to influence the extent and form of condensation including the concentration of nanoparticles in solution, the ratio of nanoparticles to DNA, and the size of nanoparticles used. In some cases, the nanoparticles are added to the DNA at a concentration greater than about 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 15 ng/ml, 20 ng/ml, 25 ng/ml, 30 ng/ml, 40 ng/ml, 50 ng/ml, 60 ng/ml, 70 ng/ml, 80 ng/ml, 90 ng/ml, 100 ng/ml, 120 ng/ml, 140 ng/ml, 160 ng/ml, 180 ng/ml, 200 ng/ml, 250 ng/ml, 300 ng/ml, 400 ng/ml, 500 ng/ml, 600 ng/ml, 700 ng/ml, 800 ng/ml, 900 ng/ml, 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 15 µg/ml, 20 µg/ml, 25 µg/ml, 30 µg/ml, 40 µg/ml, 50 µg/ml, 60 µg/ml, 70 µg/ml, 80 µg/ml, 90 µg/ml, 100 µg/ml, 120 µg/ml, 140 µg/ml, 160 µg/ml, 180 µg/ml, 200 µg/ml, 250 µg/ml, 300 µg/ml, 400 µg/ml, 500 µg/ml, 600 µg/ml, 700 µg/ml, 800 µg/ml, 900 µg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, 50 mg/ml, 60 mg/ml, 70 mg/ml, 80 mg/ml, 90 mg/ml, 100 mg/ml, or a greater concentration. In some cases, the nanoparticles are added to the DNA at a concentration less than about 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 15 ng/ml, 20 ng/ml, 25 ng/ml, 30 ng/ml, 40 ng/ml, 50 ng/ml, 60 ng/ml, 70 ng/ml, 80 ng/ml, 90 ng/ml, 100 ng/ml, 120 ng/ml, 140 ng/ml, 160 ng/ml, 180 ng/ml, 200 ng/ml, 250 ng/ml, 300 ng/ml, 400 ng/ml, 500 ng/ml, 600 ng/ml, 700 ng/ml, 800 ng/ml, 900 ng/ml, 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 15 µg/ml, 20 µg/ml, 25 µg/ml, 30 µg/ml, 40 µg/ml, 50 µg/ml, 60 µg/ml, 70 µg/ml, 80 µg/ml, 90 µg/ml, 100 µg/ml, 120 µg/ml, 140 µg/ml, 160 µg/ml, 180 µg/ml, 200 µg/ml, 250 µg/ml, 300 µg/ml, 400 µg/ml, 500 µg/ml, 600 µg/ml, 700 µg/ml, 800 µg/ml, 900 µg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, 50 mg/ml, 60 mg/ml, 70 mg/ml, 80 mg/ml, 90 mg/ml, 100 mg/ml, or a greater concentration. In some cases, the nanoparticles are added to the DNA at a weight-to-weight (w/w) ratio greater than about 1:10000, 1:5000, 1:2000, 1:1000, 1:500, 1:200, 1:100, 1:50, 1:20, 1:10, 1:5, 1:2, 1:1, 2:1, 5:1, 10:1, 20:1, 50:1, 100:1, 200:1, 500:1, 1000:1, 2000:1, 5000:1, or 10000:1. In some cases, the nanoparticles are added to the DNA at a weight-to-weight (w/w) ratio less than about 1:10000, 1:5000, 1:2000, 1:1000, 1:500, 1:200, 1:100, 1:50, 1:20, 1:10, 1:5, 1:2, 1:1, 2:1, 5:1, 10:1, 20:1, 50:1, 100:1, 200:1, 500:1, 1000:1, 2000:1, 5000:1, or 10000:1. In some cases, the nanoparticles have a diameter greater than about 1 nm 1 nm, 2 nm, 3 nm, 4 nm, 5 nm, 6 nm, 7 nm, 8 nm, 9 nm, 10 nm, 15 nm, 20 nm, 25 nm, 30 nm, 40 nm, 50 nm, 60 nm, 70 nm, 80 nm, 90 nm, 100 nm, 120 nm, 140 nm, 160 nm, 180 nm, 200 nm, 250 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, 10 µm, 15 µm, 20 µm, 25 µm, 30 µm, 40 µm, 50 µm, 60 µm, 70 µm, 80 µm, 90 µm, or 100 µm. In some cases, the nanoparticles have a diameter less than about 1 nm 1 nm, 2 nm, 3 nm, 4 nm, 5 nm, 6 nm, 7 nm, 8 nm, 9 nm, 10 nm, 15 nm, 20 nm, 25 nm, 30 nm, 40 nm, 50 nm, 60 nm, 70 nm, 80 nm, 90 nm, 100 nm, 120 nm, 140 nm, 160 nm, 180 nm, 200 nm, 250 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, 10 µm, 15 µm, 20 µm, 25 µm, 30 µm, 40 µm, 50 µm, 60 µm, 70 µm, 80 µm, 90 µm, or 100 µm.

Furthermore, the nanoparticles are often immobilized on solid substrates (e.g. beads, slides, or tube walls) by applying magnetic fields (in the case of paramagnetic nanoparticles) or by covalent attachment (e.g. by cross-linking to poly-lysine coated substrate). Immobilization of the nanoparticles improves the ligation efficiency thereby increasing the number of desired products (signal) relative to undesired (noise).

However, in a majority of cases herein, nucleoprotein complexes are isolated such that additional complex formation is supplemental or accessory rather than required, due to the preservation of previously existent nucleoprotein complexes in the sample which are partially or substantially preserved pursuant to extraction. Thus, post-extraction assembly is optional in many cases, and is often excluded from methods herein due to the preservation of complexes pursuant to the extraction process, such as an extraction process supplemented using an enzyme or enzyme protocol as disclosed herein or otherwise known in the art.

In various cases, the methods disclosed herein are used to produce read-sets comprising reads that are separated by large distances. The upper limit of this distance may be improved by the ability to collect DNA samples of large size. In some cases, the reads are separated by up to 50 kb, 60 kb, 70 kb, 80 kb, 90 kb, 100 kb, 125 kb, 150 kb, 175 kb, 200 kb, 225 kb, 250 kb, 300 kb, 400 kb, 500 kb, 600 kb, 700 kb, 800 kb, 900 kb, 1 Mb, 1.5 Mb, 2 Mb, 2.5 Mb, 3 Mb, 4 Mb, 5 Mb or more in genomic distance. In some cases, the reads are separated by up to 500 kb in genomic distance. In other cases, the reads are separated by up to 2 Mb in genomic distance. The methods disclosed herein can integrate and build upon standard techniques in molecular biology, and are further well-suited for increases in efficiency, specificity, and genomic coverage. In some cases, the read-sets are generated in less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 60, or 90 days. In some cases, the read-sets are generated in less than about 14 days. In further cases, the read-sets are generated in less about 10 days. In some cases, the methods of the present disclosure provide greater than about 5%, about 10%, about 15%, about 20%, about 30%, about 40%, about 50%, about 60%, about 70%, about 80%, about 90%, about 95%, about 99%, or about 100% of the read pairs with at least about 50%, about 60%, about 70%, about 80%, about 90%, about 95%, about 99%, or about 100% accuracy in correctly ordering and/or orientating the plurality of contigs and/or scaffolds. In some cases, the methods provide about 90 to 100% accuracy in correctly ordering and/or orientating the plurality of contigs and/or scaffolds.

Nanoparticles herein are often cross-linked to the DNA fragment isolated from a recalcitrant or fixed biological sample in an in vitro complex, and wherein the in vitro complex is immobilized on a solid support. In other aspects, the present disclosure provides a composition comprising a DNA fragment, a plurality of nanoparticles, and a DNA-binding molecule, wherein the DNA-binding molecule is bound to a predetermined sequence of the DNA fragment, and wherein the nanoparticles are cross-linked to the DNA fragment. In some cases, the DNA-binding molecule is a nucleic acid that can hybridize to the predetermined sequence. In some cases, the nucleic acid is RNA. In other cases, the nucleic acid is DNA. In further cases, the DNA-binding molecule is a small molecule. In some cases, the DNA-binding molecule is protein histone. In some cases, the nanoparticle is any nanoparticles described herein. In some embodiments, the small molecule binds to the predetermined sequence with a binding affinity less than 100 µM. In further embodiments, small molecule binds to the predetermined sequence with a binding affinity less than 1 µM. In certain cases, the nucleic acid is immobilized to a surface or a solid support.

Methods herein often also comprises adding a barcode, for example ligating a barcoded aggregate to the DNA complex. In some instances, a barcoded aggregate is added to a DNA complex using an integrase. In some cases, the barcoded aggregate comprises a plurality of barcoded polynucleotides and a plurality of aggregate molecules. In further examples, the barcoded polynucleotides are generated using Rolling Circle Amplification (RCA). In some cases, each of the barcoded polynucleotides in the barcoded aggregate comprises an identical barcode. In further cases, the barcoded polynucleotides in the barcoded aggregate are identical. In some cases, the barcoded polynucleotides are ligated to the first sequence segment and the second sequence segment. In further cases, the first sequence segment and the second sequence segment are amplified using the barcoded polynucleotides as templates. In some cases, the barcoded polynucleotides comprise the first and the second label, which can comprise an identical barcode. In some cases, the aggregate molecules comprise amino acids. In further cases, the aggregate molecules comprise peptides or proteins (e.g. histones). In other cases, the aggregate molecules comprise nanoparticles. The nanoparticles can be any nanoparticles as described herein. In some cases, a sequencing adaptor is further linked to the first sequence segment and/or the second sequence segment. In some cases, the sequence information of the first sequence segment and the second sequence segment is obtained by a sequencing method. The sequencing method can be any known sequencing method in the art, including but not limited to the sequencing technologies disclosed in the present application. Using the sequence information, in some cases, the first sequence segment and the second sequence segment are associated to one another. In some cases, the first sequence segment and the second sequence segment comprise a same label and are binned into a read-set. In some cases, the sequence information is also used to assemble a plurality of contigs and/or scaffolds. In certain cases, the sequence information is used to assemble the first DNA molecule. In further cases, the sequence information is used to assemble a genome. In some cases, the genome is assembled by aligning reads to a reference genome, or by de novo assembly. In some cases, methods that produce fragments of genomic DNA up to megabase scale are used with the methods disclosed herein. Long DNA fragments can be generated to confirm the ability of the present methods to generate read pairs spanning the longest fragments offered by those extractions. In some cases, DNA fragments beyond 150 kb in length are extracted and used to generate XLRP libraries.

Sequence tag information herein, in some cases, is used to map sequence reads to a single nucleic acid molecule from which they originated. In some embodiments, this information is independent of distance information within a single nucleic acid molecule. In some cases, the nucleic acid molecule is obtained from a population of incompletely fragmented or sheared genomic DNA, which is sheared such that overlapping nucleic acid fragments are obtained. Upon sequencing the reads which correspond to each individual overlapping nucleic acid molecule, one may assemble larger 'read position contig' information to infer phase or physical linkage information across distances beyond single sheared nucleic acid size.

The intrachromosomal interactions can be used to correlate chromosomal connectivity. Similarly, the nucleic acid fragment mapping data can be used to correlate chromosomal connectivity. Further, the intrachromosomal data can aid genomic assembly. In some cases, the chromatin is reconstructed in vitro. This can be advantageous because chromatin—particularly histones, the major protein component of chromatin—is important for DNA fixation. In some cases, chromatin forms a stable complex with DNA to capture the spatial and sequence information, which is analyzed to aid genomic assembly. Chromatin is highly non-specific in terms of sequence and can be generally assemble uniformly across the genome. In some cases, the genomes of species that do not use chromatin are assembled on a reconstructed chromatin and thereby extend the horizon for the disclosure to all domains of life.

Cross-links are created between genome regions that are in close physical proximity, in some instances. Crosslinking of proteins (e.g. histones) to the DNA molecule (e.g. genomic DNA), within chromatin is accomplished according to a suitable method described in further detail elsewhere herein or otherwise known in the art. In some cases, two or more nucleotide sequences are cross-linked via proteins bound to one or more nucleotide sequences. One approach is to expose the chromatin to ultraviolet irradiation (Gilmour et al., Proc. Nat'l. Acad. Sci. USA 81:4275-4279, 1984). Crosslinking of polynucleotide segments may also be performed utilizing other approaches, such as chemical or physical (e.g. optical) crosslinking. Suitable chemical cross-linking agents include, but are not limited to, formaldehyde and psoralen (Solomon et al., Proc. Natl. Acad. Sci. USA 82:6470-6474, 1985; Solomon et al., Cell 53:937-947, 1988). For example, cross-linking can be performed by adding a solution comprising about 2% formaldehyde to a mixture comprising the DNA molecule and chromatin proteins. Other cases of agents that are used to cross-link DNA include, but are not limited to, UV light, mitomycin C, nitrogen mustard, melphalan, 1,3-butadiene diepoxide, cis diaminedichloroplatinum (II) and cyclophosphamide. In further cases, the cross-linking agent forms cross-links that bridge relatively short distances—such as about 2 Å—thereby selecting intimate interactions that can be reversed.

The DNA molecule isolated from a recalcitrant or fixed biological sample is sometimes immunoprecipitated prior to or after crosslinking. In some cases, the DNA molecule is fragmented into two or more sequence segments. In further cases, sequence segments are contacted with a binding partner, such as an antibody that specifically recognizes and binds to acetylated histones, e.g., H3. Cases of such antibodies include, but are not limited to, Anti Acetylated Histone H3, available from Upstate Biotechnology, Lake Placid, N.Y. In some cases, the polynucleotides from the immunoprecipitate are subsequently collected from the immunoprecipitate. In some cases, prior to fragmenting the polynucleotide, the acetylated histones are cross-linked to adjacent polynucleotide sequences. In further cases, the mixture is then treated to fractionate polynucleotides in the mixture. Fractionation techniques are known in the art and include, for example, shearing techniques to generate smaller genomic fragments. Fragmentation can be accomplished using established methods for fragmenting chromatin, including, for example, sonication, shearing, contacting with enzymes or other chemicals having nonspecific endonuclease activity and/or the use of restriction enzymes. In some cases, the restriction enzyme has a restriction recognition site of 1, 2, 3, 4, 5, 6, 7, 8, or more than 8 bases long. Examples of restriction enzymes include, but are not limited to, AatII, Acc65I, AccI, AciI, AclI, AcuI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeGI, BaeI, BamHI, BanI, BanII, BbsI, BbvCI, BbvI, BccI, BceAI, BcgI, BciVI, BclI, BfaI, BfuAI, BfuCI, BglI, BglII, BlpI, BmgBI, BmrI, BmtI, BpmI, Bpu10I, BpuEI, BsaAI, BsaBI, BsaHI, BsaI, BsaJI, BsaWI, BsaXI, BscRI, BscYI, BsgI, BsiEI, BsiHKAI, BsiWI, BslI, BsmAI, BsmbI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, Cac8I, ClaI, CspCI, CviAII, CviKI-1, CviQI, DdcI, DpnI, DpnII, DraI, DraIII, DrdI, EacI, EagI, EarI, EciI, Eco53kI, EcoNI, EcoO109I, EcoP15I, EcoRI, EcoRV, FatI, FauI, Fnu4HI, FokI, FseI, FspI, HaeII, HaeIII, HgaI, HhaI, HincII, HindIII, HinfI, HinPII, HpaI, HpaII, HphI, Hpy166II, Hpy188I, Hpy188III, Hpy99I, HpyAV, HpyCH4III, HpyCH4IV, HpyCH4V, KasI, KpnI, MboI, MboII, MfeI, MluI, MlyI, MmeI, MnlI, MscI, MseI, MslI, MspAlI, MspI, MwoI, NaeI, NarI, Nb.BbvCI, Nb.BsmI, Nb.BsrDI, Nb.BtsI, NciI, NcoI, NdeI, NgoMIV, NheI, NlaIII, NlaIV, NmeAIII, NotI, NruI, NsiI, NspI, Nt.AlwI, Nt.BbvCI, Nt.BsmAI, Nt.BspQI, Nt.BstNBI, Nt.CviPII, Pacd, PaeR7I, PciI, PflFI, PflMI, PhoI, PleI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, Sbfl, ScaI, ScrFI, SexAI, SfaNI, SfcI, SfiI, SfoI, SgrAI, SmaI, SmlI, SnaBI, SpeI, SphI, SspI, StuI, StyD4I, StyI, SwaI, T, TaquI, TfiI, TliI, TseI, Tsp45I, Tsp509I, TspMI, TspRI, Tth111I, XbaI, XcmI, XhoI, XmaI, XmnI, and ZraI. The resulting sequence segments can vary in size. The resulting sequence segments may also comprise a single-stranded overhand at the 5' or 3' end.

Sonication techniques are sometimes used to obtain sequence segments of about 100 to 5000 nucleotides. Alternatively, sequence segments of about 100 to 1000, about 150 to 1000, about 150 to 500, about 200 to 500, or about 200 to 400 nucleotides are obtained. The sample can be prepared for sequencing the cross-linked sequence segments. In some cases, sequence segments that were intramolecularly cross-linked are labeled with a common label. The common label can then be detected and analyzed to determine sequence segments that were intramolecularly cross-linked. The common label can, for example, be a barcode, which can optionally be detected by sequencing methods. In some cases, the reads of sequence segments labeled with a common label are binned into a read-set.

Sequence information is obtained from the nucleic acid isolated from a recalcitrant or fixed biological sample using any suitable sequencing technique described in further detail elsewhere herein or otherwise known in the art, such as a high throughput sequencing method. In some cases, the sequence segments are subject to a sequencing technique to generate sequence reads, which are used to identify sequence segments that are cross-linked and/or are labeled with a common label. In further cases, two or more sequence segments are represented in the obtained sequence information, associating haplotyping information over a linear distance separating the two sequence segments along the polynucleotide.

The methods disclosed herein are often used in combination with an existing sequencing technology. In further cases, the methods disclosed herein are used with technologies and approaches derived from any existing sequencing technology. Cases of sequencing technologies that can be used with the methods disclosed herein include, but are not limited to, the Illumina® sequencing-by-synthesis platform (Illumina®, San Diego, Calif.), the SOLiD™ system (Applied Biosystems Corp.), pyrosequencing (e.g., 454 Life Sciences, subsidiary of Roche Diagnostics), a sequencing technique based on semiconductor detectors (e.g., the Ion Torrent® platform), nanopore sequencing (e.g., the Oxford Nanopore™ sequencing platform), DNA nanoball sequencing methods (e.g. Complete Genomics), long-read sequencing such as Pacific Biosciences (PacBio), sequencing by hybridization and any other suitable technology, or any technology that may be derived from any of the above technologies.

In addition to species-specific and cell type-specific chromatin interactions, two canonical interaction patterns have been observed in most chromatin capture techniques. One pattern, distance-dependent decay (DDD), is a general trend of decay in interaction frequency as a function of genomic distance. The second pattern, cis-trans ratio (CTR), is a significantly higher interaction frequency between loci located on the same chromosome, even when separated by tens of megabases of sequence, versus loci on different chromosomes. These patterns may reflect general polymer dynamics, where proximal loci have a higher probability of randomly interacting, as well as specific nuclear organization features such as the formation of chromosome territories, the phenomenon of interphase chromosomes tending to occupy distinct volumes in the nucleus with little mixing. Although the exact details of these two patterns may vary between species, cell types and cellular conditions, they are ubiquitous and prominent. These patterns are so strong and consistent that they are used to assess experiment quality and are usually normalized out of the data in order to reveal detailed interactions. However, in the methods disclosed herein, genome assembly can take advantage of the three-dimensional structure of genomes. In certain cases, the ubiquity, strength, and consistency of these features are used as powerful tools for estimating the genomic position of contigs and/or scaffolds.

Examination of the physical distance between intra-chromosomal read pairs sometimes indicates several useful features of the data with respect to genome assembly. First, shorter range interactions are more common than longer-range interactions. That is, each read of a read-pair is more likely to be mated with a region close by in the actual genome than it is to be with a region that is far away. Second, there is a long tail of intermediate and long-range interactions. That is, read pairs carry information about intra-chromosomal arrangement at kilobase (kb) or even megabase (Mb) distances. In some cases, read pairs provide sequence information over a span of greater than about 10 kb, about 50 kb, about 100 kb, about 200 kb, about 500 kb, about 1 Mb, about 2 Mb, about 5 Mb, about 10 Mb, or about 100 Mb. These features of the data simply indicate that regions of the genome that are nearby on the same chromosome are more likely to be in close physical proximity—an expected result because they are chemically linked to one another through the DNA backbone. It was speculated that genome-wide chromatin interaction data sets, such as those generated by chromatin capture methods, would provide long-range information about the grouping and linear organization of sequences along entire chromosomes.

The present disclosure provides a method to determine haplotype phasing. In some cases, the method comprises a step of identifying one or more sites of heterozygosity in the plurality of read pairs, wherein phasing data for allelic variants are determined by identifying read pairs that comprise a pair of heterozygous sites.

In diploid genomes, it is often important to know which allelic variants are physically linked on the same chromosome rather than mapping to the homologous position on a chromosome pair. Mapping an allele or other sequence to a specific physical chromosome of a diploid chromosome pair is known as the haplotype phasing. Short reads from high-throughput sequence data rarely allow one to directly observe which allelic variants are linked, particularly, as is most often the case, if the allelic variants are separated by a greater distance than the longest single read. Computational inference of haplotype phasing can be unreliable at long distances. Methods disclosed herein allow for preserving or preparing nucleic acids for determining which allelic variants are physically linked using allelic variants on read pairs.

The methods and compositions of the disclosure enable the haplotype phasing of diploid or polyploid genomes with regard to a plurality of allelic variants. Methods described herein thus provide for the determination of linked allelic variants based on variant information from labeled sequence segments and/or assembled contigs and/or scaffolds using the same. Cases of allelic variants include, but are not limited to, those that are known from the 1000 genomes, UK10K, HapMap and other projects for discovering genetic variation among humans. In some cases, disease association to a specific gene are revealed more easily by having haplotype phasing data as demonstrated, for example, by the finding of unlinked, inactivating mutations in both copies SH3TC2 leading to Charcot-Marie-Tooth neuropathy (Lupski J R, Reid J G, Gonzaga-Jauregui C, et al. *N. Engl. J. Med.* 362:1181-91, 2010) and unlinked, inactivating mutations in both copies of ABCG5 leading to hypercholesterolemia 9 (Rios J, Stein E, Shendure J, et al. *Hum. Mol. Genet.* 19:4313-18, 2010).

Humans are heterozygous at an average of 1 site in 1,000. In some cases, a single lane of data using high throughput sequencing methods generates at least about 150,000,000 reads. In further cases, individual reads are about 100 base pairs long. If we assume input DNA fragments average 150 kb in size and we get 100 paired-end reads per fragment, then we expect to observe 30 heterozygous sites per set, i.e., per 100 read pairs. Every read-pair containing a heterozygous site within a set is in phase (i.e., molecularly linked) with respect to all other read pairs within the same set. This property enables greater power for phasing with sets as opposed to singular pairs of reads in some cases. With approximately 3 billion bases in the human genome, and one in one-thousand being heterozygous, there are approximately 3 million heterozygous sites in an average human genome. With about 45,000,000 read pairs that contain heterozygous sites, the average coverage of each heterozygous site to be phased using a single lane of a high throughput sequence method is about (15×), using a typical high throughput sequencing machine. A diploid human genome can therefore be reliably and completely phased with one lane of a high-throughput sequence data relating sequence variants from a sample that is prepared using the methods disclosed herein. In some cases, a lane of data is a set of DNA sequence read data. In further cases, a lane of data is a set of DNA sequence read data from a single run of a high throughput sequencing instrument.

As the human genome, like most diploid genomes, consists of two homologous sets of chromosomes in its nuclear contingent, understanding the true genetic makeup of an individual requires delineation of the maternal and paternal copies or haplotypes of the genetic material. Obtaining a haplotype in an individual is useful in several ways. For example, haplotypes are useful clinically in predicting outcomes for donor-host matching in organ transplantation. Haplotypes are increasingly used to detect disease associations. In genes that show compound heterozygosity, haplotypes provide information as to whether two deleterious variants are located on the same allele (that is, 'in cis', to use genetics terminology) or on two different alleles ('in trans'), greatly affecting the prediction of whether inheritance of these variants is harmful, and impacting conclusions as to whether an individual carries a functional allele and a single nonfunctional allele having two deleterious variant positions, or whether that individual carries two nonfunctional alleles, each with a different defect. Haplotypes from groups of individuals have provided information on population structure of interest to both epidemiologists and anthropologists and informative of the evolutionary history of the human race. In addition, widespread allelic imbalances in gene expression have been reported, and suggest that genetic or epigenetic differences between allele phases may contribute to quantitative differences in expression. An understanding of haplotype structure will delineate the mechanisms of variants that contribute to allelic imbalances.

Some methods disclosed herein often comprise an in vitro technique to fix and capture associations among distant regions of a genome as needed for long-range linkage and phasing following DNA damage in nucleic acid samples isolated from a recalcitrant or fixed biological sample. In some cases, the method comprises constructing and sequencing one or more read-sets to deliver very genomically distant read pairs. In further cases, each read-set comprises two or more reads that are labeled by a common barcode, which may represent two or more sequence segments from a common polynucleotide. In some cases, the interactions primarily arise from the random associations within a single polynucleotide. In some cases, the genomic distance between sequence segments are inferred because sequence segments near to each other in a polynucleotide interact more often and with higher probability, while interactions between distant portions of the molecule are less frequent. Consequently, there is a systematic relationship between the number of pairs connecting two loci and their proximity on the input DNA. In some cases, the methods disclosed herein produce read pairs that span the largest DNA fragments in an extraction. The input DNA for this particular library had a maximum length of 150 kb, which is the longest meaningful read pair observed from the sequencing data. This suggests that the present method can link still more genomically distant loci if provided larger input DNA fragments. By applying improved assembly software tools that are specifically adapted to handle the type of data produced by the present method, a complete genomic assembly may be possible. Methods disclosed herein are used in some embodiments to label sequence segments and/or to preserve labeled sequence segments that span the largest polynucleotide from an extraction.

Methods and compositions are also provided that produce data to achieve extremely high phasing accuracy. In comparison to previous methods, the methods described herein can phase a higher proportion of the variants. In some cases, phasing is achieved while maintaining high levels of accuracy. In further cases, this physical linkage information is extended to longer ranges, for example greater than about 200 kb, about 300 kb, about 400 kb, about 500 kb, about 600 kb, about 700 kb, about 800 kb, about 900 kb, about 1 Mb, about 2 Mb, about 3 Mb, about 4 Mb, about 5 Mb, or about 10 Mb, or longer than about 10 Mb, up to and including the entire length of a chromosome. In some embodiments, more than 90% of the heterozygous SNPs for a human sample is phased at an accuracy greater than 99% using less than about 250 million reads, e.g. by using only 1 lane of Illumina® HiSeq™ data. In other cases, more than about 40%, 50%, 60%, 70%, 80%, 90%, 95% or 99% of the heterozygous SNPs for a human sample is phased at an accuracy greater than about 70%, 80%, 90%, 95%, or 99% using less than about 250 million or about 500 million reads, e.g. by using only 1 or 2 lanes of Illumina® HiSeq™ data. In some cases, more than 95% or 99% of the heterozygous SNPs for a human sample are phased at an accuracy greater than about 95% or 99% using less about 250 million or about 500 million reads. In further cases, additional variants are captured by increasing the read length to about 200 bp, 250 bp, 300 bp, 350 bp, 400 bp, 450 bp, 500 bp, 600 bp, 800 bp, 1000 bp, 1500 bp, 2 kb, 3 kb, 4 kb, 5 kb, 10 kb, 20 kb, 50 kb, or 100 kb.

Some methods herein expand the number of sample sources from which phasing or scaffolding information is obtainable. Many preserved samples, for example, have been recalcitrant to nucleic acid isolation, or have yielded nucleic acids only through protocols that both cleave nucleic acids and remove them from nucleoprotein complexes, thus losing substantial amounts of long-range phase or scaffolding information. Through practice of the methods herein, substantially more long range phase or scaffold information is available from preserved samples.

Accordingly, methods disclosed herein may be applied to intact human genomic DNA samples isolated from a recalcitrant or fixed biological sample but may also be applied to a broad diversity of nucleic acid samples, such as reverse-transcribed RNA samples, circulating free DNA samples, cancer tissue samples, crime scene samples, archaeological samples, nonhuman genomic samples, or environmental samples such as environmental samples comprising genetic information from more than one organism, such as an organism that is not easily cultured under laboratory conditions.

High degrees of accuracy required by cancer genome sequencing are achieved using the methods and systems described herein. Inaccurate reference genomes make base-calling challenges when sequencing cancer genomes. Heterogeneous samples and small starting materials, for example a sample obtained by biopsy introduce additional challenges. Further, detection of large-scale structural variants and/or losses of heterozygosity is often crucial for cancer genome sequencing, as well as the ability to differentiate between somatic variants and errors in base-calling.

The systems and methods described herein may generate accurate long sequences from complex samples containing up to 2, 3, 4, 5, 6, 7, 8, 9, 10, 12, 15, 20 or more than 20 varying genomes. Mixed samples of normal, benign, and/or tumor origin may be analyzed, optionally without the need for a normal control. In some embodiments, samples comprising less than about 1000 ng, about 500 ng, about 200 ng, about 100 ng, about 50 ng, about 20 ng, about 10 ng, or even as little as hundreds of genome equivalents, are utilized to generate accurate long sequences. Systems and methods described herein may allow for detection of large scale structural variants and rearrangements. Phased variant calls may be obtained over long sequences spanning about 1 kb, about 2 kb, about 5 kb, about 10 kb, 20 kb, about 50 kb, about 100 kb, about 200 kb, about 500 kb, about 1 Mb, about 2 Mb, about 5 Mb, about 10 Mb about 20 Mb, about 50 Mb, or about 100 Mb or more nucleotides. For example, a phase variant call may be obtained over long sequences spanning about 1 Mb or about 2 Mb.

Methods disclosed herein are used to assemble a plurality of contigs and/or scaffolds originating from a single DNA molecule. In some cases, the method comprises generating a plurality of read pairs from the single DNA molecule that is cross-linked to a plurality of nanoparticles and assembling the contigs and/or scaffolds using the read pairs. In certain cases, single DNA molecule is cross-linked outside of a cell. In some cases, at least 0.1%0, 0.2%0, 0.3%0, 0.4%, 0.5%0, 0.6%0, 0.7%0, 0.8%0, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% of the read pairs span a distance greater than 1 kb, 2 kb, 3 kb, 4 kb, 5 kb, 6 kb, 7 kb, 8 kb, 9 kb, 10 kb, 15 kb, 20 kb, 30 kb, 40 kb, 50 kb, 60 kb, 70 kb, 80 kb, 90 kb, 100 kb, 150 kb, 200 kb, 250 kb, 300 kb, 400 kb, 500 kb, 600 kb, 700 kb, 800 kb, 900 kb, or 1 Mb on the single DNA molecule. In certain cases, at least 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, or 20% of the read pairs span a distance greater than 5 kb, 6 kb, 7 kb, 8 kb, 9 kb, 10 kb, 15 kb, 20 kb, 30 kb, 40 kb, 50 kb, 60 kb, 70 kb, 80 kb, 90 kb, 100 kb, 150 kb, or 200 kb on the single DNA molecule. In further cases, at least 0.5%, 0.6%, 0.7%, 0.8%, 0.9%, 1%, 2%, 3%, 4%, or 5% of the read pairs span a distance greater than 20 kb, 30 kb, 40 kb, 50 kb, 60 kb, 70 kb, 80 kb, 90 kb, or 100 kb on the single DNA molecule. In particular cases, at least 1% or 5% of the read pairs span a distance greater than 50 kb or 100 kb on the single DNA molecule. In some cases, the read pairs are generated within 1, 2, 3, 4, 5, 6, 7, 8, 9, 10, 11, 12, 13, 14, 15, 16, 17, 18, 19, 20, 30, 40, 50 or 60 days. In certain cases, the read pairs are generated within 3, 4, 5, 6, 7, 8, 9, 10, 11, 12, 13, 14, 15, 16, 17 or 18 days. In further cases, the read-p airs are generated within 7, 8, 9, 10, 11, 12, 13, or 14 days. In particular cases, the read pairs are generated within 7 or 14 days.

Methods disclosed herein are also often used for haplotype phasing. In some cases, the method comprises generating a plurality of read pairs from a single DNA molecule isolated from a recalcitrant or fixed biological sample that is bound to a plurality of nanoparticles and cross-linked, and assembling a plurality of contigs and/or scaffolds of the DNA molecule using the read pairs. In certain cases, single DNA molecule isolated from a recalcitrant or fixed biological sample is subjected to cross-linking outside of a cell. In some cases, at least 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%1, 13%, 14%, 5%, 16%, 17%, 18%, 19%, 20%, 25%, 30%, 35%, 40%, 45%, or 50% of the read pairs span a distance greater than 1 kb, 2 kb, 3 kb, 4 kb, 5 kb, 6 kb, 7 kb, 8 kb, 9 kb, 10 kb, 15 kb, 20 kb, 30 kb, 40 kb, 50 kb, 60 kb, 70 kb, 80 kb, 90 kb, 100 kb, 150 kb, 200 kb, 250 kb, 300 kb, 400 kb, 500 kb, 600 kb, 700 kb, 800 kb, 900 kb, or 1 Mb on the single DNA molecule. In certain cases, at least 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, or 20% of the read pairs span a distance greater than 5 kb, 6 kb, 7 kb, 8 kb, 9 kb, 10 kb, 15 kb, 20 kb, 30 kb, 40 kb, 50 kb, 60 kb, 70 kb, 80 kb, 90 kb, 100 kb, 150 kb, or 200 kb on the single DNA molecule. In further cases, at least 0.5%, 0.6%, 0.7%, 0.8%, 0.9%, 1%, 2%, 3%, 4%, or 5% of the read pairs span a distance greater than 20 kb, 30 kb, 40 kb, 50 kb, 60 kb, 70 kb, 80 kb, 90 kb, or 100 kb on the single DNA molecule. In particular cases, at least 1% or 10% of the read pairs span a distance greater than 30 kb or 50 kb on the single DNA molecule. Often, the haplotype phasing is performed at greater than 70% accuracy. In some embodiments, at least 10% of the read pairs span a distance greater than 50 kb on the single DNA molecule. In other embodiments, wherein at least 1% of the read pairs span a distance greater than 100 kb on the single DNA molecule. In some cases, the haplotype phasing is performed at greater than 50%, 60%, 70%, 75%, 80%, 85%, 90%, 95%, 96%, 97%, 98%, or 99% accuracy. In certain cases, the haplotype phasing is performed at greater than 70%, 75%, 80%, 85%, 90%, or 95% accuracy. In further cases, the haplotype phasing is performed at greater than 70%, or 90% accuracy.

Haplotypes determined using the methods and systems described herein may be assigned to computational resources, for example, computational resources over a network, such as a cloud system. Similarly, in certain cases, contig and/or scaffold information is obtained using computational resources such as cloud system resources. Short variant calls are corrected, if necessary, using relevant information that is stored in the computational resources. In some cases, structural variants are detected based on the combined information from short variant calls and the information stored in the computational resources. In some cases, problematic parts of the genome, such as segmental duplications, regions prone to structural variation, the highly variable and medically relevant MHC region, centromeric and telomeric regions, and other heterochromatic regions including but not limited to those with repeat regions, low sequence accuracy, high variant rates, ALU repeats, segmental duplications, or any other relevant problematic parts known in the art, are assembled or reassembled for increased accuracy.

A sample type may be assigned to the sequence information either locally or in a networked computational resource, such as a cloud. In cases where the source of the information is known, for example, when the source of the information is from a cancer or normal tissue, the source is assigned to the sample as part of a sample type. Other sample type cases generally include, but are not limited to, tissue type, sample collection method, presence of infection, type of infection, processing method, size of the sample, etc. In cases where a complete or partial comparison genome sequence is available, such as a normal genome in comparison to a cancer genome, the differences between the sample data and the comparison genome sequence is determined and optionally output.

Haplotype phasing herein often comprises the steps of associating a first sequence segment and a second sequence segment. In some cases, the methods comprise: a. crosslinking a DNA library prepared from a nucleic acid sample isolated from a recalcitrant or fixed biological sample, said DNA library comprising a first DNA molecule, wherein the first DNA molecule comprises the first sequence segment and the second sequence segment; b. isolating the first sequence segment and the second sequence segment in a first reaction volume; and c. attaching a first label to the first sequence segment and a second label to the second sequence segment. In some cases, the methods comprise: a. crosslinking a DNA library comprising a first DNA molecule, wherein the first DNA molecule comprises the first sequence segment and the second sequence segment; b. isolating the first sequence segment and the second sequence segment in a first reaction volume; c. releasing the first sequence segment and the second sequence segment from the crosslinking; and d. linking the first sequence segment and the second sequence segment.

The methods further may comprise severing the first DNA molecule. Methods for severing the first DNA molecule are described elsewhere in the present application. In some cases, the first DNA molecule is severed into the first sequence segment and the second sequence segment, which may have blunt-ends or overhangs. In some cases, the overhangs are filled in by modified nucleotides, such as sulfated or biotinylated nucleotides. In some cases, adaptor oligonucleotides are hybridized and/or ligated to the blunt-ends or overhangs. The adaptor oligonucleotides can be any known adaptor in the art, including but not limited to those disclosed in the present application.

The first sequence segment and the second sequence segment are often cross-linked to a plurality of association molecules. Examples of association molecules are as described elsewhere in the present application. In some cases, the association molecules comprise amino acids. In further examples, the association molecules comprise peptides or proteins (e.g. histones or packing proteins such as H1 and protamine).

Often, rather than assembling such complexes, a first sequence segment and the second sequence segment are often cross-linked to a plurality of association molecules pursuant to isolating substantially in tact nucleoprotein complexes, such that de novo complexes need not be assembled.

The first reaction volume may comprise a single DNA molecule and not any other DNA molecule. In some cases, the DNA library comprises a plurality of DNA molecules that are isolated in a plurality of reaction volumes. In further cases, the DNA molecules are isolated in the reaction volumes under conditions such that a substantial percentage of the reaction volumes comprise a single DNA molecule or no DNA molecules at all. In some cases, more than about 50%, about 60%, about 70%, about 75%, about 80%, about 85%, about 90%, about 91%, about 92%, about 93%, about 94%, about 95%, about 96%, about 97%, about 98%, about 99%, about 99.9%, or more of the reaction volumes comprise 0 or 1 DNA molecules.

The first label and the second label are identical in certain instances. In other cases, the first label and the second label are different. In some cases, the first label and the second label are polynucleotides. In further examples, the first label and the second label each comprise one or more elements selected from the group consisting of a primer, a barcode, and a restriction site. In some cases, the first label and the second label each comprise a barcode. In further examples, the labels comprise specific sequences indicating the location of the barcode. In certain cases, the first label and the second label are produced from a template in the first reaction volume. In some cases, the first label and the second label are produced by amplification of a linear template (e.g. PCR). In other cases, the first label and the second label are produced by Rolling Circle Amplification (RCA) of a circular template. In further cases, the RCA product is further digested to yield a plurality of labels. In some cases, the labels are digested or modified (e.g. adenylated), such as to generate complementary overhangs for attachment to the sequence segments. In certain cases, the labels are attached to the sequence segments by ligation or by hybridization and extension with a DNA polymerase. In further cases, the labels are attached directly to the sequence segments, or indirectly to adaptor oligonucleotides that are ligated or hybridized to the sequence segments.

The first sequence segment and the second sequence segment are sometimes released from the crosslinking using heat or chemical agents. In certain cases, the crosslinks are reversed. In some cases, the first sequence segment and the second sequence segment are further digested to generate new ends (e.g. with a different restriction enzyme). In further cases, the first sequence segment and the second sequence segment are hybridized and/or linked by a ligase. In some cases, the sequence segments within a single reaction volume link to one another and generate many hybrid molecules. In some cases, the linked sequence segments may be previously distant on the original DNA molecule.

Sequencing adaptors are often further linked to the first sequence segment and/or the second sequence segment. In some cases, the sequence information of the first sequence segment and/or the second sequence segment are obtained by a sequencing method. The sequencing method can be any known sequencing method in the art, including but not limited to the sequencing technologies disclosed in the present application. In some cases, the sequencing method is a microarray analysis (e.g. comparative hybridization) or a high-throughput sequencing technique. Using the sequence information, in some cases, the first sequence segment and the second sequence segment are associated to one another. In some cases, the first sequence segment and the second sequence segment comprise a same barcode and are binned into a read-set. In further examples, the first sequence segment and the second sequence segment are associated based on the first label and the second label. In some cases, the sequence information is also used to assemble a plurality of contigs and/or scaffolds. In certain cases, the sequence information is used to assemble the first DNA molecule. In further cases, the sequence information is used to assemble a genome. In some cases, the genome is assembled by aligning reads to a reference genome, or by de novo assembly.

The labeled or linked sequence segments are often analyzed and/or characterized. In some cases, the labeled or linked sequence segments are isolated (e.g. by phase separation), filtered and/or washed to retain only the sequence segments of interest. In some cases, the size of the DNA molecules in the DNA library are estimated (e.g. by gel electrophoresis or pulsed field gel electrophoresis (PFGE)) and used to calculate an expected range (in base pairs) of the sequence segments.

In the realm of personalized medicine, the XLRS read-sets generated from sequencing nucleic acid samples isolated from a recalcitrant or fixed biological sample via methods disclosed herein represents a meaningful advance toward accurate, low-cost, phased, and rapidly produced personal genomes. Previous methods are insufficient in their ability to phase variants at long distances, thereby preventing the characterization of the phenotypic impact of compound heterozygous genotypes. Additionally, structural variants of substantial interest for genomic diseases are difficult to accurately identify and characterize with previous techniques due to their large size in comparison to the reads and read inserts used to study them. Read-sets spanning tens of kilobases to megabases or longer can help alleviate this difficulty, thereby allowing for highly parallel and personalized analyses of structural variation.

Basic evolutionary and biomedical research can be driven by technological advances in high-throughput sequencing. It is now relatively inexpensive to generate massive quantities of DNA sequence data. However, it is difficult in theory and in practice to produce high-quality, highly contiguous genome sequences with previous technologies. Further, many organisms, including humans, are diploid, wherein each individual has two haploid copies of the genome. At sites of heterozygosity (e.g. where the allele given by the mother differs from the allele given by the father), it is difficult to know which sets of alleles came from which parent (known as haplotype phasing). This information can be critically important for performing a number of evolutionary and biomedical studies such as disease and trait association studies.

The present disclosure provides methods for genome sequence assembly that combine technologies for DNA preparation isolated from a recalcitrant or fixed biological sample with tagged sequence reads for high-throughput discovery of short, intermediate, and long-term connections corresponding to sequence reads from a single physical nucleic acid molecule bound to a complex such as a chromatin complex within a given genome. The disclosure further provides methods using these connections to assist in genome sequence assembly, for haplotype phasing, and/or for metagenomic studies. While the methods presented herein can be used to determine the assembly of a subject's genome, it should also be understood that in certain cases the methods presented herein are used to determine the assembly of portions of the subject's genome such as chromosomes, or the assembly of the subject's chromatin of varying lengths. It should also be understood that, in certain cases, the methods presented herein are used to determine or direct the assembly of non-chromosomal nucleic acid molecules. Indeed, any nucleic acid the sequencing of which is complicated by the presence of repetitive regions separating non-repetitive contigs and/or scaffolds may be facilitated using the methods disclosed herein.

The methods disclosed herein sometimes comprise the step of generating a plurality of contigs and/or scaffolds from sequencing fragments of target DNA isolated from a recalcitrant or fixed biological sample from a subject. In some cases, long stretches of target DNA are fragmented by cutting the DNA with one or more restriction enzymes, incompletely digesting the DNA with one or more nonspecific endonucleases, shearing the DNA, or a combination thereof. The resulting fragments are sequenced using high throughput sequencing methods to obtain a plurality of sequencing reads. Cases of high throughput sequencing methods are described in U. S. Patent Application Number PCT/US2015/043327, which is hereby incorporated in its entirety, or any techniques known in the art.

Alternately or in combination with the above, in some cases, the methods disclosed herein are used with contig and/or scaffold information previously generated. Contig and/or scaffold information for a vast number of genomes, including the human genome, plant genome, bacteria genome, virus genome, and nematode genome. Rather than generating contig and/or scaffold information de novo, or in combination with de novo generated contig and/or scaffold data, the methods disclosed herein may be used to assist in the chromosomal assembly, ordering and orientation of these previously generated contigs and/or scaffolds.

Samples comprising target DNA isolated from a recalcitrant or fixed biological sample are often used to generate contigs and/or scaffolds are obtained from a subject by any number of means, including by taking bodily fluids (e.g., blood, urine, serum, lymph, saliva, anal and vaginal secretions, perspiration, and semen), taking tissue, biopsy, sewage, water, soil, air, or by collecting cells/organisms. The sample obtained may be comprised of a single type of cell/organism, or may be comprised multiple types of cells/organisms. In some cases, the DNA are extracted and prepared from the subject's sample. For example, the samples are treated to lyse a cell comprising the polynucleotide, using known lysis buffers, sonication techniques, electroporation, and the like. In further cases, the target DNA is further purified to remove contaminants, such as proteins, by using alcohol extractions, cesium gradients, and/or column chromatography.

The methods disclosed herein are alternatively used with chromatin isolated from a recalcitrant or fixed biological sample, or with reconstituted chromatin prepared from nucleic acids isolated from a recalcitrant or fixed biological sample. Reconstituted chromatin is differentiated from chromatin formed within a cell/organism over various features. First, for many samples, the collection of naked DNA samples can be achieved by using a variety of noninvasive to invasive methods, such as by collecting bodily fluids, swabbing buccal or rectal areas, taking epithelial samples, etc. Second, reconstituting chromatin substantially prevents the formation of inter-chromosomal and other long-range interactions that generate artifacts for genome assembly and haplotype phasing. In some cases, a sample has less than about 20, 15, 12, 11, 10, 9, 8, 7, 6, 5, 4, 3, 2, 1, 0.5, 0.4, 0.3, 0.2, 0.1% or less inter-chromosomal or intermolecular cross-linking according to the methods and compositions of the disclosure. In some cases, the sample has less than about 5% inter-chromosomal or intermolecular crosslinking. In some cases, the sample has less than about 3% inter-chromosomal or intermolecular crosslinking. In further cases, the sample has less than about 1% inter-chromosomal or intermolecular crosslinking. Third, the frequency of sites that are capable of crosslinking and thus the frequency of intramolecular cross-links within the polynucleotide can be adjusted. For example, the ratio of DNA to histones can be varied, such that the nucleosome density is adjusted to a desired value. In some cases, the nucleosome density is reduced below the physiological level. Accordingly, the distribution of cross-links can be altered to favor longer-range interactions. In some embodiments, sub-samples with varying cross-linking density may be prepared to cover both short- and long-range associations. In some cases, the crosslinking conditions is adjusted such that at least about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 40%, about 45%, about 50%, about 60%, about 70%, about 80%, about 90%, about 95%, or about 100% of the crosslinks occur between DNA segments that are at least about 50 kb, about 60 kb, about 70 kb, about 80 kb, about 90 kb, about 100 kb, about 110 kb, about 120 kb, about 130 kb, about 140 kb, about 150 kb, about 160 kb, about 180 kb, about 200 kb, about 250 kb, about 300 kb, about 350 kb, about 400 kb, about 450 kb, or about 500 kb apart on the sample DNA molecule.

Through recovery of nucleoprotein complexes, such as using recovery methods facilitated through the use of an extracellular or intercellular-acting enzyme such as a collagenase, one recovers nucleoprotein complexes suitable for improving or effecting genome sequence assembly. Such complexes are also in some cases suitable for determining physical proximity information, such as is obtained using techniques known in the art such as Hi-C techniques (reviewed and updated in Belaghzal H, Dekker J, Gibcus J H, "Hi-C 2.0: An optimized Hi-C procedure for high-resolution genome-wide mapping of chromosome conformation." *Methods*. 2017 Jul. 1; 123:56-65. doi: 10.1016/j.ymeth.2017.04.004. Epub 2017 Apr. 18, which is hereby incorporated by reference in its entirety. That is, information is recovered in various cases that facilitates contig, scaffold or even partial or whole chromosome sequence assembly, or that facilitates assessment of physical proximity information such as that determined using Hi-C techniques disclosed herein or known to one of skill in the art.

Methods for Transcriptome Reconstruction

Many eukaryotic genes are transcribed and spliced into messenger RNA. According to some studies, the average human protein-coding gene contains a mean of about 9 exons with a mean size of about 145 nucleotides. The mean intron length is 3365 nucleotide and the 5' and 3' UTR are 770 and 300 nucleotides, respectively. As a result, a typical gene can span about 27 kbp. After pre-mRNA processing, however, the average mRNA exported into the cytosol consists of a 1340 nucleotide coding sequence, 1070 nucleotide untranslated region, and a poly-A tail. In some cases, more than 90% of the pre-mRNA is removed as introns and only about 10% of the pre-mRNA is joined as exonic sequences by pre-mRNA splicing. The population of mRNA within a sample can contain many different variants encoded by the same gene. However, the variations in these sequences can be difficult to identify by current sequencing technologies because they often occur more than one read-length or read-pair apart on the same molecule.

These variants can arise from several different mechanisms, including alternative splicing, mutations, and RNA editing. The sets of all mRNA transcripts present in living cells, termed "transcriptomes," are fundamental to regulating life processes. The proteins translated from alternatively spliced mRNAs may contain differences in their amino acid sequence, and often, in their biological functions. Alternative splicing generates a tremendous amount of proteomic diversity in humans and significantly affects various functions in cellular processes, tissue specificity, developmental states, and disease conditions. Splicing variants have been associated with a variety of disease phenotypes, and numerous human diseases have been linked to changes in levels of alternative spliced isoforms. Thus, knowing which isoform is expressed in a sample is critical for accurate research and analysis. Furthermore, the determination of transcriptome sequence content may be important in addressing diverse processes such as cancer, tissue specificity, autoimmune responses, development, disease causality, treatment selection, and environmental adaptation.

However, transcriptome analysis has proven to be difficult because the abundance of mRNA transcripts can vary widely in cells and change in a context and environmentally sensitive manner. RNA sequence information has been obtained conventionally by targeted sequencing or specific transcripts or by shotgun sequencing of entire transcriptomes.

Targeted sequencing determines the complete sequence of an entire transcript, including splicing information. Targeted sequencing is impractical for large-scale applications because it is prohibitively slow and labor-intensive. The intense resource and time requirements put such approaches out of reach for most small labs and prevents studying individual subjects, individual samples, or non-model organisms.

Technological efforts to detect and quantify RNA sequence variant information using next-generation sequencing methods have largely been limited by the read lengths such methods produce. Shotgun sequencing, therefore, generates large amounts of sequence information, but it is limited in its ability to assign individual reads to the same or different molecules.

Methods disclosed herein are used alone or in combination with currently employed sequencing technology and can overcome the substantial barriers posed by the limits of next generation sequencing read lengths. For example, the methods described herein can produce very long-range read-sets and provide a more complete picture of the population of RNA species present in a sample with a single sequencing run. This cuts costs by orders of magnitude and shortens the time required to produce such data.

Methods and compositions disclosed herein contemplate the quantification and deconvolution of the population of mRNA sliced variant isoforms from a cellular transcriptome.

RNA sequencing can be improved by incorporating methods that allow for the detection of distant segments of an RNA molecule in the same read without necessarily increasing read length. Such methods can include the use of proximity information generated during sample preparation and data collection. Some methods disclosed herein include linking together distant RNA sequences from the same molecule. The method of forming these linkages generally includes the use of an RNA binding moiety that binds a first RNA segment and a second RNA segment of the same RNA molecule together in a complex independent of the segments' common phosphodiester bond. Example moieties include native or recombinant RNA binding proteins and nanoparticles. The RNA in the assembled complex can then be crosslinked to fix the long-range interactions and the sequence of RNA found within each interaction can be identified. One way to identify RNA sequences in a complex is to digest the RNA, remove segments between the two segments bound independent of their phosphodiester bond, and fuse the bound segments of RNA to each other to form a rearranged molecule. The rearranged molecule containing non-contiguous sequences can then be identified by sequencing. A benefit of this approach is that segments separated by greater than a read length, such as splice variants or edited RNA segments, can be confidently assigned to a common molecule if they appear joined by a common ligation event.

Generally, the methods described herein include adding tagging information to the RNA segments such that they can be identified as belonging to the same original RNA molecule. The tagging information can include a junction between a first RNA segment and a second RNA segment. The tagging information can also include sequencing information obtained from either side of the junction. For example, a segment can be tagged by its being ligated or directly bound to a non-adjacent segment of the transcript of origin. In some instances, a tag is added to a transcript using an integrase. In these cases, adding additional barcode information can be optional.

The tagging information sometimes includes adding a unique label, such as an RNA or DNA barcode sequence, to at least one of the RNA segments. In some cases, the methods disclosed herein labels segments using an oligonucleotide array (e.g. polynucleotide microarray) in order to identify polynucleotide fragments that are related by physical linkage and/or proximity.

The methods described herein can be used to generate and sequence molecules that are informative of longer molecules that cannot be sequenced in a single read using many traditional high-throughput sequencing platforms. For example, the sequences can be informative of distant RNA splicing events, mutations, or RNA editing events that would be difficult to detect in the same molecule using traditional next-generation sequencing techniques. This information can be helpful when trying to find correlations between events that are found in the same molecules rather than events that are simply found in a population as a whole.

Methods of Assigning Linkage Information to Distal Ribonucleic Acid Segments

Provided herein are compositions and methods for generating, isolating, and preparing RNA samples for linkage-informative analysis. Through practice of the methods herein, sequence information from segments separating greater than a dead length apart are nonetheless confidently assigned to a common molecule in using shotgun sequencing or other similar approach. The RNA molecules include at least two RNA segments that share a common phosphodiester backbone. A first RNA segment and a second RNA segment are often not adjacent on the RNA molecule. The non-adjacent RNA segments are separated by at least one nucleotide, such as an intervening RNA segment. The segment that separates the first and second RNA segment can comprise a length of nucleotides that prevents the first and second segment from being encompassed together in a single sequence read.

Provided herein are methods of determining the sequences of transcripts contained in a sample. The sequences are often partial sequences. The sequences can be part of a transcriptome, or can represent up to an entire transcriptome. The methods disclosed herein generally take advantage of the ability to cross-link RNA segments, such as in complexes comprising RNA binding moieties that physically connect different parts of a longer polynucleotide through chemical linkage such that they are held together independent of their phosphodiester backbone. Upon cleavage, one or more intervening segments are lost, and the bound segments can be ligated or mutually tagged to indicate their common origin. The RNA binding moiety can comprise an endogenous or heterologous RNA binding protein. When the cross-linked polynucleotide complexes are formed, the polynucleotide is in a compact and stable cross-linked form and behaves as a polymer unit. The complex can be manipulated while retaining the proximity of bound RNA segments. The polynucleotide can be tagged such that at least two segments of the polynucleotide can be identified as belonging to the same RNA molecule. Retaining the proximity of segments allows for the rearrangement of segments in a linear polynucleotide such that a first segment is connected to a second segment that was more than the distance of a single read away from the first segment in the non-rearranged molecule. Such rearrangements allow for the two segments to be identified by a single read as belonging to the same original RNA molecule. In these rearranged molecules, each segment is tagged by the other segment, indicating that the segments are found in a common molecule.

The proximity information is determined by sequencing the tagged segments or a substantial part thereof. When the polynucleotides comprise sequences that originate from different segments of the same RNA molecule or variant, the proximity information is useful for identifying or even quantifying RNA variants occurring in the same molecule, including alternative splice variants, mutant variants, and RNA editing variants. When two segments harboring variant sequences are commonly tagged, one may infer that the variants originated from the same RNA molecule. This information can be helpful in determining which variations occur in concert in the same species.

Tagged molecules often comprise two distinct segments of a target nucleic acid sample. Alternately, some tagged molecules comprise a segment of a target nucleic acid sample in combination with a molecular tag, such that all target nucleic acid sample reads corresponding to a common molecular tag sequence may be mapped to a common RNA molecule within a target nucleic acid sample. Accordingly, the molecular tag sequence can be used to sort target nucleic acid sample reads into "tagged bins," each of which can correspond to a single molecule of a target nucleic acid sample. Commonly tagged reads can be mapped to a single nucleic acid molecule or molecular fragment.

A nucleic acid sample is often fragmented such that multiple copies of an RNA transcript are fragmented differentially with respect to one another. Molecular tagged sequences that map to each individual RNA molecule may contain overlapping sequence spanning at least one polymorphism that may differ among homologous chromosome pairs encoding the RNA transcript. In such cases, by comparing the sequence at the position that differs among RNA transcripts, one may determine whether the overlapping sequences represent sequence that is encoded by the same physically linked chromosome or original nucleic acid of the sample.

The present disclosure provides methods for transcript sequencing that combine technologies for RNA preparation with tagged sequence reads for high-throughput discovery of short, intermediate, and long-distance linkage information corresponding to sequence reads from a single physical nucleic acid molecule bound to a complex such as an RNA-protein complex. The disclosure further provides methods using these connections to facilitate transcript assembly and quantification.

Methods disclosed herein often comprise the step of generating a plurality of reads from sequencing fragments of target RNA obtained from a subject. Long stretches of target RNA are fragmented by, for example, hydrolysis, shearing, or enzymatic digestion, incompletely digesting the RNA, other fragmentation approaches, or combinations thereof. The RNA fragments are optionally reverse-transcribed into DNA. The RNA fragments can be amplified. The resulting fragments are sequenced using any approach known in the art, including high throughput sequencing methods, to obtain a plurality of sequencing reads. High throughput sequencing methods that are used with the methods of the disclosure include, but are not limited to, 454™ pyrosequencing methods, "clusters" sequencing methods, SOLiD™ and Ion semiconductor sequencing methods, and DNA nanoball sequencing methods. The overlapping ends of different sequencing reads are then sorted by molecule of origin, generally using tagging information, and assembled to determine the complete or partial sequence of the RNA molecule of origin.

Alternately or in combination with the above, in some cases, the methods disclosed herein are used with information previously generated, such as expressed sequence tag (EST) information or other linkage-independent read generation approach. EST data is publicly available for a large number of species, including humans, and often harbors splice variant information that is not easily assigned linkage information.

Sequence tag information can be used to map sequence reads to a single nucleic acid molecule from which they originated. In some cases, the nucleic acid molecule is obtained from a population of incompletely fragmented or sheared RNA, which is sheared such that overlapping nucleic acid fragments are obtained from a plurality of RNA molecules. Upon sequencing the reads which correspond to each individual overlapping nucleic acid molecule, one may assemble larger 'read position contig' information to infer physical linkage information across distances beyond single sheared nucleic acid size.

Sequence segments that were intramolecularly cross-linked are labeled with a common label. The common label can then be detected and analyzed to determine sequence segments that were intramolecularly cross-linked. The common label can, for example, be a barcode, which can optionally be detected by sequencing methods. In some cases, the reads of sequence segments labeled with a common label are binned into a read-set and/or assigned to a common molecule.

Samples

Provided herein are methods of assigning linking information to sequences from RNA molecules in a sample. Some the methods comprise obtaining a tissue or RNA sample from a subject. Some methods incorporate expressed sequence tags during the sequence analysis. In some cases, samples comprising target RNA are obtained from a subject by any number of approaches, including by sampling bodily fluids, tissue, or by collecting cells/organisms. The sample obtained may comprise a single type of cell/organism, or may comprise multiple types of cells/organisms. For example, the sample is treated to lyse a cell comprising the polynucleotide, using known lysis buffers, sonication techniques, or electroporation. In some cases, a sample is treated with an enzyme using methods provided herein to isolate the RNA from the sample. In further cases, the target RNA is further purified to remove contaminants, such as proteins, using methods known in the art.

Sample RNA often contains two or more splice variants transcribed from a common locus. Splice variants can include retained or excised exons, differential exon border section, or intron border section, or partial or total intro retention, and different combinations of exons.

The sample often contains RNA molecules encoded by two or more alleles of a given gene. The sample may contain RNA variants that have undergone different RNA editing events.

The nucleic acids in some samples can all or substantially all be of a certain length or no more than a certain length. The sample may be enriched for shorter RNA molecules. In some embodiments, the sample includes or is enriched for RNA molecules that are no more than 30 kb, 25 kb, 20 kb, 15 kb, 10 kb, 9 kb, 8 kb, 7 kb, 6 kb, 5 kb, 4 kb, 3 kb, 2 kb, 1 kb, 0.9 kb, 0.8 kb, 0.7 kb, 0.6 kb, 0.5 kb, 0.4 kb, 0.3 kb, 0.2 kb, or 0.1 kb.

RNA Binding Moieties

Nucleic acids of the samples disclosed herein are contacted to binding moieties, such as RNA binding moieties, so as to bind a first segment to a second segment independent of a common phosphodiester bond. The RNA binding moiety binds to RNA such that proximity information can be retained. A benefit of using RNA binding moieties is that separate regions of a common RNA molecule can be held together independently of their common phosphodiester bond upon cleavage of the phosphodiester backbone. The RNA binding moiety preferentially binds to the RNA molecule at one or two sites. The RNA binding moiety can also be crosslinked to a second RNA binding moiety such that at least two segments of the RNA molecule are bound together independently of their common phosphodiester bond.

An RNA binding moiety can be an RNA binding protein. The RNA binding protein can be a heterologous or recombinantly produced RNA binding protein. Exemplary RNA binding proteins include or comprise an endogenous or recombinant heterogeneous nuclear ribonucleoprotein (hnRNP). Examples of hnRNP include hnRNP A0, hnRNP A1, hnRNP A1L1, hnRNP A1L2, hnRNP A3, hnRNP A2B1, hnRNP AB, hnRNP B1, hnRNP PC, hnRNP PCL1, hnRNP D, hnRNP DL, hnRNP PF, hnRNP PH1, hnRNP PH2, hnRNP PH3, hnRNP PK, hnRNP PL, hnRNP LL, hnRNP PM, hnRNP PR, hnRNP U, hnRNP UL1, hnRNP UL2, hnRNP UL3, FMR1, hrp36, Hrb87F, and homologs thereof, including from non-human species. In some embodiments, the RNA-binding moiety is hnRNP A1. In some embodiments, the RNA-binding moiety comprises hrp36. The RNA binding protein can bind non-specifically, preferentially, or specifically to particular sequences. The RNA binding protein can contain a variety of motifs, such as an RNA-recognition motif (RRM), Double-stranded RNA-binding motif (dsRBM), or at least one zinc-finger domain.

In some cases, the methods disclosed herein are used with RNA associated to nanoparticles. In further cases, the nanoparticles are positively charged. In certain cases, the RNA and the nanoparticles aggregate and condense. Furthermore, the nanoparticles may be immobilized on solid substrates (e.g. beads, slides, or tube walls) by applying magnetic fields (in the case of paramagnetic nanoparticles) or by covalent attachment (e.g. by cross-linking to poly-lysine coated substrate). Immobilization of the nanoparticles may improve the ligation efficiency thereby increasing the number of desired products (signal) relative to undesired (noise).

The RNA binding moiety can comprise an affinity tag. For example, the affinity tag can comprise a polypeptide tag, such as a poly-histidine tag, such as a 6×His-tag. Another exemplary polypeptide tag comprises a strep tag, such as a Strep-tag II. An exemplary Strep-Tag II comprises the amino acid sequence WSHPQFEK. Yet another polypeptide tag comprises a FLAG-tag. In some embodiments, the FLAG-tag comprises the sequence DYKDDDDK.

The ratio of RNA to RNA binding moieties can be varied such that the density of each complex is adjusted to a desired value. Accordingly, the distribution of crosslinks can be altered to favor longer-range or shorter-range interactions. Sub-samples with varying cross-linking density may be prepared to cover both short- and long-range associations. In some cases, the crosslinking conditions is adjusted such that at least about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 40%, about 45%, about 50%, about 60%, about 70%, about 80%, about 90%, about 95%, or about 100% of the crosslinks occur between RNA segments that are at least about 0.5 kb, about 0.6 kb, about 0.7 kb, about 0.8 kb, about 0.9 kb, about 1 kb, about 1.1 kb, about 1.2 kb, about 1.3 kb, about 1.4 kb, about 1.5 kb, about 1.6 kb, about 1.8 kb, about 2 kb, about 2.5 kb, about 3. kb, about 3.5 kb, about 4 kb, about 4.5 kb, about 5 kb, about 6 kb, about 7 kb, about 8 kb, about 9 kb, about 10 kb, about 15 kb, about 20 kb, or about 25 kb apart on the sample RNA molecule. In some cases, the crosslinking is reversible. In certain cases, the crosslinking is reversed using heat. In other cases, the crosslinking is reversed using a chemical agent.

RNA Isolation Using a Solid Support

The RNA bound to RNA binding moieties described above can be isolated using a solid support. Isolation allows RNA segments that are bound to RNA binding moieties to be retained, while RNA that is not bound to RNA binding moieties, and therefore not part of a complex, can be washed away. This process can increase the efficiency of the subsequent steps. A solid support can be used to bind to the RNA-RNA binding moiety complexes. The solid support may bind to an affinity tag on the RNA binding moiety. The solid support can allow the bound RNA to be retained, isolated, and/or purified during manipulation and/or washing steps of the methods described herein. The solid support can allow unbound RNA and/or contaminants to be removed from the sample.

The solid support can comprise a bead. The bead may be a magnetic bead, such as a nickel-magnetic bead. The solid support can comprise streptavidin or a synthetic streptavidin, such as Streptactin. The solid support can also comprise anti-FLAG antibodies.

Alternatively, some methods do not involve isolation or a solid support.

Crosslinking

Crosslinking stabilizes the complexes generated as described above such that a first segment and a second segment remain bound even after fragmentation, which involves cleavage of the common phosphodiester bond. In some cases, cross-links are created between segments of RNA that are not adjacent to each other on the linear polynucleotide sequence, but that are in close physical proximity to each other during the crosslinking process. Crosslinking of proteins (e.g. RNA binding proteins) to the RNA molecule (e.g. mRNA) is accomplished according to a suitable method described in further detail elsewhere herein or otherwise known in the art. Suitable chemical crosslinking agents include, but are not limited to, formaldehyde. For example, cross-linking can be performed by adding a solution comprising about 2% formaldehyde to a mixture comprising the RNA molecule and RNA binding proteins.

Polynucleotide Fragmentation

Once the complexes are stabilized as described above, the RNA can be fragmented. Fragmenting allows the molecule to be rearranged while crosslinking retaining the proximity of fragments originating from the same RNA molecule. Generally, fragmentation cleaves phosphodiester backbones, such that RNA segments bond to the RNA binding moiety are held together despite no longer being joined by a common phosphodiester backbone. These segments bound to the RNA binding moiety are retained. Segments not bound by the RNA binding moiety, such as segments in "loops" extending from the complexes, are generally released. Crosslinking thus generally allows segments bound to the RNA binding moiety to remain physically linked to one another despite cleavage and removal of intervening RNA segments.

Many fragmentation techniques are known in the art. An exemplary fragmentation technique described herein includes fragmentation by mild hydrolysis. The pH of the solution in which the RNA is being fragmented can less than 7. In some embodiments, the pH of the solution in which the RNA is being fragmented is between 1 and 2, between 2 and 3, between 3 and 4, between 4 and 5, between 5 and 6, or between 6 and 7. In some embodiments, the pH of the solution in which the RNA is being fragmented is or is about 4.0, 4.1, 4.2, 4.3, 4.4, 4.5, 4.6. 4.7, 4.8, 4.9, 5.0, 5.1, 5.2, 5.3, 5.4, 5.5. 5.6, 5.7, 5.8, 5.9, 6.0, 6.1, 6.2, 6.3, 6.4, 6.5, 6.6, 6.7, 6.8, 6.9, or 7.0. The fragmentation can be carried out using a solution containing sodium acetate. Sodium acetate solutions can be at a concentration of 1M to 5M, such as 1, 2, 3, 4, or 5M.

The pH of the solution in which the RNA is being fragmented can also be greater than 7. In some embodiments, the pH of the solution in which the RNA is being fragmented in is between 7 and 8, between 8 and 9, between 9 and 10, between 10 and 11, between 11 and 12, between 12 and 13, or between 13 and 14.

The RNA can be fragmented using a commercially available kit, including, for example, an NEBNext® Magnesium RNA Fragmentation Module. RNA can also be fragmented with sonication, heat, RNAses, and shear forces.

Phosphatase Treatment

The fragments generated as described above can be prone to ligate back to each other, and therefore phosphatases are optionally used to prevent unwanted ligation. A phosphatase removes phosphate groups from an end of an RNA fragment of the RNA molecule. Removing a phosphate group from an end of an RNA fragment can prevent or reduce the likelihood of the RNA fragment from religating to its original fragment partner before fragmentation took place. The phosphatase can remove phosphate groups from a 5', a 3', and/or a 2' position on an RNA. The phosphatase preferably removes a phosphate from a 5' position on the RNA. The phosphate can also be removed from an OH group.

Kinase Treatment

Phosphatase-treated samples are optionally contacted with a kinase to enable the fragments to be ligated to other fragments within the complex. The kinase adds a phosphate group to a 5' position on an end of an RNA fragment. The phosphate group added to a 5' position on an end of a first RNA fragment can facilitate ligation to a second RNA fragment, including a fragment that was not adjacent to the first RNA fragment in the original RNA molecule prior to fragmentation. Example kinases include T4 kinase.

Polynucleotide Tagging

The fragmented nucleic acids described above are generally labeled with a molecular tag. The tag allows fragments generated from a common molecule to be identified as originating from that common molecule with confidence. Segments can be tagged or labeled such that they can be assigned to the same original RNA molecule. A sequence read can comprise two or more segments that map to the original RNA molecule. A first sequence read often detects a first segment comprising a first label or tag and a second sequence read detects a second segment comprising a second label or tag. The first and second labels or tags can the same or different. In many cases, the first label and the second label are polynucleotides. In certain cases, the first label and the second label each comprise one or more elements selected from the group consisting of a linker, a barcode, and an adaptor. In some cases, the first label comprises a first adaptor and the second label comprises a second adaptor.

Sequence tag information is generally used to map sequence reads to a single nucleic acid molecule, such as an RNA, from which the sequence reads originated. This information can be independent of distance information within a single nucleic acid molecule. In some cases, the nucleic acid molecule is obtained from a population of incompletely fragmented or sheared RNA, which is sheared such that overlapping nucleic acid fragments are obtained. Upon sequencing the reads which correspond to each individual overlapping nucleic acid molecule, one may assemble larger 'read position contig' information to infer physical linkage information across distances beyond single sheared nucleic acid size.

In most cases, common tagging will not arise by chance, and thus most commonly tagged sequences are safely inferred to map to the same RNA molecule of origin.

Tagging with a Second RNA Segment

The tagging information can comprise sequence information from each side of the junction between the two segments of ligated RNA. The segments need not be adjacent to each other on the original nonfragmented RNA molecule. Thus, segments that were more than one read-pair apart prior to fragmentation and ligation can form junctions after ligation that can serve as tagging information for each segment. In some cases, the first RNA segment is tagged with the second RNA segment and the second RNA segment is tagged with the first RNA segment. For example, the first RNA segment can be linked to the second RNA segment. In some examples, the first RNA segment present in a first RNA fragment, which is linked to a second RNA fragment containing the second RNA segment. The fragments or segments are often linked using a ligase.

The at least two RNA fragments, each comprising at least one RNA segment bound to an RNA binding moiety, are generally joined together. As used herein, with respect to fragments, the terms "connecting", "joining", or "ligating" can refer to the covalent attachment of two separate nucleic acid segments, such as RNA segments, to produce a single larger polynucleotide with a contiguous backbone. Ligating RNA fragments generally yields an RNA molecule with segments that originated in the same RNA molecule, but which are altered in their proximity to each other compared to the original RNA molecule.

Segments that were originally more than a single read length apart in the original RNA molecule are often rearranged such that the segments are within a read length apart once fragments containing the segments are ligated to each other. In various embodiments, the methods disclosed herein generate read pairs that include sequences that were separated by extremely long distances in the original molecule. In some cases, the read pairs span up to 50, 60, 70, 80, 90, 100, 125, 150, 175, 200, 225, 250, 300, 400, 500, 600, 700, 800, 900, 1000, 1500, 2000, 2500, 3000, 4000, 5000 kbp, or more in distance in the unfragmented molecule. In some cases, the read pairs span up to 500 kbp in distance. In other cases, the read pairs span up to 2000 kbp in distance. In some cases, the segments are ligated such that they are adjacent to each other. Adjacent generally means that the segments share a common junction.

Ligation can be conducted under conditions such that the majority of ligation events involve 5' phosphorylated ends and 3' OH ends of segments that are bound together in a single complex. Methods for joining two RNA segments are known in the art, and include without limitation, enzymatic and non-enzymatic (e.g. chemical) methods.

Examples of ligation reactions that are enzymatic include the use of ligases. Exemplary ligases include RNA ligases. Multiple ligases, each having characterized reaction conditions, are known in the art, and include, without limitation $NAD^+$-dependent ligases including tRNA ligase, ATP-dependent ligases including T4 RNA ligase; novel ligases discovered by bioprospecting; and wild-type, mutant isoforms, and genetically engineered variants thereof.

In some cases, the ligation reaction is performed at a sequence segment or polynucleotide concentration of about less than about 0.1 ng/µL, about 0.2 ng/µL, about 0.3 ng/µL, about 0.4 ng/µL, about 0.5 ng/µL, about 0.6 ng/µL, about 0.7 ng/µL, about 0.8 ng/µL, about 0.9 ng/µL, about 1.0 ng/µL, about 1.2 ng/µL, about 1.4 ng/µL, about 1.6 ng/µL, about 1.8 ng/µL, about 2.0 ng/µL, about 2.5 ng/µL, about 3.0 ng/µL, about 3.5 ng/µL, about 4.0 ng/µL, about 4.5 ng/µL, about 5.0 ng/µL, about 6.0 ng/µL, about 7.0 ng/µL, about 8.0 ng/µL, about 9.0 ng/µL, about 10 ng/µL, about 15 ng/µL, about 20 ng/µL, about 30 ng/µL, about 40 ng/µL, about 50 ng/µL, about 60 ng/µL, about 70 ng/µL, about 80 ng/µL, about 90 ng/µL, about 100 ng/µL, about 150 ng/µL, about 200 ng/µL, about 300 ng/µL, about 400 ng/µL, about 500 ng/µL, about 600 ng/µL, about 800 ng/µL, or about 1000 ng/µL. In some cases, the ligation reaction is performed at a sequence segment or polynucleotide concentration of about greater than about 0.1 ng/µL, about 0.2 ng/µL, about 0.3 ng/µL, about 0.4 ng/µL, about 0.5 ng/µL, about 0.6 ng/µL, about 0.7 ng/µL, about 0.8 ng/µL, about 0.9 ng/µL, about 1.0 ng/µL, about 1.2 ng/µL, about 1.4 ng/µL, about 1.6 ng/µL, about 1.8 ng/µL, about 2.0 ng/µL, about 2.5 ng/µL, about 3.0 ng/µL, about 3.5 ng/µL, about 4.0 ng/µL, about 4.5 ng/µL, about 5.0 ng/µL, about 6.0 ng/µL, about 7.0 ng/µL, about 8.0 ng/µL, about 9.0 ng/µL, about 10 ng/µL, about 15 ng/µL, about 20 ng/µL, about 30 ng/µL, about 40 ng/µL, about 50 ng/µL, about 60 ng/µL, about 70 ng/µL, about 80 ng/µL, about 90 ng/µL, about 100 ng/µL, about 150 ng/µL, about 200 ng/µL, about 300 ng/µL, about 400 ng/µL, about 500 ng/µL, about 600 ng/µL, about 800 ng/µL, or about 1000 ng/µL. In some cases, the ligation is performed at a sequence segment or polynucleotide concentration of about 100 ng/µL, about 150 ng/µL, about 200 ng/µL, about 300 ng/µL, about 400 ng/µL, or about 500 ng/µL. In further examples, the ligation reaction is performed at a sequence segment or polynucleotide concentration of about 0.1 to 1000 ng/µL, about 1 to 1000 ng/µL, about 1 to 800 ng/µL, about 10 to 800 ng/µL, about 10 to 600 ng/µL, about 100 to 600 ng/µL, or about 100 to 500 ng/µL.

In some cases, the ligation reaction is performed for at least about 5 minutes, about 10 minutes, about 20 minutes, about 30 minutes, about 40 minutes, about 50 minutes, about 60 minutes, about 90 minutes, about 2 hours, about 3 hours, about 4 hours, about 5 hours, about 6 hours, about 8 hours, about 10 hours, about 12 hours, about 18 hours, about 24 hours, about 36 hours, about 48 hours, or about 96 hours. In certain cases, the ligation reaction is performed for less than about 5 minutes, about 10 minutes, about 20 minutes, about 30 minutes, about 40 minutes, about 50 minutes, about 60 minutes, about 90 minutes, about 2 hours, about 3 hours, about 4 hours, about 5 hours, about 6 hours, about 8 hours, about 10 hours, about 12 hours, about 18 hours, about 24 hours, about 36 hours, about 48 hours, or about 96 hours. In some cases, the ligation reaction is performed for about 30 minutes to about 90 minutes.

Tagging with Barcodes

Barcodes can allow segments to be mapped to a common molecule. In such cases, the sequence read information typically comprises barcode sequence information and segment sequence information. In some cases, the first label comprises a first barcode and the second label comprises a second barcode. In some cases, the first barcode and the second barcode are identical. Some embodiments comprise associating the first sequence segment and the second sequence segment based on the first barcode and the second barcode. The barcodes can be unique within a sample, but often do not need to be.

Certain embodiments comprise ligating a barcoded aggregate to the RNA complex. In some cases, the barcoded aggregate comprises a plurality of barcoded polynucleotides and a plurality of aggregate molecules. In certain cases, the barcoded polynucleotides are ligated to the first sequence segment and the second sequence segment. Some embodiments comprise amplifying the first sequence segment and the second sequence segment using the barcoded polynucleotides as templates.

As used herein, the term "barcode" or "molecular tag" refers to a known nucleic acid sequence that allows some feature of a polynucleotide with which the barcode is associated to be identified. In some embodiments, the feature of the polynucleotide to be identified is the sample from which the polynucleotide is derived. Barcodes can be at least 3, 4, 5, 6, 7, 8, 9, 10, 11, 12, 13, 14, 15, or more nucleotides in length. In some cases, barcodes are at least 10, 11, 12, 13, 14, or 15 nucleotides in length. Barcodes can be shorter than 10, 9, 8, 7, 6, 5, or 4 nucleotides in length. In certain examples, barcodes are shorter than 10 nucleotides in length. Barcodes associated with some polynucleotides can be of different length than barcodes associated with other polynucleotides.

In general, barcodes are of sufficient length and comprise sequences that are sufficiently different to allow the identification of samples based on barcodes with which they are associated. In some embodiments, a barcode, and the sample source with which it is associated, are identified accurately after the mutation, insertion, or deletion of one or more nucleotides in the barcode sequence, such as the mutation, insertion, or deletion of 1, 2, 3, 4, 5, 6, 7, 8, 9, 10, or more nucleotides. In some cases, 1, 2 or 3 nucleotides are mutated, inserted and/or deleted. In some embodiments, each barcode in a plurality of barcodes differ from every other barcode in the plurality at least two nucleotide positions, such as at least 2, 3, 4, 5, 6, 7, 8, 9, 10, or more positions. In some cases, each barcode differs from every other barcode by in at least 2, 3, 4 or 5 positions.

Both a first site and a second site can comprise at least one of a plurality of barcode sequences. Barcodes for second sites can be selected independently from barcodes for first adapter oligonucleotides. First sites and second sites having barcodes can be paired, such that sequences of the pair comprise the same or different one or more barcodes. The methods of the disclosure can further comprise identifying the sample from which a target polynucleotide is derived based on a barcode sequence to which the target polynucleotide is joined. In general, a barcode may comprise a nucleic acid sequence that when joined to a target polynucleotide serves as an identifier of the sample from which the target polynucleotide was derived.

The present disclosure also provides compositions comprising an emulsion of a plurality of aqueous droplets, wherein a first droplet comprises: a first nucleic acid, such as an RNA, wherein the first nucleic acid molecule comprises a first segment and a second segment; and a molecular tag sequence, such as a barcode; and wherein the first droplet is enveloped by an immiscible layer. In some cases, the first nucleic acid is complexed with an RNA binding moiety, wherein the first region and the second region of the first nucleic acid molecule are bound independently of a phosphodiester backbone of the first nucleic acid molecule; and wherein a double-stranded break of known end sequence is introduced between the first segment and the second segment of the first nucleic acid molecule. In some cases, the first nucleic acid is covalently bound to the binding agent. In various cases, the first droplet comprises a single covalently bound molecule. In some cases, the molecular tag sequence of the oligonucleotide is not present in a second droplet. In some cases, the second droplet comprises a different molecular tag sequence.

In certain cases, the droplet comprises a ligase. In some further cases, the droplet comprises ATP. The ligase often ligates the molecular tag sequence to the first segment and the molecular tag sequence to the second segment such that the first and second segments can be identified as originating from the same molecule.

In some aspects, the barcode sequence is bound to a solid surface comprising a plurality of the oligonucleotide tag sequence. In some aspects the solid surface is a nucleic acid array. In some aspects the oligonucleotide tag sequence is cross-linked to an RNA binding moiety that comprises multiple copies of the oligonucleotide tag sequence. In some aspects the RNA binding moiety comprises an RNA binding protein. In some aspects the RNA binding moiety comprises a nanoparticle. In some aspects the oligonucleotide tag sequence is contained in a vesicle.

Reversing Crosslinking

While crosslinking can preserve proximity information during tagging steps, the RNA binding moieties may interfere with sequencing steps. Thus, the crosslinking is often reversed and RNA binding moieties removed before sequencing the nucleic acids. In some cases, unbinding the RNA from the RNA binding moieties and/or reversing the crosslinking between RNA binding moieties yields a population of naked RNA molecules that include RNA molecules that have been rearranged by fragmentation and ligation. In some cases, crosslinking is reversed using a solution containing a divalent cation. Exemplary solutions contain EDTA and/or EGTA. Crosslinking can be reversed using a protease, such as proteinase K. Crosslinking can be reversed using a number of chemical reagents. Crosslinking can also be reversed using heat.

Oligo/Linearizing

A number of approaches are available for oligo linearization consistent with the disclosure herein.

Creating Complementary DNA Using Reverse Transcriptase

The RNA sequences generated by the methods described above are optionally stabilized and prepared for sequencing by reverse transcribing the RNA into DNA. DNA offers several advantages, including compatibility with many sequencing technologies and the ability to amplify individual sequences so they can be detected and identified. Methods of reverse transcribing RNA into DNA, including cDNA, are known in the art. Some reverse transcriptases utilize a double-stranded polynucleotide to initiate reverse transcription. Accordingly, the RNA is optionally contacted with a primer to form a double-stranded site on the polynucleotide. Exemplary primers include a poly-T oligo, which can also be called an oligo-T primer. In some examples, the oligo-T primer binds to the 3' poly-A tail of an RNA molecule. In some examples, a polymerase or adenyltransferase is used to add a 3' poly-A tail to the RNA. In some aspects, the method includes contacting the RNA to a primer or primer population comprising arbitrary or random sequences, such as a random hexamer primer population. The random hexamer generally hybridizes to the RNA molecule and initiates reverse transcription within the RNA sequence. In some embodiments, a target-specific primer is used. In some cases, PCR is used alone.

Some methods benefit from digesting the RNA in the sample after synthesis of complementary DNA sequences. In some cases, an RNase, such as RNase H, is used to digest the remaining RNA molecules. In some cases, an alkaline solution is used to digest the remaining RNA present in the sample. Some methods do not involve digesting the RNA.

Amplification

Individual nucleic acid molecules, such as those contained in the samples described above, can be difficult or impossible to sequence. Amplification or replication of individual molecules can provide sufficient copies of a sequence to allow for sequence signals to be detected. As used herein, the term "amplification" refers to any process by which the copy number of a nucleic acid sequence is increased. The disclosure further provides methods for amplifying polynucleotides. In some cases, the polynucleotides comprise a label. The labeled polynucleotide(s) can be obtained by the methods of the present disclosure.

In some cases, the one or more amplification and/or replication steps are used for the preparation of a library or read-set to be sequenced. Any amplification method known in the art may be used. Examples of amplification techniques that can be used include, but are not limited to, quantitative PCR, quantitative fluorescent PCR (QF-PCR), multiplex fluorescent PCR (MF-PCR), real time PCR (RTPCR), single cell PCR, restriction fragment length polymorphism PCR (PCR-RFLP), PCK-RFLPIRT-PCR-IRFLP, hot start PCR, nested PCR, in situ polony PCR, in situ rolling circle amplification (RCA), bridge PCR, ligation mediated PCR, Qb replicase amplification, inverse PCR, picotiter PCR and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid-based sequence amplification (NABSA). Other amplification methods that can be used herein include those described in U.S. Pat. Nos. 5,242,794; 5,494,810; 4,988,617; and 6,582,938.

In some cases, an amplification reaction produces only a single complimentary copy/replica of a polynucleotide. In some cases, an amplification reaction produces a plurality of complimentary copies/replicas of a polynucleotide. Such methods are well known in the art.

In some cases, one or more specific priming sequences within amplification adapters are utilized for PCR amplification. The amplification adapters may be ligated to fragmented polynucleotides. In some cases, polynucleotides comprising amplification adapters with suitable priming sequences on both ends are PCR amplified exponentially. Polynucleotides with only one suitable priming sequence due to, for example, imperfect ligation efficiency of amplification adapters comprising priming sequences, may only undergo linear amplification. Further, polynucleotides can be eliminated from amplification, for example, PCR amplification, altogether, if no adapters comprising suitable priming sequences are ligated.

Sequencing

Once the molecules are prepared by the methods described herein, they are sequenced in order to obtain sequencing information, including linkage information for distal DNA segments. Sequence information may be obtained from the sample using any suitable sequencing technique described in further detail elsewhere herein or otherwise known in the art, such as a high throughput sequencing method. In some cases, the sequence segments are subject to a sequencing technique to generate sequence reads, which are used to identify sequence segments that are cross-linked and/or are labeled with a common label or tag. In further cases, two or more sequence segments are represented in the obtained sequence information, associating information over a linear distance separating the two sequence segments along the same polynucleotide.

In some cases, the methods disclosed herein are used in combination with an existing sequencing technology. In further cases, the methods disclosed herein are used with technologies and approaches derived from any existing sequencing technology. Cases of sequencing technologies that can be used with the methods disclosed herein include, but are not limited to, the Illumina® sequencing-by-synthesis platform (Illumina®, San Diego, Calif), the SOLiD™ system (Applied Biosystems Corp.), pyrosequencing (e.g., 454™ Life Sciences, subsidiary of Roche Diagnostics), a sequencing technique based on semiconductor detectors (e.g., the Ion Torrent® platform), nanopore sequencing (e.g., the Oxford Nanopore™ sequencing platform), DNA nanoball sequencing methods (e.g. Complete Genomics™), sequencing by hybridization and any other suitable technology, or any technology that may be derived from any of the above technologies.

In some cases, at least 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% of the read-pairs span a distance less than 1 kB, 2 kB, 3 kB, 4 kB, 5 kB, 6 kB, 7 kB, 8 kB, 9 kB, 10 kB, 15 kB, 20 kB, or 30 kB. In certain cases, at least 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, or 20% of the read-pairs span a distance less than 5 kB, 6 kB, 7 kB, 8 kB, 9 kB, 10 kB, 15 kB, 20 kB, or 30 kB on the single RNA molecule.

In some cases, sequencing is accomplished through classic Sanger sequencing methods, which are well known in the art. In other cases, sequencing is accomplished using high-throughput systems some of which allow detection of a sequenced nucleotide immediately after or upon its incorporation into a growing strand, i.e., detection of sequence in real time or substantially real time. In some cases, high throughput sequencing generates at least 1,000, at least 5,000, at least 10,000, at least 20,000, at least 30,000, at least 40,000, at least 50,000, at least 100,000 or at least 500,000 sequence reads per hour. In some cases, the sequencing reads are at least about 50, about 60, about 70, about 80, about 90, about 100, about 120, about 150, about 180, about 210, about 240, about 270, about 300, about 350, about 400, about 450, about 500, about 600, about 700, about 800, about 900, about 1000, about 1500, about 2000, about 2500, about 3000, about 4000, about 5000, about 6000, about 7000, about 8000, about 9000, or about 10000 bases per read.

In some cases, high-throughput sequencing is performed using technology available by Illumina®'s Genome Analyzer IIX™, MiSeq™ personal sequencer, or HiSeq™ systems, such as those using HiSeq 2500™, HiSeq 1500™, HiSeq 2000™, or HiSeq 1000 ™ machines. These machines use reversible terminator-based sequencing by synthesis chemistry. These machines can produce 200 billion DNA reads or more in eight days. Alternatively, smaller systems may be utilized for runs within 3, 2, 1 days or less time.

In some cases, high-throughput sequencing is performed using technology available by ABI Solid System™. This genetic analysis platform that enables massively parallel sequencing of clonally-amplified DNA fragments linked to beads. The sequencing methodology is based on sequential ligation with dye-labeled oligonucleotides.

In some cases, high-throughput sequencing is performed using ion semiconductor sequencing (e.g., using technology from Life Technologies™ (Ion Torrent™)). Ion semiconductor sequencing can take advantage of the fact that when a nucleotide is incorporated into a strand of DNA, an ion can be released. In some cases, to perform ion semiconductor sequencing, a high-density array of micromachined wells is formed. In some cases, each well holds a single DNA template. In further examples, an ion sensitive layer is beneath the well, and beneath the ion sensitive layer can be an ion sensor. In certain cases, when a nucleotide is added to a DNA, H+ is released, which can be measured as a change in pH. In further cases, the H+ ion is converted to voltage and recorded by the semiconductor sensor. In some cases, an array chip is sequentially flooded with one nucleotide after another. In some cases, no scanning, light, or camera is required. In some cases, an IONPROTON™ Sequencer is used to sequence nucleic acid. In some cases, an IONPGM™ Sequencer is used. In certain examples, the Ion Torrent Personal Genome Machine (PGM) can do 10 million reads in two hours.

In some cases, high-throughput sequencing is performed using technology available by Helicos BioSciences Corporation (Cambridge, Massachusetts) such as the Single Molecule Sequencing by Synthesis (SMSS) method. SMSS is unique because it allows for sequencing the entire human genome in up to 24 hours. SMSS is described in part in US Publication Application Nos. 20060024711; 20060024678; 20060012793; 20060012784; and 20050100932.

In some cases, high-throughput sequencing is performed using technology available by 454™ Lifesciences, Inc. (Branford, Connecticut) such as the PicoTiterPlate™ device which includes a fiber optic plate that transmits chemiluminescent signal generated by the sequencing reaction to be recorded by a CCD camera in the instrument. This use of fiber optics allows for the detection of a minimum of 20 million base pairs in 4.5 hours.

Methods for using bead amplification followed by fiber optics detection are described in Marguiles, M., et al. "Genome sequencing in microfabricated high-density picolitre reactors Nature 437, 376-380 (15 Sep. 2005), doi:10.1038/nature03959; and well as in US Application Publication Nos. 20020012930; 20030068629; 20030100102; 20030148344; 20040248161; 20050079510, 20050124022; and 20060078909.

In some cases, high-throughput sequencing is performed using Clonal Single Molecule Array M (Solexa, Inc.) or sequencing-by-synthesis (SBS) utilizing reversible terminator chemistry. These technologies are described in part in U.S. Pat. Nos. 6,969,488; 6,897,023; 6,833,246; 6,787,308; and US Publication Application Nos. 20040106110; 20030064398; 20030022207; and Constans, A., The Scientist 2003, 17(13):36.

In some cases, high-throughput sequencing is performed using real-time (SMRT™) technology by Pacific Biosciences m. In certain examples of SMRT™, each of four DNA bases is attached to one of four different fluorescent dyes. In further examples, these dyes are phospho linked. In some cases, a single DNA polymerase is immobilized with a single molecule of template single stranded DNA at the bottom of a zero-mode waveguide (ZMW). In certain cases, a ZMW is a confinement structure which enables observation of incorporation of a single nucleotide by DNA polymerase against the background of fluorescent nucleotides that can rapidly diffuse in an out of the ZMW (in microseconds). In some cases, it takes several milliseconds to incorporate a nucleotide into a growing strand. During this time, the fluorescent label can be excited and produce a fluorescent signal, and in some cases the fluorescent tag is further cleaved off. In certain cases, the ZMW is illuminated from below. Attenuated light from an excitation beam can penetrate the lower 20-30 nm of each ZMW. In some cases, a microscope with a detection limit of 20 zepto liters (10" liters) is created. In certain examples, the tiny detection volume provides 1000-fold improvement in the reduction of background noise. In further examples, detection of the corresponding fluorescence of the dye indicates which base was incorporated. In many cases, the process is repeated.

In some cases, high-throughput sequencing is performed using nanopore sequencing (See, e.g., Soni G V and Meller A. (2007) Clin Chem 53: 1996-2001). In various cases, a nanopore is a small hole, of the order of about one nanometer in diameter. In certain cases, immersion of a nanopore in a conducting fluid and application of a potential across it results in a slight electrical current due to conduction of ions through the nanopore. In further cases, the amount of current which flows is sensitive to the size of the nanopore. As a DNA molecule passes through a nanopore, each nucleotide on the DNA molecule can obstruct the nanopore to a different degree. Thus, the change in the current passing through the nanopore as the DNA molecule passes through the nanopore may represent a reading of the DNA sequence. In some cases, the nanopore sequencing technology is from Oxford Nanopore Technologies m e.g., a GridION™ system. In certain examples, a single nanopore is inserted in a polymer membrane across the top of a microwell. In various examples, each microwell has an electrode for individual sensing. In further examples, the microwells are fabricated into an array chip, with 100,000 or more microwells (e.g., more than 200,000, 300,000, 400,000, 500,000, 600,000, 700,000, 800,000, 900,000, or 1,000,000) per chip. In some cases, an instrument (or node) is used to analyze the chip. In certain cases, data is analyzed in real-time. In many cases, one or more instruments are operated at a time. In some cases, the nanopore is a protein nanopore, e.g., the protein alpha-hemolysin, a heptameric protein pore. In certain examples, the nanopore is a solid-state nanopore made, e.g., a nanometer sized hole formed in a synthetic membrane (e.g., $SiN_x$, or $SiO_2$). In other examples, the nanopore is a hybrid pore (e.g., an integration of a protein pore into a solid-state membrane). In further examples, the nanopore is a nanopore with an integrated sensor (e.g., tunneling electrode detectors, capacitive detectors, or graphene based nano-gap or edge state detectors (see e.g., Garaj et al. (2010) Nature vol. 67, doi: 10.1038/nature09379)). In some cases, a nanopore is functionalized for analyzing a specific type of molecule (e.g., DNA, RNA, or protein). In certain cases, nanopore sequencing comprises "strand sequencing" in which intact DNA polymers can be passed through a protein nanopore with sequencing in real time as the DNA translocates the pore. In many cases, an enzyme separates strands of a double stranded DNA and feed a strand through a nanopore. In further cases, the DNA has a hairpin at one end, and the system can read both strands. In some cases, nanopore sequencing is "exonuclease sequencing" in which individual nucleotides are cleaved from a DNA strand by a processive exonuclease, and the nucleotides are passed through a protein nanopore. In certain examples, the nucleotides transiently bind to a molecule in the pore (e.g., cyclodextran). In various examples, a characteristic disruption in current is used to identify bases.

In further cases, nanopore sequencing technology from GENIA™ is used. In some cases, an engineered protein pore is embedded in a lipid bilayer membrane. In certain examples, "Active Control" technology is used to enable efficient nanopore-membrane assembly and control of DNA movement through the channel. In some cases, the nanopore sequencing technology is from NABsys™. In some cases, DNA is fragmented. In certain examples, the fragments are made single stranded and subsequently hybridized with a 6-mer probe. In many examples, the fragments with probes are driven through a nanopore, which can create a current-versus-time tracing. In further examples, the current tracing provides the positions of the probes on each fragment.

In some cases, high-throughput sequencing is performed using DNA nanoball sequencing (as performed, e.g., by Complete Genomics™; see e.g., Drmanac et al. (2010) Science 327: 78-81). In certain cases, DNA is isolated, fragmented, and size selected. In some cases, DNA is fragmented (e.g., by sonication) to a mean length of about 500 bp. Adaptors (Ad1) can be attached to the ends of the fragments. In certain examples, the adaptors are used to hybridize to anchors for sequencing reactions. In various examples, DNA with adaptors bound to each end is PCR amplified. In further examples, the adaptor sequences are modified so that complementary single strand ends bind to each other forming circular DNA. In some cases, the DNA is methylated to protect it from cleavage by a type IIS restriction enzyme used in a subsequent step. In certain cases, an adaptor (e.g., the right adaptor) has a restriction recognition site, and the restriction recognition site remains non-methylated. In other cases, the non-methylated restriction recognition site in the adaptor is recognized by a restriction enzyme (e.g., Acu1), and the DNA is cleaved by Acu1 13 bp to the right of the right adaptor to form linear double stranded DNA. In further cases, a second round of right and left adaptors (Ad2) is ligated onto either end of the linear DNA, and all DNA with both adapters bound are PCR amplified (e.g., by PCR). In some cases, Ad2 sequences are modified to allow them to bind each other and form circular DNA. In certain examples, the DNA is methylated, but a restriction enzyme recognition site remains non-methylated on the left Ad1 adapter. In various examples, a restriction enzyme (e.g., Acu1) is applied, and the DNA is cleaved 13 bp to the left of the Ad1 to form a linear DNA fragment. In further examples, a third round of right and left adaptor (Ad3) is ligated to the right and left flank of the linear DNA, and the resulting fragment is PCR amplified. In some cases, the adaptors are modified so that they bind to each other and form circular DNA. In certain embodiments, a type III restriction enzyme (e.g., EcoP15) is added; EcoP15 cleaves the DNA 26 bp to the left of Ad3 and 26 bp to the right of Ad2. In various embodiments, this cleavage removes a large segment of DNA and linearizes the DNA once again. In further embodiments, a fourth round of right and left adaptors (e.g., Ad4) is ligated to the DNA, the DNA is amplified (e.g., by PCR), and modified so that they bind each other and form the completed circular DNA template.

In certain cases, rolling circle replication (e.g., using Phi 29 DNA polymerase) is used to amplify small fragments of DNA. In some cases, the four adaptor sequences contain palindromic sequences that can hybridize and a single strand can fold onto itself to form a DNA nanoball (DNB™) which can be approximately 200-300 nanometers in diameter on average. In certain examples, a DNA nanoball is attached (e.g., by adsorption) to a microarray (sequencing flow cell). In further examples, the flow cell is a silicon wafer coated with silicon dioxide, titanium and hexamethyldisilazane (HMDS) and a photoresist material. In some cases, sequencing is performed by unchained sequencing by ligating fluorescent probes to the DNA. In certain cases, the color of the fluorescence of an interrogated position is visualized by a high-resolution camera. In further cases, the identity of nucleotide sequences between adaptor sequences is determined.

In some cases, high-throughput sequencing is performed using AnyDot.chips (Genovoxx, Germany). In particular, the AnyDot.chips allow for 10×-50× enhancement of nucleotide fluorescence signal detection. AnyDot.chips and methods for using them are described in part in International Publication Application Nos. WO 02088382, WO 03020968, WO 03031947, WO 2005044836, PCT/EP 05/05657, PCT/EP 05/05655; and German Patent Application Nos. DE 101 49 786, DE 102 14 395, DE 103 56 837, DE 10 2004 009 704, DE 10 2004 025 696, DE 10 2004 025 746, DE 10 2004 025 694, DE 10 2004 025 695, DE 10 2004 025 744, DE 10 2004 025 745, and DE 10 2005 012 301.

Other high-throughput sequencing systems include those disclosed in Venter, J., et al. Science 16 Feb. 2001; Adams, M. et al. Science 24 Mar. 2000; and M. J. Levene, et al. Science 299:682-686, January 2003; as well as US Publication Application No. 20030044781 and 2006/0078937. Overall such system involve sequencing a target nucleic acid molecule having a plurality of bases by the temporal addition of bases via a polymerization reaction that is measured on a molecule of nucleic acid, i.e. the activity of a nucleic acid polymerizing enzyme on the template nucleic acid molecule to be sequenced is followed in real time. In some cases, the sequence is deduced by identifying which base is being incorporated into the growing complementary strand of the target nucleic acid by the catalytic activity of the nucleic acid polymerizing enzyme at each step in the sequence of base additions. A polymerase on the target nucleic acid molecule complex is provided in a position suitable to move along the target nucleic acid molecule and extend the oligonucleotide primer at an active site. A plurality of labeled types of nucleotide analogs are provided proximate to the active site, with each distinguishable type of nucleotide analog being complementary to a different nucleotide in the target nucleic acid sequence. The growing nucleic acid strand is extended by using the polymerase to add a nucleotide analog to the nucleic acid strand at the active site, where the nucleotide analog being added is complementary to the nucleotide of the target nucleic acid at the active site. The nucleotide analog added to the oligonucleotide primer as a result of the polymerizing step is identified. The steps of providing labeled nucleotide analogs, polymerizing the growing nucleic acid strand, and identifying the added nucleotide analog are repeated so that the nucleic acid strand is further extended and the sequence of the target nucleic acid is determined.

Data Analysis and Scaffolding

The DNA sequences obtained herein are be analyzed to assign segment sequences to common molecules. Provided herein are methods for identifying sequence information that originated from the same original RNA molecule. The RNA molecule can be from a sample comprising a transcriptome. The methods herein can comprise assembling a plurality of reads into at least one RNA sequence. A plurality of reads generally comprises molecular tagging information that confers information regarding physical linkage or origination from a common RNA molecule. In some cases, a first sequence segment and a second sequence segment comprise the same label and are determined to have originated from the same RNA molecule. In some cases, more than two segments comprise the same label and are determined to have originated from the same RNA molecule. A first sequence segment and second sequence segment that are contained in the same read are often determined to have originated from the same RNA molecule.

In certain cases, the sequence information is used to assemble a sequence for at least a portion of an RNA molecule. In certain cases, the sequence information is used to identify some or all of the components of an RNA molecule, such as exons, that were present in the same RNA molecule. In some cases, the sequence information is used to identify some or all of the variations present in an RNA molecule relative to a reference sequence. In some cases, the reference sequence is a wild-type sequence, a cDNA, an EST, or a predicted transcript.

In some cases, the segment includes sequences encoding an entire exon that was present in the RNA molecule. In some cases, the segment includes a portion of an exon that was contained in the RNA molecule. In some aspects, a portion of an exon indicates the presence of a portion of or the presence of a complete exon in the RNA molecule.

A read pair can include sequence information for at least two segments of RNA. Each of the segments may include sequence information derived from an exon of the gene encoding the RNA transcript. In such cases, the two segments can allow for the identification of the two exons as being present in the original RNA molecule. One of the sequence segments can comprise a junction between one or more exons. In such cases, the junction in a single segment can allow for the identification of the two exons as being present in the original RNA molecule. The presence of two or more exons joined together in a single segment can indicate that the two exons were adjacent to each other in the original RNA molecule.

One of the segments can comprise a mutation. In some cases, at least two of the segments comprise mutations. In some cases, the mutation or mutations comprise a single nucleotide polymorphism, insertion, deletion, duplication, transposition, errors introduced by DNA damage repair mechanisms, and other types of mutations known in the art.

The methods described herein can be used to detect RNA variants comprising combinations of all of the categories of variants described herein, including variants comprising combinations of alternative splicing, mutations, RNA editing, etc.

In some cases, the sequence information is used to identify or determine the sequence of a complete RNA molecule. In some cases, the sequence information is used to assemble a plurality of contigs. In some aspects, contigs can be used to assemble the sequence of part of all of an RNA molecule.

In some aspects, the segments originating from a common RNA molecule are mapped to a cDNA sequence, open reading frame sequence, expected or predicted sequence, consensus sequence, or an untranslated region adjacent to a putative transcript. Such sequences can be known in the art or independently generated by methods known in the art.

Sequences identified by the methods described herein need not be complete sequences. In some aspects, sequences covering a portion of an RNA transcript can show correlations or linkage between the presence or absence of specific exons, splicing events, editing events, or mutations within the same RNA molecules even if the entire sequence of the RNA cannot be determined. For example, certain exons may not be present in the same mature mRNA molecule with high frequencies after splicing has occurred. Conversely, some exons may be present in the same molecule at high frequencies. Some mutations may correlate to the same allele more frequently than others, while other mutations may be present on separate alleles more frequently than they are found together. Results from the methods described herein can also be used to estimate the frequency or amounts of specific sequences, mutations, splicing events, etc., present in a sample.

Applications of Transcriptome Reconstruction

Identify Expression of Splice Variants

Alternative splicing allows the human genome to direct the synthesis of many more proteins than would be expected from its 20,000 protein-coding genes. Alternative splicing is a regulated process during gene expression that results in a single gene coding for multiple protein isoforms. One mechanism of alternative splicing involves exon skipping, wherein particular exons of a gene may be included within or excluded from the final, processed messenger RNA (mRNA) produced from that gene. Some exons may be mutually exclusive, and thus the final mRNA may retain one exon or the other, but not both. Some splicing events may be dependent on the occurrence of other splicing events. Some alternatively spliced variants can contain introns. Some alternatively spliced variants can be the result of alternative donor or acceptor sites.

Changes in the RNA processing machinery may lead to mis-splicing of multiple transcripts. Single-nucleotide alterations in splice sites or cis-acting splicing regulatory sites may lead to differences in splicing of a single gene, and thus in the mRNA produced from a mutant gene's transcripts. Consequently, the proteins translated from alternatively spliced mRNAs will contain differences in their amino acid sequence and, often, in their biological functions. Thus, information pertaining to individual RNA molecules can be informative of biological function and the processes that regulate which proteins are ultimately expressed from RNA transcripts. The methods and compositions described herein can be useful a tool in gathering such information from individual molecules rather than from populations as a whole and can therefore be more informative.

Medical Applications

Alternative splicing plays critical roles in normal development and can promote growth and survival in cancer. Aberrant splicing, including the production of noncanonical and cancer-specific mRNA transcripts, can lead to changes in biological functions necessary to prevent or suppress cancer. For example, loss-of-function in tumor suppressors due to changes in RNA splicing can affect a patient's prognosis. Likewise, activation of oncogenes and cancer pathways can be affected or caused by noncanonical and cancer-specific mRNA transcripts.

Aberrant splicing products and loss of canonically spliced variants can correlate with stage and progression in malignancy. Loss of fidelity, variation of the splicing process, and controlled switching to specific splicing alternatives may occur during tumor progression and could play a major role in carcinogenesis. Splice variants that are found predominantly in tumors can have clear diagnostic value and may provide potential drug targets. Moreover, understanding the process of aberrant splicing and the detailed characterization of the splice variants may prove crucial to our understanding of malignant transformation. The methods described herein can therefore assist in diagnosing, monitoring, determining a prognosis, stratifying patients, screening, and identifying treatment options for subjects with medical conditions caused by or correlated with alternative splicing, RNA editing, or mutations.

The methods of present disclosure can provide the advantage that many different target molecules are analyzed at one time from a single biomolecular sample. This allows, for example, for several diagnostic tests to be performed on one sample.

In one aspect, the methods and compositions of the present disclosure are used in genomics. In some cases, the methods described herein provide an answer rapidly, which is very desirable for this application. In some cases, the methods and composition described herein are used in the process of finding biomarkers that may be used for diagnostics and/or prognostics, and/or as indicators of health and disease, or as part of a pharmaceutical selection regime. In further cases, the methods and compositions described herein are used to screen for drugs, e.g., drug development, selection of treatment, determination of treatment efficacy and/or identify targets for pharmaceutical development. The ability to test gene expression on screening assays involving drugs is very important because proteins are the final gene product in the body. In some aspects, the methods and compositions described herein will measure both protein and gene expression, including variant expression, simultaneously, which will provide the most information regarding the particular screening being performed.

In another aspect, the methods and compositions of the disclosure are used in gene expression analysis. In some cases, the methods described herein are used to discriminate between nucleotide sequences. In some cases, the difference between the target nucleotide sequences is difference in alternative splicing, RNA editing, a single nucleic acid base difference, a nucleic acid deletion, a nucleic acid insertion, or a rearrangement. In further cases, such sequence differences involving more than one base are also detected. Such changes can be indicative of disease or can allow for the monitoring of disease over time.

In some cases, the present methods are applied to the analysis of biomolecular samples obtained or derived from a subject so as to determine whether a diseased cell type is present in the sample, the stage of the disease, the prognosis for the subject, the ability to the subject to respond to a particular treatment, or the best treatment for the subject. In further cases, the present methods are also applied to identify biomarkers for a particular disease, including monitoring biomarkers for a particular disease or disease state over time.

In another aspect, the methods described herein are used in the diagnosis of a condition. As used herein, the term "diagnose" or "diagnosis" of a condition may include predicting or diagnosing the condition, determining predisposition to the condition, monitoring treatment of the condition, diagnosing a therapeutic response of the disease, or prognosis of the condition, condition progression, or response to particular treatment of the condition. In some cases, a blood or tissue sample is assayed according to any of the methods described herein to determine the presence and/or quantity of markers of a disease or malignant cell type in the sample, thereby diagnosing or staging a disease or a cancer. In further examples, the methods and composition described herein are also used for the diagnosis and/or prognosis of a condition.

In numerous cases, immunologic, proliferative, and malignant diseases and disorders are amenable to the methods described herein. An exemplary disorder due to mutations in splicing machinery includes retinitis pigmentosa. Exemplary disorders due to changes in splicing include familial dysautonomia, frontotemporal lobar dementias/amyotrophic lateral sclerosis, Hutchinson-Gilford progeria syndrome, medium-chain acyl-CoA dehydrogenase (MCAD) deficiency, medium-chain acyl-CoA dehydrogenase (MCAD) deficiency, myotonic dystrophy, Prader-Willi syndrome, spinal muscular atrophy, and tauopathies. See Tazi, et al., Biochim Biophys Acta. 2009 January; 1792(1): 14-26, incorporated by reference herein.

Immunologic diseases and disorders include allergic diseases and disorders, disorders of immune function, and autoimmune diseases and conditions.

Malignant diseases and disorders that may be evaluated by the methods of the disclosure include both hematologic malignancies and solid tumors. In some cases, hematologic malignancies are amenable to the methods of the disclosure, especially when the sample is a blood sample, because such malignancies involve changes in blood-borne cells. Such malignancies include non-Hodgkin's lymphoma, Hodgkin's lymphoma, non-B cell lymphomas, and other lymphomas, acute or chronic leukemias, polycythemias, thrombocythemias, multiple myeloma, myelodysplastic disorders, myeloproliferative disorders, myelofibroses, atypical immune lymphoproliferations and plasma cell disorders. Plasma cell disorders that may be evaluated by the methods of the disclosure include multiple myeloma, amyloidosis and Waldenstrom's macroglobulinemia. Examples of solid tumors include, but are not limited to, colon cancer, breast cancer, lung cancer, prostate cancer, brain tumors, central nervous system tumors, bladder tumors, melanomas, liver cancer, osteosarcoma and other bone cancers, testicular and ovarian carcinomas, head and neck tumors, and cervical neoplasms.

In another aspect, the methods and compositions of the present disclosure are used to identify and/or quantify a target molecule whose abundance is indicative of a biological state or disease condition, for example, blood markers that are upregulated or downregulated as a result of a disease state.

In yet another aspect, the methods and compositions of the present disclosure is used for detecting cytokine expression. In some cases, the sensitivity of the methods described herein is helpful for early detection of cytokines, e.g., as biomarkers of a condition, diagnosis, or prognosis of a disease such as cancer, and the identification of subclinical conditions.

RNA Compositions

Also provided herein are compositions comprising complexes useful in the methods described herein. The compositions generally comprise at least two RNA segments bound to at least one RNA binding moiety. Some of the compositions comprise RNA segments that share a common phosphodiester backbone. Other compositions comprise fragments in which the shared common phosphodiester backbone is cleaved, but the segments remain bound to one another independent of the common phosphodiester backbone.

The RNA segments can comprise RNA variant sequences, including alternative splicing events, mutations, or the products of RNA editing.

The RNA binding moiety can be or can comprise any of the RNA binding moieties described herein, including the RNA binding proteins and nanoparticles described above. The RNA binding moiety can comprise an affinity tag, such as a polyhistidine tag or biotin.

The nucleic acid fragments of the composition generally comprises a label, such as a molecular identifier. The label can be a barcode. In some cases, the segment is labeled by virtue of being joined to another RNA segment. Segments can be joined together by ligation. Some segments may contain two or more variations within the distance of a single read pair.

In some cases, the compositions comprise nucleic acid fragments that do not have 5' phosphate groups. These complexes may have been treated with phosphatases to remove the 5' phosphate groups. In other cases, the nucleic acid fragments comprise 5' phosphate groups. These complexes may not have been treated with a phosphatase or may have been treated with a kinase, such as a T4 kinase.

The nucleic acid of the composition can comprise an adapter or a binding probe. The binding probes can be any known probe in the art, including but not limited to the probes disclosed in the present application. In some cases, the binding probes comprise feature oligonucleotides. In some cases, the feature oligonucleotides comprises one or more elements selected from the group consisting of a linker, a primer, a barcode, and a capture sequence. In certain examples, the feature oligonucleotides comprise a linker, a primer, a barcode and/or a capture sequence. Exemplary primers include P5 and P7 primers or primer sites. In some cases, the capture sequence can hybridize to the first sequence segment. In some cases, the resolved locus comprise a unique binding probe that is not found in any other resolved locus on the substrate.

The compositions provided herein also include libraries comprising a plurality of read pairs each comprising a first segment and a second segment, wherein the first segment is adjacent to the second segment on the read-pair, wherein the first and second segments of each pair originate from the same RNA molecule and wherein at least 1% of read-pairs comprise first and second segments that are not adjacent to each other on the original RNA molecule.

The libraries can be generated from original RNA molecules wherein the first segment and the second segment are at least 100, 125, 150, 200, 300, 400, 500, 1000, or more than 1000 base pairs apart from each other.

In some aspects, the present disclosure provides a composition comprising at least one aqueous droplet. In some cases, the aqueous droplet comprises an RNA comprising a first sequence segment and a second sequence segment. In some embodiments the RNA is not bound by any additional molecule, while in other embodiments the nucleic acid is bound by an RNA binding moiety configured so as to bind the first sequence segment and the second sequence segment. In many embodiments, the additional molecule is covalently bound to the nucleic acid molecule, for example by formaldehyde or psoralen. In some cases, the first sequence segment is linked to a first label and the second sequence segment is linked to a second label. In certain cases, the first segment is labeled with the second segment and the second segment is labeled with the first segment. In certain cases, the first label and the second label each comprise a barcode, which may be identical. In further cases, the first sequence segment and the second sequence segment can be linked to an adaptor oligonucleotide.

In certain cases, the aqueous droplet comprises a plurality of molecular tagged or barcoded oligonucleotides. In many cases, these molecularly tagged or barcoded oligonucleotide molecules have identical sequences. In further embodiments, the molecularly tagged or barcoded oligonucleotide molecules have identical molecular tag or barcode sequences. In other cases, the aqueous droplet comprises molecular tagged or barcoded oligonucleotides that sort into at least two populations, each population characterized by a distinct molecular tag or barcode sequence.

In some cases, the aqueous droplet is surrounded by an oil or an organic phase. In further cases, the aqueous droplet is within a microfluidic device. The aqueous droplet in many embodiments is surrounded by an immiscible layer to form a micelle or an immiscible bilayer to form a liposome.

Barcode Delivery to Nucleic Acids

Whole genome sequencing and assembly have become available to nearly every researcher by the advent of high-throughput next-generation sequencers. However, the challenge of obtaining high quality contiguous genome sequences has not been solved by this technology. Both de novo genome sequencing and assembly and obtaining haplotype phasing information are difficult to do using current sequencing methodologies.

De novo genomic assembly and phasing can be improved by incorporating long range DNA interaction data obtained by linking together distant nucleic acid sequences such as DNA and RNA sequences and tagging the junctions using integrases. One method to form these linkages is to assemble chromatin in vitro with genomic DNA and proteins such as histones. The assembled chromatin can then be cross-linked to fix long range interactions, and the sequence of the DNA found within each is identified. One way to identify DNA sequences in an aggregate is to digest the cross-linked DNA and ligate a first integrase recognition sequence to the cross-linked DNA. Barcodes are inserted into the first recognition sequence using a bead-bound second integrase recognition sequence carrying a barcode. The term "integrase recognition sequence" is used interchangeably herein with the term "integrase recognition site."

The present disclosure provides robust, cost-effective, and sample-efficient methods for producing long range sequence information, such as physical linkage information for assembled contigs, including contigs that are bound by repetitive, hard to assemble sequence regions. The methods disclosed herein address previous shortcomings while producing sequence information or physical linkage information over comparatively vast genomic distances (up to megabases) due to the stabilization offered by chromatin and cross-linking. Furthermore, the methods disclosed herein may be realized with numerous distinct platforms, each with strengths and weaknesses for particular applications or targeted outcomes.

The present disclosure provides methods for barcoding DNA sequences in a manner that preserves linkage information. The methods frequently involve introducing integration or recombination compatible DNA sequences to sample DNA molecules without losing linkage information such that sample DNA sequences can be identified as originating from the same molecule. Exemplary methods include the use of chromatin aggregates, transposases, or other methods to insert integrase recognitions sites into sample DNA while retaining linkage information. The methods are also compatible with the use of native integration or recombination compatible sites found within sample DNA sequences. Knowledge of all DNA sequences within a molecule would prove more powerful and accurate de novo genome assembly. A method for the identifying DNA sequences in a sample molecule can be achieved by attaching a label (e.g. a barcode) to the sequences found within or the fragments generated from the molecule, such as a chromatin aggregate. DNA sequencing of the labeled DNA may reveal the nature of these sequences and help group them together according to the barcode attached to them. The methods often include cleaving a longer sample DNA molecule into individual fragments, inserting the integration or recombination compatible sequences, and joining many of the fragments back together while the fragments are retained as part of a cross-linked aggregate. The methods also include inserting the integration or recombination compatible sequences into the sample DNA molecule directly, including through the use of transposases. The present disclosure provides methods and compositions for inserting integration or recombination-compatible sites to DNA molecules found within a sample.

The present disclosure also provides methods for carrying out massively-parallel barcoding of individual DNA molecules. The methods include binding the newly-introduced or native recombination or integration-compatible DNA sequences to a compatible site on a molecule labeled with a barcode. Often, libraries of barcode aggregates (also referred to as "barcode balls") each comprising multiple copies of a common barcode tag are used to attach barcode tags to the DNA fragments. Barcodes can also be attached to other forms of solid supports, such as chips, as well as emulsions and microdroplets. The barcodes can sometimes be unique for each barcode aggregate, but can also be less than unique so long as they allow for the identification of molecules with a common origin. The barcodes are capable of identifying the fragments in a manner that identifies the common origin of DNA fragments.

The present disclosure also describes methods of cleaving the barcoded fragments to generate shorter fragments that are compatible with a variety of sequencing methods. Some of the enzymes described herein include nucleolytic activity. Many of the enzymes described herein, including many of the integrases, cleave the molecules at the inserted DNA sequences during the recombination or integration process. Other examples can include the use of restriction endonucleases to cleave the enzymes at inserted restrictions sites to generate smaller fragments.

Methods of Delivering a Barcode to a Nucleic Acid Sample

Disclosed herein are methods of delivering a barcode to a nucleic acid sample. Some such methods often comprise: ligating a first polynucleotide comprising a first integrase recognition sequence to a genomic DNA sample; annealing the first integrase recognition sequence-genomic DNA to a second polynucleotide comprising a second integrase recognition sequence and a barcode; contacting the annealed first and second integrase recognition sequences with an integrase under conditions that support integrase activity; and isolating the recombined genomic DNA-barcode fragments. Such barcode labeled nucleic acid samples typically further comprise at least one sequencing primer binding site, such as P5, P7, T7, SP6, T3, or other primer sequences known in the art. The resulting nucleic acid is ready for amplification and sequencing having a label that is specific to its molecule of origin. The label allows for accurate phasing information to be obtained and for the detection of mutations or other variations within an allele without many of the challenges presented by the short read lengths inherent in today's sequencing technologies.

The methods disclosed herein are frequently used with currently employed sequencing technology. In some cases, the methods are used in combination with well-tested and/or widely deployed sequencing instruments. The methods disclosed herein are also useful with technologies and approaches derived from currently employed sequencing technology.

The methods disclosed herein can dramatically simplify de novo genomic assembly for a wide range of organisms. Using previous technologies, such assemblies are limited by the short inserts of economical mate-pair libraries. Some current methods generate read pairs at genomic distances up to the 40-50 kbp, such as methods using fosmids. These techniques are often expensive and cumbersome. The reads are also still too short to span the longest repetitive stretches, including sequences found within centromeres, which in humans range in size from 300 kbp to 5 Mbp. The methods disclosed herein often provide read pairs capable of spanning large distances (e.g., megabases or longer) and thereby overcome these scaffold integrity challenges. Accordingly, producing chromosome-level assemblies may be routine by utilizing the methods disclosed herein. Similarly, the acquisition of long-range phasing information can provide tremendous additional power to population genomic, phylogenetic, and disease studies. In certain cases, the methods disclosed herein enable accurate phasing for large numbers of individuals, thus extending the breadth and depth of our ability to probe genomes at the population and deep-time levels.

In the realm of personalized medicine, the barcoded read-sets generated from the methods disclosed herein represent a meaningful advance toward accurate, low-cost, phased, and rapidly produced personal genomes. Previous methods are insufficient in their ability to phase variants at long distances, thereby preventing the characterization of the phenotypic impact of compound heterozygous genotypes. Additionally, structural variants of substantial interest for genomic diseases are difficult to accurately identify and characterize with previous techniques due to their large size in comparison to the reads and read inserts used to study them. Read-sets spanning tens of kilobases to megabases or longer can help alleviate this difficulty, thereby allowing for highly parallel and personalized analyses of structural variation.

Basic evolutionary and biomedical research can be driven by technological advances in high-throughput sequencing. It is now relatively inexpensive to generate massive quantities of DNA sequence data. However, it is difficult to produce high-quality, highly contiguous genome sequences with previous technologies. Further, many organisms, including humans, are diploid, wherein each individual has two haploid copies of the genome. At sites of heterozygosity (e.g. where the allele given by the mother differs from the allele given by the father), it is difficult to know which sets of alleles came from which parent (known as haplotype phasing). This information can be critically important for performing a number of evolutionary and biomedical studies such as disease and trait association studies.

The present disclosure provides methods for genome assembly that combine technologies for DNA preparation with tagged sequence reads for high-throughput discovery of short, intermediate, and long-term connections corresponding to sequence reads from a single physical nucleic acid molecule bound to a complex such as a chromatin complex within a given genome. The disclosure further provides methods using these connections to assist in genome assembly, for haplotype phasing, and/or for metagenomic studies. While the methods presented herein can be used to determine the assembly of a subject's genome, it should also be understood that in certain cases the methods presented herein are used to determine the assembly of portions of the subject's genome such as chromosomes, or the assembly of the subject's chromatin of varying lengths. It should also be understood that, in certain cases, the methods presented herein are used to determine or direct the assembly of non-chromosomal nucleic acid molecules. Indeed, any nucleic acid the sequencing of which is complicated by the presence of repetitive regions separating non-repetitive contigs may be facilitated using the methods disclosed herein.

The methods disclosed herein frequently comprise the step of generating a plurality of contigs from sequencing fragments of target DNA obtained from a subject. In some cases, long stretches of target DNA are fragmented by cutting the DNA with one or more restriction enzymes, incompletely digesting the DNA with one or more nonspecific endonucleases, shearing the DNA, or a combination thereof. The resulting fragments are sequenced using high throughput sequencing methods to obtain a plurality of sequencing reads. Cases of high throughput sequencing methods which are used with the methods of the disclosure include, but are not limited to, pyrosequencing methods, "clusters" sequencing methods, SOLiD™ and Ion semiconductor sequencing methods, and DNA nanoball sequencing methods. The overlapping ends of different sequencing reads are then assembled to form a contig.

In other cases, fragmented target DNA is cloned into vectors. Cells or organisms are then transfected with the DNA vectors to form a library. After replicating the transfected cells or organisms, the vectors are isolated and sequenced to generate a plurality of sequencing reads. The overlapping ends of different sequencing reads are then assembled to form a contig.

Alternately or in combination with the above, the methods disclosed herein can be used with contig information previously generated. Contig information for a vast number of genomes, including the human genome, is publicly available (see, for example, sequence available at the National Center for Biotechnology Information, the Joint Genome Institute, the Eukaryotic Pathogen Database, or any number of species-specific genome web pages). Rather than generating contig information de novo, or in combination with de novo generated contig data, the methods disclosed herein may be used to assist in the chromosomal assembly, ordering and orientation of these previously generated contigs.

Genome assembly can be problematic, especially with high-throughput sequencing technology. The assembly often consists of thousands or tens of thousands of short contigs. The order and orientation of these contigs is generally unknown, limiting the usefulness of the genome assembly. Previous technologies for orienting these scaffolds often fail in discovering very long-range interactions.

A tissue or a DNA sample from a subject can be provided and the methods can return an assembled genome, alignments with called variants (including large structural variants), phased variant calls, and/or any additional analyses. The methods disclosed herein can provide barcoded libraries for the subject.

Provided herein are methods of generating contigs and assigning linkage information to sequences from DNA molecules in a sample. The sample is often obtained from a subject by any number of means, including by taking bodily fluids (e.g., blood, urine, serum, lymph, saliva, anal and vaginal secretions, perspiration, and semen), taking tissue, or by collecting cells/organisms. The sample obtained may be comprised of a single type of cell/organism, or may be comprised multiple types of cells/organisms. The DNA is frequently extracted and prepared from the subject's sample. For example, the sample are treated to lyse a cell comprising the polynucleotide, using known lysis buffers, sonication techniques, electroporation, and the like. In some cases, a sample is treated with an enzyme to isolate the nucleic acids from the sample without damaging long nucleic acids or chromatin structure. In further cases, the target DNA is further purified to remove contaminants, such as proteins, by using alcohol extractions, cesium gradients, and/or column chromatography.

In further cases, the methods disclosed herein allow for accurate and predictive results for genotype assembly, haplotype phasing, and metagenomics with small amounts of materials. In some cases, less than about 0.1 µg, about 0.2 µg, about 0.3 µg, about 0.4 µg, about 0.5 µg, about 0.6 µg, about 0.7 µg, about 0.8 µg, about 0.9 µg, about 1.0 µg, about 1.2 µg, about 1.4 µg, about 1.6 µg, about 1.8 µg, about 2.0 µg, about 2.5 µg, about 3.0 µg, about 3.5 µg, about 4.0 µg, about 4.5 µg, about 5.0 µg, about 6.0 µg, about 7.0 µg, about 8.0 µg, about 9.0 µg, about 10 µg, about 15 µg, about 20 µg, about 30 µg, about 40 µg, about 50 µg, about 60 µg, about 70 µg, about 80 µg, about 90 µg, about 100 µg, about 150 µg, about 200 µg, about 300 µg, about 400 µg, about 500 µg, about 600 µg, about 700 µg, about 800 µg, about 900 µg, or about 1000 µg of DNA is used with the methods disclosed herein. In some cases, the DNA used in the methods disclosed herein is extracted from less than about 1,000,000, about 500,000, about 200,000, about 100,000, about 50,000, about 20,000, about 10,000, about 5,000, about 2,000, about 1,000, about 500, about 200, about 100, about 50, about 20, or about 10 cells.

Methods to extract very high molecular weight DNA are also provided. The data from a barcoded library is sometimes improved by increasing the fragment size of the input DNA. Extracting megabase-sized fragments of DNA from a cell often produces read-sets comprising reads separated by megabases in the genome. For example, the read-sets can provide sequence information over a span of greater than about 10 kB, about 50 kB, about 100 kB, about 200 kB, about 500 kB, about 1 Mb, about 2 Mb, about 5 Mb, about 10 Mb, or about 100 Mb. The read-sets can also provide sequence information over a span of greater than about 500 kB. In further cases, the read-sets provide sequence information over a span of greater than about 2 Mb. In some cases, the very high molecular weight DNA is extracted by very gentle cell lysis (Teague, B. et al. (2010) Proc. Nat. Acad. Sci. USA 107(24), 10848-53) and agarose plugs (Schwartz, D. C., & Cantor, C. R. (1984) Cell, 37(1), 67-75). Commercially available machines that can purify DNA molecules up to megabases in length can also be used to extract very high molecular weight DNA.

In various cases, the methods disclosed herein are used to produce read-sets comprising reads that are separated by large distances. The upper limit of this distance may be improved by the ability to collect DNA samples of large size. In some cases, the reads are separated by up to 50, 60, 70, 80, 90, 100, 125, 150, 175, 200, 225, 250, 300, 400, 500, 600, 700, 800, 900, 1000, 1500, 2000, 2500, 3000, 4000, 5000 kbp, or more in genomic distance. In some cases, the reads are separated by up to 500 kbp in genomic distance. In other cases, the reads are separated by up to 2000 kbp in genomic distance. The methods disclosed herein can integrate and build upon standard techniques in molecular biology, and are further well-suited for increases in efficiency, specificity, and genomic coverage. In some cases, the read-sets are generated in less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 60, or 90 days. In some cases, the read-sets are generated in less than about 14 days. In further cases, the read-sets are generated in less than 10 days. In some cases, the methods of the present disclosure provide greater than about 5%, about 10%, about 15%, about 20%, about 30%, about 40%, about 50%, about 60%, about 70%, about 80%, about 90%, about 95%, about 99%, or about 100% of the read pairs with at least about 50%, about 60%, about 70%, about 80%, about 90%, about 95%, about 99%, or about 100% accuracy in correctly ordering and/or orientating the plurality of contigs. In some cases, the methods provide about 90 to 100% accuracy in correctly ordering and/or orientating the plurality of contigs.

The methods disclosed herein can comprise probing the physical layout of chromosomes within living cells. The methods sometimes utilize the fixation of chromatin in live cells to cement spatial relationships in the nucleus. Subsequent processing and sequencing of the products allows for recovery of a matrix of proximate associations among genomic regions. With further analysis, these associations can be used to produce a three-dimensional geometric map of the chromosomes as they are physically arranged in live nuclei. Such techniques describe the discrete spatial organization of chromosomes in live cells, and provide an accurate view of the functional interactions among chromosomal loci. The nonspecific intrachromosomal interactions are frequently captured by the methods presented herein so as to provide valuable information for assembly.

DNA Complex Formation

The present disclosure provides methods for barcoding DNA sequences in a manner that preserves linkage information. The methods frequently involve introducing integration or recombination compatible DNA sequences to sample DNA molecules without losing linkage information such that sample DNA sequences can be identified as originating from the same molecule. The methods disclosed herein frequently take advantage of the ability to cross-link sequences segments, such as in endogenous or reconstituted chromatin or other protein-polynucleotide complexes, in a way that physically connects different parts of a longer polynucleotide through chemical linkage. When the cross-linked polynucleotide complexes are formed, the polynucleotide is in a compact and stable cross-linked form and behaves as a polymer unit, which can be manipulated without fear of shearing the polynucleotide. The methods disclosed herein often label these cross-linked polynucleotide complexes using a bead comprising a plurality of barcoded oligonucleotides in order to identify polynucleotide fragments that are related by physical linkage and/or proximity. This information can be useful for applications such as genomic assembly and/or haplotype phasing.

The methods provided herein can comprise forming a complex comprising a nucleic acid and a nucleic acid binding agent. The formation of such complexes can facilitate probing the physical layout of chromosomes or other large DNA molecules.

In certain cases, the sample DNA molecule comprises a first sequence segment and a second sequence segment. The first and second sequence segments are often cross-linked within a cell. In some cases, the first sequence segment and the second sequence segment are part of chromatin obtained from whole cell or nuclear extracts. In other cases, the first sequence segment and the second sequence segment are cross-linked outside of a cell. In still further cases, polynucleotides can be isolated and cross-linked in vitro. In further examples, the crosslinking is performed using photo-irradiation methods (e.g. UV irradiation) or chemical agents (e.g. formaldehyde).

The first sequence segment and the second sequence segment can be cross-linked to a plurality of association molecules, also referred to herein as DNA binding moieties. In some cases, the association molecules comprise amino acids. Some such association molecules comprise peptides or proteins (e.g. histones). In other cases, the association molecules comprise a nanoparticle. Exemplary nanoparticles include a platinum-based nanoparticle. The nanoparticle is sometimes a DNA intercalator, or any derivatives thereof. In further examples, the nanoparticle is a bisintercalator, or any derivatives thereof. Nanoparticles can also be magnetic, which may facilitate the isolation of the cross-linked sequence segments. The association molecules can be from a different source than the first DNA molecule. For example, the first DNA molecule can be from a first human subject, whereas the association molecules can be from a second human subject. As another example, the first DNA molecule is from a mammal (e.g. human), whereas the association molecules are from another eukaryotic organism. In further examples, the first DNA molecule is from a plant cell or a prokaryote, whereas the association molecules are from a eukaryotic organism.

The methods disclosed herein are often used with chromatin isolated from a cell/organism, or with reconstituted chromatin. Reconstituted chromatin is differentiated from chromatin formed within a cell/organism over various features. First, for many samples, the collection of naked DNA samples can be achieved by using a variety of noninvasive to invasive methods, such as by collecting bodily fluids, swabbing buccal or rectal areas, taking epithelial samples, etc.

Second, reconstituting chromatin substantially prevents the formation of inter-chromosomal and other long-range interactions that generate artifacts for genome assembly and haplotype phasing. A sample sometimes has less than about 20, 15, 12, 11, 10, 9, 8, 7, 6, 5, 4, 3, 2, 1, 0.5, 0.4, 0.3, 0.2, 0.1%, or less inter-chromosomal or intermolecular crosslinking according to the methods and compositions of the disclosure. Alternatively, the sample has less than about 5% inter-chromosomal or intermolecular crosslinking. Alternatively, the sample has less than about 3% inter-chromosomal or intermolecular crosslinking. In further cases, the sample has less than about 1% inter-chromosomal or intermolecular crosslinking.

Third, the frequency of sites that are capable of cross-linking and thus the frequency of intramolecular crosslinks within the polynucleotide can be adjusted. For example, the ratio of DNA to histones can be varied, such that the nucleosome density is adjusted to a desired value. In some cases, the nucleosome density is reduced below the physiological level. Accordingly, the distribution of crosslinks can be altered to favor longer-range interactions. In some embodiments, sub-samples with varying cross-linking density may be prepared to cover both short- and long-range associations. In some cases, the crosslinking conditions is adjusted such that at least about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 40%, about 45%, about 50%, about 60%, about 70%, about 80%, about 90%, about 95%, or about 100% of the crosslinks occur between DNA segments that are at least about 50 kb, about 60 kb, about 70 kb, about 80 kb, about 90 kb, about 100 kb, about 110 kb, about 120 kb, about 130 kb, about 140 kb, about 150 kb, about 160 kb, about 180 kb, about 200 kb, about 250 kb, about 300 kb, about 350 kb, about 400 kb, about 450 kb, or about 500 kb apart on the sample DNA molecule. Often, the crosslinking is reversible. In certain cases, the crosslinking is reversed using heat. In other cases, the crosslinking is reversed using a chemical agent such as thiourea.

The basic structural unit of chromatin is the nucleosome, which consists of 146 base pairs (bp) of DNA wrapped around a histone octamer. The histone octamer consists of two copies each of the core histone H2A-H2B dimers and H3-H4 dimers. Nucleosomes are regularly spaced along the DNA in what is commonly referred to as "beads on a string".

The assembly of core histones and DNA into nucleosomes is mediated by chaperone proteins and associated assembly factors. Nearly all of these factors are core histone-binding proteins. Some of the histone chaperones, such as nucleosome assembly protein-1 (NAP-1), exhibit a preference for binding to histones H3 and H4. It has also been observed that newly synthesized histones are acetylated and then subsequently deacetylated after assembly into chromatin. The factors that mediate histone acetylation or deacetylation therefore play an important role in the chromatin assembly process.

At least two in vitro methods have been developed for reconstituting or assembling chromatin. One method is ATP-independent, while the second is ATP-dependent. The ATP-independent method for reconstituting chromatin involves the DNA and core histones plus either a protein like NAP-1 or salt to act as a histone chaperone. This method results in a random arrangement of histones on the DNA that does not accurately mimic the native core nucleosome particle in the cell. These particles are often referred to as mononucleosomes because they are not regularly ordered, extended nucleosome arrays and the DNA sequence used is usually not longer than 250 bp (Kundu, T. K. et al., Mol. Cell 6: 551-561, 2000). To generate an extended array of ordered nucleosomes on a greater length of DNA sequence, the chromatin must be assembled through an ATP-dependent process.

The ATP-dependent assembly of periodic nucleosome arrays, which are similar to those seen in native chromatin, requires the DNA sequence, core histone particles, a chaperone protein and ATP-utilizing chromatin assembly factors. ACF (ATP-utilizing chromatin assembly and remodeling factor) or RSF (remodeling and spacing factor) are two widely researched assembly factors that are used to generate extended ordered arrays of nucleosomes into chromatin in vitro (Fyodorov, D. V., and Kadonaga, J. T. Method Enzymol. 371: 499-515, 2003; Kundu, T. K. et al. Mol. Cell 6: 551-561, 2000).

As previously described, the methods disclosed herein can be used with DNA associated to nanoparticles. In further cases, the nanoparticles are positively charged. In some cases, the nanoparticles are coated with amine groups, and/or amine-containing molecules. In certain cases, the DNA and the nanoparticles aggregate and condense. In further cases, the nanoparticle-bound DNA is induced to aggregate in a fashion that mimics the ordered arrays of biological nucleosomes (e.g. chromatin). In some cases, the nanoparticle is a platinum-based nanoparticle. In other cases, the nanoparticle is a DNA intercalator, or any derivatives thereof. In further cases, the nanoparticle is a bisintercalator, or any derivatives thereof. In some cases, the nanoparticle-based method is less expensive, faster to assemble, provide a better recovery rate than using reconstituted chromatin, and/or allow for reduced DNA input requirements.

A number of factors can be varied to influence the extent and form of condensation including the concentration of nanoparticles in solution, the ratio of nanoparticles to DNA, and the size of nanoparticles used. In some cases, the nanoparticles is added to the DNA at a concentration greater than about 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 15 ng/mL, 20 ng/mL, 25 ng/mL, 30 ng/mL, 40 ng/mL, 50 ng/mL, 60 ng/mL, 70 ng/mL, 80 ng/mL, 90 ng/mL, 100 ng/mL, 120 ng/mL, 140 ng/mL, 160 ng/mL, 180 ng/mL, 200 ng/mL, 250 ng/mL, 300 ng/mL, 400 ng/mL, 500 ng/mL, 600 ng/mL, 700 ng/mL, 800 ng/mL, 900 ng/mL, 1 µg/mL, 2 µg/mL, 3 µg/mL, 4 µg/mL, 5 µg/mL, 6 µg/mL, 7 µg/mL, 8 µg/mL, 9 µg/mL, 10 µg/mL, 15 µg/mL, 20 µg/mL, 25 µg/mL, 30 µg/mL, 40 µg/mL, 50 µg/mL, 60 µg/mL, 70 µg/mL, 80 µg/mL, 90 µg/mL, 100 µg/mL, 120 µg/mL, 140 µg/mL, 160 µg/mL, 180 µg/mL, 200 µg/mL, 250 µg/mL, 300 µg/mL, 400 µg/mL, 500 µg/mL, 600 µg/mL, 700 µg/mL, 800 µg/mL, 900 µg/mL, 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 15 mg/mL, 20 mg/mL, 25 mg/mL, 30 mg/mL, 40 mg/mL, 50 mg/mL, 60 mg/mL, 70 mg/mL, 80 mg/mL, 90 mg/mL, or 100 mg/mL. In some cases, the nanoparticles is added to the DNA at a concentration less than about 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 15 ng/mL, 20 ng/mL, 25 ng/mL, 30 ng/mL, 40 ng/mL, 50 ng/mL, 60 ng/mL, 70 ng/mL, 80 ng/mL, 90 ng/mL, 100 ng/mL, 120 ng/mL, 140 ng/mL, 160 ng/mL, 180 ng/mL, 200 ng/mL, 250 ng/mL, 300 ng/mL, 400 ng/mL, 500 ng/mL, 600 ng/mL, 700 ng/mL, 800 ng/mL, 900 ng/mL, 1 µg/mL, 2 µg/mL, 3 µg/mL, 4 µg/mL, 5 µg/mL, 6 µg/mL, 7 µg/mL, 8 µg/mL, 9 µg/mL, 10 µg/mL, 15 µg/mL, 20 µg/mL, 25 µg/mL, 30 µg/mL, 40 µg/mL, 50 µg/mL, 60 µg/mL, 70 µg/mL, 80 µg/mL, 90 µg/mL, 100 µg/mL, 120 µg/mL, 140 µg/mL, 160 µg/mL, 180 µg/mL, 200 µg/mL, 250 µg/mL, 300 µg/mL, 400 µg/mL, 500 µg/mL, 600 µg/mL, 700 µg/mL, 800 µg/mL, 900 µg/mL, 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 15 mg/mL, 20 mg/mL, 25 mg/mL, 30 mg/mL, 40 mg/mL, 50 mg/mL, 60 mg/mL, 70 mg/mL, 80 mg/mL, 90 mg/mL, or 100 mg/mL. In some cases, the nanoparticles is added to the DNA at a weight-to-weight (w/w) ratio greater than about 1:10000, 1:5000, 1:2000, 1:1000, 1:500, 1:200, 1:100, 1:50, 1:20, 1:10, 1:5, 1:2, 1:1, 2:1, 5:1, 10:1, 20:1, 50:1, 100:1, 200:1, 500:1, 1000:1, 2000:1, 5000:1, or 10000:1. In some cases, the nanoparticles is added to the DNA at a weight-to-weight (w/w) ratio less than about 1:10000, 1:5000, 1:2000, 1:1000, 1:500, 1:200, 1:100, 1:50, 1:20, 1:10, 1:5, 1:2, 1:1, 2:1, 5:1, 10:1, 20:1, 50:1, 100:1, 200:1, 500:1, 1000:1, 2000:1, 5000:1, or 10000:1. In some cases, the nanoparticles have a diameter greater than about 1 nm 1 nm, 2 nm, 3 nm, 4 nm, 5 nm, 6 nm, 7 nm, 8 nm, 9 nm, 10 nm, 15 nm, 20 nm, 25 nm, 30 nm, 40 nm, 50 nm, 60 nm, 70 nm, 80 nm, 90 nm, 100 nm, 120 nm, 140 nm, 160 nm, 180 nm, 200 nm, 250 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, 10 µm, 15 µm, 20 µm, 25 µm, 30 µm, 40 µm, 50 µm, 60 µm, 70 µm, 80 µm, 90 µm, or 100 µm. In some cases, the nanoparticles have a diameter less than about 1 nm 1 nm, 2 nm, 3 nm, 4 nm, 5 nm, 6 nm, 7 nm, 8 nm, 9 nm, 10 nm, 15 nm, 20 nm, 25 nm, 30 nm, 40 nm, 50 nm, 60 nm, 70 nm, 80 nm, 90 nm, 100 nm, 120 nm, 140 nm, 160 nm, 180 nm, 200 nm, 250 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, 10 µm, 15 µm, 20 µm, 25 µm, 30 µm, 40 µm, 50 µm, 60 µm, 70 µm, 80 µm, 90 µm, or 100 µm.

Furthermore, the nanoparticles may be immobilized on solid substrates (e.g. beads, slides, or tube walls) by applying magnetic fields (in the case of paramagnetic nanoparticles) or by covalent attachment (e.g. by cross-linking to poly-lysine coated substrate). Immobilization of the nanoparticles may improve the ligation efficiency thereby increasing the number of desired products (signal) relative to undesired (noise).

Cross-links are frequently created between genome regions that are in close physical proximity. Crosslinking of proteins (e.g. histones) to the DNA molecule (e.g. genomic DNA), within chromatin is accomplished according to a suitable method described in further detail elsewhere herein or otherwise known in the art. Two or more nucleotide sequences can often be cross-linked via proteins bound to one or more nucleotide sequences. One approach is to expose the chromatin to ultraviolet irradiation (Gilmour et al., Proc. Nat'l. Acad. Sci. USA 81:4275-4279, 1984). Crosslinking of polynucleotide segments may also be performed utilizing other approaches, such as chemical or physical (e.g. optical) crosslinking. Suitable chemical cross-linking agents include, but are not limited to, formaldehyde and psoralen (Solomon et al., Proc. Natl. Acad. Sci. USA 82:6470-6474, 1985; Solomon et al., Cell 53:937-947, 1988). For example, cross-linking can be performed by adding a solution comprising about 2% formaldehyde to a mixture comprising the DNA molecule and chromatin proteins. Other cases of agents that are used to cross-link DNA include, but are not limited to, UV light, mitomycin C, nitrogen mustard, melphalan, 1,3-butadiene diepoxide, cis diaminedichloroplatinum(II) and cyclophosphamide. In further cases, the cross-linking agent forms cross-links that bridge relatively short distances-such as about 2 Å—thereby selecting intimate interactions that can be reversed.

The DNA molecule is immunoprecipitated prior to or after crosslinking in some methods. For example, the DNA molecule can be fragmented into two or more sequence segments. In further cases, sequence segments are contacted with a binding partner, such as an antibody that specifically recognizes and binds to acetylated histones, e.g., H3. Cases of such antibodies include, but are not limited to, Anti Acetylated Histone H3, available from Upstate Biotechnology, Lake Placid, N.Y. In some cases, the polynucleotides from the immunoprecipitate are subsequently collected from the immunoprecipitate. In some cases, prior to fragmenting the polynucleotide, the acetylated histones are cross-linked to adjacent polynucleotide sequences.

DNA Fragmentation

Among the methods disclosed herein, some methods include cleaving the DNA sample into smaller fragments in order to insert compatible recognition sequences. The recognition sequences can be ligated to the ends of these fragments and, in some cases, the fragments can be joined to other fragments with intervening recognition sequences. Fragmentation techniques are known in the art and include, for example, shearing, chemical, and enzymatic techniques to generate smaller genomic fragments. As used herein, the terms "fragment", "segment", or "sequence segment" can refer to a piece of polynucleotide derived or prepared from an original, larger nucleic acid molecule.

Fragmentation can be accomplished using established methods for fragmenting chromatin, including, for example, sonication, shearing, contacting with enzymes or other chemicals having nonspecific endonuclease activity and/or the use of restriction enzymes. One exemplary advantage of the methods disclosed herein is the ability to select a fragmentation method that is suited for a particular application, experiment, or sequencing method. For example, a restriction enzyme can then be selected based on the desired criteria and expected fragment characteristics or distribution. Among those characteristics is the predicted average fragment length or a distribution of fragment lengths. More specifically, in experiments in which longer fragments are desired, a restriction enzyme with relatively fewer predicted cut sites can be selected. Similarly, a restriction enzyme with relatively more frequent cut sites can be selected when shorter fragments are desired. Likewise, a restriction enzyme can also be selected based on the desired frequency of barcode insertions using the same concepts.

In some cases, the restriction enzyme has a restriction recognition site of 1, 2, 3, 4, 5, 6, 7, 8, or more than 8 bases long. Examples of restriction enzymes include, but are not limited to, AatII, Acc65I, AccI, AciI, AclI, AcuI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeGI, BaeI, BamHI, BanI, BanII, BbsI, BbvCI, BbvI, BccI, BceAI, BcgI, BciVI, BclI, BfaI, BfuAI, BfuCI, BglI, BglII, BlpI, BmgBI, BmrI, BmtI, BpmI, Bpu10I, BpuEI, BsaAI, BsaBI, BsaHI, BsaI, BsaJI, BsaWI, BsaXI, BscRI, BscYI, BsgI, BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, Cac8I, ClaI, CspCI, CviAII, CviKI-1, CviQI, DdeI, DpnI, DpnII, DraI, DraIII, DrdI, EacI, EagI, EarI, EciI, Eco53kI, EcoNI, EcoO109I, EcoP15I, EcoRI, EcoRV, FatI, FauI, Fnu4HI, FokI, FseI, FspI, HaeII, HaeIII, HgaI, HhaI, HincII, HindIII, HinfI, HinPII, HpaI, HpaII, HphI, Hpy166II, Hpy188I, Hpy188III, Hpy99I, HpyAV, HpyCH4III, HpyCH4IV, HpyCH4V, KasI, KpnI, MboI, MboII, MfeI, MluI, MlyI, MmeI, MnlI, MscI, MseI, MslI, MspA1I, MspI, MwoI, NaeI, NarI, Nb.BbvCI, Nb.BsmI, Nb.BsrDI, Nb.BtsI, NciI, NeoI, NdeI, NgoMIV, NheI, NlaIII, NlaIV, NmeAIII, NotI, NruI, NsiI, NspI, Nt.AlwI, Nt.BbvCI, Nt.BsmAI, Nt.BspQI, Nt.BstNBI, Nt.CviPII, PacI, PaeR7I, PciI, PflFI, PflMI, PhoI, PleI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScaI, ScrFI, SexAI, SfaNI, SfcI, SfiI, SfoI, SgrAI, SmaI, SmlI, SnaBI, SpeI, SphI, SspI, StuI, StyD4I, StyI, SwaI, T, TaquI, TfiI, TliI, TseI, Tsp45I, Tsp509I, TspMI, TspRI, Tth111I, XbaI, XcmI, XhoI, XmaI, XmnI, and ZraI. The resulting sequence segments can vary in size. The resulting sequence segments may also comprise a single-stranded overhand at the 5' or 3' end.

In some embodiments, using sonication techniques, sequence segments of about 100 to 5000 nucleotides are obtained. Alternatively, sequence segments of about 100 to 1000, about 150 to 1000, about 150 to 500, about 200 to 500, or about 200 to 400 nucleotides are obtained. The sample can be prepared for sequencing the cross-linked sequence segments. In some cases, sequence segments that were intramolecularly cross-linked are labeled with a common label. The common label can then be detected and analyzed to determine sequence segments that were intramolecularly cross-linked. The common label can, for example, be a barcode, which can optionally be detected by sequencing methods. In some cases, the reads of sequence segments labeled with a common label are binned into a read-set.

In some cases, a nucleic acid sample is incompletely fragmented such that multiple copies of homologous nucleic acids are fragmented differentially with respect to one another, in some cases resulting in overlapping fragments having identical sequence in their positions of overlap but having non-identical molecular ends. In some cases, molecular tagged sequences that map to each individual molecular fragment, such as overlapping sequence spanning at least one polymorphism that may differ among homologous chromosome pairs. In such cases, by comparing the sequence at the position that may differ among homologous chromosome pairs, one may determine whether the overlapping sequences represent sequence from the sample phase that is the same physically linked chromosome or original nucleic acid of the sample.

Further, the range of the associated sequence segments generated by the disclosure can be extended to span much larger genomic distances. The assembly can be produced from a standard shotgun library in addition to a library of associated sequence segments (i.e. a read-set). In some cases, the sequence segments are associated based on a label. In further cases, the sequence segments labeled with a common label are associated to one another, and optionally binned together to form a "read-set". In some cases, the label is a barcode sequence.

Further, the range of the associated sequence segments generated by the disclosure can be extended to span much larger genomic distances. The assembly can be produced from a standard shotgun library in addition to a library of associated sequence segments (i.e. a read-set). In some cases, the sequence segments are associated based on a label. In further cases, the sequence segments labeled with a common label are associated to one another, and optionally binned together to form a "read-set". In some cases, the label is a barcode sequence.

Generation of Polynucleotides Comprising Sample DNA Fragments and Integrase Recognition Sequences In one aspect, the present disclosure provides methods of delivering a molecular tag, like a barcode, to a nucleic acid sample. The molecular tags can allow multiple fragments of a common molecule to be sequenced and identified as originating from the common molecule. The sequences of fragments identified as originating from the common molecule can then be reassembled into a longer sequence.

Some of the methods described herein utilize integrases to mediate barcode addition to sample DNA fragments. In some cases, the method comprises: a. ligating a first polynucleotide comprising a first integrase recognition sequence to a genomic DNA sample; b. annealing the first integrase recognition sequence ligated to the genomic DNA sample to a second polynucleotide comprising a second integrase recognition sequence and a barcode; c. contacting the annealed integrase recognition sequences to an integrase under conditions that support integrase activity; and d. isolating the resulting polynucleotide, which comprises a barcoded genomic or sample DNA fragment.

The DNA sample that is often bound to a DNA binding moiety, as described in the present disclosure, is severed by any known method in the art, including, but not limited to, the chemical, enzymatic, and mechanical fragmentation methods disclosed in the present disclosure. As previously described, a crosslinked polynucleotide and DNA binding moiety complex is in a compact and stable cross-linked form and behaves as a polymer unit. The DNA molecule in the complex can be fragmented and rearranged by retaining the fragments in close proximity. Thus, two segments that may be up to megabases apart on the nonfragmented molecule can be brought into closer proximity by rearrangement. The rearranged fragments can be ligated to each other and to the first polynucleotides comprising the first integrase recognition sequences while still bound in the complex. Thus, the complex can preserve the physical linkage, phase, and proximity information in the ligated molecules, which can later be determined using the compositions and methods described herein.

In some cases, the genomic DNA sample comprises a first segment end and a second segment end. In some cases, the first segment end and the second segment end comprise overhang sequences. In other cases, the first segment end and the second segment end comprise blunt ends. Samples comprising a mixture of blunt and overhanging ends are also contemplated. In some cases, the overhang sequences are filled in to generate blunt ends (e.g. using a DNA polymerase). In some cases, the overhangs are filled in by modified nucleotides, such as sulfated or biotinylated nucleotides. In some cases, the overhang sequences are cut with an exonuclease to generate blunt ends.

In some cases, the first polynucleotide comprising a first integrase recognition sequence is ligated to the first segment end.

In some cases, the first polynucleotide comprises a first integrase recognition sequence, which is capable of exchange with a second polynucleotide comprising a second integrase sequence and a barcode in the presence of an integrase. Thus, the first integrase recognition sequence generally allows an integrase to attach a barcode to the adjacent sample DNA using recombination. In some cases, the first polynucleotide comprising the first integrase recognition sequence is ligated to both the first segment end and the second segment end. It can be desirable to have long chains of fragments and first polynucleotides comprising the first integrase recognition sequence ligated together. In some cases, the ligation produces nucleic acids comprising 2, 3, 4, 5, 6, 7, 8, 9, 10, 11, 12, 13, 14, 15 or more sample DNA fragments. In some cases, the ligation produces nucleic acids comprising 2, 3, 4, 5, 6, 7, 8, 9, 10, 11, 12, 13, 14, 15 or more first polynucleotides comprising the first integrase recognition sequence. Each fragment ligated to a first polynucleotide can potentially be labeled with a barcode after recombination. The chains of fragments and first integrase recognition sites allow fragments originating from the same DNA molecule, and presumably bound in the same complex of crosslinked DNA and DNA binding moieties, to be barcoded with the same molecular tag as described below.

Integrase recognition sequences are known in the art. For example, attB can recombine with attP, attR can recombine with attL, attB' can recombine with attP', and attR' can recombine with attL'. Thus, various combinations of first and second integrase recognition sequences can be used in the disclosed methods and compositions.

In some cases, the first polynucleotide further comprises at least one primer binding site, such as a sequencing primer binding site. In cases where the first polynucleotide comprises the at least one sequencing primer binding site, the sequencing primer binding site is generally exchanged with the sample DNA fragment during the integrase-mediated recombination steps described below. Examples of primer binding sites are described below.

In some cases, the 5' and/or 3' end nucleotide sequences of fragmented polynucleotides are not modified prior to ligation. In some cases, fragmentation by a restriction endonuclease is used to leave a predictable overhang, followed by ligation with a nucleic acid end comprising an overhang complementary to the predictable overhang on a polynucleotide fragment. In other examples, cleavage by an enzyme that leaves a predictable blunt end is followed by ligation of blunt-ended polynucleotide fragments to nucleic acids, such as the first polynucleotide comprising a first integrase recognition sequence described above, although other adapters, oligonucleotides, or polynucleotides comprising a blunt end are also contemplated. In some embodiments, the fragmented polynucleotide is blunt-end polished (or "end repaired") to produce DNA fragments having blunt ends, prior to being joined to the polynucleotides described above. In some cases, the blunt-end polishing step is accomplished by incubation with a suitable enzyme, such as a DNA polymerase that has both 3' to 5' exonuclease activity and 5' to 3' polymerase activity, for example T4 polymerase. In some embodiments, end repair is followed by an addition of 1, 2, 3, 4, 5, 6, 7, 8, 9, 10, 11, 12, 13, 14, 15, 16, 17, 18, 19, 20 or more nucleotides, such as one or more adenine, one or more thymine, one or more guanine, or one or more cytosine, to produce an overhang. In certain examples, the end repair is followed by an addition of 1, 2, 3, 4, 5, or 6 nucleotides.

In certain cases, polynucleotide fragments having an overhang are joined to one or more nucleic acids, such as the first polynucleotide comprising a first integrase recognition sequence described above, or other oligonucleotides, adapter oligonucleotides, or polynucleotides, having a complementary overhang, such as in a ligation reaction. In some cases, a single adenine is added to the 3' ends of end repaired DNA fragments using a template independent polymerase, followed by ligation to one or more adapters each having a thymine at a 3' end. In some cases, nucleic acids, such as oligonucleotides or polynucleotides is joined to blunt end double-stranded DNA molecules which have been modified by extension of the 3' end with one or more nucleotides followed by 5' phosphorylation. In some cases, extension of the 3' end is performed with a polymerase such as, Klenow polymerase or any of the suitable polymerases provided herein, or by use of a terminal deoxynucleotide transferase, in the presence of one or more dNTPs in a suitable buffer that can contain magnesium.

In some cases, polynucleotide fragments having blunt ends are joined to one or more recombinant polynucleotides, including a first integrase recognition sequence comprising a blunt end. In certain examples, phosphorylation of 5' ends of DNA fragment molecules is performed for example with T4 polynucleotide kinase in a suitable buffer containing ATP and magnesium. In further cases, the fragmented DNA molecules are treated to dephosphorylate 5' ends or 3' ends, for example, by using enzymes known in the art, such as phosphatases.

As used herein, with respect to two polynucleotides such as polynucleotides comprising the first integrase recognition sequence and a target polynucleotide, such as a DNA fragment from the sample or genome of interest, the terms "connecting", "joining" or "ligating" can refer to the covalent attachment of two separate nucleic acid segments to produce a single larger polynucleotide with a contiguous backbone. Methods for joining two nucleic acid segments are known in the art, and include without limitation, enzymatic and non-enzymatic (e.g. chemical) methods. Examples of ligation reactions that are non-enzymatic include the non-enzymatic ligation techniques described in U.S. Pat. Nos. 5,780,613 and 5,476,930, each of which is herein incorporated by reference in its entirety. In some embodiments, an adapter oligonucleotide is joined to a target polynucleotide by a ligase, for example a DNA ligase or RNA ligase. Multiple ligases, each having characterized reaction conditions, are known in the art, and include, without limitation NAD$^+$-dependent ligases including tRNA ligase, Taq DNA ligase, *Thermus filiformis* DNA ligase, *Escherichia coli* DNA ligase, Tth DNA ligase, *Thermus scotoductus* DNA ligase (I and II), thermostable ligase, Ampligase thermostable DNA ligase, VanC-type ligase, 9° N DNA Ligase, Tsp DNA ligase, and novel ligases discovered by bioprospecting; ATP-dependent ligases including T4 RNA ligase, T4 DNA ligase, T3 DNA ligase, T7 DNA ligase, Pfu DNA ligase, DNA ligase 1, DNA ligase III, DNA ligase IV, and novel ligases discovered by bioprospecting; and wild-type, mutant isoforms, and genetically engineered variants thereof.

In some cases, ligation is between nucleic acid segments having hybridizable sequences, such as complementary overhangs. In certain cases, ligation is between two blunt ends. In many cases, a 5' phosphate is utilized in a ligation reaction. In various cases, the 5' phosphate is provided by the target polynucleotide, the adapter oligonucleotide, or both. In further cases, 5' phosphates are added to or removed from sequence segments to be joined, as needed. Methods for the addition or removal of 5' phosphates are known in the art, and include without limitation enzymatic and chemical processes. Enzymes useful in the addition and/or removal of 5' phosphates include kinases, phosphatases, and polymerases. In some cases, both of the two ends joined in a ligation reaction (e.g. an adapter end and a target polynucleotide end) provide a 5' phosphate, such that two covalent linkages are made in joining the two ends. In other cases, only one of the two ends joined in a ligation reaction (e.g. only one of an adapter end and a target polynucleotide end) provides a 5' phosphate, such that only one covalent linkage is made in joining the two ends.

In some cases, only one strand at one or both ends of a target polynucleotide is joined to an adapter oligonucleotide. In other cases, both strands at one or both ends of a target polynucleotide are joined to an adapter oligonucleotide. In some cases, 3' phosphates are removed prior to ligation. In some cases, an adapter oligonucleotide is added to both ends of a target polynucleotide, wherein one or both strands at each end are joined to one or more adapter oligonucleotides. In certain cases, when both strands at both ends are joined to an adapter oligonucleotide, joining is followed by a cleavage reaction that leaves a 5' overhang that can serve as a template for the extension of the corresponding 3' end, which 3' end may or may not include one or more nucleotides derived from the adapter oligonucleotide. In some cases, a target polynucleotide is joined to a first adapter oligonucleotide on one end and a second adapter oligonucleotide on the other end. In other cases, two ends of a target polynucleotide are joined to the opposite ends of a single adapter oligonucleotide. In some cases, the target polynucleotide and the adapter oligonucleotide to which it is joined comprise blunt ends. In some cases, separate ligation reactions are carried out for each sample, using a different first adapter oligonucleotide comprising at least one barcode sequence for each sample, such that no barcode sequence is joined to the target polynucleotides of more than one sample. A sequence segment or a polynucleotide that has an adapter oligonucleotide joined to it is considered "tagged" by the joined adapter.

In some cases, the ligation reaction is performed at a sequence segment or polynucleotide concentration of about less than about 0.1 ng/µL, about 0.2 ng/µL, about 0.3 ng/µL, about 0.4 ng/µL, about 0.5 ng/µL, about 0.6 ng/µL, about 0.7 ng/µL, about 0.8 ng/µL, about 0.9 ng/µL, about 1.0 ng/µL, about 1.2 ng/µL, about 1.4 ng/µL, about 1.6 ng/µL, about 1.8 ng/µL, about 2.0 ng/µL, about 2.5 ng/µL, about 3.0 ng/µL, about 3.5 ng/µL, about 4.0 ng/µL, about 4.5 ng/µL, about 5.0 ng/µL, about 6.0 ng/µL, about 7.0 ng/µL, about 8.0 ng/µL, about 9.0 ng/µL, about 10 ng/µL, about 15 ng/µL, about 20 ng/µL, about 30 ng/µL, about 40 ng/µL, about 50 ng/µL, about 60 ng/µL, about 70 ng/µL, about 80 ng/µL, about 90 ng/µL, about 100 ng/µL, about 150 ng/µL, about 200 ng/µL, about 300 ng/µL, about 400 ng/µL, about 500 ng/µL, about 600 ng/µL, about 800 ng/µL, or about 1000 ng/µL. In some cases, the ligation reaction is performed at a sequence segment or polynucleotide concentration of about greater than about 0.1 ng/µL, about 0.2 ng/µL, about 0.3 ng/µL, about 0.4 ng/µL, about 0.5 ng/µL, about 0.6 ng/µL, about 0.7 ng/µL, about 0.8 ng/µL, about 0.9 ng/µL, about 1.0 ng/µL, about 1.2 ng/µL, about 1.4 ng/µL, about 1.6 ng/µL, about 1.8 ng/µL, about 2.0 ng/µL, about 2.5 ng/µL, about 3.0 ng/µL, about 3.5 ng/µL, about 4.0 ng/µL, about 4.5 ng/µL, about 5.0 ng/µL, about 6.0 ng/µL, about 7.0 ng/µL, about 8.0 ng/µL, about 9.0 ng/µL, about 10 ng/µL, about 15 ng/µL, about 20 ng/µL, about 30 ng/µL, about 40 ng/µL, about 50 ng/µL, about 60 ng/µL, about 70 ng/µL, about 80 ng/µL, about 90 ng/µL, about 100 ng/µL, about 150 ng/µL, about 200 ng/µL, about 300 ng/µL, about 400 ng/µL, about 500 ng/µL, about 600 ng/µL, about 800 ng/µL, or about 1000 ng/µL. In some cases, the ligation is performed at a sequence segment or polynucleotide concentration of about 100 ng/µL, about 150 ng/µL, about 200 ng/µL, about 300 ng/µL, about 400 ng/µL, or about 500 ng/µL. In further examples, the ligation reaction is performed at a sequence segment or polynucleotide concentration of about 0.1 to 1000 ng/µL, about 1 to 1000 ng/µL, about 1 to 800 ng/µL, about 10 to 800 ng/µL, about 10 to 600 ng/µL, about 100 to 600 ng/µL, or about 100 to 500 ng/µL.

In some cases, the ligation reaction is performed for more than about 5 minutes, about 10 minutes, about 20 minutes, about 30 minutes, about 40 minutes, about 50 minutes, about 60 minutes, about 90 minutes, about 2 hours, about 3 hours, about 4 hours, about 5 hours, about 6 hours, about 8 hours, about 10 hours, about 12 hours, about 18 hours, about 24 hours, about 36 hours, about 48 hours, or about 96 hours. In certain cases, the ligation reaction is performed for less than about 5 minutes, about 10 minutes, about 20 minutes, about 30 minutes, about 40 minutes, about 50 minutes, about 60 minutes, about 90 minutes, about 2 hours, about 3 hours, about 4 hours, about 5 hours, about 6 hours, about 8 hours, about 10 hours, about 12 hours, about 18 hours, about 24 hours, about 36 hours, about 48 hours, or about 96 hours. In some cases, the ligation reaction is performed for about 30 minutes to about 90 minutes. In certain examples, joining of an adapter to a polynucleotide produces a joined polynucleotide having a 3' overhang comprising a nucleotide sequence derived from the adapter.

Once the DNA fragments and first polynucleotides comprising the first integrase recognition sequence have been ligated together, the crosslinking is reversed in certain cases and the DNA binding moieties can be removed. In certain cases, the crosslinking is reversed using heat. In other cases, the crosslinking is reversed using a chemical agent, such as thiourea. Crosslinking can also be reversed using enzymes, such as proteases, including proteinase K.

The integrase recognition sites need not be added recombinantly. Also provided herein are methods of using native integrase recognition sequences found in the DNA sample itself to mediate barcoding.

The use of transposons to add integrase recognition sites is also encompassed in various embodiments of the methods and compositions described herein. For example, transposons can include specific recombination or integrase sites, which can then be inserted into sample DNA using transposases. Some methods using transposons do not require the use of DNA binding moieties in order to retain linkage and phase information.

This process yields rearranged polynucleotides comprising fragments of sample DNA and first integrase recognition sequences.

Barcoding Nucleic Acids Using Integrases

The polynucleotides comprising a fragment of sample DNA and at least one first integrase recognition sequence described above can be barcoded by annealing the first integrase recognition sequence to a second polynucleotide comprising a second integrase recognition sequence and a barcode and exchanging the integrase recognition sequences. The process results in the sample DNA being joined to the barcode. Barcodes can be unique to a particular bead, solid support, or molecule of origination. However, the methods disclosed herein can also identify segments arising from common or different molecules even when barcodes are not unique. For example, segments tagged with the same barcodes that map to different chromosomes can often be identified as originating from different molecules, especially when chromosomal translocations can be ruled out. Likewise, segments that map to loci that are longer than the longest predicted molecule in a sample can often be identified as originating from different molecules. Thus, while the use of unique barcodes is contemplated herein, the re-use of the same barcode sequences on a plurality of beads or chips is also contemplated herein, as is the ability to distinguish between a plurality of molecules with different origins binding to the same bead or chip. The methods described herein can identify such events with confidence.

The compositions and methods described herein have several exemplary advantages. For example, the steps of rearranging fragments originating from the same sample DNA molecules and ligating those fragments to the first polynucleotide can be done in parallel in the same reaction tube for potentially millions or billions of fragments without the need for complicated microfluidic devices. Another exemplary advantage is that the first polynucleotide comprising the first integrase recognition sequence can be the same for every molecule in the ligation reaction because the barcode is delivered in a subsequent step. These advantages can save both time and money, as the methods can generally be performed without forming individual emulsions.

As previously described, the second polynucleotide comprising the second integrase recognition sequence generally also comprises a barcode. As used herein, the term "barcode" or "molecular tag" refers to a known nucleic acid sequence that allows some feature of a polynucleotide with which the barcode is associated to be identified. For example, the feature of the polynucleotide to be identified can be the sample from which the polynucleotide is derived. In another example, the feature of the polynucleotide to be identified can be that the polynucleotide originated from the same molecule as other polynucleotides contained within the same sample. This includes identifying or determining that a plurality of DNA fragments or segments originated from the same chromosome or the same allele.

The barcodes are frequently at least 3, 4, 5, 6, 7, 8, 9, 10, 11, 12, 13, 14, 15, or more nucleotides in length. Sometimes, barcodes are at least 10, 11, 12, 13, 14, or 15 nucleotides in length. In other situations, the barcodes are shorter than 10, 9, 8, 7, 6, 5, or 4 nucleotides in length. The barcodes are often shorter than 10 nucleotides in length. The barcodes associated with some polynucleotides are of different length than barcodes associated with other polynucleotides.

In general, barcodes are of sufficient length and comprise sequences that are sufficiently different to allow the identification of samples based on barcodes with which they are associated. In some embodiments, a barcode, and the sample source with which it is associated, are identified accurately after the mutation, insertion, or deletion of one or more nucleotides in the barcode sequence, such as the mutation, insertion, or deletion of 1, 2, 3, 4, 5, 6, 7, 8, 9, 10, or more nucleotides. In some cases, 1, 2 or 3 nucleotides are mutated, inserted and/or deleted. In some embodiments, each barcode in a plurality of barcodes differ from every other barcode in the plurality at least two nucleotide positions, such as at least 2, 3, 4, 5, 6, 7, 8, 9, 10, or more positions. In some cases, each barcode differs from every other barcode by at least 2, 3, 4 or 5 positions.

In some embodiments, both a first site and a second site comprise at least one of a plurality of barcode sequences. In some embodiments, barcodes for second sites are selected independently from barcodes for first adapter oligonucleotides. In some embodiments, first sites and second sites having barcodes are paired, such that sequences of the pair comprise the same or different one or more barcodes. In some embodiments, the methods of the disclosure further comprise identifying the sample or molecule of origin from which a target polynucleotide is derived based on a barcode sequence to which the target polynucleotide is joined. In general, a barcode may comprise a nucleic acid sequence that, when joined to a target polynucleotide, serves as an identifier of the sample or molecule of origin from which the target polynucleotide was derived.

In some embodiments, the second polynucleotide comprising the second integrase recognition sequence and the barcode is attached to a bead. Often, the bead comprises a plurality of such second polynucleotides affixed to its surface. The barcodes of each of the polynucleotides attached to the bead can be the same or different so long as the target DNA sequences that ultimately get tagged with the barcodes can be traced back as originating from the same DNA molecule. The methods generally use a population of beads to increase the throughput of the labeling. As a result, each bead can have a bead-specific barcode or set of barcodes. The barcodes present on each bead can also be unique to that individual bead within the population of beads.

In some cases, the second polynucleotide comprises a linear chain of barcodes and second integrase recognition sequences. In some such cases, the second polynucleotide can be part of a population of second polynucleotides, each of which can recombine with a linear chain of target DNA fragments ligated to first integrase recognition sequences.

As a result, in some cases the first polynucleotide comprising a plurality of DNA fragments and a plurality of first integrase recognition sequences, such as those generated using the methods and compositions described above, can anneal to a plurality of second polynucleotides each containing a single second integrase recognition sequence on a bead, or a plurality of second recognition sequences in a second polynucleotide comprising a linear chain of barcodes and second integrase recognition sequences. These exchanges can result in the fragments of the first polynucleotide being labeled with the same barcode. This allows the fragments to be identified as having originated from the same sample DNA molecule, such as the same chromosome.

In some cases, the second polynucleotide further comprises at least one primer binding sequence, such as a sequencing primer binding sequence, such as P5, P7, T7, SP6, T3, or other primer sequences known in the art.

Recognition Sequences

The methods described herein use recombinant DNA sequences to mediate the delivery of barcodes. Some of these sequences are capable of mediating recombination events. For example, some of the sequences are integrase recognition sequences. Such sequences are specific to and targeted by a recombinase, such as an integrase, in order to effect strand exchange between the first integrase recognition sequence and the second integrase recognition sequence. Integrase recognition sequences are known in the art. For example, attB can recombine with attP, attR can recombine with attL, attB' can recombine with attP', and attR' can recombine with attL'. Thus, various combinations of first and second integrase recognition sequences can be used in the disclosed methods and compositions.

As an example, a first integrase recognition sequence, such as an attB sequence, is ligated to digested genomic DNA as chromatin or reconstituted chromatin. The second integrase recognition sequence, such as an attP sequence, is synthesized as a polynucleotide having a barcode and an adaptor sequence, such as a primer binding sequence. The attB and attP sequences are chosen that are most efficiently recognized by the integrase. The attB and attP sequences are exchanged or recombined to insert a barcode into the ligated donor sequence.

Exemplary attB sequences include but are not limited to GGGTGCCAGGGCGTGCCCTTGGGCTCCCCGGGCGCGTA (SEQ ID NO: 2).

Exemplary attP sequences herein include but are not limited to CCCCAACTGGGGTAACCTTTGAGTTCTCTCAGTTGGGG (SEQ ID NO: 3).

Integrases

Methods herein utilize enzymes with endonuclease activity to mediate the exchange of DNA sequences between the first polynucleotide and the second polynucleotide. Some such enzymes include recombinases, restriction enzymes, and transposases. Integrases can also promote strand exchange between a first polynucleotide comprising a first integrase recognition sequence and a second polynucleotide comprising a second integrase recognition sequence. In some cases, the first polynucleotide is ligated to a genomic DNA sample. In some cases, the second polynucleotide comprises a barcode and at least one primer binding sequence. The integrase enzymatically causes an exchange between the integrase recognition sequences, which can join the genomic DNA sample to the barcode and at least one primer binding sequence. The joining generally comprises ligating a portion of the first polynucleotide containing the DNA sample to a portion of the second polynucleotide containing the barcode and the primer binding sequence.

Integrases are enzymes which catalyze recombination between specific DNA sequences. Various integrases serve the function of site-specific integration of exogenous DNA into a host genome. Integrases can be selected based on desired properties. For example, some integrases introduce double-stranded breaks in between segments after recombination occurs. These breaks may be desirable when breaking chains of fragments into individually barcoded fragments is desirable. For example, some sequencing methods may be preferably used with shorter, individually barcoded fragments.

Integrases include but are not limited to bacteria integrons, bacteriophage integrases, and retroviral integrases. Each integrase acts upon a specific sequence or sequences that are referred to herein as integrase recognition sequences or integrase recognition sites, described below. In some cases, the integrase comprises a bacteriophage integrase. In some cases, the integrase comprises a φC31 integrase. In some cases, the integrase is a serine integrase. In some cases, the integrase is a single polypeptide integrase. In some cases, the integrase has no detectable excision activity. In some cases, the integrase is a retrovirus integrase. In some cases, the integrase is selected from one or more of an HIV-1 integrase, an HIV-2 integrase, a SIV integrase, and an RSV integrase. In some cases, the integrase comprises a φBT1, TG1, Bxb1, R4, φMR11, φRv1, TP901-1, or A118 integrase. In some cases, the integrase is a φC31 integrase and the specific sequence is an attB and attP sequence. In some cases, a recombinant directionality factor (RDF) is used in addition to the integrase. For example, in some cases the RDF facilitates the recombination of attR and attL sites. Exemplary RDFs include Bxb1 gp47 and φC31 gp3.

Integrases herein are isolated and purified, in some cases, using recombinant DNA techniques. In some cases, the integrase is purified from a host cell expressing an exogenous integrase gene, such as a φC31 integrase gene. In some cases, the integrase is encoded by a codon-optimized nucleic acid sequence encoding the amino acid sequence MDTYAGAYDRQSRERENSSAASPATQRSANED-KAADLQREVERDGGRFRFVGHFSEAP GTSAFG-TAERPEFERILNECRAGRLNMIIVYDVSRFSRLKVM-DAIPIVSELLALGVTIVSTQ EGVFRQGNVMDL-IHLIMRLDASHKESSLKSAKILDTKNLQRELG-GYVGGKAPYGFELVS ETKEITRNGRMVNVVINK-LAHSTTPLTGPFEFEPDVIRWWWREIKTHKHL-PFKPGSQAAI HPGSITGLCKRMDADAVPTRGET-IGKKTASSAWDPATVMRILRDPRIAGFAAEVIYKKK PDGTPTTKIEGYRIQRDPITLRPVELDCGPIIEPAEW-YELQAWLDGRGRGKGLSRGQAILS AMDK-LYCECGAVMTSKRGEESIKDSYRCRRRKVVDP-SAPGQHEGTCNVSMAALDKFV AERIFNKIRHA-EGDEETLALLWEAARRFGKLTEAPEKSGERANL-VAERADALNALEELY EDRAAGAYDGPVGRKH-FRKQQAALTLRQQGAEERLAELEAAEAPKLPLDQ-WFPEDAD ADPTGPKSWWGRASVDDKRVFVGLFVD-KIVVTKSTTGRGQGTPIEKRASITWAKPPTDD DED-DAQDGTEDVAA (SEQ ID NO: 1).

The methods optionally include cleaving the barcoded fragments to generate shorter fragments that are compatible with a variety of sequencing methods. Some of the enzymes described herein include nucleolytic activity. Many of the enzymes described herein, including many of the integrases, cleave the molecules at the inserted DNA sequences during the recombination or integration process. Other examples can include the use of restriction endonucleases to cleave the enzymes at inserted restrictions sites to generate smaller fragments. The method can be tailored to fragment the barcoded segments into a plurality of fragments that possess a desired size or a desired distribution of fragments sizes. Such characteristics may be useful in optimizing a library for a particular method of DNA sequencing. As such, integrases or restriction enzymes can be selected that produce the desired outcomes, as described above.

Once the integrase catalyzes the exchange between the two polynucleotides and the sample DNA is barcoded, the barcoded DNA can be separated from the bead. One method includes melting a strand of the barcoded DNA away from the bead using methods known in the art, including heat. Other methods include cleaving the DNA from the solid support, for example, by using a restriction enzyme or chemically-mediated cleavage of a linker binding the DNA to the solid support.

As a result, the polynucleotides produced by the methods described herein can include a fragment of sample DNA, a barcode, and at least one primer binding sequence. The second polynucleotide sometimes comprises a first primer binding sequence at a first end and a second primer binding sequence at a second end. In such cases, the polynucleotides that result from the recombination of the first and second polynucleotides can include the fragment of sample DNA and the barcode located between the first primer binding sequence and the second primer binding sequence. This can enable the sequencing of the sample fragment and barcode by the methods described herein.

Enrichment

The disclosure further provides methods for the enrichment and/or analysis of nucleic acids. In some cases, the first or the second polynucleotide comprises an affinity tag that is integrated into the recombined, barcoded sample DNA polynucleotide generated by the methods disclosed herein. The affinity tag can allow for the purification or enrichment of those polynucleotides that have undergone a recombination event. This purification or enrichment can reduce the amount or number of sample fragments that did not receive a barcode in the library, and thus make the sequencing and analysis steps more efficient.

In some cases, the enrichment method is a solution-based format. In certain cases, the nucleic acid is labeled with an affinity tag, such as a labeling agent. In various cases, the nucleic acid is cross-linked to one or more association molecules that are labeled with a labeling agent. Examples of labeling agents include but are not limited to biotin, polyhistidine tags, and chemical tags (e.g. alkyne and azide derivatives used in Click Chemistry methods). In further cases, the labeled target nucleic acid is captured and thereby enriched by using a capturing agent. In some cases, the capturing agent is streptavidin and/or avidin, an antibody, a chemical moiety (e.g. alkyne, azide), or any biological, chemical, physical, or enzymatic agents used for affinity purification known in the art.

In some cases, immobilized or non-immobilized nucleic acid probes are used to capture the nucleic acids. In some cases, the polynucleotides are enriched from a sample by hybridization to the probes on a solid support or in solution. In some cases, the sample is a genomic sample. In some cases, the probes comprise an amplicon. In further examples, the amplicon comprises a predetermined sequence. In further cases, the hybridized nucleic acids can be washed and/or eluted off of the probes. In some cases, the nucleic acid is a DNA, RNA, cDNA, or mRNA molecule.

In some cases, the enrichment method comprises contacting the sample comprising the nucleic acid to the probes and binding the nucleic acid to a solid support. In some cases, the sample is fragmented using chemical, physical, or enzymatic methods to yield the nucleic acids. In some cases, the probes are specifically hybridized to the nucleic acids. In some cases, the nucleic acids have an average size of about 50 to 5000, about 50 to 2000, about 100 to 2000, about 100 to 1000, about 200 to 1000, about 200 to 800, or about 300 to 800, about 300 to 600, or about 400 to 600 nucleotide residues. In further cases, the nucleic acids are separated from the unbound nucleic acids in the sample. In certain examples, the solid support are washed and/or eluted to provide the enriched nucleic acids. In some cases, the enrichment steps are repeated for about 1, 2, 3, 4, 5, 6, 7, 8, 9, or 10 times. In further examples, the enrichment steps are repeated for about 1, 2, or 3 times.

In some cases, the enrichment method comprises providing probe-derived amplicons wherein the probes for amplification are attached to a solid support. In some cases, the solid support comprises support-immobilized nucleic acid probes to capture specific polynucleotides from a sample. In certain examples, the probe derived amplicons can hybridize to the nucleic acids. In certain cases, following hybridization to the probe amplicons, the nucleic acids in the sample are enriched by capturing (e.g., via capturing agents as biotin, antibodies, etc.) and washing and/or eluting the hybridized nucleic acids from the captured probes. In further cases, the nucleic acid sequence(s) is amplified using, for example, PCR methods to produce an amplified pool of enriched PCR products.

In some cases, the solid support is a microarray, a slide, a chip, a microwell, a column, a tube, a particle, or a bead. In some cases, the solid support is coated with streptavidin and/or avidin. In some cases, the solid support is coated with an antibody. In further examples, the solid support comprises a glass, metal, ceramic or polymeric material. In some embodiments, the solid support is a nucleic acid microarray (e.g. a DNA microarray). In other embodiments, the solid support is a paramagnetic bead.

In certain cases, the enrichment method comprises digestion with a secondary restriction enzyme, self-ligation (e.g. self-circularization), and re-digestion with the original restriction enzyme. In some cases, the ligation products are linearized and available for adapter-ligation and sequencing. In other examples, the ligation junction sequence itself is used for hybridization-based enrichment using a bait-probe complimentary to the junction sequence.

Amplification

As used herein, the term "amplification" refers to any process by which the copy number of a nucleic acid sequence is increased. The disclosure further provides methods for amplifying polynucleotides. In some cases, the polynucleotides comprise a label. The labeled polynucleotide(s) can be obtained by the methods of the present disclosure.

In some cases, the one or more amplification and/or replication steps are used for the preparation of a library or read-set to be sequenced. Any amplification method known in the art may be used. Examples of amplification techniques that can be used include, but are not limited to, quantitative PCR, quantitative fluorescent PCR (QF-PCR), multiplex fluorescent PCR (MF-PCR), real time PCR (RTPCR), single cell PCR, restriction fragment length polymorphism PCR (PCR-RFLP), PCK-RFLPIRT-PCR-IRFLP, hot start PCR, nested PCR, in situ polony PCR, in situ rolling circle amplification (RCA), bridge PCR, ligation mediated PCR, Qb replicase amplification, inverse PCR, picotiter PCR, and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR), and nucleic acid-based sequence amplification (NABSA). Other amplification methods that can be used herein include those described in U.S. Pat. Nos. 5,242,794; 5,494,810; 4,988,617; and 6,582,938.

In some cases, an amplification reaction produces only a single complimentary copy/replica of a polynucleotide. Methods for primer-directed amplification of target polynucleotides are known in the art, and include without limitation, methods based on the polymerase chain reaction (PCR). In some cases, the polynucleotides comprise both a forward and a reverse sequencing primer binding site (e.g. a first and a second primer binding site). In some cases, the polynucleotides comprise a first sequencing primer binding site and a second sequencing primer binding site is added by using primer comprising a randomized primer portion and a second sequencing primer binding site. In such cases, the randomized primer can bind to the barcoded DNA fragment and the second sequencing primer binding site can be introduced into the PCR product by extension.

Exemplary sequencing primer binding sites include primer binding sites for P5, P7, T7, SP6, or T3 primers, or other primer sequences known in the art.

Conditions favorable to the amplification of target sequences by PCR are known in the art, can be optimized at a variety of steps in the process, and depend on characteristics of elements in the reaction, such as target type, target concentration, sequence length to be amplified, sequence of the target and/or one or more primers, primer length, primer concentration, polymerase used, reaction volume, ratio of one or more elements to one or more other elements, and others, some or all of which can be altered. In general, PCR involves the steps of denaturation of the target to be amplified (if double stranded), hybridization of one or more primers to the target, and extension of the primers by a DNA polymerase, with the steps repeated (or "cycled") in order to amplify the target sequence. Steps in this process can be optimized for various outcomes, such as to enhance yield, decrease the formation of spurious products, and/or increase or decrease specificity of primer annealing. Methods of optimization are well known in the art and include adjustments to the type or amount of elements in the amplification reaction and/or to the conditions of a given step in the process, such as temperature at a particular step, duration of a particular step, and/or number of cycles.

Each of the first and second primers may be of any suitable length, such as about, less than about, or more than about 10, 15, 20, 25, 30, 35, 40, 45, 50, 55, 60, 65, 70, 75, 80, 90, 100, or more nucleotides, any portion or all of which may be complementary to the corresponding target sequence (e.g. about, less than about, or more than about 5, 10, 15, 20, 25, 30, 35, 40, 45, 50, or more nucleotides). In some cases, about 10 to 50 nucleotides is complementary to the corresponding target sequence.

In some embodiments, an amplification reaction comprises at least about 1, 2, 3, 4, 5, 6, 7, 8, 9, 10, 11, 12, 13, 14, 15, 20, 25, 30, 35, 40, 50, 60, 70, 80, 90, 100, 150, 200, or more cycles. In some cases, an amplification reaction comprises at least about 20, 25, 30, 35, or 40 cycles. In some embodiments, an amplification reaction comprises no more than about 1, 2, 3, 4, 5, 6, 7, 8, 9, 10, 11, 12, 13, 14, 15, 20, 25, 30, 35, 40, 50, 60, 70, 80, 90, 100, 150, 200, or more cycles. Cycles can contain any number of steps, such as 1, 2, 3, 4, 5, 6, 7, 8, 9, 10, or more steps. Steps can comprise any temperature or gradient of temperatures, suitable for achieving the purpose of the given step, including but not limited to, 3' end extension (e.g. adapter fill-in), primer annealing, primer extension, and strand denaturation. Steps can be of any duration, including but not limited to about, less than about, or more than about 1, 5, 10, 15, 20, 25, 30, 35, 40, 45, 50, 55, 60, 70, 80, 90, 100, 120, 180, 240, 300, 360, 420, 480, 540, 600, 1200, 1800, or more seconds, including indefinitely until manually interrupted. In some cases, cycles of any number comprising different steps are combined in any order. In some embodiments, different cycles comprising different steps are combined such that the total number of cycles in the combination is about, less that about, or more than about 5, 10, 15, 20, 25, 30, 35, 40, 50, 60, 70, 80, 90, 100, 150, 200, or more cycles. In some embodiments, amplification is performed following the fill-in reaction.

In some cases, the amplification reaction is carried out on at least about 1, 2, 3, 4, 5, 6, 7, 8, 9, 10, 12, 14, 16, 18, 20, 25, 30, 40, 50, 100, 200, 300, 400, 500, 600, 800, or 1000 ng of the target DNA molecule. In some cases, the amplification reaction is carried out on less than about 1, 2, 3, 4, 5, 6, 7, 8, 9, 10, 12, 14, 16, 18, 20, 25, 30, 40, 50, 100, 200, 300, 400, 500, 600, 800, or 1000 ng of the polynucleotide. In further examples, amplification is performed before or after pooling of target polynucleotides from independent samples.

Sequencing Technologies

In one aspect, suitable sequencing methods described herein or otherwise known in the art are used to obtain sequence information from nucleic acid molecules within a sample. In some cases, sequencing is accomplished through classic Sanger sequencing methods, which are well known in the art. In other cases, sequencing is accomplished using high-throughput systems some of which allow detection of a sequenced nucleotide immediately after or upon its incorporation into a growing strand, i.e., detection of sequence in real time or substantially real time. In some cases, high throughput sequencing generates at least 1,000, at least 5,000, at least 10,000, at least 20,000, at least 30,000, at least 40,000, at least 50,000, at least 100,000, or at least 500,000 sequence reads per hour. In some cases, the sequencing reads are at least about 50, about 60, about 70, about 80, about 90, about 100, about 120, about 150, about 180, about 210, about 240, about 270, about 300, about 350, about 400, about 450, about 500, about 600, about 700, about 800, about 900, about 1000, about 1500, about 2000, about 2500, about 3000, about 4000, about 5000, about 6000, about 7000, about 8000, about 9000, or about 10000 bases per read.

In some cases, high-throughput sequencing is performed using technology available by Illumina®'s Genome Analyzer IIX™, MiSeq™ personal sequencer, or HiSeq systems, such as those using HiSeq 2500™, HiSeq 1500™, HiSeq 2000™, or HiSeq 1000™ machines. These machines use reversible terminator-based sequencing by synthesis chemistry. These machines can produce 200 billion DNA reads or more in eight days. Alternatively, smaller systems may be utilized for runs within 3, 2, 1 days or less time.

In some cases, high-throughput sequencing is performed using technology available by ABI Solid System™. This genetic analysis platform that enables massively parallel sequencing of clonally-amplified DNA fragments linked to beads. The sequencing methodology is based on sequential ligation with dye-labeled oligonucleotides.

In some cases, high-throughput sequencing is performed using ion semiconductor sequencing (e.g., using technology from Life Technologies™ (Ion Torrent™)). Ion semiconductor sequencing can take advantage of the fact that when a nucleotide is incorporated into a strand of DNA, an ion can be released. In some cases, to perform ion semiconductor sequencing, a high-density array of micromachined wells is formed. In some cases, each well holds a single DNA template. In further examples, an ion sensitive layer is beneath the well, and beneath the ion sensitive layer can be an ion sensor. In certain cases, when a nucleotide is added to a DNA, H+ is released, which can be measured as a change in pH. In further cases, the H+ ion is converted to voltage and recorded by the semiconductor sensor. In some cases, an array chip is sequentially flooded with one nucleotide after another. In some cases, no scanning, light, or cameras is required. In some cases, an IONPROTON™ Sequencer is used to sequence nucleic acid. In some cases, an IONPGM™ Sequencer is used. In certain examples, the Ion Torrent Personal Genome Machine™ (PGM) can do 10 million reads in two hours.

In some cases, high-throughput sequencing is performed using technology available by Helicos BioSciences Corporation (Cambridge, Massachusetts) such as the Single Molecule Sequencing by Synthesis (SMSS) method. SMSS is unique because it allows for sequencing the entire human genome in up to 24 hours. Finally, SMSS is described in part in US Publication Application Nos. 20060024711; 20060024678; 20060012793; 20060012784; and 20050100932.

In some cases, high-throughput sequencing is performed using technology available by 454 Lifesciences, Inc. (Branford, Connecticut) such as the PicoTiterPlate™ device which includes a fiber optic plate that transmits chemiluminescent signal generated by the sequencing reaction to be recorded by a CCD camera in the instrument. This use of fiber optics allows for the detection of a minimum of 20 million base pairs in 4.5 hours.

Methods for using bead amplification followed by fiber optics detection are described in Marguiles, M., et al. "Genome sequencing in microfabricated high-density pricolitre reactors Nature 437, 376-380 (15 Sep. 2005), doi: 10.1038/nature03959; and well as in US Application Publication Nos. 20020012930; 20030068629; 20030100102; 20030148344; 20040248161; 20050079510, 20050124022; and 20060078909.

In some cases, high-throughput sequencing is performed using Clonal Single Molecule Array™ (Solexa, Inc.) or sequencing-by-synthesis (SBS) utilizing reversible terminator chemistry. These technologies are described in part in U.S. Pat. Nos. 6,969,488; 6,897,023; 6,833,246; 6,787,308; and US Publication Application Nos. 20040106110; 20030064398; 20030022207; and Constans, A., The Scientist 2003, 17(13):36.

In some cases, high-throughput sequencing is performed using real-time (SMRT™) technology by Pacific Biosciences™. In certain examples of SMR™, each of four DNA bases is attached to one of four different fluorescent dyes. In further examples, these dyes are phosphor-linked. In some cases, a single DNA polymerase is immobilized with a single molecule of template single stranded DNA at the bottom of a zero-mode waveguide (ZMW). In certain cases, a ZMW is a confinement structure which enables observation of incorporation of a single nucleotide by DNA polymerase against the background of fluorescent nucleotides that can rapidly diffuse in an out of the ZMW (in microseconds). In some cases, it takes several milliseconds to incorporate a nucleotide into a growing strand. During this time, the fluorescent label can be excited and produce a fluorescent signal, and in some cases the fluorescent tag is further cleaved off. In certain cases, the ZMW is illuminated from below. Attenuated light from an excitation beam can penetrate the lower 20-30 nm of each ZMW. In some cases, a microscope with a detection limit of 20 zepto liters (10" liters) is created. In certain examples, the tiny detection volume provides 1000-fold improvement in the reduction of background noise. In further examples, detection of the corresponding fluorescence of the dye indicates which base was incorporated. In many cases, the process is repeated.

In some cases, high-throughput sequencing is performed using nanopore sequencing (See, e.g., Soni G V and Meller A. (2007) Clin Chem 53: 1996-2001). In various cases, a nanopore is a small hole, of the order of about one nanometer in diameter. In certain cases, immersion of a nanopore in a conducting fluid and application of a potential across it results in a slight electrical current due to conduction of ions through the nanopore. In further cases, the amount of current which flows is sensitive to the size of the nanopore. As a DNA molecule passes through a nanopore, each nucleotide on the DNA molecule can obstruct the nanopore to a different degree. Thus, the change in the current passing through the nanopore as the DNA molecule passes through the nanopore may represent a reading of the DNA sequence. In some cases, the nanopore sequencing technology is from Oxford Nanopore Technologies™; e.g., a GridlON™ system. In certain examples, a single nanopore is inserted in a polymer membrane across the top of a microwell. In various examples, each microwell has an electrode for individual sensing. In further examples, the microwells are fabricated into an array chip, with 100,000 or more microwells (e.g., more than 200,000, 300,000, 400,000, 500,000, 600,000, 700,000, 800,000, 900,000, or 1,000,000) per chip. In some cases, an instrument (or node) is used to analyze the chip. In certain cases, data is analyzed in real-time. In many cases, one or more instruments are operated at a time. In some cases, the nanopore is a protein nanopore, e.g., the protein alpha-hemolysin, a heptameric protein pore. In certain examples, the nanopore is a solid-state nanopore made, e.g., a nanometer sized hole formed in a synthetic membrane (e.g., SiNx, or SiO2). In other examples, the nanopore is a hybrid pore (e.g., an integration of a protein pore into a solid-state membrane). In further examples, the nanopore is a nanopore with integrated sensors (e.g., tunneling electrode detectors, capacitive detectors, or graphene based nano-gap or edge state detectors (see e.g., Garaj et al. (2010) Nature vol. 67, doi: 10.1038/nature09379)). In some cases, a nanopore is functionalized for analyzing a specific type of molecule (e.g., DNA, RNA, or protein). In certain cases, nanopore sequencing comprises "strand sequencing" in which intact DNA polymers can be passed through a protein nanopore with sequencing in real time as the DNA translocates the pore. In many cases, an enzyme separates strands of a double stranded DNA and feed a strand through a nanopore. In further cases, the DNA has a hairpin at one end, and the system can read both strands. In some cases, nanopore sequencing is "exonuclease sequencing" in which individual nucleotides are cleaved from a DNA strand by a processive exonuclease, and the nucleotides are passed through a protein nanopore. In certain examples, the nucleotides transiently bind to a molecule in the pore (e.g., cyclodextran). In various examples, a characteristic disruption in current is used to identify bases.

In further cases, nanopore sequencing technology from GENIA™ is used. In some cases. an engineered protein pore is embedded in a lipid bilayer membrane. In certain examples, "Active Control" technology is used to enable efficient nanopore-membrane assembly and control of DNA movement through the channel. In some cases, the nanopore sequencing technology is from NABsys™. In some cases, genomic DNA is fragmented into strands of average length of about 100 kb. In certain examples, the 100 kb fragments are made single stranded and subsequently hybridized with a 6-mer probe. In many examples, the genomic fragments with probes are driven through a nanopore, which can create a current-versus-time tracing. In further examples, the current tracing provides the positions of the probes on each genomic fragment. In some cases, the genomic fragments are lined up to create a probe map for the genome. In certain cases, the process is done in parallel for a library of probes. In further cases, a genome-length probe map for each probe is generated. In many cases, errors are fixed with a process termed "moving window Sequencing By Hybridization™ (mwSBH™)." In some cases, the nanopore sequencing technology is from IBM/Roche™. In certain examples, an electron beam is used to make a nanopore sized opening in a microchip. In some cases, an electrical field is used to pull or thread DNA through the nanopore. In various examples, a DNA transistor device in the nanopore comprises alternating nanometer sized layers of metal and dielectric. In some cases, discrete charges in the DNA backbone are trapped by electrical fields inside the DNA nanopore. In further cases, turning off and on gate voltages allows the DNA sequence to be read.

In some cases, high-throughput sequencing is performed using DNA nanoball sequencing (as performed, e.g., by Complete Genomics; see e.g., Drmanac et al. (2010) Science 327: 78-81). In certain cases, DNA is isolated, fragmented, and size selected. In some cases, DNA is fragmented (e.g., by sonication) to a mean length of about 500 bp. Adaptors (Ad1) can be attached to the ends of the fragments. In certain examples, the adaptors are used to hybridize to anchors for sequencing reactions. In various examples, DNA with adaptors bound to each end is PCR amplified. In further examples, the adaptor sequences are modified so that complementary single strand ends bind to each other forming circular DNA. In some cases, the DNA is methylated to protect it from cleavage by a type IIS restriction enzyme used in a subsequent step. In certain cases, an adaptor (e.g., the right adaptor) has a restriction recognition site, and the restriction recognition site remains non-methylated. In other cases, the non-methylated restriction recognition site in the adaptor is recognized by a restriction enzyme (e.g., Acu1), and the DNA is cleaved by Acu1 13 bp to the right of the right adaptor to form linear double stranded DNA. In further cases, a second round of right and left adaptors (Ad2) is ligated onto either end of the linear DNA, and all DNA with both adapters bound are PCR amplified (e.g., by PCR). In some cases, Ad2 sequences are modified to allow them to bind each other and form circular DNA. In certain examples, the DNA is methylated, but a restriction enzyme recognition site remains non-methylated on the left Ad1 adapter. In various examples, a restriction enzyme (e.g., Acu1) is applied, and the DNA is cleaved 13 bp to the left of the Ad1 to form a linear DNA fragment. In further examples, a third round of right and left adaptor (Ad3) is ligated to the right and left flank of the linear DNA, and the resulting fragment is PCR amplified. In some embodiments, the adaptors are modified so that they bind to each other and form circular DNA. In certain embodiments, a type III restriction enzyme (e.g., EcoP15) is added; EcoP15 cleaves the DNA 26 bp to the left of Ad3 and 26 bp to the right of Ad2. In various embodiments, this cleavage removes a large segment of DNA and linearizes the DNA once again. In further embodiments, a fourth round of right and left adaptors (e.g., Ad4) is ligated to the DNA, the DNA is amplified (e.g., by PCR), and modified so that they bind each other and form the completed circular DNA template.

In certain cases, rolling circle replication (e.g., using Phi 29 DNA polymerase) is used to amplify small fragments of DNA. In some cases, the four adaptor sequences contain palindromic sequences that can hybridize and a single strand can fold onto itself to form a DNA nanoball (DNB™) which can be approximately 200-300 nanometers in diameter on average. In certain examples, a DNA nanoball is attached (e.g., by adsorption) to a microarray (sequencing flow cell). In further examples, the flow cell is a silicon wafer coated with silicon dioxide, titanium and hexamethyldisilazane (HMDS) and a photoresist material. In some cases, sequencing is performed by unchained sequencing by ligating fluorescent probes to the DNA. In certain cases, the color of the fluorescence of an interrogated position is visualized by a high-resolution camera. In further cases, the identity of nucleotide sequences between adaptor sequences is determined.

In some cases, high-throughput sequencing is performed using AnyDot.chips (Genovoxx, Germany). In particular, the AnyDot.chips allow for 10×-50× enhancement of nucleotide fluorescence signal detection. AnyDot.chips and methods for using them are described in part in International Publication Application Nos. WO 02088382, WO 03020968, WO 03031947, WO 2005044836, PCT/EP 05/05657, PCT/EP 05/05655; and German Patent Application Nos. DE 101 49 786, DE 102 14 395, DE 103 56 837, DE 10 2004 009 704, DE 10 2004 025 696, DE 10 2004 025 746, DE 10 2004 025 694, DE 10 2004 025 695, DE 10 2004 025 744, DE 10 2004 025 745, and DE 10 2005 012 301.

Other high-throughput sequencing systems include those disclosed in Venter, J., et al. Science 16 Feb. 2001; Adams, M. et al. Science 24 Mar. 2000; and M. J. Levene, et al. Science 299:682-686, January 2003; as well as US Publication Application No. 20030044781 and 2006/0078937. Overall such system involve sequencing a target nucleic acid molecule having a plurality of bases by the temporal addition of bases via a polymerization reaction that is measured on a molecule of nucleic acid, i.e. the activity of a nucleic acid polymerizing enzyme on the template nucleic acid molecule to be sequenced is followed in real time. In some cases, the sequence is deduced by identifying which base is being incorporated into the growing complementary strand of the target nucleic acid by the catalytic activity of the nucleic acid polymerizing enzyme at each step in the sequence of base additions. A polymerase on the target nucleic acid molecule complex is provided in a position suitable to move along the target nucleic acid molecule and extend the oligonucleotide primer at an active site. A plurality of labeled types of nucleotide analogs are provided proximate to the active site, with each distinguishable type of nucleotide analog being complementary to a different nucleotide in the target nucleic acid sequence. The growing nucleic acid strand is extended by using the polymerase to add a nucleotide analog to the nucleic acid strand at the active site, where the nucleotide analog being added is complementary to the nucleotide of the target nucleic acid at the active site. The nucleotide analog added to the oligonucleotide primer as a result of the polymerizing step is identified. The steps of providing labeled nucleotide analogs, polymerizing the growing nucleic acid strand, and identifying the added nucleotide analog are repeated so that the nucleic acid strand is further extended and the sequence of the target nucleic acid is determined.

Using Sequencing Reads to Order and Orient Contigs

Traditional paired-end sequencing data sets comprise pairs of reads sampled from the genome so as to indicate approximately the probability distribution of their separation on the genome. Barcode Tagged sequence read data sets yield "sets" or "bins" of sequence tagged reads, where each set is defined in practice by sharing a ligated barcode molecular tag sequence. The reads in each "set" sample a particular nucleic acid molecule (a subset of the genome or other target sequence sample) approximately uniformly. The subset of the genome being sampled may be a single segment corresponding to a single molecule of input DNA, or it may be multiple input segments.

One way to define the ordering and orientation problem is: given a pair of sequence contigs, how can we distinguish whether (test the hypothesis that) they come from adjacent segments of the genome, with a particular choice of the four possible relative orientations?

Given a set of sequence reads sharing a common molecular tag and mapping to a common region of the target sequence or to two or more contigs in an obtained contig set (a common region of the genome, or a set of contigs known or believed to map to the same general vicinity, or even a set of contigs for which no mapping information is known), one may determine an order among the contigs as follows.

Provided that the nucleic acid molecules do not correspond directly to assembled contigs in content and in their endpoints, barcoded sequence sets derived from these nucleic acid molecules are in some embodiments used to assemble contig order and orientation. Individual sequence reads on a sequence set are each individually mapped to a locus on a contig in the contig set corresponding to the target sequence of a sample. Commonly tagged sequences that derive from a single nucleic acid molecule are likely to map nearby to one another on a contig or contigs. If a commonly tagged set of sequence reads maps to more than one contig, in some embodiments the contigs are presumed to be near one another in the genomic sequence. In some embodiments, if a set of sequence reads maps to the ends of two contigs, the contigs are presumed to be adjacent and oriented such that the ends to which sequence reads map are adjacent to one another. In some embodiments, if a sequence read set spans three or more than three contigs, then the contig or contigs demonstrating complete coverage are placed in the interior of the contig order, and any one or two contigs demonstrating partial coverage, such as coverage biased toward an end of each contig, are positioned at an end or on opposite ends of the contig order. In some embodiments, middle contigs are unoriented. In some embodiments, if a sequence read set spans three or more than three contigs, then the contig or contigs demonstrating complete coverage are placed in the interior of the contig order and are unoriented, and any one or two contigs demonstrating partial coverage, such as coverage biased toward an end of each contig, are positioned at an end or on opposite ends of the contig order and are oriented such that the end of each contig demonstrating partial coverage is positioned adjacent to the internal contigs demonstrating full coverage.

In some embodiments each read set corresponds to a unique molecular tag or barcode. However, in some embodiments multiple sets may have the same molecular tag or barcode. Contigs that are unlinked on the genome may share barcode sets by chance, or because of read mapping errors, and the number of shared barcodes coming from these "noise" sources can also be calculated. In particular, sequence read sets that share a common molecular barcode or tag are nonetheless easily assembled without affecting final conclusions as to molecule phase or physical linkage, provided that the commonly tagged sets do not also overlap in their mapping to a single contig sequence. In cases of commonly tagged, genomically overlapping segments of disparate origins (for example a set from mom's chromosome and a set from dad's that overlap), the presence of overlap occurrence is nonetheless detectable and disentangleable by scanning for significant coverage density fluctuations (for example, twice as many reads mapping to a contig or set of contigs than expected or than observed elsewhere) or by detecting significant levels of heterozygosity in the region, such as levels of heterozygosity above those expected from sequencing error. Alternately, a single molecule or DNA complex can be multiply tagged with more than one tag sequence without affecting final physical linkage or phasing conclusions, as the sequence reads will map to a common contig or contigs, and the molecular tag or barcode sequence is likely to be randomly or fairly randomly distributed among the sets such that it becomes clear that the sequence reads correspond to a single molecule or DNA complex.

In some embodiments more quantitative approaches are used to order, orient or order and orient contigs. For example, the expected separation on the genome between consecutive (on the genome) reads sampled from the same molecule is approximately equal to L/n, where L is the mean length of input DNA fragments, and n in the mean number of reads sampled from each chromatin aggregate. This can be used to identify which relative orientation of a pair of contigs that share many barcodes is most consistent with the data. A misoriented contig manifests itself as unexpectedly long gaps between successive reads from many shared barcodes:

The expected separation between the most distant pair of reads sampled from the same input molecule is L (n−1)/n. This expression embodies on the of the advantages of sequence read sets or binned sequences over, for example, paired end sequences. When generating binned sequence sets, one may expect many chromatin aggregates to provide linking information on the same length scale as the input DNA.

Additional approaches to ordering contigs in light of molecular-tag sorted sequence read sets are contemplated and are consistent with the disclosure herein.

As some embodiments of the diversity of approaches for positioning and/or orienting contigs along a single physically linked nucleic acid molecule, the present disclosure further provides methods comprising constructing an adjacency matrix of contigs using the read-mapping data from the read-sets. In some embodiments, an adjacency matrix uses a weighting scheme for read-sets that incorporate the tendency for short-range interactions to occur more frequently than long-range interactions. In some cases, a function describing the probability of a particular distance is fit using the read-mapping data that map to a single contig to learn this distribution. Therefore, one important feature of the reads within a read-set that map to different contigs is the position on the contig where they map. For sequence segments that both map near an end of their respective contigs, the inferred distance between these contigs can be short and therefore the distance between the joined reads may be inferred to be small. Since shorter distances between reads within a read-set are more common than longer distances, this configuration provides stronger evidence that these two contigs are adjacent than would reads mapping far from the edges of the contig. Therefore, in some embodiments the connections in the adjacency matrix are further weighted by the distance of the reads to the edge of the contigs. In further embodiments, the adjacency matrix is scaled to down-weigh the high number of contacts on some contigs that represent promiscuous regions of the genome. These regions of the genome, identifiable by having a high proportion of reads mapping to them, are a priori more likely to contain spurious read mappings that might misinform assembly. In yet further embodiments, this scaling is directed by searching for one or more conserved binding sites for one or more agents that regulate the scaffolding interactions of chromatin, such as transcriptional repressor CTCF, endocrine receptors, cohesins, or covalently modified histones.

In some embodiments, the methods disclosed herein comprise analyzing the adjacency matrix to determine a path through the contigs, or an ordering and/or orientation of the contigs that represents their order and/or orientation along a nucleic acid molecule, such as a chromosome. In some cases, the path through the contigs is chosen so that each contig is visited exactly once. In some cases, the path through the contigs is chosen so that the path through the adjacency matrix maximizes the sum of edge-weights visited. In this way, the most probable contig connections are proposed for the correct assembly. In further cases, the path through the contigs is chosen so that each contig is visited exactly once and that edge-weighting of adjacency matrix is maximized. In some embodiments an adjacency matrix is constructed to facilitate or to guide contig ordering or contig ordering and orientation, while in other embodiments contig ordering or contig ordering and orientation is determined using read-to-contig mapping information without the construction of an adjacency matrix.

Phase Data and Uses

In diploid genomes, it is often important to know which allelic variants are physically linked on the same chromosome rather than mapping to the homologous position on a chromosome pair. Mapping an allele or other sequence to a specific physical chromosome of a diploid chromosome pair is known as the haplotype phasing. Short reads from high-throughput sequence data rarely allow one to directly observe which allelic variants are linked, particularly, as is most often the case, if the allelic variants are separated by a greater distance than the longest single read. Computational inference of haplotype phasing can be unreliable at long distances. Methods disclosed herein allow for determining which allelic variants are physically linked using allelic variants on read pairs.

In various cases, the methods and compositions of the disclosure enable the haplotype phasing of diploid or polyploid genomes with regard to a plurality of allelic variants. Methods described herein thus provide for the determination of linked allelic variants based on variant information from labeled sequence segments and/or assembled contigs using the same. Cases of allelic variants include, but are not limited to, those that are known from the 1000 genomes, UK10K, HapMap and other projects for discovering genetic variation among humans. In some cases, disease association to a specific gene are revealed more easily by having haplotype phasing data as demonstrated, for example, by the finding of unlinked, inactivating mutations in both copies SH3TC2 leading to Charcot-Marie-Tooth neuropathy (Lupski J R, Reid J G, Gonzaga-Jauregui C, et al. N. Engl. J. Med. 362:1181-91, 2010) and unlinked, inactivating mutations in both copies of ABCG5 leading to hypercholesterolemia 9 (Rios J, Stein E, Shendure J, et al. Hum. Mol. Genet. 19:4313-18, 2010).

Humans are heterozygous at an average of 1 site in 1,000. In some cases, a single lane of data using high throughput sequencing methods generates at least about 150,000,000 reads. In further cases, individual reads are about 100 base pairs long. If we assume input DNA fragments average 150 kbp in size and we get 100 paired-end reads per fragment, then we expect to observe 30 heterozygous sites per set, i.e., per 100 read-pairs. Every read-pair containing a heterozygous site within a set is in phase (i.e., molecularly linked) with respect to all other read-pairs within the same set. This property enables greater power for phasing with sets as opposed to singular pairs of reads in some cases. With approximately 3 billion bases in the human genome, and one in one-thousand being heterozygous, there are approximately 3 million heterozygous sites in an average human genome. With about 45,000,000 read pairs that contain heterozygous sites, the average coverage of each heterozygous site to be phased using a single lane of a high throughput sequence method is about (15×), using a typical high throughput sequencing machine. A diploid human genome can therefore be reliably and completely phased with one lane of a high-throughput sequence data relating sequence variants from a sample that is prepared using the methods disclosed herein. In some cases, a lane of data is a set of DNA sequence read data. In further cases, a lane of data is a set of DNA sequence read data from a single run of a high throughput sequencing instrument.

As the human genome consists of two homologous sets of chromosomes, understanding the true genetic makeup of an individual requires delineation of the maternal and paternal copies or haplotypes of the genetic material. Obtaining a haplotype in an individual is useful in several ways. For example, haplotypes are useful clinically in predicting outcomes for donor-host matching in organ transplantation. Haplotypes are increasingly used to detect disease associations. In genes that show compound heterozygosity, haplotypes provide information as to whether two deleterious variants are located on the same allele (that is, 'in cis', to use genetics terminology) or on two different alleles ('in trans'), greatly affecting the prediction of whether inheritance of these variants is harmful, and impacting conclusions as to whether an individual carries a functional allele and a single nonfunctional allele having two deleterious variant positions, or whether that individual carries two nonfunctional alleles, each with a different defect. Haplotypes from groups of individuals have provided information on population structure of interest to both epidemiologists and anthropologists and informative of the evolutionary history of the human race. In addition, widespread allelic imbalances in gene expression have been reported, and suggest that genetic or epigenetic differences between allele phase may contribute to quantitative differences in expression. An understanding of haplotype structure will delineate the mechanisms of variants that contribute to allelic imbalances.

In certain embodiments, the methods disclosed herein comprise an in vitro technique to fix and capture associations among distant regions of a genome as needed for long-range linkage and phasing. In some cases, the method comprises constructing and sequencing one or more read-sets to deliver very genomically distant read pairs. In further cases, each read-set comprises two or more reads that are labeled by a common barcode, which may represent two or more sequence segments from a common polynucleotide. In some cases, the interactions primarily arise from the random associations within a single polynucleotide. In some cases, the genomic distance between sequence segments are inferred because sequence segments near to each other in a polynucleotide interact more often and with higher probability, while interactions between distant portions of the molecule are less frequent. Consequently, there is a systematic relationship between the number of pairs connecting two loci and their proximity on the input DNA. In some cases, the methods disclosed herein produce read pairs that span the largest DNA fragments in an extraction. For example, if the input DNA for a particular library has a maximum length of 150 kbp, then this is the longest meaningful read pair that can be observed from the sequencing data. By applying improved assembly software tools that are specifically adapted to handle the type of data produced by the present method, a complete genomic assembly may be possible. Methods disclosed herein are used in some embodiments to label sequence segments that span the largest polynucleotide from an extraction.

In some aspects, the disclosure provides methods and compositions that produce data to achieve extremely high phasing accuracy. In comparison to previous methods, the methods described herein can phase a higher proportion of the variants. In some cases, phasing is achieved while maintaining high levels of accuracy. In further cases, this phase information is extended to longer ranges, for example greater than about 200 kbp, about 300 kbp, about 400 kbp, about 500 kbp, about 600 kbp, about 700 kbp, about 800 kbp, about 900 kbp, about 1 Mbp, about 2 Mbp, about 3 Mbp, about 4 Mbp, about 5Mbp, or about 10 Mbp, or longer than about 10 Mbp, up to and including the entire length of a chromosome. In some embodiments, more than 90% of the heterozygous SNPs for a human sample is phased at an accuracy greater than 99% using less than about 250 million reads, e.g. by using only 1 lane of Illumina® HiSeq data. In other cases, more than about 40%, 50%, 60%, 70%, 80%, 90%, 95% or 99% of the heterozygous SNPs for a human sample is phased at an accuracy greater than about 70%, 80%, 90%, 95%, or 99% using less than about 250 million or about 500 million reads, e.g. by using only 1 or 2 lanes of Illumina® HiSeq data. In some cases, more than 95% or 99% of the heterozygous SNPs for a human sample are phased at an accuracy greater than about 95% or 99% using less about 250 million or about 500 million reads. In further cases, additional variants are captured by increasing the read length to about 200 bp, 250 bp, 300 bp, 350 bp, 400 bp, 450 bp, 500 bp, 600 bp, 800 bp, 1000 bp, 1500 bp, 2 kbp, 3 kbp, 4 kbp, 5 kbp, 10 kbp, 20 kbp, 50 kbp, or 100 kbp.

In other embodiments of the disclosure, the data from a barcoded library are used to confirm the phasing capabilities of the long-range read pairs.

In another aspect, the methods and compositions disclosed herein allow for the investigation of meta-genomes, for example, those found in the human gut. In some cases, the partial or whole genomic sequences of some or all organisms that inhabit a given ecological environment are investigated. Cases include random sequencing of all gut microbes, the microbes found on certain areas of skin, and the microbes that live in toxic waste sites. In some cases, the composition of the microbe population in these environments is determined using the compositions and methods described herein and as well as the aspects of interrelated biochemistries encoded by their respective genomes. In further cases, the methods described herein enable metagenomic studies from complex biological environments, for example, those that comprise more than 2, 3, 4, 5, 6, 7, 8, 9, 10, 12, 15, 20, 25, 30, 40, 50, 60, 70, 80, 90, 100, 125, 150, 175, 200, 250, 300, 400, 500, 600, 700, 800, 900, 1000, 5000, 10000 or more organisms and/or variants of organisms.

Accordingly, methods disclosed herein may be applied to intact human genomic DNA samples but may also be applied to a broad diversity of nucleic acid samples, such as reverse-transcribed RNA samples, circulating free DNA samples, cancer tissue samples, crime scene samples, archaeological samples, nonhuman genomic samples, or environmental samples such as environmental samples comprising genetic information from more than one organism, such as an organism that is not easily cultured under laboratory conditions.

In some cases, high degrees of accuracy required by cancer genome sequencing are achieved using the methods and systems described herein. Inaccurate reference genomes make base-calling challenges when sequencing cancer genomes. Heterogeneous samples and small starting materials, for example a sample obtained by biopsy introduce additional challenges. Further, detection of large-scale structural variants and/or losses of heterozygosity is often crucial for cancer genome sequencing, as well as the ability to differentiate between somatic variants and errors in base-calling.

The systems and methods described herein may generate accurate long sequences from complex samples containing 2, 3, 4, 5, 6, 7, 8, 9, 10, 12, 15, 20 or more than 20 varying genomes. Mixed samples of normal, benign, and/or tumor origin may be analyzed, optionally without the need for a normal control. In some embodiments, samples comprising less than about 1000 ng, about 500 ng, about 200 ng, about 100 ng, about 50 ng, about 20 ng, about 10 ng, or even as little as hundreds of genome equivalents, are utilized to generate accurate long sequences. Systems and methods described herein may allow for detection of large scale structural variants and rearrangements. Phased variant calls may be obtained over long sequences spanning about 1 kbp, about 2 kbp, about 5 kbp, about 10 kbp, 20 kbp, about 50 kbp, about 100 kbp, about 200 kbp, about 500 kbp, about 1 Mbp, about 2 Mbp, about 5 Mbp, about 10 Mbp, about 20 Mbp, about 50 Mbp, or about 100 Mbp or more nucleotides. For example, a phase variant call may be obtained over long sequences spanning about 1 Mbp or about 2 Mbp.

In certain aspects, the methods disclosed herein are used to assemble a plurality of contigs originating from a single DNA molecule. In some cases, the method comprises generating a plurality of read-pairs from the single DNA molecule that is cross-linked to a plurality of nanoparticles and assembling the contigs using the read-pairs. In certain cases, single DNA molecule is cross-linked outside of a cell. In some cases, at least 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% of the read-pairs span a distance greater than 1 kB, 2 kB, 3 kB, 4 kB, 5 kB, 6 kB, 7 kB, 8 kB, 9 kB, 10 kB, 15 kB, 20 kB, 30 kB, 40 kB, 50 kB, 60 kB, 70 kB, 80 kB, 90 kB, 100 kB, 150 kB, 200 kB, 250 kB, 300 kB, 400 kB, 500 kB, 600 kB, 700 kB, 800 kB, 900 kB, or 1 MB on the single DNA molecule. In certain cases, at least 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, or 20% of the read-pairs span a distance greater than 5 kB, 6 kB, 7 kB, 8 kB, 9 kB, 10 kB, 15 kB, 20 kB, 30 kB, 40 kB, 50 kB, 60 kB, 70 kB, 80 kB, 90 kB, 100 kB, 150 kB, or 200 kB on the single DNA molecule. In further cases, at least 0.5%, 0.6%, 0.7%, 0.8%, 0.9%, 1%, 2%, 3%, 4%, or 5% of the read-pairs span a distance greater than 20 kB, 30 kB, 40 kB, 50 kB, 60 kB, 70 kB, 80 kB, 90 kB, or 100 kB on the single DNA molecule. In particular cases, at least 1% or 5% of the read pairs span a distance greater than 50 kB or 100 kB on the single DNA molecule. In some cases, the read-pairs are generated within 1, 2, 3, 4, 5, 6, 7, 8, 9, 10, 11, 12, 13, 14, 15, 16, 17, 18, 19, 20, 30, 40, 50 or 60 days. In certain cases, the read-pairs are generated within 3, 4, 5, 6, 7, 8, 9, 10, 11, 12, 13, 14, 15, 16, 17 or 18 days. In further cases, the read-p airs are generated within 7, 8, 9, 10, 11, 12, 13, or 14 days. In particular cases, the read-pairs are generated within 7 or 14 days.

In other aspects, the methods disclosed herein are used for haplotype phasing. In some cases, the method comprises generating a plurality of read-pairs from a single DNA molecule that is cross-linked to plurality of nanoparticles and assembling a plurality of contigs of the DNA molecule using the read-pairs. In certain cases, single DNA molecule is cross-linked outside of a cell. In some cases, at least 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% of the read-pairs span a distance greater than 1 kB, 2 kB, 3 kB, 4 kB, 5 kB, 6 kB, 7 kB, 8 kB, 9 kB, 10 kB, 15 kB, 20 kB, 30 kB, 40 kB, 50 kB, 60 kB, 70 kB, 80 kB, 90 kB, 100 kB, 150 kB, 200 kB, 250 kB, 300 kB, 400 kB, 500 kB, 600 kB, 700 kB, 800 kB, 900 kB, or 1 MB on the single DNA molecule. In certain cases, at least 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, or 20% of the read-pairs span a distance greater than 5 kB, 6 kB, 7 kB, 8 kB, 9 kB, 10 kB, 15 kB, 20 kB, 30 kB, 40 kB, 50 kB, 60 kB, 70 kB, 80 kB, 90 kB, 100 kB, 150 kB, or 200 kB on the single DNA molecule. In further cases, at least 0.5%, 0.6%, 0.7%, 0.8%, 0.9%, 1%, 2%, 3%, 4%, or 5% of the read-pairs span a distance greater than 20 kB, 30 kB, 40 kB, 50 kB, 60 kB, 70 kB, 80 kB, 90 kB, or 100 kB on the single DNA molecule. In particular cases, at least 1% or 10% of the read pairs span a distance greater than 30 kB or 50 kB on the single DNA molecule. the haplotype phasing is performed at greater than 70% accuracy. In some embodiments, at least 10% of the read-pairs span a distance greater than 50 kB on the single DNA molecule. In other embodiments, wherein at least 1% of the read-pairs span a distance greater than 100 kB on the single DNA molecule. In some cases, the haplotype phasing is performed at greater than 50%, 60%, 70%, 75%, 80%, 85%, 90%, 95%, 96%, 97%, 98%, or 99% accuracy. In certain cases, the haplotype phasing is performed at greater than 70%, 75%, 80%, 85%, 90%, or 95% accuracy. In further cases, the haplotype phasing is performed at greater than 70%, or 90% accuracy.

Haplotypes determined using the methods and systems described herein may be assigned to computational resources, for example, computational resources over a network, such as a cloud system. Similarly, in certain cases, contig information are obtained using computational resources such as cloud system resources. Short variant calls are corrected, if necessary, using relevant information that is stored in the computational resources. In some cases, structural variants are detected based on the combined information from short variant calls and the information stored in the computational resources. In some cases, problematic parts of the genome, such as segmental duplications, regions prone to structural variation, the highly variable and medically relevant MHC region, centromeric and telomeric regions, and other heterochromatic regions including but not limited to those with repeat regions, low sequence accuracy, high variant rates, ALU repeats, segmental duplications, or any other relevant problematic parts known in the art, are assembled or reassembled for increased accuracy.

In some cases, a sample type is assigned to the sequence information either locally or in a networked computational resource, such as a cloud. In cases where the source of the information is known, for example, when the source of the information is from a cancer or normal tissue, the source is assigned to the sample as part of a sample type. Other sample type cases generally include, but are not limited to, tissue type, sample collection method, presence of infection, type of infection, processing method, size of the sample, etc. In cases where a complete or partial comparison genome sequence is available, such as a normal genome in comparison to a cancer genome, the differences between the sample data and the comparison genome sequence is determined and optionally output.

In another aspect, the methods of the present disclosure are used in the analysis of genetic information of selective genomic regions of interest as well as genomic regions which may interact with the selective region of interest. In some cases, amplification methods as disclosed herein are used in the devices, kits, and methods known to the art for genetic analysis, such as, but not limited to those found in U.S. Pat. Nos. 6,449,562, 6,287,766, 7,361,468, 7,414,117, 6,225,109, and 6,110,709. In some cases, amplification methods of the present disclosure are used to amplify target nucleic acid for DNA hybridization studies to determine the presence or absence of polymorphisms. In further cases, the polymorphisms, or alleles, are associated with diseases or conditions such as genetic disease. In other cases, the polymorphisms are associated with susceptibility to diseases or conditions, for example, polymorphisms associated with addiction, degenerative and age-related conditions, cancer, and the like. In other cases, the polymorphisms are associated with beneficial traits such as increased coronary health, or resistance to diseases such as HIV or malaria, or resistance to degenerative diseases such as osteoporosis, Alzheimer's or dementia.

In yet another aspect, the methods and compositions of the disclosure are used for diagnostic, prognostic, therapeutic, patient stratification, drug development, treatment selection, and screening purposes. In some cases, the methods of present disclosure provide the advantage that many different target molecules are analyzed at one time from a single biomolecular sample using the methods of the disclosure. This allows, for example, for several diagnostic tests to be performed on one sample.

In one aspect, the methods and compositions of the present disclosure are used in genomics. In some cases, the methods described herein provide an answer rapidly, which is very desirable for this application. In some cases, the methods and composition described herein are used in the process of finding biomarkers that may be used for diagnostics and/or prognostics, and/or as indicators of health and disease, or as part of a pharmaceutical selection regime. In further cases, the methods and compositions described herein are used to screen for drugs, e.g., drug development, selection of treatment, determination of treatment efficacy and/or identify targets for pharmaceutical development. The ability to test gene expression on screening assays involving drugs is very important because proteins are the final gene product in the body. In some embodiments, the methods and compositions described herein will measure both protein and gene expression simultaneously, which will provide the most information regarding the particular screening being performed.

In another aspect, the methods and compositions of the disclosure are used in gene expression analysis. In some cases, the methods described herein are used to discriminate between nucleotide sequences. In some cases, the difference between the target nucleotide sequences is a single nucleic acid base difference, a nucleic acid deletion, a nucleic acid insertion, or rearrangement. In further cases, such sequence differences involving more than one base are also detected. The process of the present disclosure is able to detect infectious diseases, genetic diseases, and cancer. It is also useful in environmental monitoring, forensics, and food science. Examples of genetic analyses that can be performed on nucleic acids include e.g., SNP detection, STR detection, RNA expression analysis, promoter methylation, gene expression, virus detection, viral subtyping, and drug resistance.

In some cases, the present methods are applied to the analysis of biomolecular samples obtained or derived from a subject so as to determine whether a diseased cell type is present in the sample, the stage of the disease, the prognosis for the subject, the ability to the subject to respond to a particular treatment, or the best treatment for the subject. In further cases, the present methods are also applied to identify biomarkers for a particular disease.

In another aspect, the methods described herein are used in the diagnosis of a condition. As used herein, the term "diagnose" or "diagnosis" of a condition may include predicting or diagnosing the condition, determining predisposition to the condition, monitoring treatment of the condition, diagnosing a therapeutic response of the disease, or prognosis of the condition, condition progression, or response to particular treatment of the condition. In some cases, a blood sample are assayed according to any of the methods described herein to determine the presence and/or quantity of markers of a disease or malignant cell type in the sample, thereby diagnosing or staging a disease or a cancer. In further examples, the methods and composition described herein are also used for the diagnosis and/or prognosis of a condition.

In numerous cases, immunologic, proliferative, and malignant diseases and disorders are amenable to the methods described herein. Immunologic diseases and disorders include allergic diseases and disorders, disorders of immune function, and autoimmune diseases and conditions. Allergic diseases and disorders include but are not limited to allergic rhinitis, allergic conjunctivitis, allergic asthma, atopic eczema, atopic dermatitis, and food allergy. Immunodeficiencies include but are not limited to severe combined immunodeficiency (SCID), hypereosinophilic syndrome, chronic granulomatous disease, leukocyte adhesion deficiency I and II, hyper IgE syndrome, Chediak Higashi, neutrophilias, neutropenias, aplasias, Agammaglobulinemia, hyper-IgM syndromes, DiGeorge/Velocardial-facial syndromes and Interferon gamma-TH1 pathway defects. Autoimmune and immune dysregulation disorders include but are not limited to rheumatoid arthritis, diabetes, systemic lupus erythematosus, Graves' disease, Graves ophthalmopathy, Crohn's disease, multiple sclerosis, psoriasis, systemic sclerosis, goiter and struma lymphomatosa (Hashimoto's thyroiditis, lymphadenoid goiter), alopecia aerata, autoimmune myocarditis, lichen sclerosis, autoimmune uveitis, Addison's disease, atrophic gastritis, myasthenia gravis, idiopathic thrombocytopenic purpura, hemolytic anemia, primary biliary cirrhosis, Wegener's granulomatosis, polyarteritis nodosa, and inflammatory bowel disease, allograft rejection and tissue destructive from allergic reactions to infectious microorganisms or to environmental antigens.

Proliferative diseases and disorders that may be evaluated by the methods of the disclosure include, but are not limited to, hemangiomatosis in newborns; secondary progressive multiple sclerosis; chronic progressive myelodegenerative disease; neurofibromatosis; ganglioneuromatosis; keloid formation; Paget's Disease of the bone; fibrocystic disease (e.g., of the breast or uterus); sarcoidosis; Peronies and Duputren's fibrosis, cirrhosis, atherosclerosis, and vascular restenosis.

Malignant diseases and disorders that may be evaluated by the methods of the disclosure include both hematologic malignancies and solid tumors. In some cases, hematologic malignancies are amenable to the methods of the disclosure, especially when the sample is a blood sample, because such malignancies involve changes in blood-borne cells. Such malignancies include non-Hodgkin's lymphoma, Hodgkin's lymphoma, non-B cell lymphomas, and other lymphomas, acute or chronic leukemias, polycythemias, thrombocythemias, multiple myeloma, myelodysplastic disorders, myeloproliferative disorders, myelofibroses, atypical immune lymphoproliferations and plasma cell disorders. Plasma cell disorders that may be evaluated by the methods of the disclosure include multiple myeloma, amyloidosis and Waldenstrom's macroglobulinemia. Examples of solid tumors include, but are not limited to, colon cancer, breast cancer, lung cancer, prostate cancer, brain tumors, central nervous system tumors, bladder tumors, melanomas, liver cancer, osteosarcoma and other bone cancers, testicular and ovarian carcinomas, head and neck tumors, and cervical neoplasms.

In some cases, genetic diseases are also detected by the process of the present disclosure. In some cases, this is carried out by prenatal or post-natal screening for chromosomal and genetic aberrations or for genetic diseases. Examples of detectable genetic diseases include: 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia, Tay-Sachs Disease, thalassemia, Klinefelter Syndrome, Huntington Disease, autoimmune diseases, lipidosis, obesity defects, hemophilia, inborn errors of metabolism, and diabetes.

In one aspect, the methods described herein are used to diagnose pathogen infections (e.g. infections by intracellular bacteria and viruses) by determining the presence and/or quantity of markers of bacterium or virus, respectively, in the sample.

In further cases, a wide variety of infectious diseases are detected by the process of the present disclosure. In some cases, the infectious disease is caused by bacterial, viral, parasite, or fungal infectious agents. The resistance of various infectious agents to drugs can also be determined using the present disclosure.

Bacterial infectious agents which can be detected by the present disclosure include *Escherichia coli, Salmonella, Shigella, Klebsiella, Pseudomonas, Listeria monocytogenes, Mycobacterium tuberculosis, Mycobacterium aviumintracellulare, Yersinia, Francisella, Pasteurella, Brucella, Clostridia, Bordetella pertussis, Bacteroides, Staphylococcus aureus, Streptococcus pneumonia*, B-Hemolytic strep., *Corynebacteria, Legionella, Mycoplasma, Ureaplasma, Chlamydia, Neisseria* gonorrhea, *Neisseria meningitides, Hemophilus influenza, Enterococcus faecalis, Proteus vulgaris, Proteus mirabilis, Helicobacter pylori, Treponema palladium, Borrelia burgdorferi, Borrelia recurrentis, Rickettsial pathogens, Nocardia*, and *Acitnomycetes*.

Fungal infectious agents which can be detected by the present disclosure include *Cryptococcus neoformans, Blastomyces dermatitidis, Histoplasma capsulatum, Coccidioides immitis, Paracoccidioides brasiliensis, Candida albicans, Aspergillus fumigautus, Phycomycetes (Rhizopus), Sporothrix schenckii, Chromomycosis*, and *Maduromycosis*.

Viral infectious agents which can be detected by the present disclosure include human immunodeficiency virus, human T-cell lymphocytotrophic virus, hepatitis viruses (e.g., Hepatitis B Virus and Hepatitis C Virus), Epstein-Barr virus, cytomegalovirus, human papillomaviruses, orthomyxo viruses, paramyxo viruses, adenoviruses, corona viruses, rhabdo viruses, polio viruses, toga viruses, bunya viruses, arena viruses, rubella viruses, and reo viruses.

Parasitic agents which can be detected by the present disclosure include *Plasmodium falciparum, Plasmodium malaria, Plasmodium vivax, Plasmodium ovale, Onchoverva volvulus, Leishmania, Trypanosoma* spp., *Schistosoma* spp., *Entamoeba histolytica, Cryptosporidium, Giardia* spp., *Trichimonas* spp., *Balatidium coli, Wuchereria bancrofti, Toxoplasma* spp., *Enterobius vermicularis, Ascaris lumbricoides, Trichuris trichiura, Dracunculus medinesis, trematodes, Diphyllobothrium latum, Taenia* spp., *Pneumocystis carinii*, and *Necator americanis*.

In one aspect, the present disclosure is also useful for detection of drug resistance by infectious agents. For example, vancomycin-resistant *Enterococcus faecium*, methicillin-resistant *Staphylococcus aureus*, penicillin-resistant *Streptococcus pneumoniae*, multi-drug resistant *Mycobacterium tuberculosis*, and AZT-resistant human immunodeficiency virus may all be identified with the present disclosure. Thus, in some cases, the target molecules detected using the compositions and methods of the disclosure are either patient markers (such as a cancer marker) or markers of infection with a foreign agent, such as bacterial or viral markers.

In another aspect, the methods and compositions of the present disclosure are used to identify and/or quantify a target molecule whose abundance is indicative of a biological state or disease condition, for example, blood markers that are upregulated or downregulated as a result of a disease state.

In yet another aspect, the methods and compositions of the present disclosure is used for detecting cytokine expression. In some cases, the sensitivity of the methods described herein is helpful for early detection of cytokines, e.g., as biomarkers of a condition, diagnosis, or prognosis of a disease such as cancer, and the identification of subclinical conditions.

Integrase Compositions

Also provided herein are compositions comprising a first segment of a nucleic acid molecule and a second segment of the nucleic acid molecule separated by an integrase site, wherein the first segment and the second segment are held together independent of their phosphodiester bonds via a crosslinked nucleic acid binding complex. In some cases, the crosslinked nucleic acid binding complex comprises native chromatin. In some cases, the crosslinked nucleic acid binding complex comprises reconstituted chromatin. In some cases, the nucleic acid molecule is interrupted by at least 3 integrase sites. In some cases, the nucleic acid molecule is interrupted by at least 10 integrase sites. In some cases, the integrase site is a phage integrase site. In some cases, the phage integrase site is a lambda phage integrase site. In some cases, the phage integrase site is a phi integrase site. In some cases, the phi integrase site is a phiC31 integrase site. In some cases, the integrase site comprises an att sequence. In some cases, the integrase site comprises an attB integrase site. In some cases, the integrase site is a retroviral integrase site. In some cases, the composition is contacted to a protease.

Also provided herein are compositions comprising a first segment of a nucleic acid molecule and a second segment of the nucleic acid molecule separated by an integrase site, wherein the first segment and the second segment are derived from a nucleic acid sample, and wherein the integrase site is not present in the sample. In some cases, the integrase site is a phage integrase site. In some cases, the phage integrase site is a lambda phage integrase site. In some cases, the phage integrase site is a phi integrase site. In some cases, the phi integrase site is a phi31 integrase site. In some cases, the integrase site comprises an att sequence. In cases, the integrase site comprises an attB integrase site. In some cases, the integrase site is a retroviral integrase site. In some cases, the composition comprises at least one bead having population of oligos on its surface, said population of oligos sharing a compatible integrase site. In some cases, the composition comprises at least one bead having population of oligos on its surface, said population of oligos sharing an att integrase site. In some cases, the composition comprises at least one bead having population of oligos on its surface, said population of oligos sharing an attP integrase site. In some cases, the composition comprises at least one bead having population of oligos on its surface, said population of oligos sharing a compatible integrase site and a barcode common to the bead. In some cases, the composition comprises at least one bead having population of oligos on its surface, said population of oligos sharing a compatible integrase site and a barcode specific to the bead. In some cases, the composition comprises at least one bead having population of oligos on its surface, said population of oligos sharing a sequencing primer binding site, a compatible integrase site and a barcode specific to the bead.

Beads

Also provided herein are populations of beads, each member of said population comprising a plurality of oligos affixed to its surface, each oligo of said plurality comprising barcode and an integrase compatible site. In some cases, the oligo comprises a sequencing primer binding site. In some cases, the oligo comprises two primer binding sites. In some cases, the two primer binding sites comprise a forward primer binding site and a reverse primer binding site. In some cases, the barcode and the integrase recognition sequence are in between a first primer binding site and a second primer binding site. Exemplary primer binding sequences include P5, P7, T7, SP6, or T3 primer binding sequences, or other primer binding sequences known in the art.

In some cases, said integrase compatible site is a retroviral integrase compatible site. In some cases, said integrase compatible site is a phage integrase-compatible site. In some cases, said phage integrase compatible site is an att compatible site. In some cases, said phage integrase compatible site is an attP, attB, attP', attB', attR, attL, attR', or attL' site.

In some cases, the oligo is double-stranded. In some cases, the bead is bound to or connected to a single strand of the double stranded oligo. The oligo can be covalently or non-covalently bound to the bead.

Samples

In some cases, the polynucleotides used in the methods disclosed herein are derived from multiple samples from the same individual, samples from different individuals, or combinations thereof. In some cases, a sample comprises a plurality of polynucleotides from a single individual. In some cases, a sample comprises a plurality of polynucleotides from two or more individuals. An individual is any organism or portion thereof from which target polynucleotides can be derived, non-limiting examples of which include plants, animals, fungi, protists, monerans, viruses, mitochondria, and chloroplasts. In further cases, sample polynucleotides are isolated from a subject, such as a cell sample, tissue sample, or organ sample derived therefrom, including, for example, cultured cell lines, biopsy, blood sample, or fluid sample containing a cell. In certain cases, the subject is an animal, including but not limited to, an animal such as a cow, a pig, a mouse, a rat, a chicken, a cat, a dog, etc., or a mammal, such as a human. In other cases, samples are artificially derived, such as by chemical synthesis. In some embodiments, the samples comprise DNA. In some embodiments, the samples comprise genomic DNA. In some embodiments, the samples comprise mitochondrial DNA, chloroplast DNA, plasmid DNA, bacterial artificial chromosomes, yeast artificial chromosomes, oligonucleotide tags, or combinations thereof. In some embodiments, the samples comprise DNA generated by primer extension reactions using any suitable combination of primers and a DNA polymerase, including but not limited to polymerase chain reaction (PCR), reverse transcription, and combinations thereof. In cases wherein the template for the primer extension reaction is RNA, the product of reverse transcription is referred to as complementary DNA (cDNA). In many cases, primers useful in primer extension reactions comprise sequences specific to one or more targets, random sequences, partially random sequences, and combinations thereof. Reaction conditions suitable for primer extension reactions are known in the art. In general, sample polynucleotides comprise any polynucleotide present in a sample, which may or may not include target polynucleotides.

In some embodiments, nucleic acid template molecules (e.g., DNA or RNA) are isolated from a biological sample containing a variety of other components, such as proteins, lipids, and non-template nucleic acids. In many embodiments, nucleic acid template molecules are obtained from any cellular material, obtained from an animal, plant, bacterium, fungus, or any other cellular organism. Biological samples for use in the present disclosure include viral particles or preparations. In further embodiments, nucleic acid template molecules are obtained directly from an organism or from a biological sample obtained from an organism, e.g., from blood, urine, cerebrospinal fluid, seminal fluid, saliva, sputum, stool, and tissue. Any tissue or body fluid specimen may be used as a source for nucleic acid for use in the disclosure. In certain cases, nucleic acid template molecules are isolated from cultured cells, such as a primary cell culture or a cell line. In various cases, the cells or tissues from which template nucleic acids are obtained are infected with a virus or other intracellular pathogen. In many cases, a sample is total RNA extracted from a biological specimen, a cDNA library, viral, or genomic DNA. In other cases, a sample is isolated DNA from a non-cellular origin, e.g. amplified/isolated DNA from the freezer.

Methods for the extraction and purification of nucleic acids are well known in the art. In some cases, nucleic acids are purified by organic extraction with phenol, phenol/chloroform/isoamyl alcohol, or similar formulations, including TRIzol™ and TriReagent®. Other non-limiting examples of extraction techniques include: (1) organic extraction followed by ethanol precipitation, e.g., using a phenol/chloroform organic reagent (Ausubel et al., 1993), with or without the use of an automated nucleic acid extractor, e.g., the Model 341 DNA Extractor available from Applied Biosystems (Foster City, Calif.); (2) stationary phase adsorption methods (U.S. Pat. No. 5,234,809; Walsh et al., 1991); and (3) salt-induced nucleic acid precipitation methods (Miller et al., (1988), such precipitation methods being typically referred to as "salting-out" methods. In other examples, nucleic acid isolation and/or purification comprises the use of magnetic particles to which nucleic acids can specifically or non-specifically bind, followed by isolation of the beads using a magnet, and washing and eluting the nucleic acids from the beads (see e.g. U.S. Pat. No. 5,705,628). In some cases, an enzyme is used to dissociate cells from each other prior to nucleic acid purification using methods provided herein. In some embodiments, the above isolation methods are preceded by an enzyme digestion step to help eliminate unwanted protein from the sample, e.g., digestion with proteinase K, or other like proteases. See, e.g., U.S. Pat. No. 7,001,724. If desired, RNase inhibitors may be added to the lysis buffer. For certain cell or sample types, it is desirable to add a protein denaturation/digestion step to the protocol. In certain cases, purification methods are directed to isolate DNA, RNA, or both. When both DNA and RNA are isolated together during or subsequent to an extraction procedure, further steps may be employed to purify one or both separately from the other. In further cases, sub-fractions of extracted nucleic acids are generated, for example, purification by size, sequence, or other physical or chemical characteristic. In addition to an initial nucleic isolation step, in many cases, purification of nucleic acids are performed after any step in the methods of the disclosure, such as to remove excess or unwanted reagents, reactants, or products.

Nucleic acid template molecules can be obtained as described in U.S. Patent Application Publication Number US2002/0190663 A1, published Oct. 9, 2003. In various cases, nucleic acid are extracted from a biological sample by a variety of techniques such as those described by Maniatis, et al., Molecular Cloning: A Laboratory Manual, Cold Spring Harbor, N.Y., pp. 280-281 (1982). In some cases, the nucleic acids are first extracted from the biological samples and then cross-linked in vitro. In some cases, native association proteins (e.g. histones) are further removed from the nucleic acids.

In some cases, the methods disclosed herein are applied to any high molecular weight double stranded DNA including, for example, DNA isolated from tissues, cell culture, bodily fluids, animal tissue, plant, bacteria, fungi, viruses, etc.

In some cases, each of the plurality of independent samples independently comprise at least about 1 ng, 2 ng, 5 ng, 10 ng, 20 ng, 30 ng, 40 ng, 50 ng, 75 ng, 100 ng, 150 ng, 200 ng, 250 ng, 300 ng, 400 ng, 500 ng, 1 µg, 1.5 µg, 2 µg, 5 µg, 10 µg, 20 µg, 50 µg, 100 µg, 200 µg, 500 µg, or 1000 µg, or more of nucleic acid material. In some embodiments, each of the plurality of independent samples independently comprise less than about 1 ng, 2 ng, 5 ng, 10 ng, 20 ng, 30 ng, 40 ng, 50 ng, 75 ng, 100 ng, 150 ng, 200 ng, 250 ng, 300 ng, 400 ng, 500 ng, 1 µg, 1.5 µg, 2 µg, 5 µg, 10 µg, 20 µg, 50 µg, 100 µg, 200 µg, 500 µg, or 1000 µg, or more of nucleic acid.

Adapters

As used herein, the term "adapter oligonucleotide" refers to any oligonucleotide having a sequence, at least a portion of which is known, that can be joined to a target polynucleotide. In some cases, adaptor oligonucleotides comprise DNA, RNA, nucleotide analogues, non-canonical nucleotides, labeled nucleotides, modified nucleotides, or combinations thereof. In certain cases, adaptor oligonucleotides are single-stranded, double-stranded, or partial duplex. In many cases, a partial-duplex adapter comprises one or more single-stranded regions and one or more double-stranded regions. In some cases, double-stranded adapters comprise two separate oligonucleotides hybridized to one another (also referred to as an "oligonucleotide duplex"). In further examples, the hybridization leaves one or more blunt ends, one or more 3' overhangs, one or more 5' overhangs, one or more bulges resulting from mismatched and/or unpaired nucleotides, or any combination of these. In some embodiments, a single-stranded adapter comprises two or more sequences that are able to hybridize with one another. When two such hybridizable sequences are contained in a single-stranded adapter, hybridization yields a hairpin structure (hairpin adapter). When two hybridized regions of an adapter are separated from one another by a non-hybridized region, a "bubble" structure results. In various cases, adaptors adopt a bubble structure comprising a single adapter oligonucleotide that comprises internal hybridizations, or comprise two or more adapter oligonucleotides hybridized to one another. In certain cases, internal sequence hybridization, such as between two hybridizable sequences in an adapter, produce a double-stranded structure in a single-stranded adapter oligonucleotide.

In some cases, adaptors of different kinds can be used in combination, such as a hairpin adapter and a double-stranded adapter, or adapters of different sequences. Hybridizable sequences in a hairpin adapter may or may not include one or both ends of the oligonucleotide. When neither of the ends are included in the hybridizable sequences, both ends are "free" or "overhanging." When only one end is hybridizable to another sequence in the adapter, the other end forms an overhang, such as a 3' overhang or a 5' overhang. When both the 5'-terminal nucleotide and the 3'-terminal nucleotide are included in the hybridizable sequences, such that the 5'-terminal nucleotide and the 3'-terminal nucleotide are complementary and hybridize with one another, the end is referred to as "blunt." In some embodiments, end repair is performed to generate blunt end 5' phosphorylated nucleic acid ends using commercial kits, such as those available from Epicentre Biotechnologies' (Madison, WI).

In certain cases, different adapters are joined to target polynucleotides in sequential reactions or simultaneously. In some cases, the first and second adapters are added to the same reaction. In certain examples, adaptors can be manipulated prior to combining with target polynucleotides. In further examples, terminal phosphates are added or removed.

In many cases, adaptors contain one or more of a variety of sequence elements, including but not limited to, one or more amplification primer annealing sequences or complements thereof, one or more sequencing primer annealing sequences or complements thereof, one or more barcode sequences, one or more common sequences shared among multiple different adapters or subsets of different adapters, one or more restriction enzyme recognition sites, one or more overhangs complementary to one or more target polynucleotide overhangs, one or more probe binding sites (e.g. for attachment to a sequencing platform, such as a flow cell for massive parallel sequencing, such as developed by Illumina®, Inc.), one or more random or near-random sequences (e.g. one or more nucleotides selected at random from a set of two or more different nucleotides at one or more positions, with each of the different nucleotides selected at one or more positions represented in a pool of adapters comprising the random sequence), and combinations thereof. In some cases, two or more sequence elements are non-adjacent to one another (e.g. separated by one or more nucleotides), adjacent to one another, partially overlapping, or completely overlapping. In certain examples, an amplification primer annealing sequence serves as a sequencing primer annealing sequence. In some cases, sequence elements are located at or near the 3' end, at or near the 5' end, or in the interior of the adapter oligonucleotide. In certain cases, when an adapter oligonucleotide is capable of forming secondary structure, such as a hairpin, sequence elements are located partially or completely outside the secondary structure, partially or completely inside the secondary structure, or in between sequences participating in the secondary structure. In some cases, when an adapter oligonucleotide comprises a hairpin structure, sequence elements are located partially or completely inside or outside the hybridizable sequences (the "stem"), including in the sequence between the hybridizable sequences (the "loop").

In some cases, the first adapter oligonucleotides in a plurality of first adapter oligonucleotides having different barcode sequences comprise a sequence element common among all first adapter oligonucleotides. In some embodiments, all second adapter oligonucleotides comprise a sequence element common among all second adapter oligonucleotides that is different from the common sequence element shared by the first adapter oligonucleotides. A difference in sequence elements can be any such that at least a portion of different adapters do not completely align, for example, due to changes in sequence length, deletion, or insertion of one or more nucleotides, or a change in the nucleotide composition at one or more nucleotide positions (such as a base change or base modification).

In some embodiments, an adapter oligonucleotide comprises a 5' overhang, a 3' overhang, or both that is complementary to one or more target polynucleotides. In some cases, complementary overhangs are one or more nucleotides in length, including but not limited to 1, 2, 3, 4, 5, 6, 7, 8, 9, 10, 11, 12, 13, 14, 15, or more nucleotides in length. In further examples, the complementary overhangs are about 1, 2, 3, 4, 5 or 6 nucleotides in length. In some cases, complementary overhangs comprise a fixed sequence. In other cases, complementary overhangs comprise a random sequence of one or more nucleotides, such that one or more nucleotides are selected at random from a set of two or more different nucleotides at one or more positions, with each of the different nucleotides selected at one or more positions represented in a pool of adapters with complementary overhangs comprising the random sequence. In some embodiments, an adapter overhang is complementary to a target polynucleotide overhang produced by restriction endonuclease digestion. In some embodiments, an adapter overhang consists of an adenine or a thymine.

Adapter oligonucleotides can have any suitable length, at least sufficient to accommodate the one or more sequence elements of which they are comprised. In some embodiments, adapters are about, less than about, or more than about 10, 15, 20, 25, 30, 35, 40, 45, 50, 55, 60, 65, 70, 75, 80, 90, 100, 200, or more nucleotides in length. In some cases, the adaptors are about 10 to about 50 nucleotides in length. In further examples, the adaptors are about 20 to about 40 nucleotides in length.

Tagged Genomic DNA

Provided herein are tagged genomic DNA samples. In some cases, tagged genomic DNA samples comprise a fragment of genomic DNA, a donor sequence, a first integrase recognition sequence, and a barcode. In some cases, the genomic DNA is a crosslinked chromatin or a reconstituted chromatin. In some cases, the first integrase recognition sequence and the donor sequence are derived from a bacteriophage. In some cases, the first integrase recognition sequence comprises an attB. In some cases, the donor sequence comprises an attP. In some cases, the first integrase recognition sequence has a nucleic acid sequence selected from at least one of GGGTGCCAGGGCGTGCCC-TTGGGCTCCCCGGGCGCGTA (SEQ ID NO: 2). In some cases, the donor sequence has a nucleic acid sequence selected from CCCCAACTGGGGTAACCTTT-GAGTTCTCTCAGTTGGGG (SEQ ID NO: 3). In some cases, the first integrase recognition sequence and the donor sequence each comprise no more than 25 nucleotides in length.

In some cases, the tagged genomic DNA sample further comprises an integrase. In some cases, the integrase comprises a bacteriophage integrase. In some cases, the integrase comprises a φC31 integrase. In some cases, the integrase is a serine integrase. In some cases, the integrase is a single polypeptide integrase. In some cases, the integrase has no detectable excision activity. In some cases, the integrase is a retrovirus integrase. In some cases, the integrase is selected from one or more of an HIV-1 integrase, an HIV-2 integrase, a SIV integrase, and an RSV integrase.

In some cases, the tagged genomic DNA sample is biotinylated. In some cases, the tagged genomic DNA sample further comprises a sequencing primer. In some cases, the tagged genomic DNA sample further comprises a second sequencing primer. In some cases, the sequencing primer is selected from a P5 and a P7. In some cases, the P5 has a nucleic acid sequence comprising AATGATACGGCGACCACCGA (SEQ ID NO: 4). In some cases, the P7 has a nucleic acid sequence comprising CAAGCAGAAGACGGCATACGAGAT (SEQ ID NO: 5).

In some cases, the tagged genomic DNA sample further comprises a bead.

In some cases, the fragment of genomic DNA comprises a first segment and a second segment of a nucleic acid molecule that are held together independently of their common phosphodiester backbone. In some cases, the first integrase recognition sequence is between the first segment and the second segment. In some cases, the tagged genomic DNA sample comprises a sequencing library which preserves contig assembly information. In some cases, the barcode is indicative of a nucleic acid molecule of the sample.

Nucleic Acid Libraries

Also provided herein are nucleic acid libraries. In some cases, nucleic acid libraries comprise a fragment of genomic DNA, a first integrase recognition sequence, a donor sequence, and a barcode. In some cases, the first integrase recognition sequence and the donor sequence are derived from a bacteriophage. In some cases, the first integrase recognition sequence comprises an attB. In some cases, the donor sequence comprises an attP. In some cases, the first integrase recognition sequence has a nucleic acid sequence selected from at least one of GGGTGCCAGGGCGTGCCCTTGGGCTCCCCGGGCGCGTA (SEQ ID NO: 2). In some cases, the donor sequence has a nucleic acid sequence selected from CCCCAACTGGGGTAACCTTTGAGTTCTCTCAGTTGGGG (SEQ ID NO: 3). In some cases, the first integrase recognition sequence and the donor sequence each comprise no more than 25 nucleotides in length.

In some cases, the nucleic acid library further comprises an integrase. In some cases, the integrase comprises a bacteriophage integrase. In some cases, the integrase comprises a φC31 integrase. In some cases, the integrase is a serine integrase. In some cases, the integrase is a single polypeptide integrase. In some cases, the integrase has no detectable excision activity. In some cases, the integrase is a retrovirus integrase. In some cases, the integrase is selected from one or more of an HIV-1 integrase, an HIV-2 integrase, a SIV integrase, and an RSV integrase.

In some cases, the nucleic acid library is biotinylated. In some cases, the nucleic acid library further comprises a sequencing primer. In some cases, the nucleic acid library further comprises a second sequencing primer. In some cases, the sequencing primer is selected from a P5 and a P7. In some cases, the P5 has a nucleic acid sequence comprising AATGATACGGCGACCACCGA (SEQ ID NO: 4). In some cases, the P7 has a nucleic acid sequence comprising CAAGCAGAAGACGGCATACGAGAT (SEQ ID NO: 5).

In some cases, the nucleic acid library further comprises a bead.

In some cases, the fragment of genomic DNA comprises a first segment and a second segment of a nucleic acid molecule that are held together independently of their common phosphodiester backbone. In some cases, the first integrase recognition sequence is between the first segment and the second segment. In some cases, the nucleic acid library comprises a sequencing library which preserves contig assembly information. In some cases, the barcode is indicative of a nucleic acid molecule of the sample.

Also provided herein, are nucleic acid sample sequencing libraries. In some cases, the sequencing library comprises a plurality of nucleic acid molecules, wherein the nucleic acid library molecules comprise a post-integration junction and an independently varying segment of a nucleic acid sample. In some cases, the nucleic acid sample is a genomic nucleic acid sample. In some cases, the post-integration junction and an independently varying segment of a nucleic acid sample are adjacent on the nucleic acid library molecules. In some cases, the nucleic acid library molecules comprise a barcoding segment. In some cases, the barcoding segment is indicative of a bead of origin of at least part of the post-integration junction. In some cases, the barcoding segment is indicative of a nucleic acid of origin of the independently varying segment of a nucleic acid sample. In some cases, the nucleic acid library molecules each comprise a sequencing primer binding site. In some cases, the sequencing primer binding site is adjacent to a post-integration junction. In some cases, the sequencing primer binding site is adjacent to barcoding segment. In some cases, the barcoding segment is between the sequencing primer binding site and the post-integration junction. In some cases, the sequencing primer binding site is a p5 primer binding site. In some cases, the sequencing primer binding site is adjacent to an independently varying segment of a nucleic acid sample. In some cases, the sequencing primer binding site is a p7 primer binding site.

One exemplary advantage of the methods disclosed herein is the ability to vary the length of sample DNA fragments within a library by selecting a fragmentation method that is suited for a particular application, experiment, or sequencing method. For example, a restriction enzyme can be selected based on the desired criteria and expected fragment characteristics or distribution. Among those characteristics is the predicted average fragment length or a distribution of fragment lengths. More specifically, in experiments in which longer fragments are desired, a restriction enzyme with relatively fewer predicted cut sites can be selected. Similarly, a restriction enzyme with relatively more frequent cut sites can be selected when shorter fragments are desired. Likewise, a restriction enzyme can also be selected based on the desired frequency of barcode insertions using the same concepts.

FIG. 1 depicts an exemplary workflow for protocols herein. Roughly 4 hours on Day 1, and 2.5 hours on Day 2 are hands-off incubations. Steps that include an optional stopping point are marked using a symbol.

FIGS. 2A-2D depict data resulting from extraction of chromatin from fixed tissue samples using collagenase. For each table, the results of 6 replicates of sample 170, 3 replicates of sample 213, 3 replicates of sample 272 and 3 replicates of sample 472 are shown, for a total of 15 sample analysis runs. At FIG. 2A, one sees the percentage of PCR duplication artifacts in each sample. A target percentage is less than 1%, as indicated in parentheses at top. Each of the four samples yielded a PCR duplicate rate of well under the 1% target, indicating the efficacy of the extraction using collagenase. At FIG. 2B, one sees the percentage of paired end reads that map to different scaffolds on a reference set each sample. A target percentage is less than 15%, as indicated in parentheses at top. Each of the four samples yielded a different scaffold rate of no more than half of the 15% target, indicating the efficacy of the extraction using collagenase. At FIG. 2C, one sees the percentage of paired end reads that map within 1 kb of one another on a reference set each sample. A target percentage is less than 50%, as indicated in parentheses at top. Each of the four samples yielded a 'within 1 kb' rate of at or only 10% above the 50% target, indicating the efficacy of the extraction using collagenase. At FIG. 2D, one sees the percentage of paired end reads that map to greater than 1 kb from one another on a reference set each sample. A target percentage is greater than 5%, as indicated in parentheses at top. Each of the four samples yielded a 'greater than 1 kb' rate of between almost 2× and almost 5× that of the target rate, indicating the efficacy of the extraction using collagenase.

Figure 4:
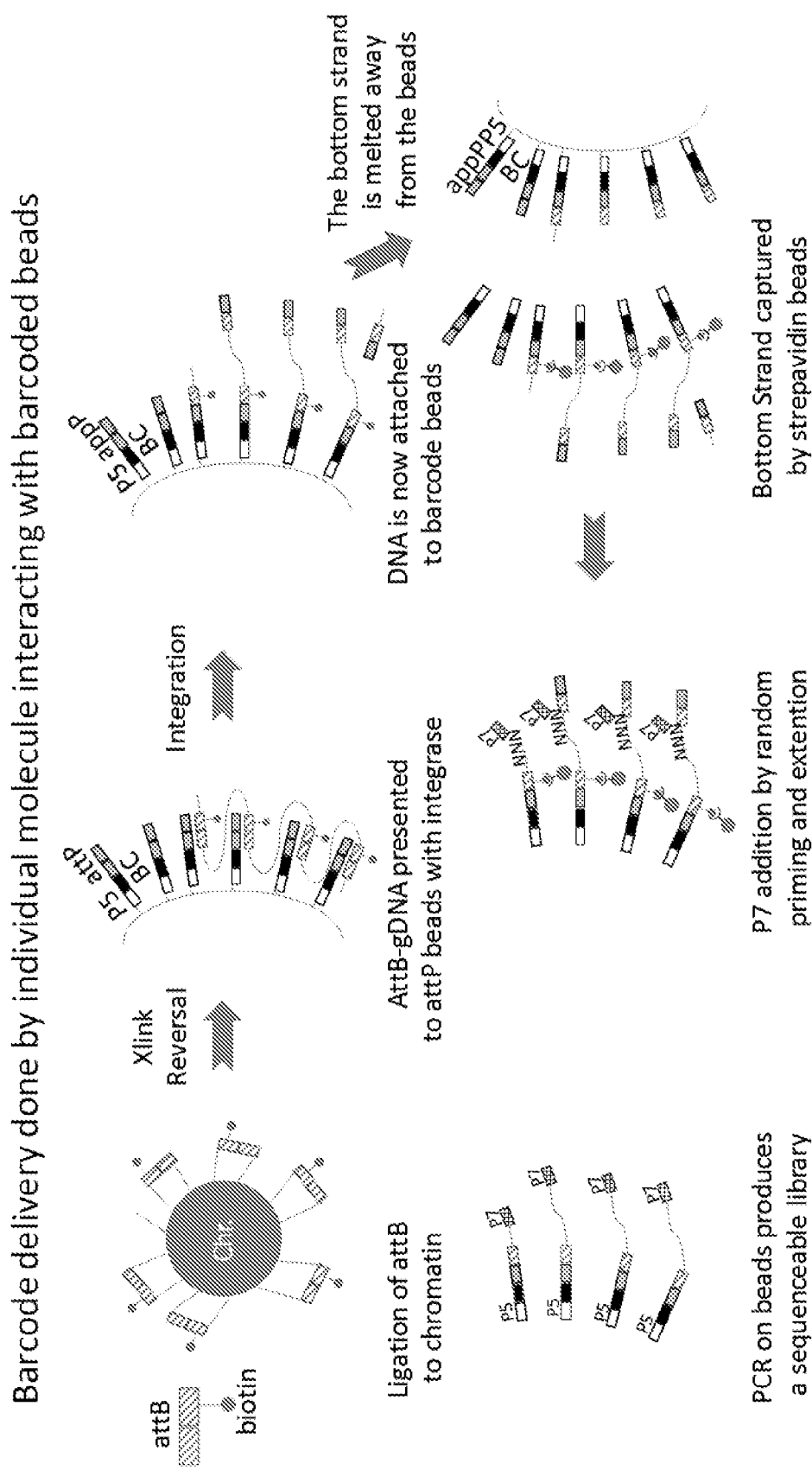
FIG. 4 shows barcode delivery done by individual molecule interacting with barcoded beads.

FIG. 4 shows barcode delivery done by individual molecule interacting with barcoded beads. The first panel shows a polynucleotide comprising an attB site and a biotinylated nucleotide. The polynucleotide is ligated to genomic DNA fragments that are fixed to histones in a chromatin complex. The ligation forms long chains of genomic DNA fragments with intervening attB sites and biotinylated nucleotides. The crosslinking is reversed. The top middle panel shows the long chain of genomic fragments and attB sites bound to double stranded oligonucleotides attached to a bead. The oligonucleotides comprise a P5 primer binding site, a barcode, and an attP site. The attP and attB sites are recombined using an integrase. The top right panel shows the recombined products, which include the P5 primer binding site, the barcode, the att site and biotinylated nucleotide, the genomic DNA fragment, and the second att site. The bottom strand of the recombined molecule is melted away from the bead. The bottom right panel shows that the single-stranded DNA molecules comprising the biotinylated nucleotide are captured by streptavidin beads. Once purified, a P7 primer binding site is added by random priming and extension (bottom middle panel). The molecules are amplified by PCR to produce a library ready for sequencing (bottom left panel).

Figure 5:
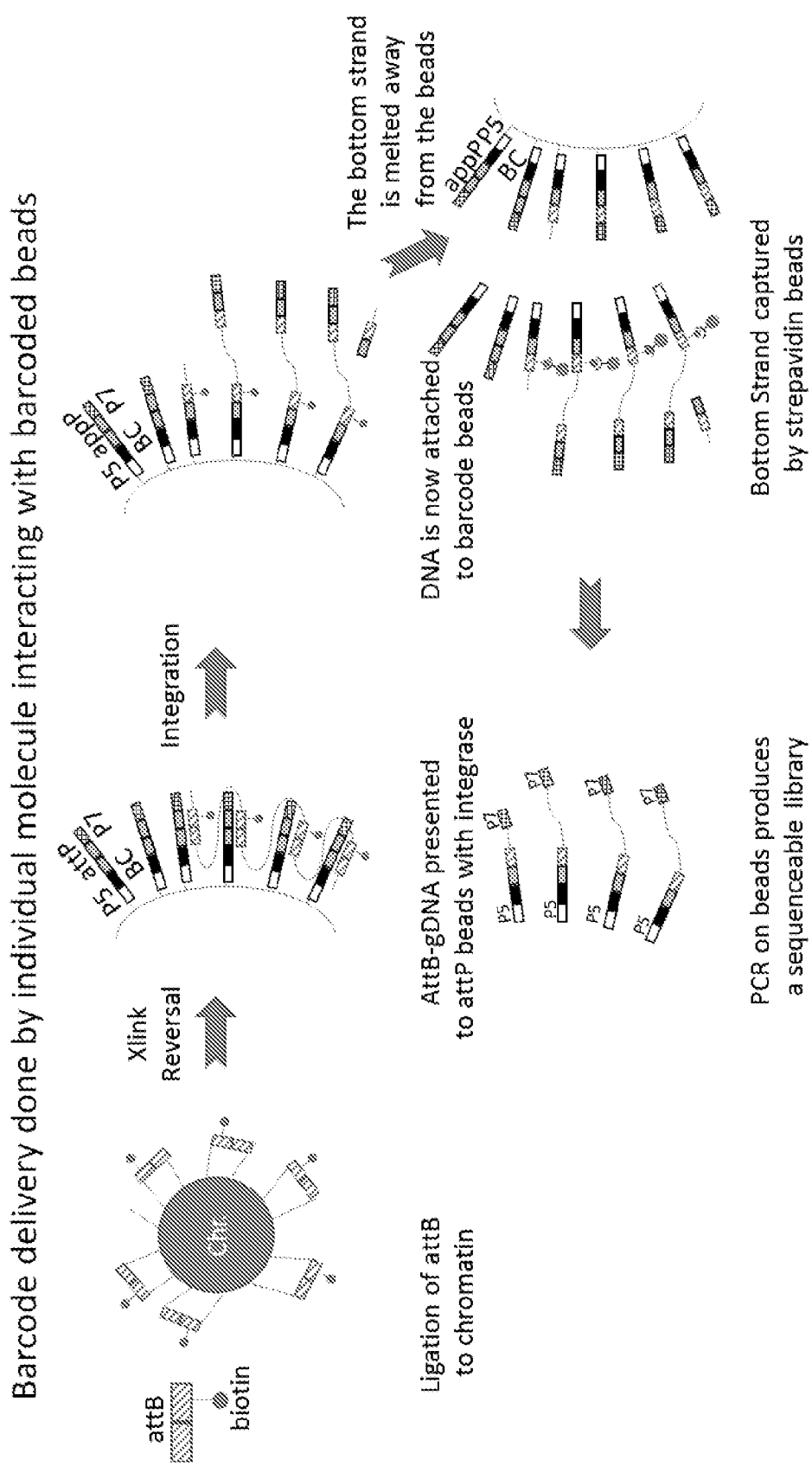
FIG. 5 shows an alternate method of barcode delivery done by individual molecule interacting with barcoded beads.

FIG. 5 shows an alternate method of barcode delivery done by individual molecule interacting with barcoded beads. The first panel shows a polynucleotide comprising an attB site and a biotinylated nucleotide. The polynucleotide is ligated to genomic DNA fragments that are fixed to histones in a chromatin complex. The ligation forms long chains of genomic DNA fragments with intervening attB sites and biotinylated nucleotides. The crosslinking is reversed. The top middle panel shows the long chain of genomic fragments and attB sites bound to double stranded oligonucleotides attached to a bead. The oligonucleotides comprise a P5 primer binding site, a barcode, an attP site, and a P7 primer binding site. The attP and attB sites are recombined using an integrase. The top right panel shows the recombined products, which include the P5 primer binding site, the barcode, the att site and biotinylated nucleotide, the genomic DNA fragment, the second att site, and the P7 primer binding site. The bottom strand of the recombined molecule is melted away from the bead. The bottom right panel shows that the single-stranded DNA molecules comprising the biotinylated nucleotide are captured by streptavidin beads. Once purified, the molecules are amplified by PCR to produce a library ready for sequencing (bottom left panel).

As used herein and in the appended claims, the singular forms "a," "and," and "the" include plural referents unless the context clearly dictates otherwise. Thus, for example, reference to "contig" includes a plurality of such contigs and reference to "probing the physical layout of chromosomes" includes reference to one or more methods for probing the physical layout of chromosomes and equivalents thereof known to those skilled in the art, and so forth.

Also, the use of "and" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

It is to be further understood that where descriptions of various embodiments use the term "comprising," those skilled in the art would understand that in some specific instances, an embodiment can be alternatively described using language "consisting essentially of" or "consisting of."

As used herein, the term "at least one of" a, b, c, and d means a, b, c, or d alone, or combinations thereof up to and including all of a, b, c, and d.

The term "about" as used herein to describe a number, unless otherwise specified, refers to a range of values including that number plus or minus 10% of that number. When used in the context of a range, the term refers to 10% lower than the lower extent of the range, and 10% greater than the upper extent of the range as listed.

As used herein, "obtaining" a nucleic acid sample is given a broad meaning in some cases, such that it refers to receiving an isolated nucleic acid sample, as well as receiving a raw human or environmental sample, for example, and isolating nucleic acids therefrom.

The term "read," "sequence read," or "sequencing read" as used herein, refers to the sequence of a fragment or segment of DNA or RNA nucleic acid that is determined in a single reaction or run of a sequencing reaction.

The term "contigs" as used herein, refers to contiguous regions of DNA sequence. "Contigs" can be determined by any number methods known in the art, such as, by comparing sequencing reads for overlapping sequences, and/or by comparing sequencing reads against a database of known sequences in order to identify which sequencing reads have a high probability of being contiguous. For many genomes and other large-scale sequencing projects, contigs are available and can be readily obtained, but physical linkage information regarding whether two or more contigs represent sequence from a single physical nucleic acid molecule, and how the contigs are to be positioned relative to one another, is difficult to obtain. This difficulty is largely due to the presence of repetitive regions comprising sequence information that does not uniquely map to any single contig.

The terms "polynucleotide," "nucleotide," "nucleic acid" and "oligonucleotide" are often used interchangeably. They generally refer to a polymeric form of nucleotides of any length, either deoxyribonucleotides or ribonucleotides, or analogs thereof. Polynucleotides comprise base monomers that are joined at their ribose backbones by phosphodiester bonds. Polynucleotides may have any three-dimensional structure, and may perform any function, known or unknown. The following are non-limiting examples of polynucleotides: coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, complementary DNA (cDNA), which is a DNA representation of mRNA, usually obtained by reverse transcription of messenger RNA (mRNA) or by amplification; DNA molecules produced synthetically or by amplification, genomic DNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. Generally, an oligonucleotide comprises only a few bases, while a polynucleotide can comprise any number but is generally longer, while a nucleic acid can refer to a polymer of any length, up to and including the length of a chromosome or an entire genome. Also, the term nucleic acid is often used collectively, such that a nucleic acid sample does not necessarily refer to a single nucleic acid molecule; rather it may refer to a sample comprising a plurality of nucleic acid molecules. The term nucleic acid can encompass double- or triple-stranded nucleic acids, as well as single-stranded molecules. In double- or triple-stranded nucleic acids, the nucleic acid strands need not be coextensive, e.g., a double-stranded nucleic acid need not be double-stranded along the entire length of both strands. The term nucleic acid can encompass any chemical modification thereof, such as by methylation and/or by capping. Nucleic acid modifications can include addition of chemical groups that incorporate additional charge, polarizability, hydrogen bonding, electrostatic interaction, and functionality to the individual nucleic acid bases or to the nucleic acid as a whole. Such modifications may include base modifications such as 2'-position sugar modifications, 5-position pyrimidine modifications, 8-position purine modifications, modifications at cytosine exocyclic amines, substitutions of 5-bromo-uracil, backbone modifications, unusual base pairing combinations such as the isobases including isocytidine, isoguanidine, and the like.

The term "nanoparticles" as used herein can refer to nanometer-scale spheres that can be modified to bind DNA. The nanoparticles can be positively charged on the surface (e.g. by coating with amine-containing molecules). See Zinchenko, A. et al. (2005) "Compaction of Single-Chain DNA by Histone-Inspired Nanoparticles" *Physical Review Letters*, 95(22), 228101, which is herein incorporated by reference in its entirety. In some cases, the nanoparticle is a platinum-based nanoparticle, such cisplatin, oxaliplatin, satraplatin, picoplatin, nedaplatin, triplatin, lipoplatin, transplatin, carboplatin or any other platinum-based DNA-binding nanoparticle, or derivatives thereof. In other cases, the nanoparticle can be a DNA intercalator (e.g. berberine, chlorambucil, ethidium bromide, mitoxantrone, proflavine, daunomycin, doxorubicin, thalidomide, nimustine, tirapazamine, carmustine, angelicin, daunorubicin, carminomycin, aclacinomycin, chlorambucil, cyclophosphamide, methotrexate, 5-uracil, arabinosyl cytosine, mitomycin, procarbazine, vinblastine, vincristine, plicamycin (Mithracin®), daptomycin (Cubicin®) anthracycline, furocoumarins, psoralen), or any derivatives thereof. In further cases, the nanoparticle can be a bisintercalator (e.g. bisacridine, echinomycin), or any derivatives thereof.

The term "subject" as used herein can refer to any eukaryotic or prokaryotic (eubacterial or archaeal) organism. For example, a subject can be a mammal, such as a human.

The term "naked DNA" as used herein can refer to DNA that is substantially free of complexed DNA binding proteins. For example, it can refer to DNA complexed with less than about 10%, about 5%, or about 1% of the endogenous proteins found in the cell nucleus, or less than about 10%, about 5%, or about 1% of the endogenous DNA-binding proteins regularly bound to the nucleic acid in vivo, or less than about 10%, about 5%, or about 1% of an exogenously added nucleic acid binding protein or other nucleic acid binding moiety, such as a nanoparticle. In some cases, naked DNA refers to DNA that is not complexed to DNA binding proteins.

The terms "polypeptide" and "protein" are often used interchangeably and generally refer to a polymeric form of amino acids, or analogs thereof bound by polypeptide bonds. Polypeptides and proteins can be polymers of any length. Polypeptides and proteins can have any three-dimensional structure, and may perform any function, known or unknown. Polypeptides and proteins can comprise modifications, including phosphorylation, lipidation, prenylation, sulfation, hydroxylation, acetylation, formation of disulfide bonds, and the like. In some cases, "protein" refers to a polypeptide having a known function or known to occur naturally in a biological system, but this distinction is not always adhered to in the art.

As used herein, nucleic acids are "stabilized" if they are bound by a binding moiety or binding moieties such that separate segments of a nucleic acid are held in a single complex independent of their common phosphodiester backbone. Stabilized nucleic acids in complexes remain bound independent of their phosphodiester backbones, such that treatment with a restriction endonuclease does not result in disintegration of the complex, and internal double-stranded DNA breaks are accessible without the complex losing its integrity.

Alternately or in combination, nucleic acid complexes comprising nucleic acids and nucleic acid binding moieties are "stabilized" by treatment that increases their binding or renders them otherwise resistant to degradation or dissolution. An example of stabilizing a complex comprises treating the complex with a fixative such as formaldehyde or psoralen, or treating with UV light so as to induce cross-linking between nucleic acids and binding moieties, or among binding moieties, such that the complex or complexes are resistant to degradation or dissolution, for example following restriction endonuclease treatment or treatment to induce nucleic acid shearing.

The term "scaffold" as used herein generally refers to contigs separated by gaps of known length but unknown sequence or separated by unknown length but known to reside on a single molecule, or ordered and oriented sets of contigs that are linked to one another by mate pairs of sequencing reads. In cases where contigs are separated by gaps of known length, the sequence of the gaps may be determined by various methods, including PCR amplification followed by sequencing (for smaller gaps) and bacterial artificial chromosome (BAC) cloning methods followed by sequencing (for larger gaps).

The term "stabilized sample" as used herein refers to a nucleic acid that is stabilized in relation to an association molecule via intermolecular interactions such that the nucleic acid and association molecule are bound in a manner that is resistant to molecular manipulations such as restriction endonuclease treatment, DNA shearing, labeling of nucleic acid breaks, or ligation. Nucleic acids known in the art include but are not limited to DNA and RNA, and derivatives thereof. The intermolecular interactions can be covalent or non-covalent. Exemplary methods of covalent binding include but are not limited to crosslinking techniques, coupling reactions, or other methods that are known to one of ordinary skill in the art. Exemplary methods of noncovalent interactions involve binding via ionic interactions, hydrogen bonding, halogen bonding, Van der Waals forces (e.g. dipole interactions), π-effects (e.g. π-π interactions, cation-π and anion-π interactions, polar π interactions, etc.), hydrophobic effects, and other noncovalent interactions that are known to one of ordinary skill in the art. Examples of association molecules include, but are not limited to, chromosomal proteins (e.g. histones), transposases, and any nanoparticle that is known to covalently or non-covalently interact with nucleic acids.

The term "heterogeneous sample" as used herein refers a biological sample comprising a diverse population of nucleic acids (e.g. DNA, RNA), cells, organisms, or other biological molecules. In many cases the nucleic acids originate from one than one organism. For example, a heterogeneous nucleic acid sample can comprise at least about 1000, 2000, 3000, 4000, 5000, 6000, 7000, 8000, 9000, 10,000, 20,000, 50,000, 100,000, 200,000, 500,000, 1,000,000, 2,000,000, 5,000,000, 10,000,000, or more DNA molecules. Further, each of the DNA molecules can comprise the full or partial genome of at least one or at least two or more than two organisms, such that the heterogeneous nucleic sample can comprise the full or partial genome of at least about 1000, 2000, 3000, 4000, 5000, 6000, 7000, 8000, 9000, 10,000, 20,000, 50,000, 100,000, 200,000, 500,000, 1,000, 000, 2,000,000, 5,000,000, 10,000,000, or more different organisms. Examples of heterogeneous samples are those obtained from a variety of sources, including but not limited to a subject's blood, sweat, urine, stool, or skin; or an environmental source (e.g. soil, seawater); a food source; a waste site such as a garbage dump, sewer, or public toilet; or a trash can.

A "partial genome" of an organism can comprise at least about 10%, 20%, 30%, 40%, 50%, 60%, 70%, 80%, 90%, 95%, 99% or more the entire genome of an organism, or can comprise a sequence data set comprising at least about 10%, 20%, 30%, 40%, 50%, 60%, 70%, 80%, 90%, 95%, 99% or more of the sequence information of the entire genome.

The term "reconstituted chromatin" as used herein can refer to forming chromatin formed by complexing isolated nuclear proteins to naked DNA.

The term "tagged sequence" as used herein can refer to a DNA sequence that comprises an added sequence that can be used to identify or associate the sequence for analytical purposes. For example, a group of tagged sequences that share the same tag can be binned together. In some examples, the tagged sequences that are in the same bin are further assigned a common phase or are assigned to a common molecule of origin. Exemplary methods of "tagging" include but are not limited to introducing a tag using an enzyme (e.g. transposase, ligase), and/or covalently linking DNA segments to each other to obtain read-pairs. A tagged sequence is 'sequenced' by, for example, obtaining end reads wherein one end read comprises tag sequence and the other end read comprises sequence of the segment to which the tag has been added. In some cases, the entire tag, the tag-segment junction, and the entire segment are sequenced. However, this is not always necessary for tagging and sequencing to be effective. On the contrary, in many cases, sequencing of an identifiable portion of the tag end and an identifiable portion of the segment end is sufficient to effect 'sequencing of the tagged segment,' particularly but not exclusively when contig information is available, such as previously generated or concurrently generated contig information. Similarly, a paired-end tag sequence is 'sequenced' in some cases by obtaining end reads where each end read comprises recognizable sequence of a ligated segment. Paired end fragments may be completely sequenced such that the junction sequence is obtained, but this is not always necessary for paired end tagging and sequencing to be effective. Accordingly, as used herein, 'sequencing a tagged segment' or 'sequencing a paired-end read' need not comprise obtaining a complete end-to-end sequence of the ligated molecule. So long as identifiable sequences of either end of the molecule be obtained such that the identity of the nucleic acids joined to form the ligated molecule are obtained, the joined fragment may be referred to as having been 'sequenced'. In some cases, the sequencing comprises end-to-end sequencing that spans the ligation junction. In some cases, the sequencing comprises generating reads from either end of the joined molecule.

The term "read set", "read-set", "read pair" or "read-pair" as used herein can refer to two or more elements, or a library of elements, that are linked to provide sequence information. In some cases, the number of read-sets or read-pairs can refer to the number of mappable read-sets or read-pairs. In other cases, the number of read-sets or read-pairs can refer to the total number of generated read-sets or read-pairs. In some cases, the linked elements in a read-set or read-pair can share a common label such as a barcode.

The terms "bind", "binding", "associate", "association", or "associating", or derivatives thereof, as used herein refers to stabilizing a molecule to another molecule via intermolecular interactions. The intermolecular interactions can be covalent or non-covalent in nature. Exemplary methods of covalent binding include but are not limited to crosslinking techniques, coupling reactions, or other methods that are known to one of ordinary skill in the art. Exemplary methods of noncovalent interactions include ionic interactions, hydrogen bonding, halogen bonding, Van der Waals forces (e.g. dipole interactions), π-effects (e.g. π-π interactions, cation-π and anion-π interactions, polar π interactions, etc.), hydrophobic effects, and other noncovalent interactions that are known to one of ordinary skill in the art.

The term "immobilizing" or "immobilization" as used herein refers to stabilizing a molecule or complex in relation to an object. For example, a DNA complex is immobilized to a solid support when the DNA complex is stabilized in relation to the solid support. In some cases, the immobilized DNA complex will remain stabilized in relation to the solid support even when subjected to various wash steps.

The term "bridge amplification" as used herein can refer to an amplification reaction where one or more of template and primer molecules are immobilized on a support, thereby forming a bridge-like structure during amplification. An example of bridge amplification is described in U.S. Pat. No. 8,652,810, which is herein incorporated by reference in its entirety.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

Partial List of Numbered Embodiments

The disclosure herein is further clarified in reference to a partial list of numbered embodiments as follows. 1. A method of recovering nucleic acid phase information from a preserved sample, comprising: subjecting the sample to an enzymatic treatment so as to degrade intercellular material while leaving a substantial portion of nucleic acids bound in nucleoprotein complexes. 2. The method of embodiment 1, comprising subjecting the preserved sample to an enzymatic treatment under conditions insufficient to release a substantial portion of nucleic acids bound in nucleoprotein complexes. 3. The method of embodiment 2, wherein the enzyme is proteinase k and wherein the reaction conditions comprise a reaction time insufficient to degrade a substantial portion of nucleosomes. 4. The method of embodiment 1, wherein the enzymatic treatment comprises contacting the sample to an enzyme that degrades intercellular material while leaving a substantial portion of nucleic acids bound in nucleoprotein complexes. 5. The method of embodiment 4, wherein the enzyme does not degrade intracellular proteins. 6. The method of embodiment 4, wherein the enzyme does not degrade cell membranes. 7. The method of embodiment 4, wherein the enzyme exhibits collagenase activity. 8. The method of embodiment 7, wherein the enzyme is a collagenase. 9. The method of embodiment 4, wherein the enzyme exhibits actin degradation activity. 10. The method of embodiment 4, wherein the enzyme exhibits myosin degradation activity. 11. The method of embodiment 4, wherein the enzyme does not degrade nuclear proteins. 12. The method of embodiment 4, wherein the enzyme does not degrade nucleosomes. 13. The method of embodiment 4, wherein the enzyme does not degrade nucleoprotein complexes. 14. The method of embodiment 4, wherein the enzyme does not degrade chromatin. 15. The method of embodiment 1, wherein the nucleic acids bound in nucleoprotein complexes comprise a first segment of a chromosome and a second segment of the chromosome bound in a common nucleoprotein complex. 16. The method of embodiment 15, wherein the first segment and the second segment do not share a common phosphodiester bond. 17. The method of embodiment 15, wherein the first segment and the second segment share a common phosphodiester bond. 18. The method of embodiment 15, comprising treating a nucleoprotein complex to cleave a phosphodiester backbone. 19. The method of embodiment 18, wherein treating comprises contacting to a restriction endonuclease. 20. The method of embodiment 18, wherein treating comprises contacting to a nonspecific endonuclease. 21. The method of embodiment 18, wherein treating comprises contacting to a transposase. 22. The method of embodiment 18, wherein treating comprises contacting to an invertase. 23. The method of embodiment 18, wherein treating comprises shearing. 24. The method of embodiment 18, wherein treating comprises sonicating. 25. The method of embodiment 18, wherein treating comprises exposing to radiation. 26. The method of embodiment 1, wherein the nucleic acids bound in nucleoprotein complexes comprise a first segment of a first chromosome and a second segment of a second chromosome bound in a common nucleoprotein complex. 27. The method of embodiment 26, wherein the first chromosome and the second chromosome are in physical proximity in a tissue nucleus. 28. A method of releasing nucleic acids from a fixed biological sample comprising contacting the fixed tissue sample to an enzyme. 29. The method of embodiment 28, wherein the nucleic acids comprise molecules at least 100 kb in length. 30. The method of embodiment 28, wherein the nucleic acids comprise molecules at least 500 kb in length. 31. The method of any one of embodiments 28 to 30, wherein the nucleic acids comprise molecules at least 1000 kb in length. 32. The method of any one of embodiments 28 to 31, wherein the nucleic acids comprise molecules bound to nucleic acid binding proteins. 33. The method of embodiment 32, wherein the nucleic acid binding proteins comprise a histone protein. 34. The method of embodiment 33, wherein the histone protein is selected from a histone H1, a histone H2A, a histone H2B, a histone H3, a histone H4, and combinations thereof. 35. The method of embodiment 32, wherein the nucleic acid binding proteins are selected from a transposase, a topoisomerase, a transcription factor, a methylase, a histone deacetylase, and combinations thereof. 36. The method of any one of embodiments 28 to 35, wherein the nucleic acids comprise molecules at least partially assembled into chromatin. 37. The method of any one of embodiments 28 to 36, wherein the nucleic acids comprise molecules bound such that a first segment and a second segment of a nucleic acid molecule are held together independent of their common phosphodiester backbone. 38. The method of any one of embodiments 28 to 37, wherein the enzyme has collagenase activity. 39. The method of embodiment 38, wherein the enzyme is a collagenase. 40. The method of embodiment 38 or embodiment 39, wherein the enzyme is a *Clostridium* collagenase. 41. The method of embodiment 38 or embodiment 39, wherein the enzyme is a mammalian collagenase. 42. The method of embodiment 38 or embodiment 39, wherein the enzyme is a stromelysin. 43. The method of embodiment 38 or embodiment 39, wherein the enzyme is a matrilysin. 44. The method of embodiment 38 or embodiment 39, wherein the enzyme is a gelatinase. 45. The method of embodiment 38 or embodiment 39, wherein the enzyme is a matrix metalloproteinase. 46. The method of embodiment 38 or embodiment 39, wherein the enzyme is a membrane bound matrix metalloproteinase. 47. The method of embodiment 38 or embodiment 39, wherein the enzyme is a disintegrin and metalloproteinase with thrombospondin motifs (ADAMTS). 48. The method of any one of embodiments 28 to 37, wherein the enzyme has aggrecanase activity. 49. The method of any one of embodiments 28 to 37, wherein the enzyme has gelatinase activity. 50. The method of any one of embodiments 28 to 37, wherein the enzyme has elastinase activity. 51. The method of any one of embodiments 28 to 37, wherein the enzyme has fibronectinase activity. 52. The method of any one of embodiments 28 to 37, wherein the enzyme has lamininase activity. 53. The method of any one of embodiments 28 to 37, wherein the enzyme has cellulase activity. 54. The method of embodiment 40, wherein the enzyme is a cellulase. 55. The method of any one of embodiments 28 to 54, wherein the biological sample is a tissue sample. 56. The method of embodiment 55, wherein the tissue sample is selected from a skin sample, a muscle sample, a bone sample, a brain sample, a liver sample, a kidney sample, a stomach sample, an intestine sample, an ovarian sample, a testicular sample, an oral tissue sample, a lymph node sample, a thymus sample, a spleen sample, a bone marrow sample, a lung sample, a breast tissue sample, and a cartilage sample. 57. The method of embodiment 55 or embodiment 56, wherein the tissue sample is a tumor sample. 58. The method of any one of embodiments 28 to 54, wherein the biological sample is a blood sample. 59. The method of any one of embodiments 28 to 54, wherein the biological sample comprises cultured cells. 60. The method of any one of embodiments 1 to 59, wherein the enzyme is not a proteinase K. 61. The method of any one of embodiments 28 to 60, wherein the enzyme does not digest chromatin. 62. The method of any one of embodiments 28 to 61, wherein the enzyme does not degrade nucleosomes. 63. The method of any one of embodiments 28 to 61, wherein the released nucleic acids comprise at least one nucleosome. 64. The method of any one of embodiments 28 to 63, wherein the enzyme breaks intercellular bonds. 65. The method of any one of embodiments 28 to 64, wherein the enzyme digests extracellular proteins. 66. The method of any one of embodiments 28 to 65, wherein the enzyme digests cytoplasmic proteins. 67. The method of any one of embodiments 28 to 66, wherein the method preserves linkage information in the nucleic acids. 68. A method of preparing reconstituted chromatin from a fixed biological sample, comprising contacting the fixed biological sample to an enzyme to create a digested biological sample, isolating nucleic acid from the digested biological sample, contacting the nucleic acid to an isolated nuclear protein to create reconstituted chromatin. 69. The method of embodiment 68, wherein the nucleic acids comprise molecules at least 100 kb in length. 70. The method of embodiment 68 or embodiment 69, wherein the nucleic acids comprise molecules at least 500 kb in length. 71. The method of any one of embodiments 68 to 70, wherein the nucleic acids comprise molecules at least 1000 kb in length. 72. The method of any one of embodiments 68 to 71, wherein the isolated nuclear protein comprises a nucleic acid binding protein. 73. The method of embodiment 72, wherein the nucleic acid binding protein comprises a histone protein. 74. The method of embodiment 73, wherein the histone protein is selected from a histone H1, a histone H2A, a histone H2B, a histone H3, a histone H4, and combinations thereof. 75. The method of embodiment 72, wherein the nucleic acid binding protein is selected from a transposase, a topoisomerase, a transcription factor, a methylase, a histone deacetylase, and combinations thereof. 76. The method of any one of embodiments 68 to 75, wherein the reconstituted chromatin comprises molecules bound such that a first segment and a second segment of a nucleic acid molecule are held together independent of their common phosphodiester backbone. 77. The method of any one of embodiments 68 to 76, wherein the enzyme has collagenase activity. 78. The method of embodiment 77, wherein the enzyme is a collagenase. 79. The method of embodiment 77 or embodiment 78, wherein the enzyme is a *Clostridium* collagenase. 80. The method of embodiment 77 or embodiment 78, wherein the enzyme is a mammalian collagenase. 81. The method of embodiment 77 or embodiment 78, wherein the enzyme is a stromelysin. 82. The method of embodiment 77 or embodiment 78, wherein the enzyme is a matrilysin. 83. The method of embodiment 77 or embodiment 78, wherein the enzyme is a gelatinase. 84. The method of embodiment 77 or embodiment 78, wherein the enzyme is a matrix metalloproteinase. 85. The method of embodiment 77 or embodiment 78, wherein the enzyme is a membrane bound matrix metalloproteinase. 86. The method of embodiment 77 or embodiment 78, wherein the enzyme is a disintegrin and metalloproteinase with thrombospondin motifs (ADAMTS). 87. The method of any one of embodiments 68 to 76, wherein the enzyme has aggrecanase activity. 88. The method of any one of embodiments 68 to 76, wherein the enzyme has gelatinase activity. 89. The method of any one of embodiments 68 to 76, wherein the enzyme has elastinase activity. 90. The method of any one of embodiments 68 to 76, wherein the enzyme has fibronectinase activity. 91. The method of any one of embodiments 68 to 76, wherein the enzyme has lamininase activity. 92. The method of any one of embodiments 68 to 76, wherein the enzyme has cellulase activity. 93. The method of embodiment 92, wherein the enzyme is a cellulase. 94. The method of any one of embodiments 68 to 93, wherein the biological sample is a tissue sample. 95. The method of embodiment 94, wherein the tissue sample is selected from a skin sample, a muscle sample, a bone sample, a brain sample, a liver sample, a kidney sample, a stomach sample, an intestine sample, an ovarian sample, a testicular sample, an oral tissue sample, a lymph node sample, a thymus sample, a spleen sample, a bone marrow sample, a lung sample, a breast tissue sample, and a cartilage sample. 96. The method of embodiment 94 or embodiment 95, wherein the tissue sample is a tumor sample. 97. The method of any one of embodiments 68 to 93, wherein the biological sample is a blood sample. 98. The method of any one of embodiments 68 to 93, wherein the biological sample comprises cultured cells. 99. The method of any one of embodiments 68 to 98, wherein the enzyme is not a proteinase K. 100. The method of any one of embodiments 68 to 99, wherein the enzyme does not digest chromatin. 101. The method of any one of embodiments 68 to 100, wherein the enzyme does not degrade nucleosomes. 102. The method of any one of embodiments 68 to 100, wherein the released nucleic acids comprise at least one nucleosome. 103. The method of any one of embodiments 68 to 102, wherein the enzyme breaks intercellular bonds. 104. The method of any one of embodiments 68 to 103, wherein the enzyme digests extracellular proteins. 105. The method of any one of embodiments 68 to 104, wherein the enzyme digests cytoplasmic proteins. 106. The method of any one of embodiments 68 to 105, wherein the method preserves linkage information in the nucleic acids. 107. A method of releasing nucleic acids from a biological sample comprising contacting the fixed tissue sample to an enzyme. 108. The method of embodiment 107, wherein the nucleic acids comprise molecules at least 100 kb in length. 109. The method of embodiment 107 or embodiment 108, wherein the nucleic acids comprise molecules at least 500 kb in length. 110. The method of any one of embodiments 107 to 109, wherein the nucleic acids comprise molecules at least 1000 kb in length. 111. The method of any one of embodiments 107 to 110, wherein the nucleic acids comprise molecules bound to nucleic acid binding proteins. 112. The method of embodiment 111, wherein the nucleic acid binding proteins comprise a histone protein. 113. The method of embodiment 112, wherein the histone protein is selected from a histone H1, a histone H2A, a histone H2B, a histone H3, a histone H4, and combinations thereof 114. The method of embodiment 111, wherein the nucleic acid binding proteins are selected from a transposase, a topoisomerase, a transcription factor, a methylase, a histone deacetylase, and combinations thereof. 115. The method of any one of embodiments 107 to 114, wherein the nucleic acids comprise molecules at least partially assembled into chromatin. 116. The method of any one of embodiments 107 to 115, wherein the nucleic acids comprise molecules bound such that a first segment and a second segment of a nucleic acid molecule are held together independent of their common phosphodiester backbone. 117. The method of any one of embodiments 107 to 116, wherein the enzyme has collagenase activity. 118. The method of embodiment 117, wherein the enzyme is a collagenase. 119. The method of embodiment 117 or embodiment 118, wherein the enzyme is a *Clostridium* collagenase. 120. The method of embodiment 117 or embodiment 118, wherein the enzyme is a mammalian collagenase. 121. The method of embodiment 117 or embodiment 118, wherein the enzyme is a stromelysin. 122. The method of embodiment 117 or embodiment 118, wherein the enzyme is a matrilysin. 123. The method of embodiment 117 or embodiment 118, wherein the enzyme is a gelatinase. 124. The method of embodiment 117 or embodiment 118, wherein the enzyme is a matrix metalloproteinase. 125. The method of embodiment 117 or embodiment 118, wherein the enzyme is a membrane bound matrix metalloproteinase. 126. The method of embodiment 117 or embodiment 118, wherein the enzyme is a disintegrin and metalloproteinase with thrombospondin motifs (ADAMTS). 127. The method of any one of embodiments 107 to 116, wherein the enzyme has aggrecanase activity. 128. The method of any one of embodiments 107 to 116, wherein the enzyme has gelatinase activity. 129. The method of any one of embodiments 107 to 116, wherein the enzyme has elastinase activity. 130. The method of any one of embodiments 107 to 116, wherein the enzyme has fibronectinase activity. 131. The method of any one of embodiments 107 to 116, wherein the enzyme has lamininase activity. 132. The method of any one of embodiments 107 to 116, wherein the enzyme has cellulase activity. 133. The method of embodiment 132, wherein the enzyme is a cellulase. 134. The method of any one of embodiments 107 to 133, wherein the biological sample is fixed. 135. The method of any one of embodiments 107 to 134, wherein the biological sample is a tissue sample. 136. The method of embodiment 135, wherein the tissue sample is selected from a skin sample, a muscle sample, a bone sample, a brain sample, a liver sample, a kidney sample, a stomach sample, an intestine sample, an ovarian sample, a testicular sample, an oral tissue sample, a lymph node sample, a thymus sample, a spleen sample, a bone marrow sample, a lung sample, a breast tissue sample, and a cartilage sample. 137. The method of embodiment 135 or embodiment 136, wherein the tissue sample is a tumor sample. 138. The method of any one of embodiments 107 to 134, wherein the biological sample is a blood sample. 139. The method of any one of embodiments 107 to 134, wherein the biological sample comprises cultured cells. 140. The method of any one of embodiments 107 to 139, wherein the enzyme is not a proteinase K. 141. The method of any one of embodiments 107 to 140, wherein the enzyme does not digest chromatin. 142. The method of any one of embodiments 107 to 141, wherein the enzyme does not degrade nucleosomes. 143. The method of any one of embodiments 107 to 141, wherein the released nucleic acids comprise at least one nucleosome. 144. The method of any one of embodiments 107 to 143, wherein the enzyme breaks intercellular bonds. 145. The method of any one of embodiments 107 to 144, wherein the enzyme digests extracellular proteins. 146. The method of any one of embodiments 107 to 145, wherein the enzyme digests cytoplasmic proteins. 147. The method of any one of embodiments 107 to 146, wherein the method preserves linkage information in the nucleic acids. 148. A method of generating a linkage-informative tagged library for an RNA sample comprising: a. obtaining a sample comprising an RNA molecule, wherein the RNA molecule comprises a first RNA segment and a second RNA segment sharing a common phosphodiester backbone, wherein the first RNA segment and second RNA segment are not adjacent on the RNA molecule; b. contacting the RNA molecule to at least one RNA-binding moiety such that the first RNA segment and second RNA segment are bound to one another independent of the common phosphodiester backbone, thereby forming a complex; c. cleaving the RNA molecule such that the first RNA segment and second RNA segment are not joined by the common phosphodiester backbone; and d. adding tagging information to the first RNA segment and to the second RNA segment, such that the tagging information identifies the first RNA segment and the second RNA segment as originating from the RNA molecule. 149. The method of embodiment 1, comprising sequencing at least a portion of the first RNA segment and at least a portion of the second RNA segment. 150. The method of embodiment 149, further comprising identifying a first variant in the sequence of the first RNA segment. 151. The method of embodiment 150, further comprising assigning the first variant to the RNA molecule. 152. The method of embodiment 150, wherein identifying the first variant in the sequence of the first RNA segment comprises identifying a point mutation relative to a predicted RNA molecule sequence. 153. The method of embodiment 150, wherein identifying the first variant in the sequence of the first RNA segment comprises identifying a retained intron sequence relative to a predicted RNA molecule. 154. The method of embodiment 150, wherein identifying the first variant in the sequence of the first RNA segment comprises identifying a junction between a first exon and a second exon in the first segment, wherein the junction between the first exon and the second exon is not present in a predicted RNA sequence. 155. The method of embodiment 151, further comprising identifying a second variant in the sequence of the second RNA segment. 156. The method of embodiment 155, further comprising assigning the second variant to the RNA molecule. 157. The method of embodiment 155, wherein identifying the second variant in the sequence of the second RNA segment comprises identifying a point mutation relative to a predicted RNA molecule sequence. 158. The method of embodiment 155, wherein identifying the second variant in the sequence of the second RNA segment comprises identifying a retained intron sequence relative to a predicted RNA molecule. 159. The method of embodiment 155, wherein identifying the second variant in the sequence of the second RNA segment comprises identifying a junction between a first exon and a second exon in the second segment, wherein the junction between the first exon and the second exon is not present in a predicted RNA sequence. 160. The method of embodiment 148, wherein the RNA molecule comprises at least a first segment and a second segment of an mRNA molecule sharing a common phosphodiester backbone. 161. The method of embodiment 160, wherein the mRNA or portion thereof comprises at least a portion of an mRNA species transcribed from a gene that encodes a plurality of alternatively spliced mRNA species. 162. The method of embodiment 161, wherein identifying the segments of the RNA molecule further comprises identifying the alternatively spliced mRNA species or portion thereof. 163. The method of embodiment 162, wherein identifying the alternatively spliced mRNA species or portion thereof comprises identifying at least one exon present in the alternatively spliced mRNA species or portion thereof 164. The method of embodiment 163, wherein the alternatively spliced mRNA species comprises at least two exons, and wherein identifying the alternatively spliced mRNA species or portion thereof comprises identifying a junction between a first exon and a second exon. 165. The method of embodiment 163, wherein identifying the alternatively spliced mRNA species or portion thereof comprises identifying a junction between a first exon and a first predicted untranslated region. 166. The method of embodiment 148, further comprising quantifying an amount of the RNA molecule present in the sample. 167. The method of embodiment 148, wherein at least one RNA-binding moiety comprises an RNA-binding protein. 168. The method of embodiment 167, wherein the RNA-binding protein comprises a native RNA-binding protein. 169. The method of embodiment 167, wherein the RNA-binding protein comprises a recombinant RNA-binding protein. 170. The method of embodiment 169, wherein the recombinant RNA-binding protein comprises a heterogeneous nuclear ribonucleoprotein (hnRNP). 171. The method of embodiment 170, wherein the hnRNP is selected from a group consisting of: hnRNP A0, hnRNP A1, hnRNP A1L1, hnRNP A1L2, hnRNP A3, hnRNP A2B1, hnRNP AB, hnRNP B1, hnRNP PC, hnRNP PCL1, hnRNP D, hnRNP DL, hnRNP PF, hnRNP PH1, hnRNP PH2, hnRNP PH3, hnRNP PK, hnRNP PL, hnRNP LL, hnRNP PM, hnRNP PR, hnRNP U, hnRNP UL1, hnRNP UL2, hnRNP UL3, FMR1, hrp36, Hrb87F, and homologs thereof 172. The method of embodiment 148, wherein the RNA-binding moiety is hnRNP A1. 173. The method of embodiment 148, wherein the RNA-binding moiety comprises hrp36 174. The method of embodiment 173, wherein the hrp36 comprises a polyhistidine tag. 175. The method of embodiment 148, wherein the linking comprises contacting at least one RNA-binding moiety with a cross-linking agent. 176. The method of embodiment 175, wherein the cross-linking agent comprises formaldehyde. 177. The method of embodiment 148, wherein the linking comprises linking a first RNA-binding moiety bound to the first RNA segment to a second RNA-binding moiety bound to the second RNA segment. 178. The method of embodiment 148, wherein the method further comprises attaching at least one of the first RNA segment or the second RNA segment to an affinity tag prior to sequencing. 179. The method of embodiment 178, wherein the attaching at least one of the first RNA segment or second RNA segment to an affinity tag comprises attaching a nucleotide comprising the affinity tag to the RNA molecule. 180. The method of embodiment 178, wherein the affinity tag comprises a polyhistidine tag. 181. The method of embodiment 178, further comprising isolating the RNA molecule using the affinity tag. 182. The method of embodiment 178, further comprising contacting the complex with a solid surface. 183. The method of embodiment 182, wherein the solid surface comprises a bead. 184. The method of embodiment 183, wherein the bead comprises a magnetic nickel bead. 185. The method of embodiment 148, wherein cleaving the RNA molecule comprises alkaline hydrolysis of the RNA molecule. 186. The method of embodiment 148, wherein cleaving the RNA molecule comprises contacting the RNA molecule with an endonuclease. 187. The method of embodiment 148, wherein cleaving the RNA molecule comprises shearing the RNA molecule. 188. The method of embodiment 148, further comprising contacting the cleaved RNA molecule with a phosphatase. 189. The method of embodiment 188, wherein the phosphatase removes at least one phosphate group from the RNA molecule. 190. The method of embodiment 189, wherein removing the at least one phosphate group comprises removing at least one 5' phosphate group from the cleaved RNA molecule. 191. The method of embodiment 148, further comprising contacting the cleaved RNA molecule with a phosphotransferase. 192. The method of embodiment 191, wherein the phosphotransferase is a T4 polynucleotide kinase. 193. The method of embodiment 148, further comprising attaching a nucleotide comprising an affinity tag to the RNA molecule. 194. The method of embodiment 148, wherein adding tagging information comprises joining the first RNA segment to the second RNA segment such that the first RNA segment is adjacent to the second RNA segment, thereby forming a junction between the first RNA segment and second RNA segment. 195. The method of embodiment 194, wherein joining comprises ligating an end of the first RNA segment to an end of the second RNA segment with an RNA ligase, wherein the first RNA segment and the second RNA segment are joined by a common phosphodiester backbone. 196. The method of embodiment 148, wherein the tagging information comprises a junction between the first RNA segment and the segment RNA segment. 197. The method of embodiment 196, wherein the tagging information added to the first RNA segment comprises sequence information from the second RNA segment and the tagging information added to the second RNA segment comprises sequence information from the first RNA segment. 198. The method of embodiment 148, wherein adding tagging information comprises adding barcode information to the first RNA segment and to the second RNA segment such that the first RNA segment and second RNA segment can be identified as originating from the RNA molecule. 199. The method of embodiment 148, wherein sequencing at least a portion of the first RNA segment and at least a portion of the second RNA segment further comprises sequencing the tagging information added to the first RNA segment and the tagging information added to the second RNA segment. 200. The method of embodiment 148, further comprising disrupting the linking from step (b). 201. The method of embodiment 200, wherein disrupting the linking comprises adding a salt solution. 202. The method of embodiment 148, further comprising reverse transcribing the first RNA segment and the second RNA segment, wherein sequencing at least the portion of the first RNA segment and at least the portion of the second RNA segment comprises sequencing the reverse-transcribed portions of the first and second RNA segments. 203. The method of embodiment 148, further comprising adding a chelating agent to the joined RNA molecule. 204. The method of embodiment 203, wherein the chelating agent comprises Ethylenediaminetetraacetic acid (EDTA). 205. The method of embodiment 203, wherein the chelating agent comprises egtazic acid (EGTA). 206. The method of embodiment 203, wherein the chelating agent comprises EDTA and EGTA. 207. The method of embodiment 148, further comprising ligating an oligo to the joined RNA molecule. 208. The method of embodiment 207, further comprising circularizing the joined RNA molecule with the oligo using an RNA ligase. 209. The method of embodiment 207, wherein the oligo comprises pre-adenylated DNA. 210. The method of embodiment 207, further comprising cleaving the linker. 211. The method of embodiment 148, further comprising amplifying the first RNA segment and the second RNA segment. 212. The method of embodiment 148, wherein sequencing comprises obtaining read-pair information. 213. The method of embodiment 212, further comprising obtaining standard paired-end read distance frequency data. 214. The method of embodiment 212, further comprising scaffolding a group of contigs such that read pair distance frequency data for read pairs that map to separate contigs approximates the standard paired-end read distance frequency data. 215. The method of embodiment 148, wherein the RNA molecule is shorter than 30 kilobases long. 216. The method of embodiment 215, wherein the RNA molecule is shorter than 20 kilobases long. 217. The method of embodiment 216, wherein the RNA molecule is less than 10 kilobases long. 218. The method of embodiment 148, wherein the sample comprises a plurality of RNA molecules and wherein at least 95% of the RNA molecules are shorter than 30 kilobases long. 219. The method of embodiment 218, wherein at least 95% of the RNA molecules are shorter than 20 kilobases long. 220. The method of embodiment 219, wherein at least 95% of the RNA molecules are shorter than 10 kilobases long. 221. The method of embodiment 148, wherein the sample further comprises a plurality of RNA molecule species. 222. The method of embodiment 221, wherein the plurality of RNA molecule species comprises a second RNA molecule that comprises a third RNA segment and a fourth RNA segment, wherein the third RNA segment and fourth RNA segment are not adjacent on the second RNA molecule, and wherein the method further comprises: a. linking the third RNA segment to the fourth RNA segment using at least one RNA-binding moiety such that the third RNA segment and fourth RNA segment are bound to one another independent of a second common phosphodiester backbone of the second RNA molecule, thereby forming a second complex; b. cleaving the second RNA molecule such that the third RNA segment and fourth RNA segment are not joined by the second common phosphodiester backbone; c. adding tagging information to the third RNA segment and the fourth RNA segment, such that the tagging information identifies the third RNA segment and the fourth RNA segment as originating from the second RNA molecule; and d. sequencing at least a portion of the third RNA segment and at least a portion of the fourth RNA segment, thereby identifying the segments of the second RNA molecule. 223. The method of embodiment 222, wherein the second RNA molecule comprises a second alternatively spliced mRNA species and wherein identifying the segments of the second RNA molecule further comprises identifying the second alternatively spliced mRNA species. 224. The method of embodiment 222, further comprising comparing the identity the first RNA segment to the identity of the third RNA segment and comparing the identity of the second RNA segment to the identity of the fourth RNA segment. 225. The method of embodiment 222, further comprising quantifying an amount of the first RNA molecule and an amount of the second RNA molecule present in the sample 226. An in vitro library comprising a plurality of read-pairs each comprising at least a first segment and a second segment, wherein the first segment is adjacent to the second segment on the read-pair, wherein the first and second segments of each pair originate from the same RNA molecule and wherein at least 1% of read-pairs comprise first and second segments that are not adjacent to each other on the original RNA molecule. 227. The in vitro library of embodiment 226, wherein the first and second segments are separated by at least 100 base pairs on the original RNA molecule. 228. The in vitro library of embodiment 226, wherein the first and second segments are separated by at least 125 base pairs on the original RNA molecule. 229. The in vitro library of embodiment 226, wherein the first and second segments are separated by at least 150 base pairs on the original RNA molecule. 230. The in vitro library of embodiment 226, wherein the first and second segments are separated by at least 200 base pairs on the original RNA molecule. 231. The in vitro library of embodiment 226, wherein the first and second segments are separated by at least 300 base pairs on the original RNA molecule. 232. The in vitro library of embodiment 226, wherein the first and second segments are separated by at least 400 base pairs on the original RNA molecule. 233. The in vitro library of embodiment 226, wherein the first and second segments are separated by at least 500 base pairs on the original RNA molecule. 234. The in vitro library of embodiment 226, wherein the first and second segments are separated by at least 1000 base pairs on the original RNA molecule. 235. The in vitro library of embodiment 226, wherein the read pairs further comprise a barcode. 236. The in vitro library of embodiment 226, wherein the read pairs further comprise a P5 primer site and a P7 primer site. 237. A method of assigning RNA sequence variant information to a common molecule of an RNA sample, comprising a. obtaining read pair information from a population of RNA molecules that have been individually bound such that a first segment and a second segment of an RNA molecule of the population are held together independent of their phosphodiester backbone, treated so as to cleave the phosphodiester backbone between the first segment and the second segment, religated, and sequenced to generate read pair information comprising sequence corresponding to the first segment and to the second segment; b. identifying a first segment comprising tagging information indicating the first segment is from a first RNA molecule; c. identifying a second segment comprising tagging information indicating the second segment is from the first RNA molecule; and d. assigning the first segment and the second segment to the first RNA molecule. 238. The method of embodiment 237, wherein the first segment comprises a variant relative to a predicted RNA sequence. 239. The method of embodiment 238, wherein identifying the variant in a sequence corresponding to the first segment comprises identifying a point mutation that is not present in a predicted RNA molecule sequence. 240. The method of embodiment 238, wherein identifying the variant in a sequence corresponding to the first segment comprises identifying a retained intron sequence that is not present in a predicted RNA molecule sequence. 241. The method of embodiment 238, wherein identifying the variant in a sequence corresponding to the first segment comprises identifying an exon-exon junction that is not present in a predicted RNA molecule sequence. 242. The method of embodiment 238, wherein identifying the variant in a sequence corresponding to the first segment comprises identifying an allelic variant relative to a predicted RNA molecule sequence. 243. A method of delivering a barcode to a nucleic acid sample, the method comprising: ligating a first polynucleotide comprising a first integrase recognition site sequence to a target nucleic acid; contacting the first polynucleotide to a second polynucleotide comprising a second integrase recognition site and a barcode; contacting the first and second polynucleotides to an integrase under conditions that support integrase activity to form a third polynucleotide comprising a barcoded target nucleic acid; and isolating the barcoded target nucleic acid. 244. The method of embodiment 243, further comprising sequencing at least a portion of the barcoded target nucleic acid. 245. The method of embodiment 243, wherein the target nucleic acid comprises genomic DNA. 246. The method of embodiment 243, further comprising contacting the target nucleic acid to at least one DNA binding moiety such that a first DNA segment and a second DNA segment are bound to one another independent of a common phosphodiester backbone, thereby forming a complex. 247. The method of embodiment 246, wherein the complex comprises reconstituted chromatin. 248. The method of embodiment 246, further comprising crosslinking the DNA binding moiety to the target nucleic acid. 249. The method of embodiment 243, further comprising digesting the target nucleic acid with an enzyme to create at least one exposed double strand end. 250. The method of embodiment 249, wherein the enzyme is a restriction endonuclease. 251. The method of embodiment 243, wherein at least one of the first and second integrase recognition sites is derived from a bacteriophage. 252. The method of embodiment 243, wherein one of the first and second integrase recognition sites comprises an attB site. 253. The method of embodiment 252, wherein the other of the first and second integrase recognition sites comprises an attP site. 254. The method of embodiment 243, wherein one of the first and second integrase recognition sites comprises an attR site. 255. The method of embodiment 252, wherein the other of the first and second integrase recognition sites comprises an attL site. 256. The method of embodiment 243, wherein at least one of the first and second integrase recognition sites comprises a nucleic acid sequence selected from at least one of GGGTGCCAGGGCGTGCCCTTGGGCTCCCCGG-GCGCGTA (SEQ ID NO: 2). 257. The method of embodiment 243, wherein at least one of the first and second integrase recognition sites comprises a nucleic acid sequence selected from at least one of CCC-CAACTGGGGTAACCTTTGAGTTCTCTCAGTTGGGG (SEQ ID NO: 3). 258. The method of embodiment 243, wherein the integrase comprises a bacteriophage integrase. 259. The method of embodiment 243, wherein the integrase is a serine integrase. 260. The method of embodiment 243, wherein the integrase comprises a φC31 integrase. 261. The method of embodiment 243, wherein the integrase is a single polypeptide integrase. 262. The method of embodiment 243, wherein the integrase has no detectable excision activity. 263. The method of embodiment 243, wherein the integrase is a retrovirus integrase. 264. The method of embodiment 243, wherein the integrase is selected from one or more of an HIV-1 integrase, an HIV-2 integrase, a SIV integrase, and an RSV integrase. 265. The method of embodiment 243, wherein the first polynucleotide comprises biotin. 266. The method of embodiment 243, wherein the second polynucleotide comprises biotin. 267. The method of embodiment 243, wherein the barcoded target nucleic acid is isolated using a bead. 268. The method of embodiment 243, wherein the second polynucleotide comprises a first sequencing primer. 269. The method of embodiment 268, wherein the sequencing primer is selected from a P5 and a P7 sequencing primer. 270. The method of embodiment 268, further comprising adding a second sequencing primer to the barcoded target nucleic. 271. The method of embodiment 270, wherein the adding comprises annealing. 272. The method of embodiment 270, wherein the adding comprises nucleic acid synthesis. 273. The method of embodiment 270, wherein the adding comprises nucleic acid amplification. 274. The method of embodiment 273, wherein the adding comprises random primer extension 275. The method of embodiment 270, wherein the second sequencing primer comprises P7 or P5 sequencing primer. 276. The method of embodiment 269, wherein the method further comprises adding a second sequencing primer to the barcoded target nucleic acid, wherein the second sequencing primer is the other of a P7 or P5 sequencing primer. 277. The method of embodiment 246, wherein the first integrase recognition site is ligated to the first segment and the second segment. 278. The method of embodiment 243, wherein the barcode is indicative of a nucleic acid molecule of a sample. 279. The method of embodiment 246, wherein the first DNA segment maps to a first contig and the second DNA segment maps to a second DNA contig. 280. The method of embodiment 279, further comprising assigning the first contig and the second contig to a common DNA scaffold. 281. The method of embodiment 280, further comprising assigning the first contig and the second contig to a common DNA molecule. 282. The method of embodiment 243, wherein the barcode is not inserted at a random position. 283. A complex comprising a DNA binding moiety, a plurality of DNA fragments originating from a common target nucleic acid molecule, and at least one first integrase recognition site ligated to at least two of the plurality of DNA fragments originating from the common target nucleotide. 284. The complex of embodiment 283, wherein the complex comprises reconstituted chromatin. 285. The complex of embodiment 283, wherein the DNA binding moiety is crosslinked to at least one of the DNA fragments. 286. The complex of embodiment 283, wherein the first integrase recognition site is derived from a bacteriophage. 287. The complex of embodiment 283, wherein the first integrase recognition site comprises an attP site. 288. The complex of embodiment 283, wherein the first integrase recognition site comprises an attB site. 289. The complex of embodiment 283, wherein the first integrase recognition site comprises an attR site. 290. The complex of embodiment 283, wherein the first integrase recognition site comprises an attL site. 291. The complex of embodiment 283, wherein the first integrase recognition site comprises a nucleic acid sequence selected from at least one of CCC-CAACTGGGGTAACCTTTGAGTTCTCTCAGTTGGGG (SEQ ID NO: 3). 292. The complex of embodiment 283, wherein the first integrase recognition site further comprises an affinity tag. 293. The complex of embodiment 292, wherein the affinity tag comprises biotin. 294. A solid support comprising an oligonucleotide, wherein the oligonucleotide comprises a first sequencing primer site, a barcode, and a first integrase recognition site. 295. The solid support of embodiment 294, wherein the solid support comprises a plurality of the oligonucleotides. 296. The solid support of embodiment 294, wherein the solid support comprises a bead. 297. The solid support of embodiment 294, wherein the oligonucleotide further comprises a second sequencing primer site. 298. The solid support of embodiment 294, wherein the first sequencing primer site is selected from a P5 or a P7 sequencing primer site. 299. The solid support of embodiment 298, wherein the oligonucleotide further comprises a second sequencing primer site selected from the other of a P5 or a P7 sequencing primer site. 300. The solid support of embodiment 298, wherein the solid support comprises a plurality of the oligonucleotides. 301. The solid support of embodiment 298, wherein the solid support comprises a bead. 302. A complex comprising a nucleic acid and a solid support, wherein the nucleic acid comprises a plurality of DNA fragments originating from the same target nucleic acid molecule, and at least one integrase recognition site ligated to at least two fragments of the plurality of DNA fragments originating from the same target nucleotide; and the solid support comprises an oligonucleotide, wherein the oligonucleotide comprises a first sequencing primer site, a barcode, and first integrase recognition site. 303. The complex of embodiment 302, wherein the first integrase recognition is derived from a bacteriophage. 304. The complex of embodiment 302, wherein the first integrase recognition comprises an attP site. 305. The complex of embodiment 302, wherein the first integrase recognition comprises an attB site. 306. The complex of embodiment 302, wherein the first integrase recognition comprises an attR site. 307. The complex of embodiment 302, wherein the first integrase recognition comprises an attL site. 308. The complex of embodiment 302, wherein the first integrase recognition comprises a nucleic acid sequence selected from at least one of CCCCAACTGGGGTAACCTTT-GAGTTCTCTCAGTTGGGG (SEQ ID NO: 3). 309. The complex of embodiment 302, wherein the first integrase recognition further comprises an affinity tag. 310. The complex of embodiment 309, wherein the affinity tag comprises biotin. 311. The complex of embodiment 302, wherein the solid support comprises a plurality of the oligonucleotides. 312. The complex of embodiment 302, wherein the solid support comprises a bead. 313. The complex of embodiment 302, wherein the oligonucleotide further comprises a second sequencing primer site. 314. The complex of embodiment 302, wherein the first sequencing primer site is selected from a P5 or a P7 sequencing primer site. 315. The complex of embodiment 314, wherein the oligonucleotide further comprises a second sequencing primer site selected from the other of a P5 or a P7 sequencing primer site. 316. The complex of embodiment 314, wherein the solid support comprises a plurality of the oligonucleotides. 317. The complex of embodiment 314, wherein the solid support comprises a bead. 318. The complex of embodiment 314, further comprising an integrase. 319. The complex of embodiment 318, wherein the integrase comprises a bacteriophage integrase. 320. The complex of embodiment 318, wherein the integrase comprises a φC31 integrase. 321. The complex of embodiment 318, wherein the integrase is a serine integrase. 322. The complex of embodiment 318, wherein the integrase is a single polypeptide integrase. 323. The complex of embodiment 318, wherein the integrase has no detectable excision activity. 324. The complex of embodiment 318, wherein the integrase is a retrovirus integrase. 325. The complex of embodiment 318, wherein the integrase is selected from one or more of an HIV-1 integrase, an HIV-2 integrase, a SIV integrase, and an RSV integrase. 326. A tagged DNA molecule comprising a fragment of target DNA, a first integrase recognition site, a second integrase recognition site, and a barcode. 327. The tagged DNA molecule of embodiment 326, wherein the target DNA comprises genomic DNA. 328. The tagged DNA molecule of embodiment 326, wherein the target DNA comprises crosslinked chromatin or a reconstituted chromatin. 329. The tagged DNA molecule of embodiment 326, wherein the first integrase recognition site and the second integrase recognition site are derived from the recombination of a third integrase recognition site and a fourth integrase recognition site. 330. The tagged DNA molecule of embodiment 329, wherein the first integrase recognition site is selected from the group consisting of an attB, attP, attR, and attL site. 331. The tagged DNA molecule of embodiment 329, wherein the second integrase recognition site is selected from the group consisting of an attB, attP, attR, and attL site. 332. The tagged DNA molecule of embodiment 329, wherein the third integrase recognition site is selected from the group consisting of an attB, attP, attR, and attL site. 333. The tagged DNA molecule of embodiment 329, wherein the fourth integrase recognition site is selected from the group consisting of an attB, attP, attR, and attL site. 334. The tagged DNA molecule of embodiment 329, wherein the first integrase recognition site has a nucleic acid sequence selected from at least one of GGGTGCCAGGGCGTGCCCTTGGGCTCCCCGGGCGCGTA (SEQ ID NO: 2). 335. The tagged DNA molecule of embodiment 329, wherein the second integrase recognition site has a nucleic acid sequence selected from CCCCAACTGGGGTAACCTTTGAGTTCTCTCAGTTGGGG (SEQ ID NO: 3). 336. The tagged DNA molecule of embodiment 329, wherein the tagged DNA molecule is biotinylated. 337. The tagged DNA molecule of embodiment 329, wherein the tagged DNA molecule further comprises a sequencing primer site. 338. The tagged DNA molecule of embodiment 329, wherein the sequencing primer site is selected from a P5 and a P7 primer site. 339. The tagged DNA molecule of embodiment 329, wherein the tagged genomic DNA sample further comprises a second sequencing primer site. 340. The tagged DNA molecule of embodiment 338, wherein the second sequencing primer site is selected from the other of a P5 and a P7 primer site. 341. The tagged DNA molecule of embodiment 329, wherein the fragment of target DNA comprises a first segment and a second segment of a nucleic acid molecule that are held together independently of their common phosphodiester backbone. 342. The tagged DNA molecule of embodiment 329, wherein the barcode is indicative of a nucleic acid molecule of the sample. 343. The tagged DNA molecule of embodiment 329, wherein the tagged target DNA molecule is bound to a bead. 344. A nucleic acid library comprising a plurality of the tagged DNA molecule described in any of embodiments 326-343. 345. A method of generating a nucleic acid molecule having an internal integrase recognition site comprising: binding a target nucleic acid molecule comprising a first segment and a second segment such that the first segment and the second segment are held together independent of their common phosphodiester bond; cleaving the target nucleic acid molecule between the first segment and the second segment to create exposed ends; contacting the bound target nucleic acid molecule to the at least one nucleic acid comprising the integrase recognition site; and forming a phosphodiester bond between an exposed end of the target nucleic acid molecule and the at least one nucleic acid comprising the integrase site. 346. The method of embodiment 345, wherein binding comprises contacting a complex of native chromatin comprising the target nucleic acid molecule to a crosslinking agent. 347. The method of embodiment 345, wherein binding comprises contacting the target nucleic acid molecule to a nucleic acid binding agent. 348. The method of embodiment 347, further comprising contacting the nucleic acid binding agent to a crosslinking agent. 349. The method of embodiment 345, wherein cleaving comprises contacting the target nucleic acid with an enzyme having endonuclease activity. 350. The method of embodiment 349, wherein the enzyme having endonuclease activity comprises a restriction endonuclease. 351. The method of embodiment 349, wherein the enzyme having endonuclease activity comprises a transposase. 352. The method of embodiment 349, wherein the enzyme having endonuclease activity comprises a nonspecific endonuclease. 353. The method of embodiment 349, wherein forming the phosphodiester bond comprises ligating the at least one nucleic acid comprising an integrase site between the first segment and the second segment. 354. A composition comprising a first segment of a nucleic acid molecule and a second segment of the nucleic acid molecule separated by an integrase recognition site, wherein the first segment and the second segment are held together independent of their phosphodiester bonds via a crosslinked nucleic acid binding complex. 355. The composition of embodiment 354, wherein the crosslinked nucleic acid binding complex comprises native chromatin. 356. The composition of embodiment 354, wherein the crosslinked nucleic acid binding complex comprises reconstituted chromatin. 357. The composition of embodiment 354, wherein the nucleic acid molecule is interrupted by at least 3 integrase recognition sites. 358. The composition of embodiment 357, wherein the nucleic acid molecule is interrupted by at least 10 integrase recognition sites. 359. The composition of embodiment 354, wherein the integrase recognition site is a phage integrase recognition site. 360. The composition of embodiment 359, wherein the phage integrase recognition site is a lambda phage integrase recognition site. 361. The composition of embodiment 359, wherein the phage recognition integrase site is a phi recognition integrase site. 362. The composition of embodiment 361, wherein the phi integrase recognition site is a phiC31 integrase recognition site. 363. The composition of embodiment 354, wherein the integrase recognition site comprises an att sequence. 364. The composition of embodiment 363, wherein the att sequence comprises a recognition site selected from the group consisting of an attB, attP, attL and attR site. 365. The composition of embodiment 354, wherein the integrase recognition site is a retroviral integrase recognition site. 366. A recombinant nucleic acid comprising a first segment of a target nucleic acid molecule and a second segment of the target nucleic acid molecule separated by a recombinant integrase recognition site. 367. The composition of embodiment 366, wherein the target nucleic acid comprises a genomic DNA sequence. 368. The composition of embodiment 366, wherein the integrase recognition site is a phage integrase recognition site. 369. The composition of embodiment 367, wherein the phage integrase recognition site is a lambda phage integrase recognition site. 370. The composition of embodiment 367, wherein the phage integrase recognition site is a phi integrase recognition site. 371. The composition of embodiment 370, wherein the phi integrase recognition site is a phi31 integrase recognition site. 372. The composition of embodiment 366, wherein the integrase site comprises an att sequence. 373. The composition of embodiment 372, wherein the integrase site comprises an attB integrase site. 374. The composition of embodiment 366, wherein the integrase site is a retroviral integrase site. 375. A bead comprising the composition of any one of embodiments 366 to 374, wherein bead comprises a plurality of oligos on its surface, said plurality of oligos comprising a common integrase site. 376. The bead of embodiment 375, wherein the integrase recognition site comprises an att integrase recognition site. 377. The bead of embodiment 375, wherein the integrase recognition site comprises an attB, attP, attR, or attL integrase site. 378. The bead of embodiment 375, wherein the integrase recognition site comprises a retroviral recognition integrase compatible site. 379. The bead of embodiment 375, wherein the plurality of oligos further comprises a common barcode. 380. The bead of embodiment 375, wherein the plurality of oligos further comprises a sequencing primer binding site. 381. A complex comprising the bead of any of embodiments 375-380 bound to a nucleic acid comprising a first sample segment, an integrase complement segment, and a second sample segment. 382. The complex of embodiment 381, wherein said nucleic acid comprises a plurality of integrase complement segments. 383. The complex of embodiment 381, further comprising an integrase. 384. A nucleic acid library comprising a plurality of oligonucleotides, the oligonucleotide comprising: a target nucleic acid; a barcode; a forward primer binding site and a reverse primer binding site; and a first integrase product site and a second integrase product site. 385. The nucleic acid library of embodiment 384, wherein the first integrase product site comprises an attR sequence or an attL sequence. 386. The nucleic acid library of embodiment 384, wherein the second integrase product site comprises an attR sequence or an attL sequence. 387. The nucleic acid library of embodiment 384, wherein the forward primer binding site comprises a P5 sequence or a P7 sequence. 388. The nucleic acid library of embodiment 384, wherein the reverse primer binding site comprises a P5 sequence or a P7 sequence. 389. The nucleic acid library of embodiment 384, wherein the oligonucleotide comprises an affinity tag. 390. The nucleic acid library of embodiment 384, wherein the affinity tag comprises biotin. 391. The nucleic acid library of embodiment 384, wherein a plurality of the target nucleic acids originated in the same DNA molecule. 392. A method of delivering a barcode to a nucleic acid sample, the method comprising: contacting a first polynucleotide comprising a first integrase recognition site sequence and a target nucleic acid to a second polynucleotide comprising a second integrase recognition site and a barcode; contacting the first and second polynucleotides to an integrase under conditions that support integrase activity to form a third polynucleotide comprising a barcoded target nucleic acid; and isolating the barcoded target nucleic acid. 393. A method of delivering a barcode to a nucleic acid sample, the method comprising: obtaining a first polynucleotide comprising a first target nucleic acid; inserting a barcode from a second polynucleotide into the first polynucleotide, wherein the insertion is not a random insertion. 394. A method of delivering a barcode to a nucleic acid sample, the method comprising: obtaining a first polynucleotide comprising a first target nucleic acid; inserting a barcode from a second polynucleotide into the first polynucleotide, wherein the insertion occurs at a specific position encoding a specific sequence in the first polynucleotide.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Further understanding of the disclosure herein is gained through reference to the Exemplary kits and protocols below.

Example 1. Exemplary Kit Contents

Kits for use in methods disclosed herein contain reagents boxed according to storage needs and compatibility. Exemplary kit components and suggested storage conditions are provided below.

TABLE 1

Box 1 (Store at 2° C. to 8° C.)

| Item | Item |
|---|---|
| TE Buffer pH 8.0 | Chromatin Capture Beads |
| Wash Buffer | Crosslink Reversal Buffer |
| TWB Solution | Streptavidin Beads |
| 2X NTB Solution | 10X RBC Lysis Buffer |
| LWB Solution | 40 mM Calcium Chloride |
| NWB Solution | 20% SDS |

TABLE 2

Box 2 (Store at −30° C. to −10° C.)

| Item | Item |
|---|---|
| Restriction Digest Buffer | Restriction Digest Enzyme Mix |
| End Fill-in Buffer | End Fill-in Enzyme Mix |
| Intra-Aggregate Ligation Buffer | Intra-Aggregate Ligation Enzyme Mix |
| 250 DTT | Adaptor |
| End Repair Enzyme Buffer | End Repair Enzyme Mix |
| Ligation Enhancer | Ligation Enzyme Mix |
| Universal PCR Primer | HotStart PCR Ready Mix |
| USER Enzyme Mix | Proteinase K |
| Index Primer 2 | Index Primer 7 |
| Index Primer 4 | Index Primer 8 |

TABLE 2-continued

Box 2 (Store at −30° C. to −10° C.)

| Item | Item |
|---|---|
| Index Primer 5 | Index Primer 12 |
| Index Primer 6 | Index Primer 19 |

TABLE 3

Box 3 (Store at −30° C. to −10° C.)
Item

Collagenase

Items to be provided by users in addition to standard molecular biology equipment and reagents include the following: Agencourt™ AMPure™ XP Beads (Beckman Coulter, Inc., cat. no. A63880); 37% formaldehyde solution (Sigma-Aldrich, product no. F8775); 1× PBS; 80% ethanol; and DNAse and RNAse free water. Molecular biology equipment and materials include: 1.5 ml DNA low binding microcentrifuge tubes; 0.2 ml PCR microcentrifuge tubes; thermal mixer; thermal cycler; vortex; pipets and pipet tips; microcentrifuge; dry ice/petri dish/razor or liquid, nitrogen/mortar and pestle (for animal tissue samples); hemocytometer (for cell culture or blood samples); 15 ml centrifuge tubes (for blood samples); magnetic separation stand for 1.5 ml microcentrifuge tubes; and magnetic separation stand for 0.2 ml microcentrifuge tubes. Genomics equipment includes: Illumina® sequencer and sequencing reagents; Qubit® Fluorometer and Qubit® dsDNA HS (High Sensitivity) Assay Kit (Thermo Fisher Scientific, cat. nos. Q32851, Q32854); Agilent TapeStation™ System or Bioanalyzer; Bioruptor® Pico Ultrasonicator for DNA fragmentation; DNA size selection system such Sage Science Pippin Prep™ for size selecting DNA in the 350-850 nt range (alternatively, AMPure™ XP beads can be used to size select). Sequencing Platform: the Hi-C Kit is designed to create Illumina®-compatible Hi-C sequencing libraries, although other platforms and libraries are consistent with the disclosure herein.

Example 2: Exemplary Protocol

As written, most of the protocol is performed in 1.5 ml low bind microcentrifuge tubes. There are 3 stages on Day 2 where it is easiest to switch to a 0.2 ml PCR tube. The protocol lists the suggested smaller microcentrifuge tube size for each of those stages on Day 2. DNA Quantification. A Qubit® Flourometer or similar instrument can be necessary in some cases to quantify DNA levels in the Hi-C protocol. DNA Sizing. An Agilent TapeStation™, Bioanalyzer, or similar assay is used to accurately determine the size distribution of the DNA. DNA Fragmentation. The Hi-C Protocol was validated using a Bioruptor® Pico Ultrasonicator to fragment the sample DNA. Alternative Stage 9 includes suggestions for using a Covaris® M220. DNA Size-Selection. A Sage Science Pippin Prep™ or similar instrument is recommended for size selecting the final library. A Size Selection protocol below includes an alternative protocol for size selecting the library using AMPure™ XP beads. This kit supports mammalian tissue, blood, and cell culture samples. Modified kits support plant, fungal, non-mammalian animal, bacterial soil, or other sample sources. Below are additional details on these supported sample types. Tissue samples with high cellularity and low-fat content perform extremely well, especially muscle, brain, heart, spleen, or liver. Tissue samples should be taken from a live, or very recently deceased, specimen and snap frozen in liquid nitrogen as soon as possible after harvest. Store samples at −80° C., the library and data quality will decrease for samples stored at or above −20° C. Avoid freeze-thaw cycles of tissue samples. If shipping, do so overnight on dry ice. Fat, bone, or similar tissue types often involve modification to the kits and protocols herein, as do samples which have been preserved in RNAlater™, Ethanol, or which have been freeze-dried. Blood samples should be taken from a live or very recently deceased specimen and have an anti-coagulant added. EDTA is the preferred anti-coagulant, samples have also been successfully tested with Heparin and Citrate (ACD-A). If using blood collection tubes, follow the manufacturer's instructions to ensure proper mixing of the anticoagulant. Flash freeze blood samples in liquid nitrogen and keep at −80° C. if the sample will be stored before preparing the library. If shipping frozen blood do so overnight on dry ice, ship fresh blood overnight on wet ice to ensure the blood remains cold throughout the shipment. For tissue culture samples, adherent cells can be disassociated using trypsin. Wash the cells with 1× PBS before starting the Hi-C protocol.

First day protocol. Day 1 should take roughly 7 hours for cells or 8 hours for tissue or blood samples. Kit-supplied reagents are listed in bold blue, user-supplied reagents are listed in bold black. Use standard practices for molecular biology including thawing, vortexing, and quick spinning down reagents before use. There are two optional stopping points listed for day 1. If one is prepping several samples in tandem consider preparing a master mix at the start of each step. An 'agitating thermal mixer' should be set at 1250 rpm for 1.5 ml tubes, 1450 rpm for 0.2 ml/PCR tubes. All centrifugation steps occur in a standard table-top microcentrifuge. The times listed for resting tubes on the magnet are a recommendation. Wait until the solution is visibly devoid of beads before continuing with the protocol. To wash beads, follow these steps: add the listed reagent to the sample tube containing beads; vortex or pipet to resuspend the beads; and quick spin the sample tube to remove liquid from the tube cap. Place tube on an appropriate magnet for 1-3 minutes. Carefully pipet off and discard the supernatant Table 4 lists the equipment and reagents you will need for day 1.

TABLE 4

| User Supplied Reagents and Equipment for Day 1 | |
|---|---|
| User Supplied Material or Equipment | Stage Used In |
| Low-bind microcentrifuge 1.5 ml tubes | Throughout |
| PCR Tubes (optional for day 1) | Throughout |
| Magnet holders for tubes | Throughout |
| Thermal mixer | Throughout |
| 1x PBS | 1 |
| 37% Formaldehyde Solution | 1 |
| Dry ice, petri dish, razor blade OR liquid nitrogen, mortar, pestle | 1 Tissue sample |
| Hemocytometer | 1 Cell/Blood samples |
| DNAse and RNAse free water | 1 Blood sample |
| Beckman-Coulter AMPure ™ XP Beads | 8 |
| 80% Ethanol | 8 |
| Qubit ® | 8 |

Protocol for Stage 1 Crosslink Tissue and Prepare Chromatin:

In Stage 1 the sample will be crosslinked and chromatin prepared. Make sure the PBS/formaldehyde added to each sample is freshly mixed, and keep the timing of the crosslinking consistent across all samples. There are three separate protocols for crosslinking: one each for tissue, blood, and cell culture found in detail below. Follow the protocol for the desired sample type and then continue the protocol at Stage 2.

Stage 1: Crosslinking Animal Tissue Samples. Note: keep animal tissue frozen until it is in the formaldehyde-containing solution. Incubate the kit-supplied 20% SDS at 37° C. for 15 min before use. Weigh out 20-40 mg of frozen tissue sample. Disrupt the tissue either by coarsely chopping it with a razor blade on a petri dish placed on dry ice, or by grinding it with mortar and pestle in liquid nitrogen. Transfer the disrupted tissue sample to a 1.5 ml microcentrifuge tube. Add to sample tube: 1 ml 1× PBS and 40.5 µl 37% formaldehyde. Vortex mix tube. Rotate tube for 20 min at room temperature. Tissue should not settle. Pellet tissue for 1 min at 13,000 rpm (~15,000×g). Repeat spin if any debris are floating. Pipet off and discard supernatant. Add 300 µl Wash Buffer to tube, vortex to resuspend the tissue. Pellet tissue for 1 min at 13,000 rpm (~15,000×g). Pipet off and discard supernatant. Repeat wash steps twice, for a total of 3 washes. Add to sample tube: 99 µl wash buffer, 1 µl 40 mM calcium chloride, 25 µl 1 mg/ml collagenase. Incubate for 1 hour at 37° C. in an agitating thermal mixer. Do not spin tube, transfer the liquid fraction to new tube. Tube containing the liquid fraction is now the sample. Discard remaining tissue. Add 6.3 µl 20% SDS to sample. Vortex tube for >30 sec. Use a pipet to break up any large clumps. Continue protocol at Stage 2: Normalize Chromatin All Samples.

Stage 1: Crosslinking Cell Culture Samples. Note: Incubate the kit-supplied 20% SDS at 37° C. for 15 min before use. Pellet 0.5×10^6 cells for 5 min at 5,200 rpm (~2,500×g). Pipet off and discard supernatant. Add to pellet: 1 ml 1× PBS, 40.5 µl 37% Formaldehyde. Pipet gently to resuspend pellet. Rotate tube at room temperature for 20 min. Cells should not settle. Pellet cells for 5 min at 5,200 rpm (~2,500×g). Pipet off and discard supernatant. Add 1 ml Wash Buffer and pipet gently to resuspend pellet. Pellet cells for 5 min at 5,200 rpm (~2,500×g). Pipet off and discard supernatant. Add to pellet: 50 µl Wash Buffer, 2.5 µl 20% SDS. Vortex tube for >30 sec. Use a pipet to break up any large clumps. Continue protocol at Stage 2: Normalize Chromatin All Samples.

Stage 1: Crosslinking Blood Samples. Notes: The sample should be normalized to 0.5×10^6 white blood cells (see below). This will generally require 300 µl-1000 µl of blood. If less input is used, the yield will be decreased. Make 1× RBC Lysis Buffer by diluting the kit-supplied 10× RBC Lysis Buffer to 1× in DNAse and RNAse free water. Incubate the kit-supplied 20% SDS at 37° C. for 15 min before use. Place in 15 ml tube: 1 volume Fresh or thawed mammalian blood sample, 10 volumes 1× RBC Lysis Buffer. Pipet mix the sample and incubate at room temperature for 5 min. Pellet sample for 5 min at 2,300 rpm (~500 × g). Pipet off and discard supernatant. Use a 100 µl pipet tip to remove any remaining red blood lysate. Resuspend cell pellet in 1 ml 1× PBS. Carefully remove any cell clumps that do not break apart with pipetting. Normalize the sample to contain 0.5× 10^6 white blood cells. Pellet sample for 5 min at 5,200 rpm (~2,500×g). Pipet off and discard supernatant. Add to sample pellet: 1 ml 1× PBS, 40.5 µl 37% Formaldehyde. Pipet gently to resuspend pellet. Rotate tube at room temperature for 20 min. Cells should not settle. Pellet sample for 5 min at 5,200 rpm (~2,500×g). Pipet off and discard supernatant. Add 1 ml Wash Buffer, gently pipet to resuspend pellet. Pellet sample for 5 min at 5,200 rpm (~2,500×g). Pipet off and discard supernatant. Add to pellet: 50 µl Wash Buffer, 2.5 µl 20% SDS. Vortex mix for >30 sec. Pipet to break up any clumps. Continue protocol at Stage 2: Normalize Chromatin All Samples.

Stage 2. Normalize Chromatin All Samples (Box 1) Note: See Alternative Stage 2 below for an alternative protocol to normalize chromatin. Quantify 1 µl of the crosslinked sample using a Qubit® and Qubit® dsDNA HS Kit. Add 500 ng of sample DNA to a new tube. Bring the total volume in the sample tube up to 50 µl with Wash Buffer. If a tissue sample contains 50-500 ng total DNA, use all of the sample up to 100 µl in Stage 3. If less than 50 ng total DNA is extracted do not continue with the sample. Store remaining chromatin at 4° C. for up to 5 days.

Stage 3. Bind Chromatin to Chromatin Capture Beads (Box 1) Add 100 µl Chromatin Capture Beads to sample tube containing 50-100 µl of normalized chromatin. Fully resuspend the beads and incubate for 5 min at room temperature off magnet. Quick spin the tube and place on the magnet for 2-5 min. Pipet off and discard supernatant. The pellet may be loose—switch to a 10 µl pipet tip to remove as much liquid as possible. Wash beads twice with 200 µl Wash Buffer. Optional Stopping Point: Sample can be resuspended in 200 µl of Wash Buffer and stored overnight at 4° C. Pipet off and discard supernatant before starting Stage 4.

Stage 4. Restriction Enzyme Digest (Box 2, Purple Caps) After the last wash has been removed, add to sample tube: 50 µl Restriction Digest Buffer, 1 µl Restriction Digest Enzyme Mix. Fully resuspend the beads and incubate for 1 hour at 37° C. in an agitating thermal mixer.

Stage 5. End Fill-In (Box 2, Green Caps) Quick spin the tube and place on the magnet for 2-5 min. Pipet off and discard supernatant. Wash beads twice with 200 µl Wash Buffer. Add to sample tube: 50 µl End Fill-in Buffer, 1 µl End Fill-in Enzyme Mix. Fully resuspend the beads and incubate for 30 min at 25° C. in an agitating thermal mixer.

Stage 6. Intra-Aggregate DNA End Ligation (Box 2, Clear Caps) Quick spin the tube and place on the magnet for 2-5 min. Pipet off and discard supernatant. Wash beads twice with 200 µl Wash Buffer. Add to sample tube: 250 µl Intra-Aggregate Ligation Buffer 1 µl Intra-Aggregate Ligation Enzyme Mix. Fully resuspend the beads and incubate for 1 hr at 16° C. in an agitating thermal mixer. Optional Stopping Point: Sample can be incubated at 16° C. in agitating thermal mixer for up to 16 hr.

Stage 7. Crosslink Reversal (Box 1& 2, Brown Caps) Note: Incubate the Crosslink Reversal Buffer for 10 min at 50° C. before use. Quick spin the tube and place on the magnet for 2-5 min. Pipet off and discard supernatant. Add to sample tube: 50 µl Crosslink Reversal Buffer, 1 µl Proteinase K. Fully resuspend the beads. Incubate for 15 min at 55° C., followed by 45 min at 68° C., in an agitating thermal mixer. Quick spin the tube and place on the magnet for 2-5 min. Transfer 50 µl of the supernatant to a new tube. The tube containing the supernatant is now the sample. Discard beads.

Stage 8. DNA Purification on AMPure™ XP Beads (Box 1) Add 100 µl resuspended AMPure™ XP Beads to the sample tube. Fully resuspend the beads and incubate for 5 min at room temperature off magnet. Quick spin the tube and place on the magnet for 2-5 min. Pipet off and discard supernatant. Leave tube on the magnet, and wash beads twice with 250 µl 80% Ethanol. There is no need to resuspend the beads for these washes. Quick spin the tube and place on the magnet for 1 min. Use a thin pipet tip to remove traces of Ethanol. Air dry beads for 5 min on the magnet. Add 54 µl TE Buffer pH 8.0 to sample tube. Fully resuspend the beads and incubate for 2 min at room temperature off magnet. Quick spin the tube and place on the magnet for 2-5 min. Transfer 52 µl of the supernatant to a new tube. The tube containing the supernatant is now the sample. Discard beads. Quantify 1 µl of the sample using a Qubit® Fluorometer and Qubit® dsDNA HS Kit. For each sample you should recover more than 200 ng DNA. If less than 100 ng of sample DNA is recovered do not continue with sample. Store the purified DNA sample at −20° C.

Second Day Protocol Day 2 should take roughly 7 hours. Allow an additional 2 hours if size selecting and QC sequencing. Kit-supplied reagents are listed in bold blue, user-supplied reagents are listed in bold black. Use standard practices for molecular biology including thawing, vortexing, and quick spinning down reagents before use. There is one optional stopping point listed for Day 2. If one is prepping several samples in tandem consider preparing a master mix at the start of each step. An 'agitating thermal mixer' should be set at 1250 rpm for 1.5 ml tubes or 1450 rpm for 0.2 ml/PCR tubes. The times listed for leaving tubes on the magnets are a recommendation. In all cases wait until the solution is visibly devoid of beads before continuing with the protocol. To wash beads, follow these steps: add the listed reagent to the sample tube containing beads; vortex or pipet to resuspend the beads and quick spin the sample tube to remove liquid from the tube cap; place tube on an appropriate magnet for 1-3 min; and carefully pipet off and discard the supernatant. Table 2 lists the equipment and reagents you will need for Day 2.

TABLE 5

User Supplied Reagents and Equipment for Day 2

| User Supplied Material or Equipment | Stage Used In |
|---|---|
| Low-bind Eppendorf 1.5 ml Tubes | Throughout |
| PCR Tubes | Throughout |
| Magnet holders for tubes | Throughout |
| Thermal cycle | 10, 11, 15 |
| Thermal mixer | 12 |
| Diagenode Bioruptor Pico | 9 |
| Agilent TapeStation or Bioanalyzer | 9, 17 |
| Beckman-Coulter AMPure XP Beads | 12, 16 |
| 80% Ethanol | 12, 16 |
| Pippin Prep or AMPure XP Beads | 17 |
| Qubit | 17 |

Stage 9. Fragmentation (Box 1) Notes: See below for suggestions on fragmenting samples using a Covaris® M220 Focused-ultrasonicator. See below for examples of sufficient and insufficient sample fragmentation. Cool the Diagenode Bioruptor Pico to 4° C. Transfer 200 ng of Day 1 purified DNA to a 0.1 ml Bioruptor tube. Use TE Buffer pH 8.0 to bring the total volume in each Bioruptor tube to 50 µl. If sample has less than 200 ng DNA, use up to 50 µl of the sample. Cool DNA in Bioruptor tubes for 10 min on ice. Fragment the sample as follows: Fragment 4 cycles of 30 sec ON/30 sec OFF. Remove tubes from carousel. Quick spin and pipet mix Fragment 4 cycles of 30 sec ON/30 sec OFF. Check the size distribution of 2 µl of the fragmented samples on a TapeStation™ or Bioanalyzer. If the fragmented samples are centered substantially larger than 250-450 bp, refragment those samples for 3 more cycles of 30 sec ON/30 sec OFF. Confirm the size distribution of re-fragmented samples. Save remaining DNA at 4° C. for up to 6 months or more.

Stage 10. End Repair (Box 2, Blue Caps) Place in clean 0.2 ml tube: 48 µl Fragmented Sample from Stage 9, 7 µl End Repair Buffer, 3 µl End Repair Enzyme Mix, and 0.5 µl 250 mM DTT. Vortex and quick spin sample tube. Incubate for 30 min at 20° C., followed by 30 min at 65° C. in a thermal cycler. Hold at 12° C.

Stage 11. Adapter Ligation & USER Digest (Box 2, Red Caps) Note: add the adapters for Illumina® directly into the sample tube, do not make a master mix. Add to 0.2 ml tube containing 58.5 µl of end-repaired sample: 2.5 µl Adapters for Illumina®, 30 µl Ligation Enzyme Mix, and 1 µl Ligation Enhancer. Vortex and quick spin sample tube. Incubate for 15 min at 20° C. Hold at 12° C. Add 3 µl of USER Enzyme Mix to sample and pipet mix. Incubate for 15 min at 37° C. Hold at 12° C.

Stage 12. DNA Purification (Box 1) Add 70 µl resuspended AMPure™ XP Beads to the sample tube. Fully resuspend the beads and incubate for 5 min at room temperature off magnet. Quick spin the tube and place on the magnet for 2-5 min. Pipet off and discard supernatant. Leave tube on the magnet, and wash beads twice with 100 µl 80% Ethanol. There is no need to resuspend the beads for these washes. Quick spin the tube and place on the magnet for 1 min. Use a thin pipet tip to remove traces of Ethanol. Air dry the beads for 5 min on the magnet. Add 102 µl TE Buffer pH 8.0 to sample tube. Fully resuspend the beads and incubate for 2 min at room temperature off magnet. Quick spin the tube and place on the magnet for 2-5 min. Transfer 100 µl of the supernatant to a new 1.5 ml tube. The tube containing the supernatant is now the sample. Discard the AMPure™ XP Beads. Optional Stopping Point: Sample can be stored at −20° C. overnight.

Stage 13. Ligation Capture (Box 1) Notes: Stage 13 does not involve any sample DNA until the fifth step. For each sample, add 25 µl resuspended Streptavidin Beads to a new and empty 1.5 ml tube. Place tube containing Streptavidin Beads on the magnet for 2-5 min. Pipet off and discard supernatant. Wash the Streptavidin Beads twice with 200 µl TWB. Add 100 µl 2× NTB to the Streptavidin Beads. Transfer 100 µl of the sample supernatant from Stage 12 to the tube containing the washed Streptavidin Beads and 100 µl of 2× NTB. This is now your sample tube. Fully resuspend the Streptavidin Beads in the sample tube and incubate for 30 min in a 25° C. agitating thermal mixer.

Stage 14. Wash Sample on Streptavidin Beads (Box 1) Quick spin tube and place on magnet for 2-5 min. Pipet off and discard supernatant. Wash beads once with 200 µl LWB. Wash beads twice with 200 µl NWB. Wash beads twice with 200 µl Wash Buffer.

Stage 15. Index PCR (Box 2, Black & White Caps) Note: See Tables 6 and 7 to choose Index Primers. After the last wash has been removed, add to the sample tube: 15 µl DNAse and RNAse free water, 25 µl HotStart PCR Ready Mix, 5 µl Universal PCR Primer, 5 µl Index Primer (Unique to each sample). Transfer sample, including Streptavidin Beads, to a 0.2 ml PCR tube. Fully resuspend the beads. Amplify sample in a thermal cycler as follows: 3 min at 98° C., 11 cycles of: 20 sec at 98° C., 30 sec at 65° C., 30 sec at 72° C., 1 min at 72° C.; Hold at 12° C.

Stage 16 DNA Purification on AMPure™ XP Beads (Box 1) Quick spin the tube and place on the magnet for 2-5 min. Transfer 50 µl of the supernatant to a new 1.5 ml tube. The tube containing the supernatant is now the sample. Discard beads. Add 100 µl resuspended AMPure™ XP Beads to the sample tube. Fully resuspend the beads and incubate for 5 min at room temperature off magnet. Quick spin the tube and place on the magnet for 2-5 min. Pipet off and discard supernatant. Leave tube on the magnet, and wash beads twice with 200 µl 80% Ethanol. There is no need to resuspend the beads for these washes. Quick spin the tube and place on the magnet for 1 min. Use a thin pipet tip to remove traces of Ethanol. Air dry beads for 5 min on the magnet. Add 45 µl TE Buffer pH 8.0 to sample tube. Fully resuspend the beads and incubate for 2 min at room temperature off magnet. Quick spin the tube and place on the magnet for 2-5 min. Transfer 43 µl of the supernatant to a new 1.5 ml tube. The tube containing the supernatant is now the Hi-C sequencing library.

Stage 17. Size Select and Quantify Final Library Quantify 1 µl of the sequencing library using a Qubit® and Qubit® dsDNA HS Kit. Total DNA in library should be in the 1-3 µg range. Size select half of the total DNA in your sequencing library to 350-850 base pairs using a Sage Science Pippin Prep or similar instrument OR using AMPure™ XP Beads following the Size Selection protocol below. Qubit® 1 µl of the size-selected library. Use a Tapestation™ or Bioanalyzer to determine the average size, DNA concentration, and molarity of your size-selected library. Average the Qubit® and TapeStation™ results to determine library molarity as follows: (Qubitng®/µl× TapeSationnM)/TapeStationng/µl=Average FinalnM LibraryQC library on an Illumina® MiSeq™ or MiniSeq™ Instrument following manufacturer's instructions. Aim to acquire 1-2 million read pairs per library for the QC step. Store the library and any remaining DNA at −20° C. Chromatin normalization: if more accurate chromatin normalization is desired the following alternative process can be used, it will require about 2 hours of time.

Alternative Stage 2. Normalize Chromatin All Samples (Box 1) Remove 10% of your sample from Stage 1 and place into a new 1.5 ml tube. This is now your sample quantification tube. Use 13.1 µl from a tissue sample, 5.3 µl from a blood or cell culture sample. To each sample quantification tube add the following: 50 µl Crosslink Reversal Buffer, 1 µl Proteinase K. Fully resuspend the beads and quick spin the tube. Incubate for 15 min at 55° C. in agitating thermal mixer. Incubate for 45 min at 68° C. in agitating thermal mixer. Perform an AMPure™ XP bead cleanup using the following protocol (similar to Stage 8). Add 100 µl resuspended AMPure™ XP Beads to the sample quantification tube. Fully resuspend the beads and incubate for 5 min at room temperature off magnet. Quick spin the tube and place on the magnet for 2-5 min. Pipet off and discard supernatant. Leave tube on the magnet, and wash beads twice with 250 µl 80% Ethanol. There is no need to resuspend the beads for these washes. Quick spin the tube and place on the magnet for 1 min. Use a thin pipet tip to remove traces of Ethanol. Air dry beads for 5 min on the magnet. Add 21 µl TE Buffer pH 8.0 to sample tube. Fully resuspend the beads and incubate for 5 min at room temperature off magnet. Quick spin the tube and place on the magnet for 2-5 min. Transfer 20 µl of the supernatant to a new tube. The tube containing the supernatant is now the sample to quantify. Discard beads. Quantify 1-5 µl of the purified crosslink sample using a Qubit® Fluorometer and Qubit® dsDNA HS Kit. Back calculate the amount of DNA in your sample tube from Stage 1 using your results from the sample quantification tube: (Sample Quantification Tube Qubitng®/ul×20 µl×10=Total ng in sample tube from the end of Stage 1). Divide the total ng of DNA in the sample tube by the volume of material in your sample tube to get your DNA concentration in ng/µl. Proceed to Stage 2, step 2 of the main protocol.

Figure 3A:
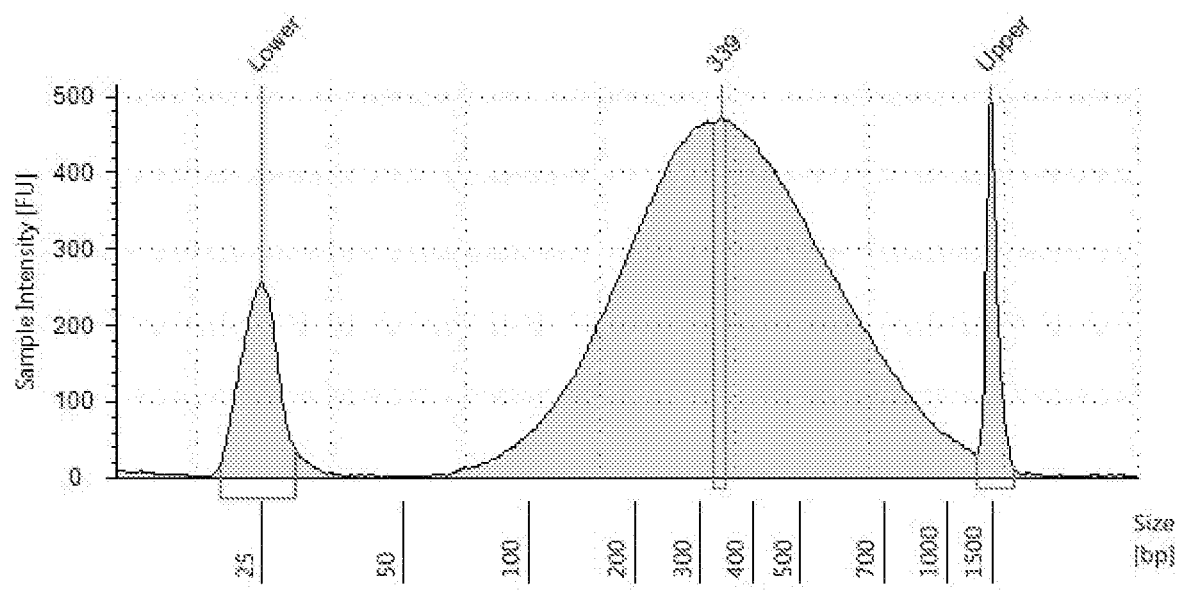
FIG. 3A presents DNA size distributions after fragmentation.
Figure 3B:
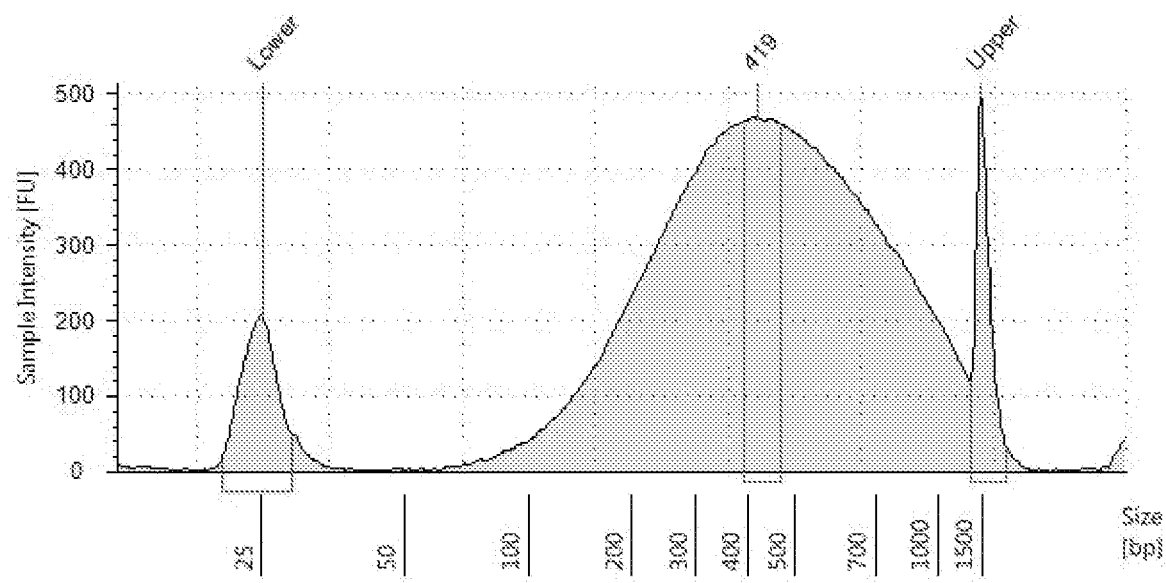
FIG. 3B presents DNA size distributions after fragmentation.
Figure 3C:
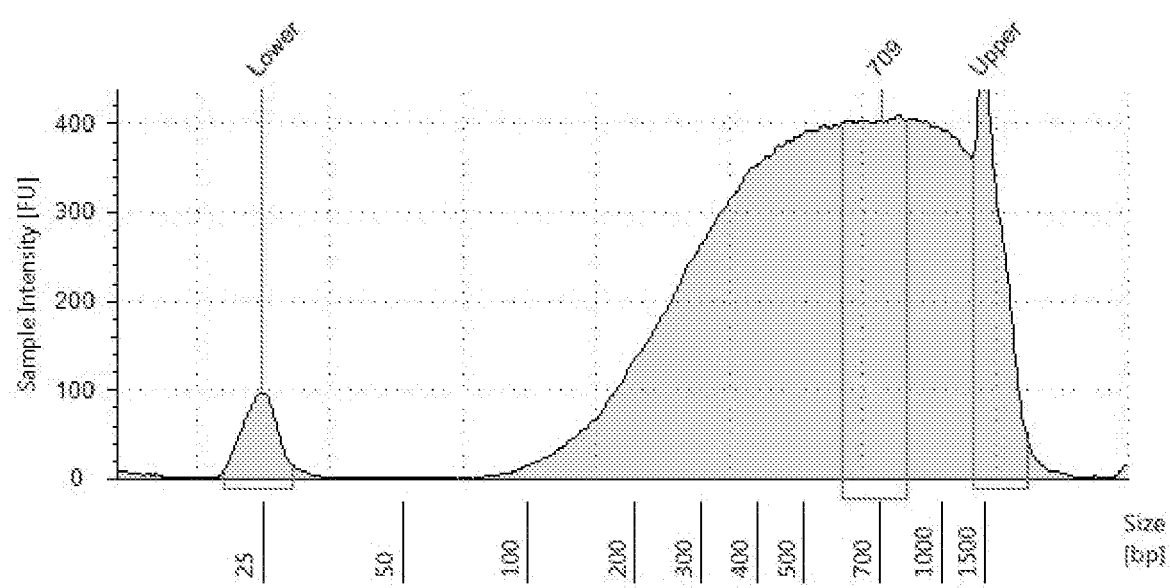
FIG. 3C presents DNA size distributions after fragmentation.

Alternative Stage 9. Covaris M220 Fragmentation The fragmentation protocol listed in Stage 9 has been optimized and validated using a Bioruptor® Pico Ultrasonicator. Covaris® instruments vary in recommended settings based on the instrument model and the volume being sonicated. To fragment DNA using a Covaris® M220 we have successfully used the following protocol. Users who plan to fragment with a Covaris should consult the documentation for their specific instrument. Transfer 200 ng of Day 1 purified DNA to a microTUBE AFA Fiber Snap-Cap (part no. 520045). Use TE Buffer pH 8.0 to bring the total volume in each tube to 55 µl. If sample has less than 200 ng DNA, use all of the sample and add buffer up to 55 µl. Fragment using a Covaris M220 Focused-ultrasonicator at the following settings: Peak Incident Power (W): 50 Duty Factor: 20% Cycles per Burst: 200 Treatment time (s): 100 Temperature (° C.): 20 Sample volume (µl): 50 Check the size distribution of 2 µl of the fragmented samples on a TapeStation™ or Bioanalyzer. If the fragmented samples are centered substantially larger than 250-450 bp, refragment those samples. Use 48 µl of the fragmented sample when continuing on to Stage 10. Save remaining DNA at 4° C. for up to 6 months. Sample fragmentation occurs in Stage 9. Samples should be fragmented to an average size of 250-450 bp. FIG. 3A, FIG. 3B, and FIG. 3C show examples of DNA size distributions after fragmentation. FIG. 3A and FIG. 3B show samples that were sufficiently fragmented. FIG. 3C shows a sample that was under-fragmented, this sample was refragmented before continuing on to End Repair (Stage 10).

Exemplary Indexing primers for nucleic acid manipulation are provided in Tables 6 and 7 below.

TABLE 6

Index Primers in the Hi-C kit

| Index Primer | Sequence |
| --- | --- |
| Index Primer 2 | CGATGT |
| Index Primer 4 | TGACCA |
| Index Primer 5 | ACAGTG |
| Index Primer 6 | GCCAAT |
| Index Primer 7 | CAGATC |
| Index Primer 8 | ACTTGA |
| Index Primer 12 | CTTGTA |
| Index Primer 19 | GTGAAA |

TABLE 7

Index Primers to use for multiplexing

| Libraries to Plex | Index Primer Combination |
| --- | --- |
| 2 | 6 and 12 |
| 2 | 5 and 19 |
| 3 | 2, 7, and 19 |
| 3 | Either of the 2-plex options and any other Index Primer |
| 4 | 5, 6, 12, and 19 |
| 4 | Either of the 3-plex options and any other Index Primer |

Size selection. Size selecting the final sequencing library to between 350-850 base pairs is often preferable, for example using a Sage Selection Pippin Prep or AMPure™ XP Beads. An exemplary protocol is as follows. Select away larger DNA fragments: Use a Qubit® to quantify the amount of DNA in the library. Place 500 ng of the library in a new tube. Bring the volume of the tube up to 100 μl using TE Buffer pH 8.0. Add 60 μl resuspended AMPure™ XP Beads to tube containing the library. Fully resuspend the beads. Incubate for 10 min at room temperature. Quick spin the tube and place on the magnet for 2-5 min. Transfer 160 μl of the supernatant to a new tube. The tube containing the supernatant is now the library. Discard beads. Select for DNA of the desired size: Add 32 μl of resuspended AMPure™ XP Beads to the library. Fully resuspend the beads. Incubate for 10 min at room temperature. Quick spin the tube, place on the magnet for 2-5 min. Pipet off and discard supernatant. Leave tube on the magnet and wash beads twice with 200 μl of 80% Ethanol. There is no need to resuspend the beads for these washes. Quick spin the tube and place on the magnet for 1 min. Use a thin pipet tip to remove traces of Ethanol. Air dry beads for 5 min on the magnet. Add 20 μl TE Buffer pH 8.0 to tube. Fully resuspend the beads and incubate for 2 min at room temperature off magnet. Quick spin the tube and place on the magnet for 2-5 min. Transfer 16 μl of the supernatant to a new 1.5 ml tube. The tube containing the supernatant is your size selected library. Discard the beads. Continue the main protocol at Stage 17 at the third step.

Example 3: Methods of Generating cDNA Libraries of mRNA Splice Variants Present in a Cellular Transcriptome A sample comprising mRNA splice variants from a human subject is used to prepare a library for subsequent sequencing. In this example, the sample contains two different splice variants of the same gene in which the alternative splicing events occur at a distance from each other, encoded by an intervening exon, is greater than the length of a single read. The gene encodes five exons, numbered 1, 2, 3, 4, and 5. The first splice variant contains exons 1, 2, 3, and 5. The second splice variant contains exons 1, 3, 4, and 5.

Cellular RNA is isolated from the human subject. A reverse transcriptase is used to reverse transcribe the RNA sample into DNA. This process results in a cDNA library. Illumina® sequencing adapters are ligated to the cDNA products. The reverse-transcribed cDNA product is amplified using PCR to generate sufficient quantities of the product for high-throughput sequencing. The cDNA products are then sequenced using traditional shotgun sequencing methods. The sequences produced include sequences across the junctions of adjacent exons from each of the molecules present in the sample. In this case, the data include junction between exons in the first RNA molecule, which include exons 1 and 2, exons 2 and 3, and exons 3 and 5. The data also include junctions between exons in the second RNA molecule, which include exons 1 and 3, exons 3 and 4, and exons 4 and 5.

In this example, the length of exon 3 is greater than the length of a single read. Thus, a single read does not detect the presence or absence of both exon 2 and exon 4 in the same molecule. Because the presence or absence of exons 2 and 4 cannot be detected using a single read, the method is unable to determine if the sample contains RNA molecules with both exons 2 and 4, only exon 2 but not exon 4, only exon 4 but not exon 2, or neither exon 2 nor exon 4.

This example illustrates how traditional sequencing methods are unable to identify each of the splice variants present in a sample.

Example 4: Methods of Generating Read-Pair Libraries from mRNA Splice Variants Present in a Cellular Transcriptome A sample comprising mRNA splice variants from a human subject is used to prepare a library for subsequent sequencing. In this example, the sample contains the same splice variants as example 3. The method in this example is used to generate sequences where the distances between the alternative splicing events that result in inclusion or exclusion of exons 2 and 4 are reduced in some molecules such that the presence or absence of the exons can be read from the same read pair and attributed to the same original molecule.

Cellular RNA is isolated from the human subject. The cellular RNA is incubated recombinant hrp36 comprising a polyhistidine tag (6his-hrp36) or under comparable conditions using comparable reagents. This results in the formation of RNA nucleo particles containing RNA and RNA binding proteins.

Nickel-magnetic beads, which bind to the nucleo particles via the polyhistidine tags on the RNA binding moiety, are added to the sample. The sample is incubated to bind the nickel-magnetic beads to the his-tagged hrp36 components of the RNA-protein complexes. Incubations at a range of temperatures and durations are consistent with the disclosure herein. The sample is then washed, such that complexes comprising RNA molecules bound to the nickel-magnetic beads are retained. Unbound RNA molecules are discarded in the wash.

A formaldehyde solution is added to crosslink the RNA nucleo particles such that a first segment and a second segment of a given transcript are held together independent of their common phosphodiester backbone. The sample is incubated in some cases to effect the reaction.

RNA segments of the crosslinked sample are fragmented via alkaline hydrolysis through addition of a 3M sodium acetate solution (pH 5.2) or comparable reagent. The fragmentation cleaves phosphodiester backbones, such that RNA segments bound to hnp36 proteins in complexes are held together despite no longer being joined by a common phosphodiester backbone. Segments not bound by the RNA binding protein, such as segments in "loops" extending from the proteins of the complexes, are released from the complexes, while bound segments remain in the complexes. As a result, despite internal RNA segment ends being exposed, the bound segments remain physically linked to one another via their RNA binding proteins. The sample is optionally washed prior to phosphate treatment.

The fragmented sample is treated with a phosphatase to remove phosphate groups from 5', 3' and 2' hydroxyl groups. Phosphatase treatment reduces the likelihood that fragments will relegate into native sequences. The tube containing the sample is then subjected to a magnetic field. The sample is washed and nucleoparticles secured by magnetic beads are selectively retained. At this stage in the process, nucleoparticles are retained while free RNA segments, either from unbound RNA molecules or of "loop" or "end" segments released from complexes through alkaline fragmentation, are not retained.

A T4 kinase is used to add a phosphate group to the 5' end of the fragments, so as to facilitate ligation of 5' ends of RNA to OH groups. Next, an RNA ligase is used to ligate phosphorylated 5' ends to exposed RNA OH groups. Ligation is conducted under conditions such that the vast majority of ligation events involve 5' phosphorylated ends and OH ends of segments that are bound in a common nucleoparticle complex.

The sample is optionally again washed using a magnet to isolate the nucleoparticles secured by the magnetic beads. The supernatant is discarded and the nucleoparticles are retained. Beads are removed at this step in some embodiments.

The crosslinking is reversed using a solution containing a divalent cation, EDTA, and EGTA. Following reversal of crosslinking and release of bound proteins, one has generated a population of RNA molecules comprising segments that were present in a common RNA molecule of origin in the starting sample, but in many cases the segments are altered in their proximity relative to one another, such that segments which were greater than a read-length apart from one another are now adjacent.

A population of pre-adenylated DNA oligos is added to the sample, and the sample is contacted to a thermostable RNA ligase to ligate at least some of the DNA oligos to exposed ends of RNA constituents of the complexes. The oligos contain P5 and P7 primer sites and a restriction site in some cases, which are now attached to the RNA molecule. The RNA is circularized using a circ-ligase. Small single-stranded DNA (ssDNA) molecules that are complementary to the DNA oligo are added to the circularized nucleic acids to form double-stranded DNA (dsDNA) segments within the otherwise single-stranded, circularized RNA-DNA hybrid molecules. This generates short double-stranded DNA regions in otherwise largely single-stranded, circular RNA molecules. The dsDNA is then cleaved by contact to a restriction endonuclease having specificity for bases of the double-stranded region generated through oligo hybridization, so as to linearize the nucleic acids. The result of this process is a linear RNA-DNA hybrid molecule with binding sites such as a P5 primer site at one end and a P7 primer site at the other end.

A reverse transcriptase is used to reverse transcribe the RNA sample into DNA. The reverse-transcribed DNA product is amplified using PCR to generate sufficient quantities of the product for high-throughput sequencing. The reverse-transcription-generated DNA products are then sequenced so as to obtain sequence read information from a segment on either side of a ligation event.

This example illustrates how read-pair sequence libraries are generated.

Example 5: Assigning Splice-Variant Information to Common Molecules

'Read pair' sequence information comprising a sequence read from each side of ligated, reverse-transcribed RNA molecules in example 4 is obtained and analyzed. The read pair information also includes the tagging information, which in this example includes sequence information from each side of the junction between the two segments of ligated RNA. It is observed that the sequence reads of a given read pair do not overlap to form contigs. Nonetheless, by mapping the sequences to known or independently generated cDNA or predicted Open Reading Frame sequence and adjacent predicted untranslated region of a putative transcript, it is observed that, for a given read pair, the vast majority of the sequences on either side of a ligation event map to a common ORF or cDNA transcript.

It is observed that multiple read pairs map to a common predictive transcript. In this example, the first segment of the first RNA molecule contains a junction between exons 1 and 2 and the second segment of the first RNA molecule contains a junction between exons 3 and 5 of the gene. Thus, when the first RNA molecule is cleaved and tagging information indicating that the segments originated from the same molecule is added, the read-pair data generated by the method indicate that exons 1, 2, 3, and 5 are all present on the same first RNA molecule, but that exon 4 has been removed during splicing.

Likewise, in this example the first segment of the second RNA molecule contains a junction between exons 1 and 3 and the second segment of the second RNA molecule contains a junction between exons 3 and 5 of the gene. Thus, when the second RNA molecule is cleaved and tagging information indicated the seconds originated from the same molecule is added, the read pair data generated by the method indicate that exons 1, 3, 4, and 5 are all present on the same second RNA molecule and exon 2 has been removed during splicing. Neither molecules containing only exons 1, 3, and 5 nor molecules containing all exons 1, 2, 3, 4, and 5 are detected. Thus, the unlike shotgun sequencing, the method described in this example is able to determine if the sample contains RNA molecules with both exons 2 and 4, only exon 2 but not exon 4, only exon 4 but not exon 2, or neither exon 2 nor exon 4.

Example 6: Assigning Two Splicing Events from a Double Splice Variant to a Common Molecule A sample comprising mRNA splice variants from a human subject is used to prepare a library for subsequent sequencing. As with examples 2 and 3, the sample contains two different splice variants of the same gene in which the alternative splicing events occur at a distance from each other, encoded by an intervening exon, is greater than the length of a single read. The gene encodes five exons, numbered 1, 2, 3, 4, and 5. In this example, the first splice variant contains exons 1, 3, and 5. The second splice variant contains exons 1, 2, 3, 4, and 5. Traditional shotgun sequencing detects that some molecules do not encode exon 2 and that some molecules do not encode exon 4. However, because exon 3 is longer than the length of a single read, it is difficult to determine if the sample contains molecules that contain both exons 2 and 4.

The sample is prepared as described in Example 4. "Read pair" sequence information comprising a sequence read from each side of ligated, reverse-transcribed RNA molecules is obtained and analyzed. It is observed that the sequence reads of a given read pair do not overlap to form contigs. Nonetheless, by mapping the sequences to known or independently generated cDNA or predicted Open Reading Frame sequence and adjacent predicted untranslated region of a putative transcript, it is observed that, for a given read pair, the vast majority of the sequences on either side of a ligation event map to a common ORF or cDNA transcript.

It is observed that multiple read pairs map to a common predictive transcript. In this example, a plurality of read pairs are detected which include a segment from exon 2 and a segment from exon 4. These sequencing data indicate that mRNA molecules that encode both exons 2 and 4 are present within the sample.

Example 7: Assigning Multiple Single Nucleotide Polymorphisms to Specific Alleles in Heterozygous Individuals In this example, a subject is determined to be heterozygous for a gene of interest. It is determined by shotgun sequencing that the individual contains two different point mutations in the same gene. The first mutation is an A to C mutation near the 5' end of the gene. The second mutation is a C to G mutation near the 3' end of the gene. However, because the point mutations are separated by a distance longer than the length of a single read, traditional shotgun sequencing is unable to determine if the subject has a wild-type allele and a double-mutant allele or if the individual has two different single-mutant alleles.

The methods described in example 4 are used to generate a DNA library from a sample containing mRNA encoding transcripts of each allele. A first RNA molecule includes two segments. The first segment of the first RNA molecule includes the A to C mutation near the 5' end and the second segment includes the C to G mutation near the 3' end of the gene. A first RNA binding protein binds to the first segment and a second RNA binding protein binds to the second segment. The RNA binding proteins are crosslinked, the intervening sequence is cleaved and removed, and the first RNA segment is ligated to the second RNA segment, as described in Example 4.

A second RNA molecule includes two segments. The first segment of the second RNA molecule includes the wild-type A near the 5' end and the second segment includes the wild-type C near the 3' end of the gene. A first RNA binding protein binds to the first segment and a second RNA binding protein binds to the second segment. The RNA binding proteins are crosslinked, the intervening sequence is cleaved and removed, and the first RNA segment is ligated to the second RNA segment, as described in Example 4. The sample containing the first and second RNA molecules is reverse transcribed and prepared as described in Example 4.

"Read pair" sequence information comprising a sequence read from each side of each of the ligated, reverse transcribed RNA molecule and the junction between the two ligated segments is obtained as tagging information for each molecule. In this example, a first read pair corresponds to the first RNA molecule. The information in the first read pair shows that the first segment of the first RNA molecule includes the A to C mutation and the second segment includes the C to G mutation. Because the tagging information allows the mutations to be mapped back to the same first RNA molecule, it is determined that the first allele includes both mutations.

Likewise, a second read pair corresponds to the second RNA molecule. The information in the second read pair shows that the first segment of the second RNA molecule includes the wild-type A and the second segment includes the wild-type C. The tagging information allows the two wild-type segments to be mapped back to the same molecule. Thus, it is determined that the second allele is a wild-type allele.

No read pairs are detected in which a wild-type segment and a segment containing a single mutation are observed. The result of this experiment determines that the subject-derived sample contains cells having one allele with two mutations and a second allele that is wild-type at these two positions.

Example 8: Methods for Associating Sequence Segments in an Emulsion

In this example, the sample contains two different splice variants of the same gene in which the alternative splicing events occur at a distance from each other, encoded by an intervening exon, is greater than the length of a single read. The gene encodes five exons, numbered 1, 2, 3, 4, and 5. The first splice variant contains exons 1, 2, 3, 4, and 5. The second splice variant contains exons 1, 3, and 5. Shotgun sequencing reveals that some transcripts are missing exon 2 and some transcripts are missing exon 4. Because exon 3 is longer than a single read, shotgun sequencing is unable to reveal if exons 2 and 4 are missing on the same or different transcripts.

Messenger RNA is obtained from the subject and contacted with hnp36 RNA binding proteins as described in Example 4. The ribonucleoparticles are then crosslinked using formaldehyde and fragmented using a mild alkaline solution. The fragmented RNA is treated with a phosphatase to remove phosphate groups from 5', 3' and 2' hydroxyl groups. Phosphatase treatment reduces the likelihood that fragments will relegate into native sequences.

The treated ribonucleoparticles are added to an aqueous droplet along with the following reagents: 1) a T4 kinase; 2) an oligo; and 3) an RNA ligase. Each oligo added to the droplet contains the same randomly-generated DNA barcode, forward and reverse priming sites, and a known sequence to mark the position of the barcode.

Oil and other reagents required for the emulsion are added to the prepared solution and an emulsion is generated through blending, vortexing, etc. This yields many "nanoreactors", or reaction volumes, which are solution compartments in the emulsion containing some number of ribonucleoparticles and synthetic constructs. A substantial percentage of the reaction volumes contain a single ribonuclearparticle.

The T4 kinase adds a phosphate group to the 5' end of the fragments so as to facilitate ligation of 5' ends to exposed OH groups on the oligo. The oligo is ligated to the RNA fragments by raising the temperature of the sample to 37° C., which activates the RNA ligase. Alternate embodiments vary in temperature of ligase activation.

After a period of time, the temperature is raised to 80° C. for 20 minutes to completely inactivate the kinase and the ligase. The emulsion is broken and the products collected for reverse transcription. The resulting DNA molecules are amplified by PCR, which also adds P5 and P7 primer sites to the ends of the DNA molecules. The resulting DNA sequences are characterized by high throughput sequencing.

Example 9: Assembling Transcript Sequences Using Barcodes

The sequencing data from Example 8 is analyzed to combine reads corresponding to the same original RNA molecule into longer sequences. Connections between segments of fragments are recovered by gathering all reads with identical barcodes, which are analyzed as reads from the same initial emulsion, and therefore most likely from the same initial RNA molecule.

The results reveal three different alternative splice variants. A first set of read pairs reveals segments containing portions of exons 1, 3, and 5 tagged with the same first barcode. A second set of read pairs reveals segments containing portions of exons 1, 2, 3, and 5 tagged with the same second barcode. A third set of read pairs reveals segments containing portions of exons 1, 2, 3, 4, and 5 tagged with the same third barcode.

Thus, the experiment reveals at least three distinct species produced by alternative splicing of the same gene. Exons 1, 3, and 5 are present in all three species. Exon 2 is present in two out of the three species. Exon 4 is present in one species, and detectable in molecules that also contain exon 2.

For some transcripts, all read information of all read pairs assembles into a common contig, indicating that there is no variation among transcripts from that locus in the sample.

In many cases, however, sequence differences are observed between one or both reads of a read pair and the predicted sequence for a given transcript. Sequence differences are observed to correspond to retained intron sequence, splice junctions where an expected exon sequence has been removed, point mutations, and insertions and deletions. These differences are analyzed to determine linkage information for the transcript populations.

These sequence differences are indicative of the qualitative and often quantitative diversity of transcripts from a given locus.

Example 10: Barcode Delivery to Create a Sequenceable Library of Genomic DNA

Reconstituted chromatin is created from a sample genome using methods in the art. The reconstituted chromatin is digested with MboI to create overhang ends. The overhang ends are ligated to biotinylated adapter oligonucleotides having an attB sequence. The fragments and adapter sequences are ligated to form chains of fragments and adapter polynucleotides. Some of the DNA fragments ligated together originate from distant genomic loci that looped together in three-dimensional space.

The crosslinking is reversed and the chains of fragments and adapter polynucleotides are presented with a population of beads. Each bead comprises double stranded oligonucleotides having a P5 primer binding sequence, a barcode sequence unique to the individual bead, and an attP sequence. One of the two strands of the double-stranded oligonucleotide is bound to the bead, leaving the other strand free.

The attB sequences on the polynucleotide are allowed to anneal to the attP sequences on the oligonucleotides. A soluble φC31 integrase is presented to the annealed complex and exchange occurs between the attB and attP sequences. The integrase also introduces double-stranded breaks between the attR and attL sites created by the exchange. This results in bead-bound nucleic acids having a P5 primer binding site, a common barcode, a biotinylated nucleotide, and a fragment of genomic DNA. The strand that is not attached to the bead is melted away from the bead. The biotinylated nucleotide on the free strand is bound and captured by a streptavidin bead. A P7 primer binding site is added to the captured DNA by random priming and extension. PCR amplification on the streptavidin bead-captured sample synthesizes a second strand and produces a sequenceable library. This workflow is shown in FIG. 4. The library is sequenced using shotgun sequencing.

Example 11: Alternative Barcode Delivery to Create a Sequenceable Library of Genomic DNA Reconstituted chromatin is created from a sample genome using methods in the art. The reconstituted chromatin is digested with MboI to create overhang ends. The overhang ends are ligated to biotinylated adapter oligonucleotides having an attB sequence. The fragments and adapter sequences are ligated to form chains of fragments and adapter polynucleotides. Some of the DNA fragments ligated together originate from distant genomic loci that looped together in three-dimensional space.

The crosslinking is reversed and the chains of fragments and adapter polynucleotides are presented with a population of beads. Each bead comprises double stranded oligonucleotides having a P5 primer binding sequence, a barcode sequence unique to the individual bead, an attP sequence, and a P7 primer binding sequence. One of the two strands of the double-stranded oligonucleotide is bound to the bead, leaving the other strand free.

The attB sequences on the polynucleotide are allowed to anneal to the attP sequences on the oligonucleotides. A soluble φC31 integrase is presented to the annealed complex and exchange occurs between the attB and attP sequences. The integrase also introduces double-stranded breaks between the attR and attL sites created by the exchange. This results in a bead-bound nucleic acid having a p5, a barcode, a biotinylated nucleotide, a fragment of genomic DNA, and a p7. The strand that is not attached to the bead is melted away from the bead. The biotinylated nucleotide on the free strand is bound and captured by a streptavidin bead. PCR amplification on the streptavidin bead-captured sample synthesizes a second strand and produces a sequenceable library. This workflow is shown in FIG. 5. The library is sequenced using shotgun sequencing.

Example 12: Contig Ordering Using Sequence Read Information

An example using the methods herein to assemble contigs into a linear order is provided. Contig information for the sequenced non-diploid human genome is obtained from a publicly-available source such as the National Center for Biotechnology Information. Individuals harboring at least one wild-type allele of the full-length version of the gene are able to metabolize the drug, while individuals lacking a wild-type allele of the gene accumulate the drug to levels detrimental to individual health. The gene comprises a 100 kb region of the human genome, and the coding region is interrupted by a number of long, AT-dinucleotide repetitive introns that complicate assembly of the locus.

Two deleterious mutation sites are known in the gene in many populations. The two deleterious mutations are separated by 10s of thousands of kb of sequence, spanning a number of introns harboring the repeat sequence. One of the two deleterious mutations is in the coding region, while the other is in the putative promoter region and affects transcript accumulation only when the drug is administered. An individual's genomic sample is sequenced using locus-targeted PCR spanning two regions of the gene known to harbor deleterious mutations in some individuals. Sequences of the PCR amplicons indicate that, at each region of the gene, the individual is heterozygous for a deleterious mutation.

A genomic DNA sample is obtained from the individual identified as being heterozygous for deleterious mutations at two positions in the gene relevant to the metabolism of the drug. Nucleic acids are extracted, separated from native chromatin, partially sheared by treatment with an endonuclease, and then artificial chromatin is reassembled by the addition of nucleosomes to the partially sheared nucleic acid sample. The nucleic acid-artificial chromatin complexes are cross-linked by treatment with formaldehyde and contacted with the restriction endonuclease MboI.

A library of barcoded genomic DNA is generated as described in Example 10.

It is observed that sequence read sets sharing a common barcode sequence map to a common set of contigs. In some instances, a sequence read set comprises sequence reads that map to two distinct sets of contigs believed to map to distinct regions of the genome. This outcome indicates that two separate DNA complexes, representing two distinct nucleic acid molecules, annealed to the same bead. The molecules, or the distinct read subsets among the population of sequence reads having the molecular tag, are easily distinguished in light of their mapping to two distinct sets of contigs.

It is observed that a sequence read indicating a mutant coding region maps to a contig corresponding to the locus of the drug resistance gene. Similarly, a sequence read indicating a wild-type coding region also maps to a contig corresponding to the locus of the drug resistance gene. A sequence corresponding to a mutant promoter region maps to a contig corresponding to the promoter of the drug resistance gene, and a sequence corresponding to a wild-type promoter region maps to a contig corresponding to the promoter of the drug resistance gene.

The feature-specific barcode of each sequence read is investigated. No two feature-specific reads match, indicating that no two reads resulted from the same post-shearing nucleic acid molecule.

However, it is found that the read corresponding to the mutant coding region shares a feature-specific barcode with a number of reads spanning single-nucleotide polymorphisms (SNPs). The SNPs do not have any known function and map to the drug resistance gene at a location 5' of the coding region mutation. This indicates that the coding region mutation and the SNPs are physically linked, or in phase, with one another.

It is also found that the read corresponding to the mutant promoter region shares a feature-specific barcode with a number of reads spanning a second set of SNPs of unknown function. These SNPs map to the drug resistance gene at a location 3' of the coding region mutation. This indicates that the coding region mutation and the SNPs are physically linked, or in phase, with one another.

The sequences of the two inferred physically-linked molecules are compared and found to share SNP sequences in common. It is inferred that the gene of interest was cut during the endonuclease/shearing process multiple times, generating multiple overlapping fragments.

It is concluded that the drug-resistance gene-coding region mutation and the drug resistance gene promoter mutation map to a single allele of the drug resistance gene on a single physical chromosome.

Similarly, it is found that the read corresponding to the wild-type coding region shares a feature-specific barcode with a number reads spanning a third set of SNPs of unknown function, which are different from those mentioned above. These SNPs also map to the drug resistance gene at a location 5' of the coding region site. This indicates that the coding region mutation and the SNPs are physically linked, or in phase, with one another. It is also found that the read corresponding to the wild-type promoter region shares a feature-specific barcode with a number of reads spanning the third set of SNPs. The SNPs also map to the drug resistance gene at a location 3' of the promoter region. This indicates that the wild-type coding region and the third set of SNPs are physically linked, or in phase, with one another.

The sequences of the two inferred physically linked molecules are compared and found to share SNP sequences in common. It is inferred that the gene of interest was cut during the endonuclease/shearing process multiple times, generating multiple overlapping fragments.

It is concluded that the wild-type drug-resistance gene coding region sequence and the wild-type drug resistance gene promoter map to a single allele of the drug resistance gene on a single physical chromosome.

It is further concluded that the individual's genome encodes a functional drug-resistance gene.

Example 13: Methods to Generate Chromatin In Vitro

Two approaches to reconstitute chromatin are of particular attention: one approach uses ATP-independent random deposition of histones onto DNA, while the other approach uses ATP-dependent assembly of periodic nucleosomes. The disclosure allows the use of either approach with one or more methods disclosed herein. Examples of both approaches to generate chromatin can be found in Lusser et al. ("Strategies for the reconstitution of chromatin," Nature Methods (2004), 1(1):19-26), which is incorporated herein by reference in its entirety, including the references cited therein.

Example 14: Methods for Haplotype Phasing

A library of barcoded genomic DNA is generated and sequenced as described in Example 10.

A haplotype reconstruction using the proximity-ligation sequencing data generated in Example 10 is performed using a probabilistic algorithm. It is observed that some paired-end sequencing reads have genomic fragments marked with the same barcode that range from several hundred base pairs to tens of millions of base pairs. Thus, the short DNA fragments generated as described in Example 10 yield small fragments that provide information regarding much longer stretches of the same molecule. The barcoding information is used to link the small fragments together.

These fragments are arranged using the barcoding information to link these small blocks together. Because the library has sufficient sequencing coverage, the method is able to link variants in discontinuous blocks and assemble every such block into a single haplotype. This data is then combined with a probabilistic algorithm for haplotype assembly. The probabilistic algorithm utilizes a graph in which nodes correspond to heterozygous variants and edges correspond to overlapping sequence fragments that may link the variants. This graph contains spurious edges resulting from sequencing errors or trans interactions. A max-cut algorithm is then used to predict parsimonious solutions that are maximally consistent with the haplotype information provided by the set of input sequencing reads. Because barcoding generates larger graphs than conventional genome sequencing or mate-pair sequencing, computing time and number of iterations are modified so that the haplotypes are predicted with reasonable speed and high accuracy. The resulting data are then used to guide local phasing using Beagle software and sequencing data from the genome project to generate chromosome-spanning haplotypes with high resolution and accuracy.

Example 15: Methods for Meta-Genomic Assembly

Microbes are collected from an environment and fixed with a fixative agent, such as formaldehyde, in order to form cross-links within the microbial cells. A plurality of contigs from the microbes is generated by using high-throughput sequencing. A barcoded library is also generated using the method described in Example 10. A plurality of read pairs are generated from the barcoded library. Barcoded sequences that map to different contigs indicate which contigs are from the same species.

Example 16: Methods for Producing Barcoded Read Pairs Using Reconstituted Chromatin Using commercially available kits, DNA is extracted and fragmented with sizes up to 150 kbp. The DNA is assembled into a reconstituted chromatin structure in vitro using a commercial kit from Activ Motif. The chromatin is fixed with formaldehyde. The DNA fragments are digested with a restriction enzyme and incubated overnight.

The resulting sticky ends are ligated to adapters as described in Example 11 and immobilized onto streptavidin beads. The reconstituted chromatin is digested with a proteinase to recover the ligated DNA. The DNA is extracted from the beads. The biotinylated fragments are purified by a pull-down with streptavidin beads. The chains of fragments and adapter polynucleotides are presented with a population of beads, and the attB sequences on the polynucleotides are recombined with the attP sequences on the beads using an integrase. This results in a library of barcoded genomic fragments. The fragments are PCR amplified for high-throughput sequencing using the P5 and P7 primer sites to generate the extremely long-range read pairs.

The distribution of the extremely long-range read pairs generated from the barcoded fragments is analyzed. Further, the read pairs are used to phase heterozygous SNPs with greater than 99% accuracy for read pairs spanning up to 150 kb.

Example 17: Methods for Producing Barcoded Read Pairs Using Nanoparticles

In another example, the DNA is assembled onto nanoparticles ("Baldwin" nanoparticles) in vitro to form a DNA complex, which is then cross-linked with di-tert-butyl peroxide (DTBP). The DNA complex is digested with a restriction enzyme and incubated overnight.

The resulting sticky ends are ligated to adapters as described in Example 11. The DNA complex is incubated in a DTT solution to reverse the crosslinks. The DNA is extracted from the nanoparticles. The biotinylated fragments are purified by a pull-down with streptavidin beads. The chains of fragments and adapter polynucleotides are presented with a population of beads, and the attB sequences on the polynucleotides are recombined with the attP sequences on the beads using an integrase. This results in a library of barcoded genomic fragments. The fragments are PCR amplified for high-throughput sequencing using the P5 and P7 primer sites to generate the barcoded read pairs.

The distribution of read pairs generated from the barcoded fragments were analyzed. Further, the read pairs were used to phase heterozygous SNPs with greater than 99% accuracy for read pairs spanning up to 150 kb.

Example 18: Methods for Producing a High-Quality Human Genome Assembly

With the knowledge that read pairs containing the same barcode but spanning considerable genomic distances can be generated by the disclosure, the utilization of this information for genomic assembly is tested. The disclosure significantly improves the linkage of de novo assemblies, potentially including chromosome-length scaffolds. An assessment is performed on how complete an assembly can be produced and how much data is required using the disclosure. To evaluate the efficacy of the present method for producing data that is valuable for assembly, a standard Illumina® shotgun library and a barcoded library are generated and sequenced.

In one case, data from one Illumina® HiSeq lane each of a standard shotgun library and a barcoded library generated as described above are used. The data generated from each method is tested and compared with various existing assemblers. Optionally, a new assembler is also written to specifically tailor to the unique data produced by the disclosure. Optionally, a well-characterized human sample is used to provide a reference to compare the assembly produced by the present method against to assess its accuracy and completeness. Using the knowledge gained in the previous analyses, an assembler is produced to increase efficient and effective utilization the barcode and shotgun data. A genome assembly is generated using methods described herein with at least the quality of the December 2002 mouse genome draft.

One sample that can be used for this analysis is NA12878. DNA from sample cells are extracted using a variety of published techniques designed to maximize DNA fragment length. A standard Illumina® TruSeq™ shotgun library and a barcoded library are each built. A single HiSeq lane of 2×150 bp sequence is obtained for each library, which yields approximately 150 million read pairs per library. The shotgun data are assembled into contigs using algorithms for whole genome assembly. Examples of such algorithms include: Meraculous as described in Chapman et al. (PLOS ONE 6(8):e2350 (2011)) or SGA as described in Simpson et al. (Genome research 22(3):549-56 (2012)). The barcoded library reads are aligned to the contigs produced by the initial assembly. The alignments are used to further link the contigs. Once the effectiveness of the barcoded library for connecting contigs is ascertained, the Meraculous assembly is extended to integrate both the shotgun and barcoded libraries simultaneously into a single assembly process. Meraculous provides a strong foundation for the assembler. Optionally, an all-in-one assembler is produced to suit the specific needs of the disclosure. The human genome assembled by the disclosure is compared to any known sequence to evaluate the quality in the assembly of the genome.

Example 19: Methods for Phasing of Heterozygous SNPs for a Human Sample at High Accuracy from a Small Data Set In one experiment, the heterozygous variants in a test human sample dataset are phased. All or nearly all phasing variants that are within one read-length's distance of a restriction site are captured. By using in silico analysis, more variants for phasing can be captured by using longer read lengths and using one or more combinations restriction enzymes for digestion. Using a combination of restriction enzymes with different restriction sites increases the proportion of the genome (and therefore heterozygous sites) that is within range of one of the two restriction sites that participate in each read pair. In silico analysis shows that the methods of the disclosure can phase more than 95% of known heterozygous positions using various combinations of two restriction enzymes. Additional enzymes and greater read lengths further increase the fraction of heterozygous sites that are observed and phased, up to a complete coverage and phasing.

Heterozygous site coverages achievable with various combinations of two restriction enzymes are calculated. The top three combinations, in terms of heterozygous sites in read proximity, are tested with the protocol. For each of these combinations, a barcoded library is produced and sequenced. The resulting reads are aligned to a human reference genome and compared to the known haplotypes of the sample to determine the accuracy of the protocol. Up to 90% or more of the heterozygous SNPs for a human sample are phased at an accuracy of 99% or greater using only 1 lane of Illumina® HiSeq data. In addition, further variants are captured by increasing the read length to 300 bp. The read area around the observable restriction sites is effectively doubled. Additional restriction enzyme combinations are implemented increasing the coverage and accuracy.

Example 20: Extraction and Effects of High Molecular Weight DNA

Nucleic acids up to 150 kbp are extracted with commercially available kits. The methods disclosed herein are expected to be capable of generating read pairs from even longer stretches of DNA than 150 kbp. There are numerous well-developed processes for high molecular weight DNA recovery, and these methods can be used with the methods or protocols disclose herein. Using an extraction method to produce large fragment lengths of DNA, a barcoded library is created from these fragments and the read pairs that are produced can be evaluated. For example, large molecular weight DNA can be extracted by, (1) gentle lysis of the cells according to Teague et al. (Proc. Nat. Acad. Sci. USA 107(24): 10848-53 (2010)) or Zhou et al. (PLOS Genetics, 5(11):e1000711 (2009)); and (2) agarose gel plugs according to Wing et al. (The Plant Journal: for Cell and Molecular Biology, 4(5):893-8 (1993)), which references are incorporated herein in-full, including any references cited therein, or by using the Aurora System from Boreal Genomics. These methods are capable of generating long DNA fragments beyond what is routinely required for next generation sequencing; however, any other suitable methods known in the art can be substituted for achieving similar results. The Aurora System provides exceptional results and can separate and concentrate DNA from tissue or other preparations up to, and beyond, a megabase in length. DNA extractions are prepared using each of these methodologies, beginning from a single GM12878 cell culture to control for possible differences at the sample level. The size distribution of the fragments can be evaluated by pulsed field gel electrophoresis according to Herschleb et al. (Nature Protocols 2(3): 677-84 (2007)). Using the foregoing methods, extremely large stretches of DNA can be extracted and used to build barcoded libraries. The barcoded library is then sequenced and aligned. The resulting read data are analyzed by comparing the genomic distance between read pairs to the fragment sizes observed from the gel.

Example 21: Sample Collection, Subsequent Analysis, and Treatment Selection

A patient undergoes surgery to remove a tissue. The tissue is excised in a sterile environment and deposited in formalin. No homogenization of the tissue occurs pursuant to collection.

The tissue is preserved and the patient is monitored. The patient is observed to undergo regrowth at the site of excision. The tissue is subjected to analysis in a laboratory setting, including excision of nucleic acid protein complexes from positions including the interior and the perimeter of the preserved tissue. The protein complexes comprise DNA and chromatin that are fixed together. The fixation preserves proximity information. The DNA includes double-stranded breaks that resulted from degradation due to storage conditions and the fixation process.

The ends of the DNA molecules are ligated biotinylated adapter oligonucleotides having an attB sequence. The fragments and adapter sequences are ligated to form chains of fragments and adapter polynucleotides. Some of the DNA fragments ligated together originate from distant genomic loci that looped together in three-dimensional space. The DNA is isolated and barcoded as described in Example 10.

Genomic information is obtained from nucleic acid protein complexes obtained from the preserved tissue. A genomic rearrangement is identified from perimeter tissue that indicates a particular genomic configuration implicated in tumor metastasis.

A chemotherapeutic treatment is selected based upon known efficacy relative to the genomic configuration implicated in tumor metastasis. The patient is administered the chemotherapeutic treatment and the tumor is observed to cease regrowth.

Example 22: Ongoing Monitoring of a Patient Suspected of Having a Tumor

A biopsy is taken from a patient suspected of having a tumor. The tissue is excised in a sterile environment and deposited in formalin. The sample is processed and analyzed as described in Example 21, the patient is diagnosed with cancer, and a chemotherapeutic agent is selected based upon the genomic rearrangement identified from the tissue. The patient undergoes a round of chemotherapy and the tumor is observed to go into remission.

A year later the patient relapses. The same therapeutic agent is used to treat the patient based on its prior success, but the patient fails to respond to the therapy. A further biopsy is taken from the patient. The tissue is excised in a sterile environment and deposited in formalin. The sample is processed and analyzed as described in Example 21, and a further genomic abnormality is identified in the tumor that was not detected in the initial biopsy. A different chemotherapeutic agent is selected based upon the further genetic abnormality identified from the tissue. The patient undergoes a round of chemotherapy and the tumor is again observed to go into remission.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed. It is intended that the following claims define the scope of the invention and that methods and structures within the scope of these claims and their equivalents be covered thereby.

What is claimed is:

1. A method of recovering nucleic acid phase information from a crosslinked sample, comprising:
   (a) cutting or grinding a tissue sample to produce a disrupted tissue sample;
   (b) contacting the disrupted tissue sample to a crosslinking agent to produce a crosslinked sample;
   (c) contacting the crosslinked sample to a collagenase to degrade intercellular material;
   (d) isolating nucleic acids bound in nucleoprotein complexes from the crosslinked sample;
   (e) contacting the nucleoprotein complexes to an enzyme to cleave one or more phosphodiester bonds of the nucleic acids bound in nucleoprotein complexes to create a plurality of segments;
   (f) ligating at least a first segment and a second segment of the plurality of segments at a junction; and
   (g) obtaining sequence on each side of the junction to generate a read pair, thereby recovering nucleic acid phase information from the crosslinked sample.

2. The method of claim 1 wherein (e) comprises a reaction time insufficient to degrade a portion of nucleosomes of the nucleoprotein complexes.

3. The method of claim 1, wherein the collagenase does not degrade intracellular proteins.

4. The method of claim 1, wherein the collagenase does not degrade cell membranes.

5. The method of claim 1, wherein the collagenase does not degrade nuclear proteins.

6. The method of claim 1, wherein the collagenase does not degrade nucleosomes.

7. The method of claim 1, wherein the collagenase does not degrade nucleoprotein complexes.

8. The method of claim 1, wherein the collagenase does not degrade chromatin.

9. The method of claim 1, wherein the nucleic acids bound in nucleoprotein complexes comprise a first segment of a chromosome and a second segment of the chromosome bound in a common nucleoprotein complex.

10. The method of claim 9, wherein the first segment of the chromosome and the second segment of the chromosome do not share a common phosphodiester bond.

11. The method of claim 9, wherein the first segment of the chromosome and the second segment of the chromosome share a common phosphodiester bond.

12. The method of claim 1, wherein the enzyme comprises at least one of a restriction endonuclease, a nonspecific endonuclease, a transposase, or an invertase.

13. The method of claim 1, wherein the nucleic acids bound in nucleoprotein complexes comprise a first segment of a first chromosome and a second segment of a second chromosome bound in a common nucleoprotein complex.

14. The method of claim 13, wherein the first chromosome and the second chromosome are in physical proximity in a tissue nucleus.

* * * * *

SEQUENCE LISTING

<160> NUMBER OF SEQ ID NOS: 8

<210> SEQ ID NO 1
<211> LENGTH: 605
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 1

Met Asp Thr Tyr Ala Gly Ala Tyr Asp Arg Gln Ser Arg Glu Arg Glu
1               5                   10                  15

Asn Ser Ser Ala Ala Ser Pro Ala Thr Gln Arg Ser Ala Asn Glu Asp
            20                  25                  30

Lys Ala Ala Asp Leu Gln Arg Glu Val Glu Arg Asp Gly Gly Arg Phe
        35                  40                  45

Arg Phe Val Gly His Phe Ser Glu Ala Pro Gly Thr Ser Ala Phe Gly
    50                  55                  60

Thr Ala Glu Arg Pro Glu Phe Glu Arg Ile Leu Asn Glu Cys Arg Ala
65                  70                  75                  80

Gly Arg Leu Asn Met Ile Ile Val Tyr Asp Val Ser Arg Phe Ser Arg
                85                  90                  95

Leu Lys Val Met Asp Ala Ile Pro Ile Val Ser Glu Leu Leu Ala Leu
            100                 105                 110

Gly Val Thr Ile Val Ser Thr Gln Glu Gly Val Phe Arg Gln Gly Asn
        115                 120                 125

Val Met Asp Leu Ile His Leu Ile Met Arg Leu Asp Ala Ser His Lys
    130                 135                 140

Glu Ser Ser Leu Lys Ser Ala Lys Ile Leu Asp Thr Lys Asn Leu Gln
145                 150                 155                 160

Arg Glu Leu Gly Gly Tyr Val Gly Gly Lys Ala Pro Tyr Gly Phe Glu
                165                 170                 175

Leu Val Ser Glu Thr Lys Glu Ile Thr Arg Asn Gly Arg Met Val Asn
            180                 185                 190

Val Val Ile Asn Lys Leu Ala His Ser Thr Thr Pro Leu Thr Gly Pro
        195                 200                 205

Phe Glu Phe Glu Pro Asp Val Ile Arg Trp Trp Arg Glu Ile Lys
    210                 215                 220

Thr His Lys His Leu Pro Phe Lys Pro Gly Ser Gln Ala Ala Ile His
225                 230                 235                 240

Pro Gly Ser Ile Thr Gly Leu Cys Lys Arg Met Asp Ala Asp Ala Val
                245                 250                 255

Pro Thr Arg Gly Glu Thr Ile Gly Lys Lys Thr Ala Ser Ser Ala Trp
            260                 265                 270

Asp Pro Ala Thr Val Met Arg Ile Leu Arg Asp Pro Arg Ile Ala Gly
        275                 280                 285

Phe Ala Ala Glu Val Ile Tyr Lys Lys Pro Asp Gly Thr Pro Thr
    290                 295                 300

Thr Lys Ile Glu Gly Tyr Arg Ile Gln Arg Asp Pro Ile Thr Leu Arg
305                 310                 315                 320

Pro Val Glu Leu Asp Cys Gly Pro Ile Ile Glu Pro Ala Glu Trp Tyr
                325                 330                 335

Glu Leu Gln Ala Trp Leu Asp Gly Arg Gly Arg Gly Lys Gly Leu Ser
            340                 345                 350

Arg Gly Gln Ala Ile Leu Ser Ala Met Asp Lys Leu Tyr Cys Glu Cys
        355                 360                 365

Gly Ala Val Met Thr Ser Lys Arg Gly Glu Glu Ser Ile Lys Asp Ser
    370                 375                 380

Tyr Arg Cys Arg Arg Lys Val Val Asp Pro Ser Ala Pro Gly Gln
385                 390                 395                 400

His Glu Gly Thr Cys Asn Val Ser Met Ala Ala Leu Asp Lys Phe Val
                405                 410                 415

Ala Glu Arg Ile Phe Asn Lys Ile Arg His Ala Glu Gly Asp Glu Glu
            420                 425                 430

Thr Leu Ala Leu Leu Trp Glu Ala Ala Arg Arg Phe Gly Lys Leu Thr
        435                 440                 445

Glu Ala Pro Glu Lys Ser Gly Glu Arg Ala Asn Leu Val Ala Glu Arg
    450                 455                 460

Ala Asp Ala Leu Asn Ala Leu Glu Glu Leu Tyr Glu Asp Arg Ala Ala
465                 470                 475                 480

Gly Ala Tyr Asp Gly Pro Val Gly Arg Lys His Phe Arg Lys Gln Gln
                485                 490                 495

Ala Ala Leu Thr Leu Arg Gln Gln Gly Ala Glu Glu Arg Leu Ala Glu
            500                 505                 510

Leu Glu Ala Ala Glu Ala Pro Lys Leu Pro Leu Asp Gln Trp Phe Pro
        515                 520                 525

Glu Asp Ala Asp Ala Asp Pro Thr Gly Pro Lys Ser Trp Trp Gly Arg
    530                 535                 540

Ala Ser Val Asp Asp Lys Arg Val Phe Val Gly Leu Phe Val Asp Lys
545                 550                 555                 560

Ile Val Val Thr Lys Ser Thr Thr Gly Arg Gly Gln Gly Thr Pro Ile
                565                 570                 575

Glu Lys Arg Ala Ser Ile Thr Trp Ala Lys Pro Pro Thr Asp Asp Asp
            580                 585                 590

Glu Asp Asp Ala Gln Asp Gly Thr Glu Asp Val Ala Ala
        595                 600                 605

<210> SEQ ID NO 2
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 2
gggtgccagg gcgtgccctt gggctccccg ggcgcgta                     38

<210> SEQ ID NO 3
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 3
ccccaactgg ggtaaccttt gagttctctc agttgggg                     38

<210> SEQ ID NO 4

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
aatgatacgg cgaccaccga                                              20

<210> SEQ ID NO 5
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
caagcagaag acggcatacg agat                                         24

<210> SEQ ID NO 6
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 6

His His His His His His
1               5

<210> SEQ ID NO 7
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Trp Ser His Pro Gln Phe Glu Lys
1               5

<210> SEQ ID NO 8
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Asp Tyr Lys Asp Asp Asp Asp Lys
1               5
```